US011485812B2

(12) United States Patent
Abe et al.

(10) Patent No.: US 11,485,812 B2
(45) Date of Patent: Nov. 1, 2022

(54) PYRANOQUINAZOLINE DERIVATIVES AND NAPHTHOPYRAN DERIVATIVES

(71) Applicant: KANTO KAGAKU KABUSHIKI KAISHA, Tokyo (JP)

(72) Inventors: Jiro Abe, Kanagawa (JP); Yuki Inagaki, Kanagawa (JP); Takayoshi Suga, Tokyo (JP); Hiroto Nagasawa, Tokyo (JP)

(73) Assignee: KANTO KAGAKU KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/494,290

(22) PCT Filed: Jan. 31, 2018

(86) PCT No.: PCT/JP2018/003141
§ 371 (c)(1),
(2) Date: Sep. 14, 2019

(87) PCT Pub. No.: WO2018/168232
PCT Pub. Date: Sep. 20, 2018

(65) Prior Publication Data
US 2020/0131193 A1 Apr. 30, 2020

(30) Foreign Application Priority Data

Mar. 14, 2017 (JP) .............................. JP2017-049113
Aug. 31, 2017 (JP) .............................. JP2017-167925

(51) Int. Cl.
*C08F 220/18* (2006.01)
*C07D 309/24* (2006.01)
*C07D 405/10* (2006.01)
*C07D 491/052* (2006.01)

(52) U.S. Cl.
CPC ...... *C08F 220/1804* (2020.02); *C07D 309/24* (2013.01); *C07D 405/10* (2013.01); *C07D 491/052* (2013.01)

(58) Field of Classification Search
CPC .. C07D 309/24; C07D 311/92; C07D 405/10; C07D 491/052; C07D 519/00; C08F 220/18; C09K 9/02; G02B 1/04; G02B 5/23
See application file for complete search history.

(56) References Cited

U.S. PATENT DOCUMENTS 8,217,188 B2   7/2012  Das et al.
8,308,995 B2  11/2012  Kasai et al.

FOREIGN PATENT DOCUMENTS

| JP | H08-3616 A | 1/1996 | |
| JP | 8-176139 A * | 7/1996 | ........... C07D 311/92 |
| JP | H08-176139 A | 7/1996 | |
| JP | H10-122860 A | 5/1998 | |
| JP | 2000-229973 A | 8/2000 | |
| JP | 2004-210657 A | 7/2004 | |
| JP | 2007-525462 A | 9/2007 | |
| JP | 2012-501326 A | 1/2012 | |
| JP | 2015-127371 A | 7/2015 | |
| JP | 2015-137259 A | 7/2015 | |
| WO | 2004/099172 A1 | 11/2004 | |
| WO | 2009/136668 A1 | 11/2009 | |

OTHER PUBLICATIONS

Arai, K et al., "Rational molecular designs for drastic acceleration of the color-fading speed of photochromic naphthopyrans," Chemical Communications, vol. 51, Issue 15, pp. 3057-3060, (2015).
Chamontin, K. et al., "Synthesis and Reactivity of Formyl-Substituted Photochromic 3,3-Diphenyl-[3H]-naphtho[2, 1-b]pyrans", Tetrahedron, vol. 55, Issue 18, pp. 5821-5830, (Apr. 1999).
Crano, J. C. et al., "Photochromic compounds: Chemistry and application in ophthalmic lenses", Pure & Applied Chemistry, vol. 68, Issue 7, pp. 1395-1398, (1996).
Hobza, P. and Havlas, Z., "Blue-Shifting Hydrogen Bonds", Chemical Reviews, vol. 100, Issue 11, pp. 4253-4264, (Nov. 2000).
Inagaki, Y et al., "A Simple and Versatile Strategy for Rapid Color Fading and Intense Coloration of Photochromic Naphthopyran Families", Journal of the American Chemical Society, vol. 139, Issue 38, pp. 13429 13441, (2017).
Joseph, J. and Jemmis, E.D., "Red-, Blue-, or No-Shift in Hydrogen Bonds: A Unified Explanation", Journal of the American Chemical Society, vol. 129, Issue 15, pp. 4620-4632, (2007).
Lewis, F.D. et al., "Molecular structure and photochemistry of (E)- and (Z)-2-(2-(2-pyridyl)ethenyl)indole. A case of hydrogen bond dependent one-way photoisomerization", Journal of the American Chemical Society, vol. 117, Issue 11, pp. 3029-3036, (1995).
Norikane, Y. et al., "Quantum Chemical Studies on Photoinduced Cis-Trans Isomerization and Intramolecular Hydrogen Atom Transfer of 2'-Hydroxychalcone", The Journal of Physical Chemistry A, vol. 107, Issue 41, pp. 3659-8664, (2003).

(Continued)

Primary Examiner — Erich A Leeser
(74) Attorney, Agent, or Firm — Maschoff Brennan

(57) ABSTRACT

A problem is presented in that conventional photochromic compounds cannot be considered adequate in terms of the colorizing/decolorizing rate and durability, and the production process therefore has many steps. The present invention provides an industrially applicable photochromic compound that has both a rapid colorizing/decolorizing reaction and high durability and can also be synthesized at a low cost. This compound is characterized in that etheric oxygen atoms are bonded to the carbon atoms at position 1 of a pyranoquinazoline (8H-pyrano[3,2-f]quinazoline) skeleton and position 10 of a naphthopyran (3H-naphtho[2,1-b]pyran) skeleton, said compound having photochromic properties and being a photochromic compound that has both a rapid colorizing/decolorizing reaction and high durability. Also provided is an industrially applicable photochromic compound that can be synthesized at a low cost.

2 Claims, 61 Drawing Sheets

(56) References Cited

OTHER PUBLICATIONS

Shinohara, Y.S. et al., "Effect of Methoxy Substituents on the Excited State Properties of Stilbene", Bulletin of the Chemical Society of Japan, vol. 81, Issue 11, pp. 1500-1504, (2008).

Oliveira, M. M. et al., "Remarkable thermally stable open forms of photochromic new N-substituted benzopyranocarbazoles", Journal of Photochemistry and Photobiology A: Chemistry, vol. 198, Issues 2-3, pp. 242-249, (Aug. 2008).

* cited by examiner

PYRANOQUINAZOLINE DERIVATIVES AND NAPHTHOPYRAN DERIVATIVES

FIELD OF THE INVENTION

The present invention relates to a photochromic compound, having both high-speed decolorizing property and high durability, whose $1^{st}$ position of pyranoquinazoline(8H-pyrano[3,2-f]quinazoline) skeleton and the $10^{th}$ of naphthopyran(3H-naphtho[2,1-b]pyran) skeleton are bonded to an etheric oxygen atom.

BACKGROUND OF THE INVENTION

Photochromism is a phenomenon which enables, by a light operation, a single chemical species to reversibly generate two isomers having different colors without changing the molecular weight. When one isomer is irradiated by light of a specific wavelength, the bonding mode or electronic state is changed to convert to the other isomer having different molecular structure such that the color is changed due to the variation of absorption spectrum. Said the other isomer generated as mentioned above by light irradiation may return, by being irradiated with light having other wavelength or by being treated with a thermal process, to the isomer of the original molecular structure so as to return to the original color. A compound having above properties is called a photochromic compound. The above phenomenon is wildly applied in various fields such as light control materials, rewritable optical memory materials, hologram materials, optical elements, security ink materials and decorative articles.

For photochromic compounds applied in light controlling lens materials, hologram materials and security ink materials, and so on, the following characteristic features are required including: high colorizing density as being irradiated by ultraviolet, a short time period from the beginning of irradiating ultraviolet to the colorizing density reaching saturation, a short time period from stopping irradiating ultraviolet to returning to the original colorless state, and good repeating durability.

The plastic light control lenses used indoors and outdoors, such as intraocular lenses and contact lenses, are manufactured by having a polymer containing a photochromic compound which processes photochromism.

For the photochromic compound, naphthopyran derivative is used as light control material of plastic light controlling lens because adjustment of its thermal decolorization speed and color tone is comparative easy, and repeating durability is high (patent document 1-7).

After light irradiates colorless naphthopyran, the following two isomers including cis-transoid (TC) and trans-transoid (TT) are generated as chromogen. In the following formula, "hv→" indicates that the compound of the present invention absorbs energy such as ultraviolet to perform photoisomerization by which a metastable cis-transoid form or trans-transoid form is transformed. "←Δ" means that cis-transoid or trans-transoid absorbs heat energy to reversibly shift to naphthopyran, which is the original decolorized form and is stable in terms of energy.

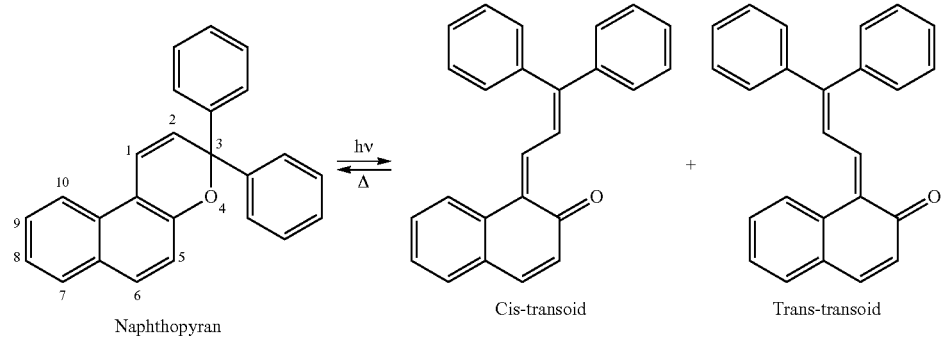

Naphthopyran      Cis-transoid      Trans-transoid

The colorless pyranoquinazoline also generates the following two isomers of cis-transoid and trans-transoid as chromogen when being irradiated.

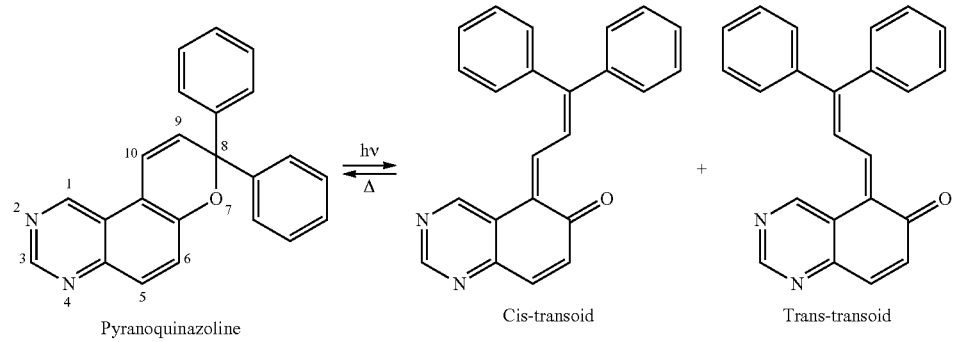

Pyranoquinazoline      Cis-transoid      Trans-transoid

As the energetically unstable cis-transoid rapidly returns to original decolorized form by thermal reaction, since trans-transoid, which is the other chromogen generated by photochemical reaction of cis-transoid, is thermally stable and is able to remain for a long time, the decolorize reaction takes at least several seconds to several minutes.

Conventional naphthopyran derivatives generate trans-transoid in high proportions by irradiation such that, when is used as an optical switch material, it will have a problem that the colorization is being remained for a long time. And when is used as a light control material, it has a problem of time consuming as switching.

PRIOR ART DOCUMENTS

Patent Document 1: JP-A-1994-135967
Patent Document 2: JP-A-1996-295690
Patent Document 3: JP-A-2004-210657
Patent Document 4: JP-A-2007-525462
Patent Document 5: JP-A-2012-501326
Patent Document 6: JP-A-2015-137259
Patent Document 7: WO2009-136668

SUMMARY OF THE INVENTION

Accordingly, an object of the present invention is to provide an industrially usable photochromic compound that solves the above problems and has both high-speed decolorizing property and high durability.

The inventors of the present invention have made extensive studies to solve the above-mentioned problems, and have found that when an etheric oxygen atom is introduced to the $1^{st}$ position of the 8H-pyrano[3,2-]quinazoline skeleton and the $10^{th}$ position of the 3H-naphtho[2,1-b]pyran skeleton, the cis-tansoid is stabilized by the effect of intramolecular hydrogen bonding, and the generation of the trans-transoid is greatly suppressed so as to have a fast colorizing/decolorizing reaction and high durability. According to the above, a further research is performed to obtain the present invention.

That is, the present invention relates to:
[1] A compound represented by the following general formulas (1), (2) or (3):

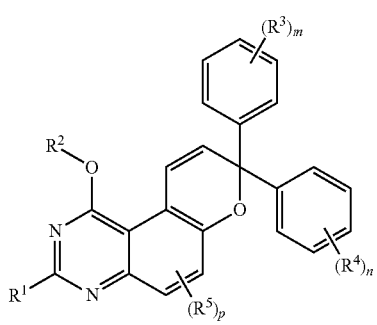
(1)

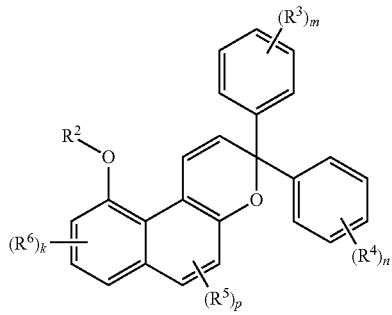
(2)

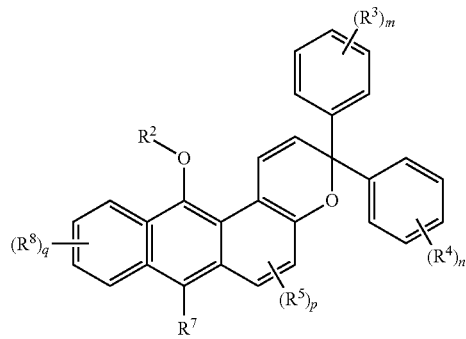
(3)

wherein, in the formulas, the substituent R1, R6 and R8 are:

alkyl group or alkoxy group, or alkyl group having substituent W or alkoxy group having substituent W; or aromatic group or heterocyclic group, or aromatic group having substituent W or heterocyclic group having substituent W, wherein the substituents W are independent to each other and are identical or different from each other, and (1) the substituent(s) W is one or more substituent selected from the group consisting of:

hydrogen atom, halogen atom, nitro group, cyano group, trifluoromethyl group, hydroxyl group, thiol group, amino group and carbazole group, straight chain or branched chain alkyl group, alkylamino group, alkoxy group and cycloether ring having carbon number from 1 to 20, —Y1-SiZ1Z2Z3 group, —Y1-SiY2Z1Z2 group and —Y1-SiY2Y3Z1 group, aromatic ring, heterocyclic ring, and alicyclic ring which forms rings by combining with each other, wherein Y1 to Y3 and Z1 to Z3 are independent to each other and are identical to or different from each other, and Y1 to Y3 represent straight chain, branched chain or cyclic alkyl group or alkylene group having carbon number from 1 to 20, and Z1 to Z3 represent hydrogen atom or halogen atom, or straight chain or branched chain alkoxy group having carbon number from 1 to 8, or (2) the substituent(s) W is one or more substituent selected from the group consisting of substituents represented by the following structural formulas (i), (ii) and (iii):

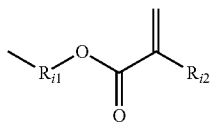
(i)

wherein Ri1 represents alkyl group, alkylene group or alkoxylene group having carbon number from 1 to 20, and Ri2 represents hydrogen or alkyl group having carbon number from 1 to 3;

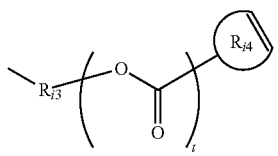
(ii)

wherein Ri3 represents alkyl group, alkylene group or alkoxylene group having carbon number from 1 to 20, Ri4 represents cyclic olefins having a total of carbon and silicon number of 5 to 10, and t represents of 0 or 1; and

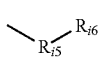
(iii)

wherein Ri5 represents alkyl group, alkylene group or alkoxylene group having carbon number from 1 to 20, Ri6 represents ethylene group or acetylene group, the substituent W is formed integrally with the carbon atom bonded thereto and other substituent to not form or form aromatic ring, heterocyclic ring or alicyclic ring on which there is not or is a substituent having the same meaning as the substituent having aryl group, R2 is:

straight chain, branched chain or cyclic alkyl group, aromatic ring group or heterocyclic group having carbon number from 1 to 20, or straight chain, branched chain or cyclic alkyl group, aromatic ring group or heterocyclic group having substituent W and having carbon number from 1 to 20, R3, R4, R5 and R7 are independent to each other, identical or different from each other, and one or more substituent selected from the group consisting of:

halogen atom, nitro group, cyano group, trifluoromethyl group, hydroxyl group, thiol group, amino group, carbazole group, and straight chain or branched chain alkyl group, alkylamino group and alkoxy group having carbon number from 1 to 20, —Y1-SiZ1Z2Z3 group, —Y1-SiY2Z1Z2 group and —Y1-SiY2Y3Z1 group, wherein Y1 to Y3 are independent to each other, identical to or different from each other, and represent straight chain, branched chain or cyclic alkyl group or alkylene group having carbon number from 1 to 20, and Z1 to Z3 are independent to each other, identical to or different from each other, and represent hydrogen atom or halogen atom or straight chain or branched chain alkoxy group having carbon number from 1 to 8, bonding of R2 with R6 and bonding of R2 with R8 may form 5- to 7-membered ring, or 5-to 7-membered ring having substituent W, bonding of two or more R5, bonding of two or more R6, bonding of one or more R5 and R6, bonding of one or more R5 and R7, and bonding of one or more R7 and R8 may form unsaturated 5- or 6-membered ring or aromatic ring, or unsaturated 5- or 6-membered ring having substituent W, in the unsaturated 5- or 6-membered ring or aromatic ring formed by bonding of one or more R5 and R6, bonding of one or more R5 and R7 and bonding of one or more R7 and R8, unsaturated 5- or 6-membered ring or aromatic ring, or unsaturated 5- or 6-membered ring having substituent W may be formed, m and n are an integer from 1 to 5,
k is an integer from 1 to 3,
p is an integer from 1 to 2, and
q is an integer from 1 to 4.

[2] A compound formed by copolymerizing the compound as described in [1].

[3] A solvent comprising the compound as described in [1] or [2].

[4] A resin comprising the compound as described in [1] or [2].

[5] A photo chromic material comprising the compound as described in [1] or [2].

[6] A photo chromic lens comprising the compound as described in [1] or [2].

[7] An optical switch comprising the compound as described in [1] or [2].

The etheric oxygen atom in the present invention indicates oxygen atom that forms ether bond. It has been found that, for example, for cis-transoid having 8H-pyrano[3,2-f] quinazoline derivative containing methoxy group at the 1st position and 3H-naphtho[2,1-b]pyran derivative containing methoxy group at the 10th position as shown in below, the etheric oxygen atom of methoxy group forms a hydrogen bond with the methylene hydrogen atom bonded to a carbon-carbon double bond such that the cis-transoid is stabilized.

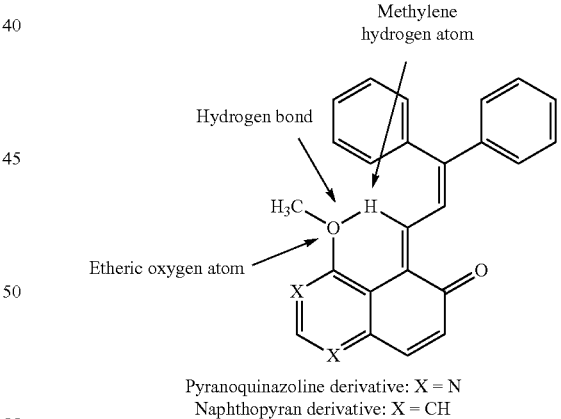

Pyranoquinazoline derivative: X = N
Naphthopyran derivative: X = CH

The cis-trans photoisomerization reaction involving the carbon-carbon double bond of olefins is a process as follows. The cis-transoid in the electronic ground state absorbs light energy to excite to a high-energy electronical excited state so as to loosen the carbon-carbon double bond such that a rotation occurs along the carbon-carbon bond axis.

It has been known that when the methylene hydrogen atom, which bonds to the carbon-carbon double bond of olefin, forms an intramolecular hydrogen bond and the rotation along the carbon-carbon bond axis is structurally inhibited, the efficiency of photoisomerization reaction from the cis-transoid to the trans-transoid is significantly reduced. Typical examples are described in papers, such as Y. M. Shinohara, T. Arai, Bull. Chem. Soc. Jpn., 81 (11), 1500-1504, 2008; Y. M. Norikane, N., Nakayama, N., Tamaoki, T., Arai, U. Nagashima, J. Phys. Chem. A, 107 (41), 8659-8664, 2003; and F. D. Lewis, B. A. Yoon, T. Arai, T. Iwasaki, K. Tokumaru, J. Am. Chem. Soc., 117 (11), 3029-3036, 1995.

Cis-transoid of pyranoquinazoline and naphthopyran absorb light energy to excite to an electronical (JC: 請全文對應修改) excited state so as to rotate along the bond axis of a carbon-carbon double bond such that isomerize turns into trans-transoid, which is thermally stable and could be remained for a long time.

Since the methylene hydrogen atom, which is bonded in a carbon-carbon double bonding manner by having a methylene carbon atom bonding to the cis-transoid of pyranoquinazoline or naphthopyran, could form intramolecular hydrogen bond with the etheric oxygen atom of the methoxy group introduced to the $1^{st}$ position of pyranoquinazoline or the $10^{th}$ position of naphthopyran, it is predicted that the rotation along the bond axis of the carbon-carbon double bond is structurally inhibited, and the efficiency of the photoisomerization reaction from the cis-transoid to the trans-transoid is significantly reduced.

Under a condition that the quantum chemistry calculation program (Gaussian09) is applied to perform the density functional calculation (M06-2X/6-31 ++ G (d, p)), it is predicted that a hydrogen bond is formed between the etheric oxygen atom of the methoxy group and the methylene hydrogen atom. Specifically, after the most stable structure of the cis-transoid, represented by the following structural formulas (a) to (d) is obtained, and the interatomic distance ($R_{O1-H1}$) between the etheric oxygen atom ($O_1$) and the methylene hydrogen atom ($H_1$), the charge q of the methylene hydrogen atom ($H_1$) and the interatomic distance ($R_{C1-H1}$) between the methylene carbon atom ($C_1$) and the methylene hydrogen atom ($H_1$), which involves in the photoisomerization reaction, are obtained, it is found that forming of the hydrogen bond could be predicted.

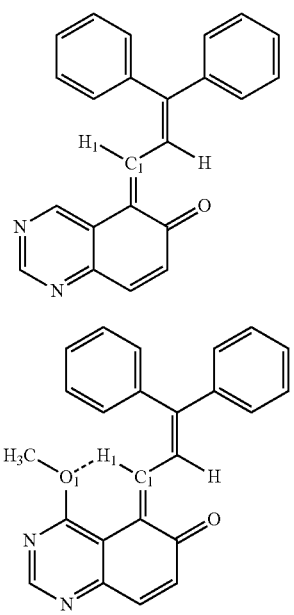

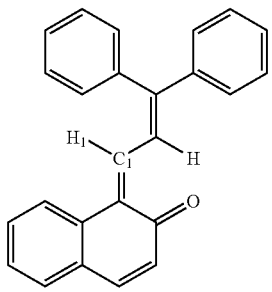

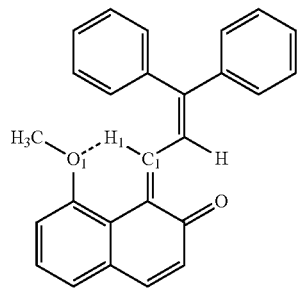

It is known that regarding the C—H . . . O type hydrogen bond, since a hydrogen bond is formed, the C—H bond distance decreases with the increase of the charge of a hydrogen atom, as described in Hobza, Z., Havlas, Chem. Rev., 100 (11), 4253-4264, 2000; and J. Mol. Joseph, E. D. Jemis, J. Am. Chem. Soc., 129 (15), 4620-4632, 2007.

The result of the density functional calculation is shown in table 1.

TABLE 1

| Structural formula | $R_{O1-H1}$ (Å) | q | $R_{C1-H1}$ (Å) |
|---|---|---|---|
| (a) | — | +0.057 | 1.087 |
| (b) | 2.046 | +0.211 | 1.082 |
| (c) | — | +0.115 | 1.087 |
| (d) | 2.055 | +0.225 | 1.082 |

$R_{O1-H1}$ of (b) and (d) having a methoxy group are 2.046 (Å) and 2.055 (Å) respectively, which are shorter than 2.72 (Å) as the sum of van der Waals radius of the oxygen atom of 1.52 (Å) and the van der Waals radius of the hydrogen atom of 1.20 (Å). And accordingly, the standard interatomic distance range of C—H . . . O-type hydrogen bonds is supported.

Compared with (a) and (c), which have no hydrogen bonds due to the lack of methoxy group, it is found that, in (b) and (d), since $R_{C1-H1}$ decreases with the increase of the charge (q) of the methylene hydrogen atom, the etheric oxygen atom of the methoxy group and the methylene hydrogen atom forming a hydrogen bond is predicted.

According to the result of the density functional calculation described above, it can be predicted that, by introducing etheric oxygen atom to the $1^{st}$ position of the 8H-pyrano[3,2-f]quinazoline skeleton and the $10^{th}$ position of the 3H-naphtho[2,1-b]pyran skeleton, the methylene hydrogen atoms bonding to the etheric oxygen atoms with a carbon-carbon double bonds form intramolecular hydrogen bonds, the rotation of the carbon-carbon double bond along the bond axis is structurally suppressed, and the efficiency of the photoisomerization reaction from cis-transoid to trans-transoid is significantly reduced in the cis-transoid, which is one of the chromophores generated by light irradiation.

The compound of the present invention is characterized in that an etheric oxygen atom is bonded to the $1^{st}$ position of the 8H-pyrano[3,2-f]quinazoline skeleton and the $10^{th}$ position of the 3H-naphtho[2,1-b]pyran skeleton.

It is found that when the compound of the present invention is irradiated with light, not only a cis-transoid as a chromogen is generated in a high efficiency, but also the generation of a long time existing trans-transoid is suppressed. As a result, an industrially usable photochromic having both high-speed decolorizing property and high durability as compared with conventional photochromic compounds could be achieved.

Therefore, the compound of the present invention can be applied to a wide range of fields such as a light control lens material, a hologram material, a security ink material, and an optical switch material.

BRIEF DESCRIPTION OF THE DRAWINGS

FIG. 6 is a graph of the $^1$H NMR spectrum (400 MHz) of 1-phenoxy-3,8-diphenyl-8-(4-(piperidin-1-yl)phenyl)-8H-pyrano[3,2-f]quinazoline (Compound 6), solvent: deuterated dimethyl sulfoxide.

DETAILED DESCRIPTION OF THE PREFERRED EMBODIMENTS

Figure 1:
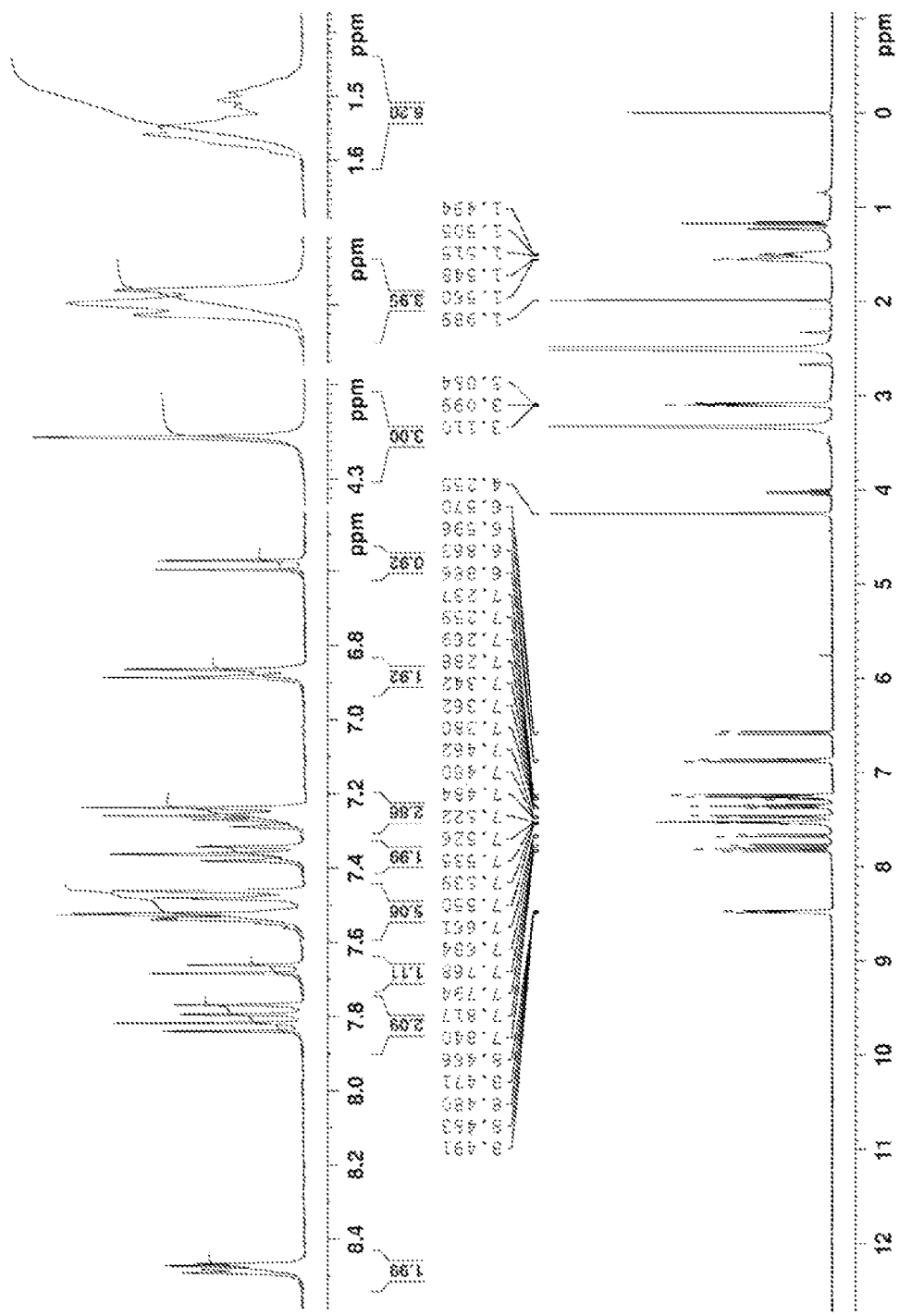
FIG. 1 is a graph of the $^1$H NMR spectrum (400 MHz) of 1-methoxy-3,8-diphenyl-8-(4-(piperidin-1-yl)phenyl)-8H-pyrano[3,2-f]quinazoline (Compound 1), solvent: deuterated dimethyl sulfoxide.
Figure 2:
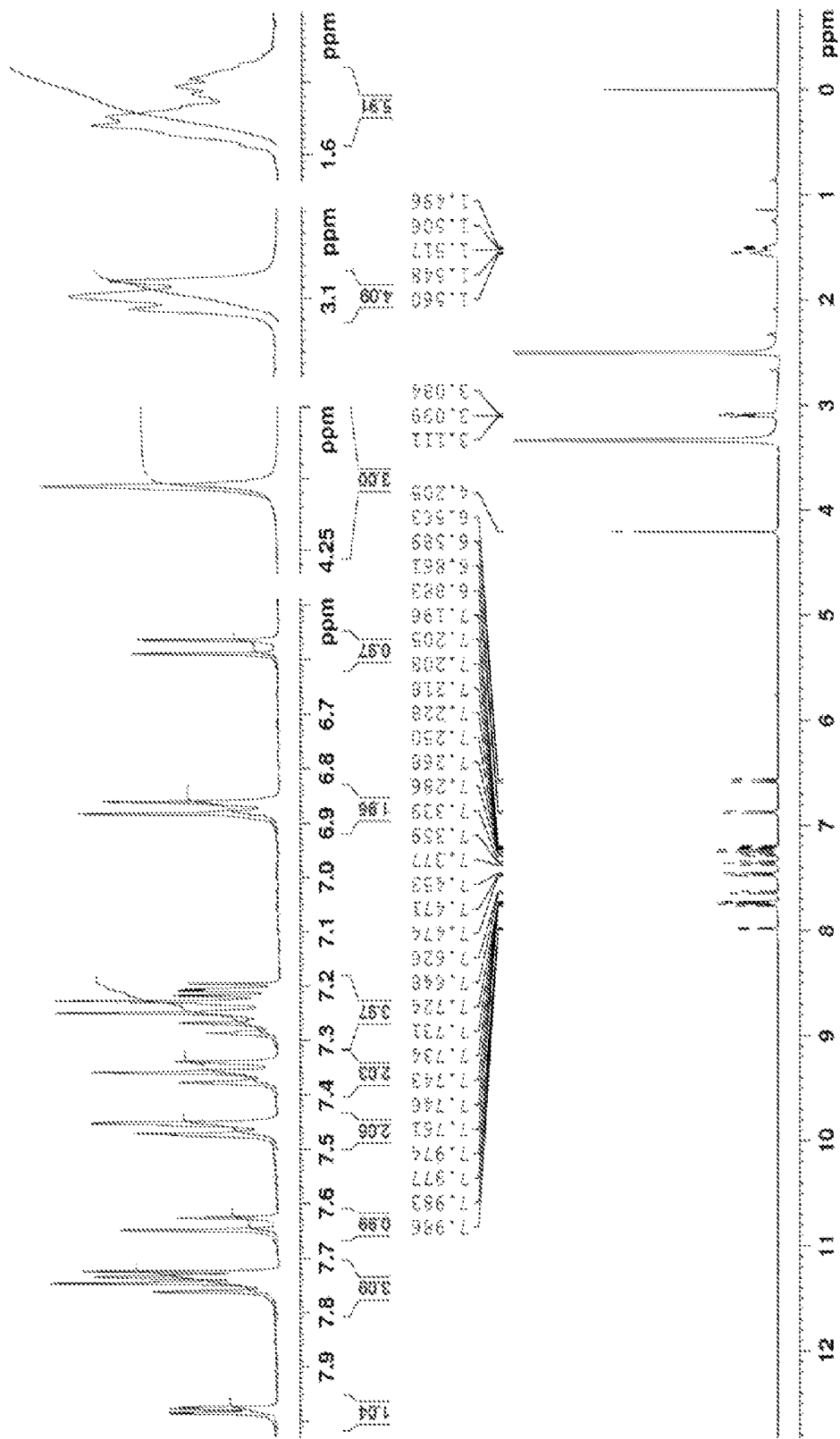
FIG. 2 is a graph of the $^1$H NMR spectrum (400 MHz) of 1-methoxy-8-phenyl-8-(4-(piperidin-1-yl)phenyl)-3-(thiophen-2-yl)-8H-pyrano[3,2-f]quinazoline (Compound 2), solvent: deuterated dimethyl sulfoxide.
Figure 3:
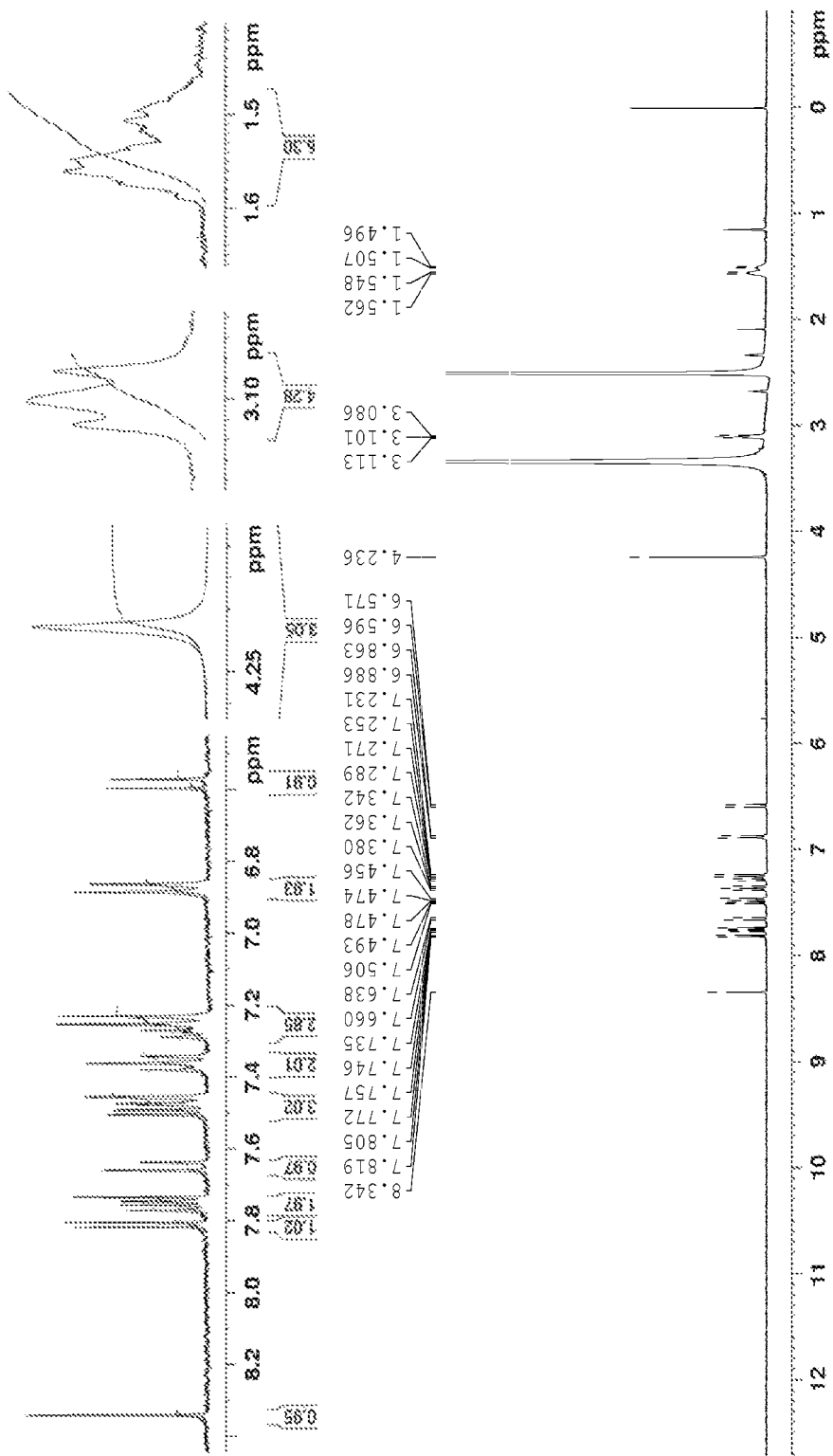
FIG. 3 is a graph of the $^1$H NMR spectrum (400 MHz) of 1-methoxy-8-phenyl-8-(4-(piperidin-1-yl)phenyl)-3-(thieno[3,2-b]thiophen-2-yl)-8H-pyrano[3,2-f]quinazoline (Compound 3), solvent: deuterated dimethyl sulfoxide.
Figure 4:
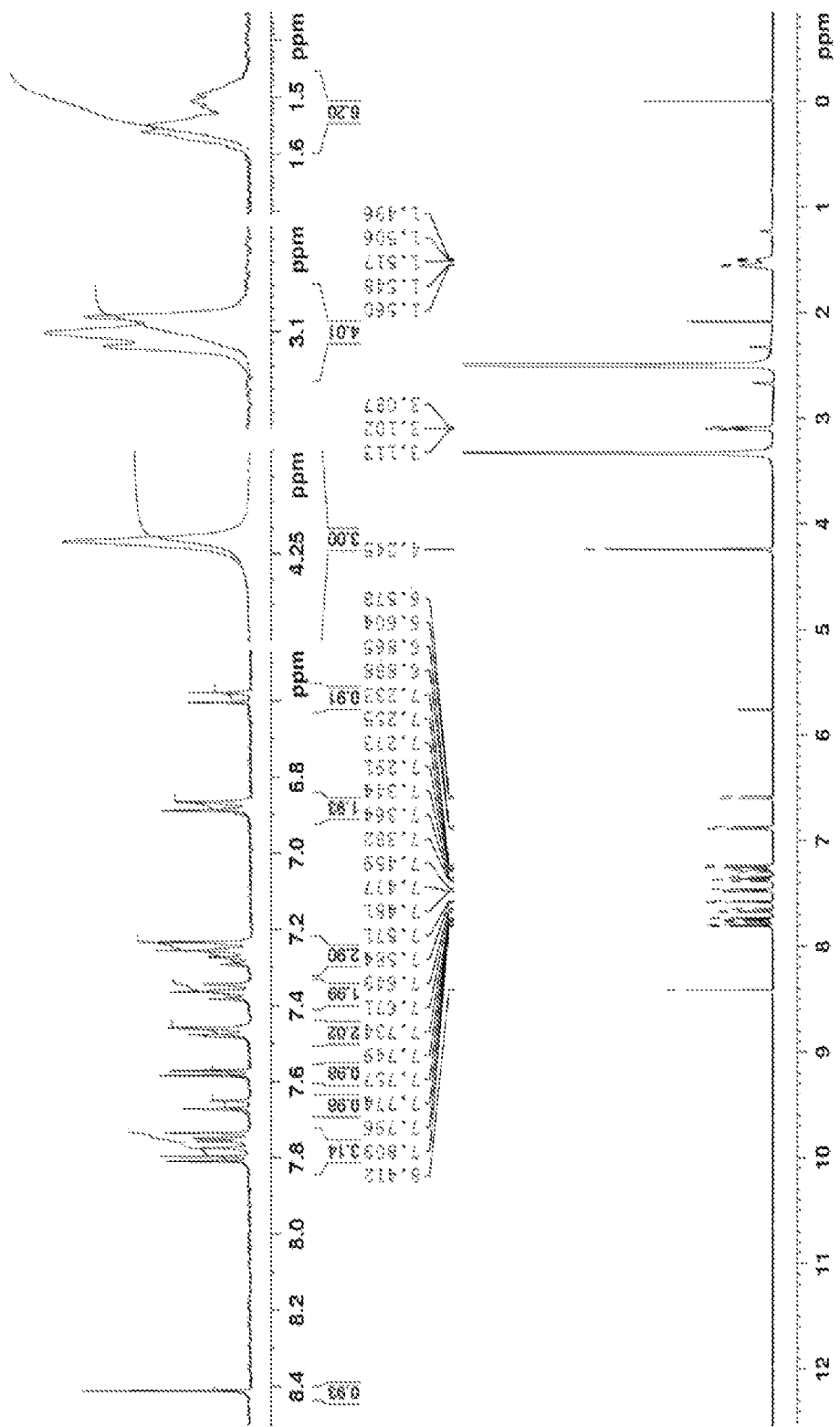
FIG. 4 is a graph of the $^1$H NMR spectrum (400 MHz) of 3-(dithieno[3,2-b:2',3'-d]-1-methoxy-8-phenyl-8-(4-(piperidin-1-yl)phenyl)-8H-pyrano[3,2-f]quinazoline (compound 4), solvent: deuterated dimethyl sulfoxide.
Figure 5:
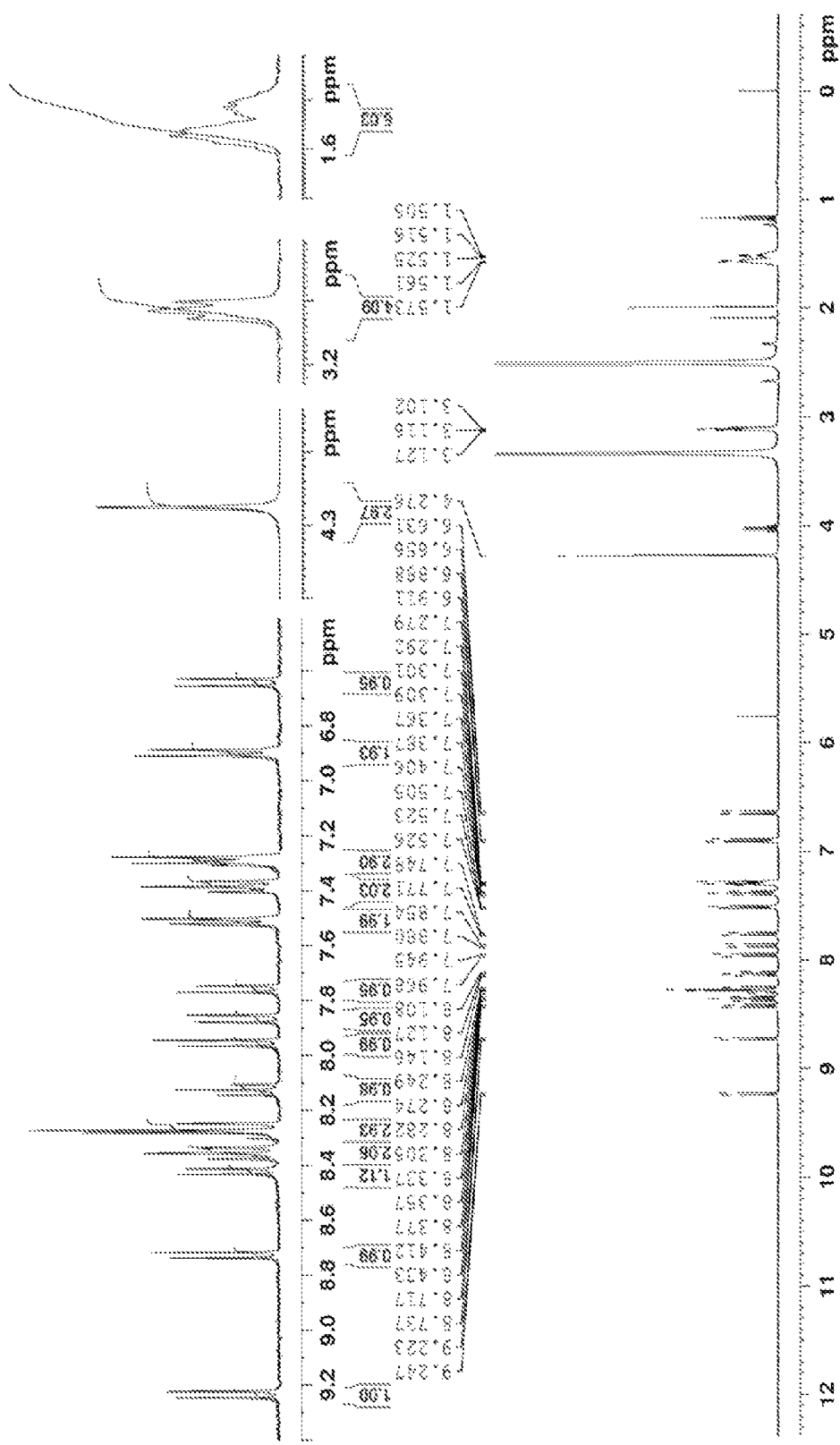
FIG. 5 is a graph of the $^1$H NMR spectrum (400 MHz) of 3-(3a,8a-dihydropyren-1-yl)-1-methoxy-8-phenyl-8-(4-(piperidin-1-yl)phenyl)-8H-pyrano[3,2-]quinazoline (compound 5), solvent: deuterated dimethyl sulfoxide.
Figure 6:
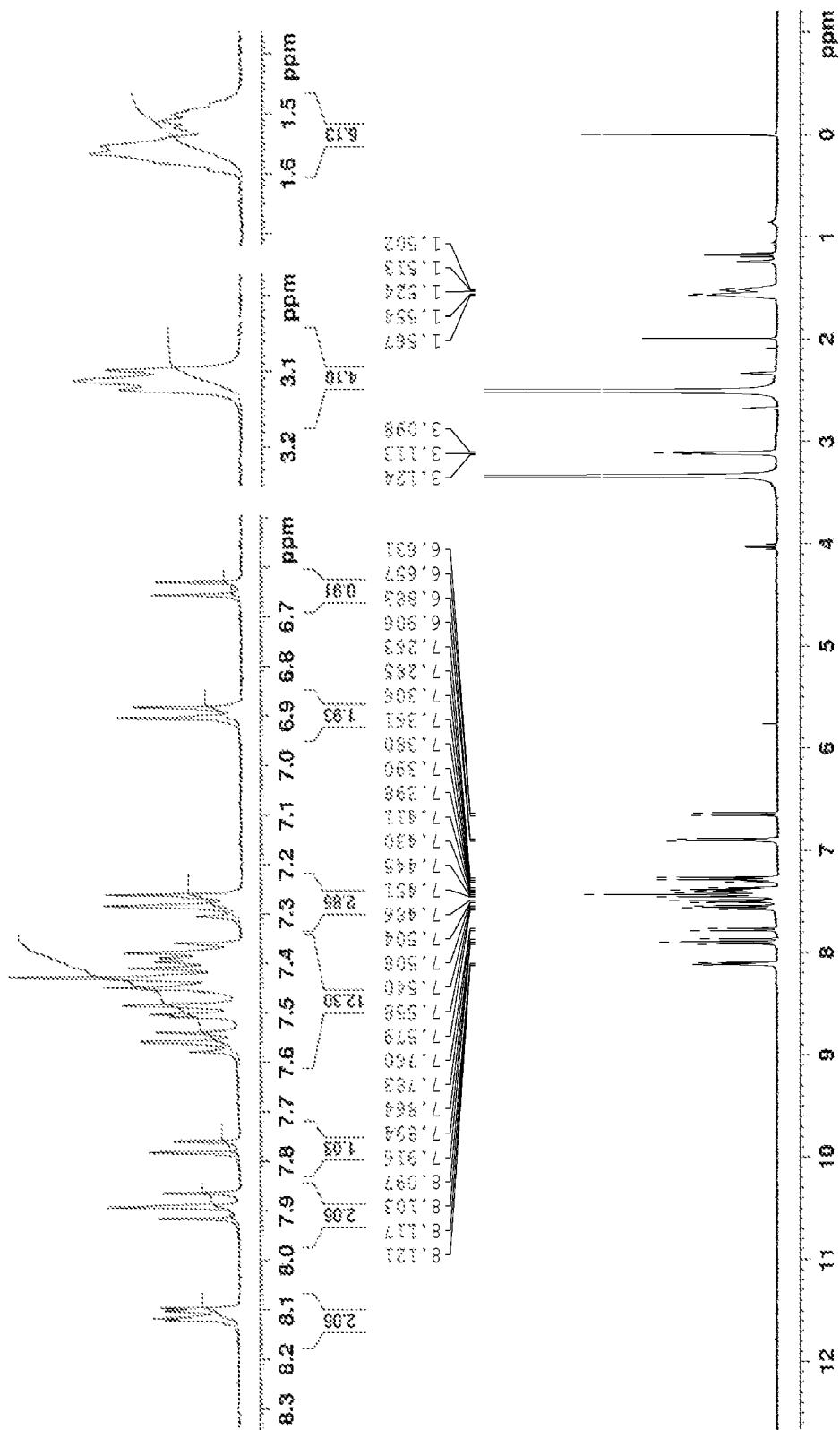
FIG. 6 is a graph of the $^1$H NMR spectrum (400 MHz) of, solvent: deuterated dimethyl sulfoxide.
Figure 7:
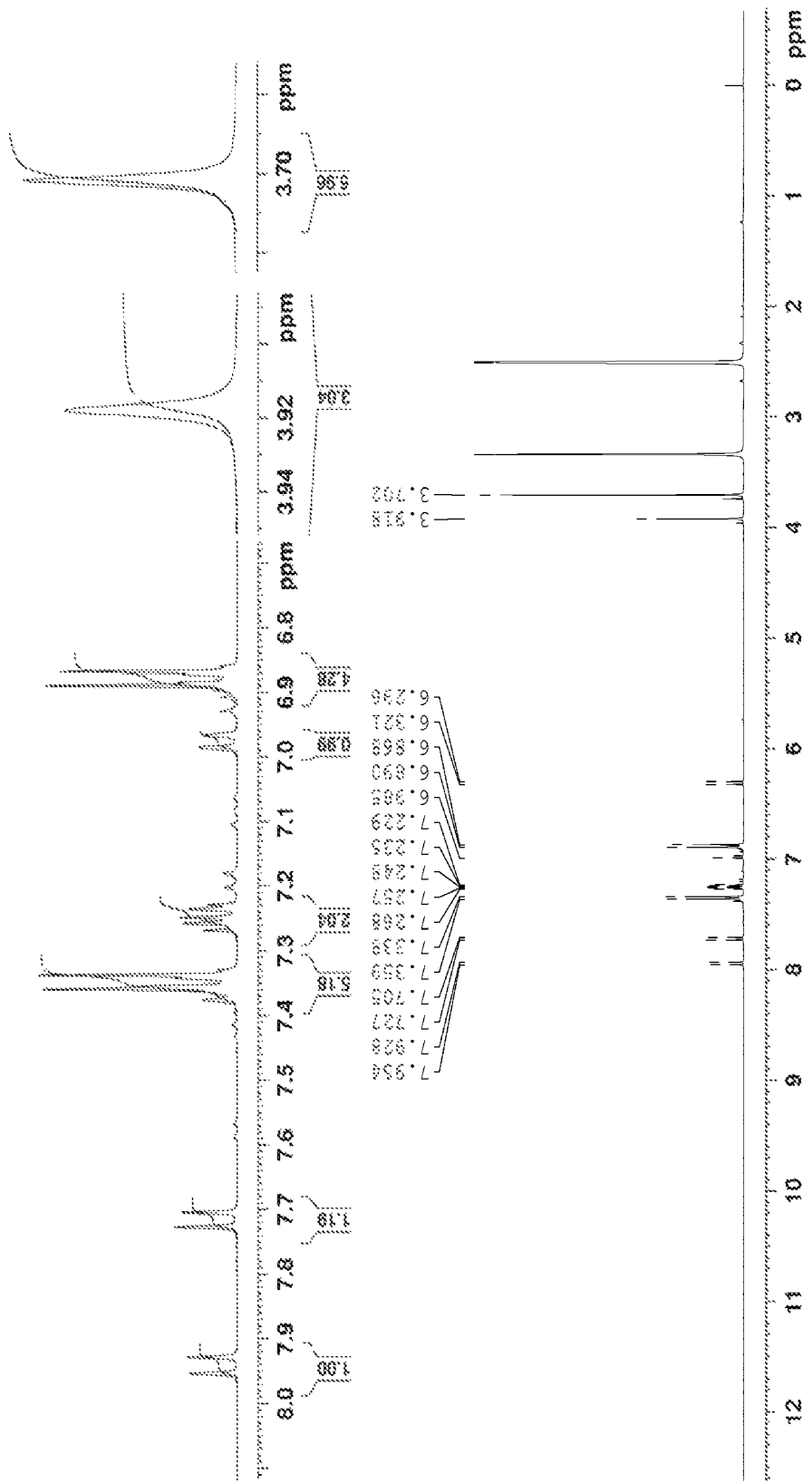
FIG. 7 is a graph of the $^1$H NMR spectrum (400 MHz) of 10-methoxy-3,3-bis(4-methoxyphenyl)-3H-benzo[f]chromene (compound 7), solvent: deuterated dimethyl sulfoxide.
Figure 8:
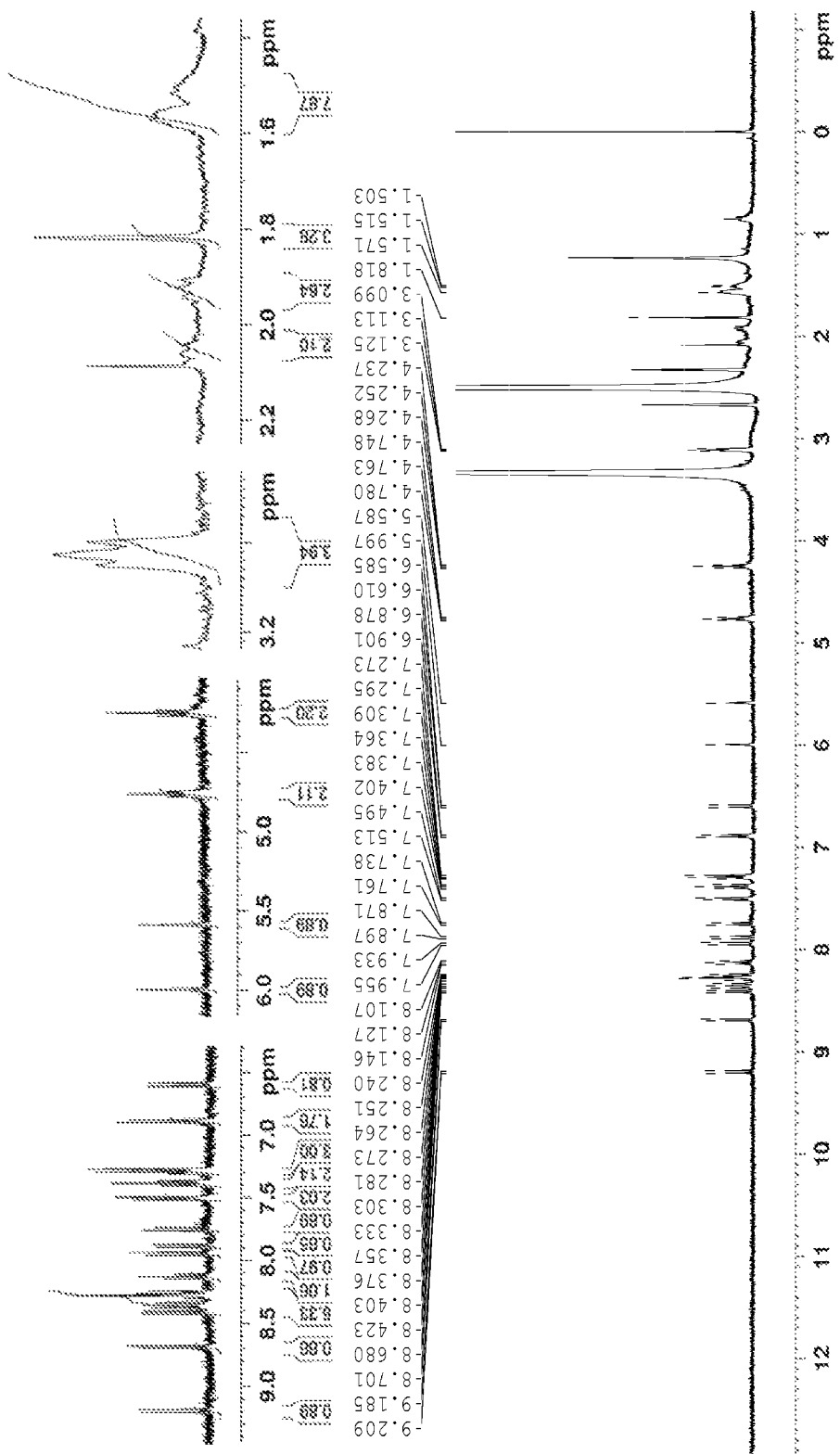
FIG. 8 is a graph of the $^1$H NMR spectrum (400 MHz) of 4-((8-phenyl-8-(4-(piperidin-1-yl)phenyl)-3-(pyren-1-yl)-8H-pyrano[3,2-f]quinazolin-1-yl)oxy)Butylmethacrylate (compound 8), solvent: deuterated dimethyl sulfoxide.
Figure 9:
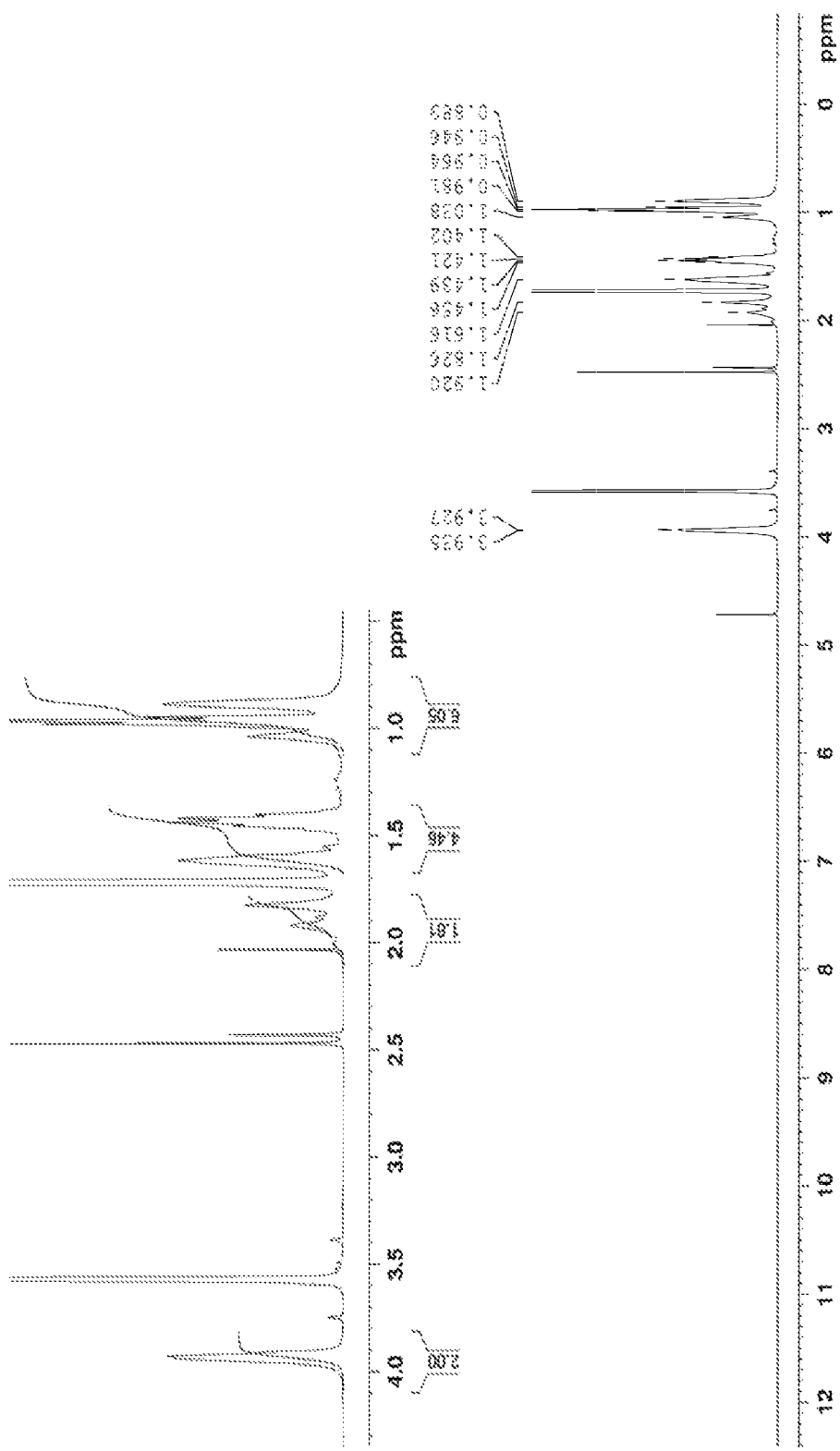
FIG. 9 is a graph of the $^1$H NMR spectrum (400 MHz) of Photochromic polymer (compound 9), solvent: deuterated tetrahydrofuran.
Figure 10:
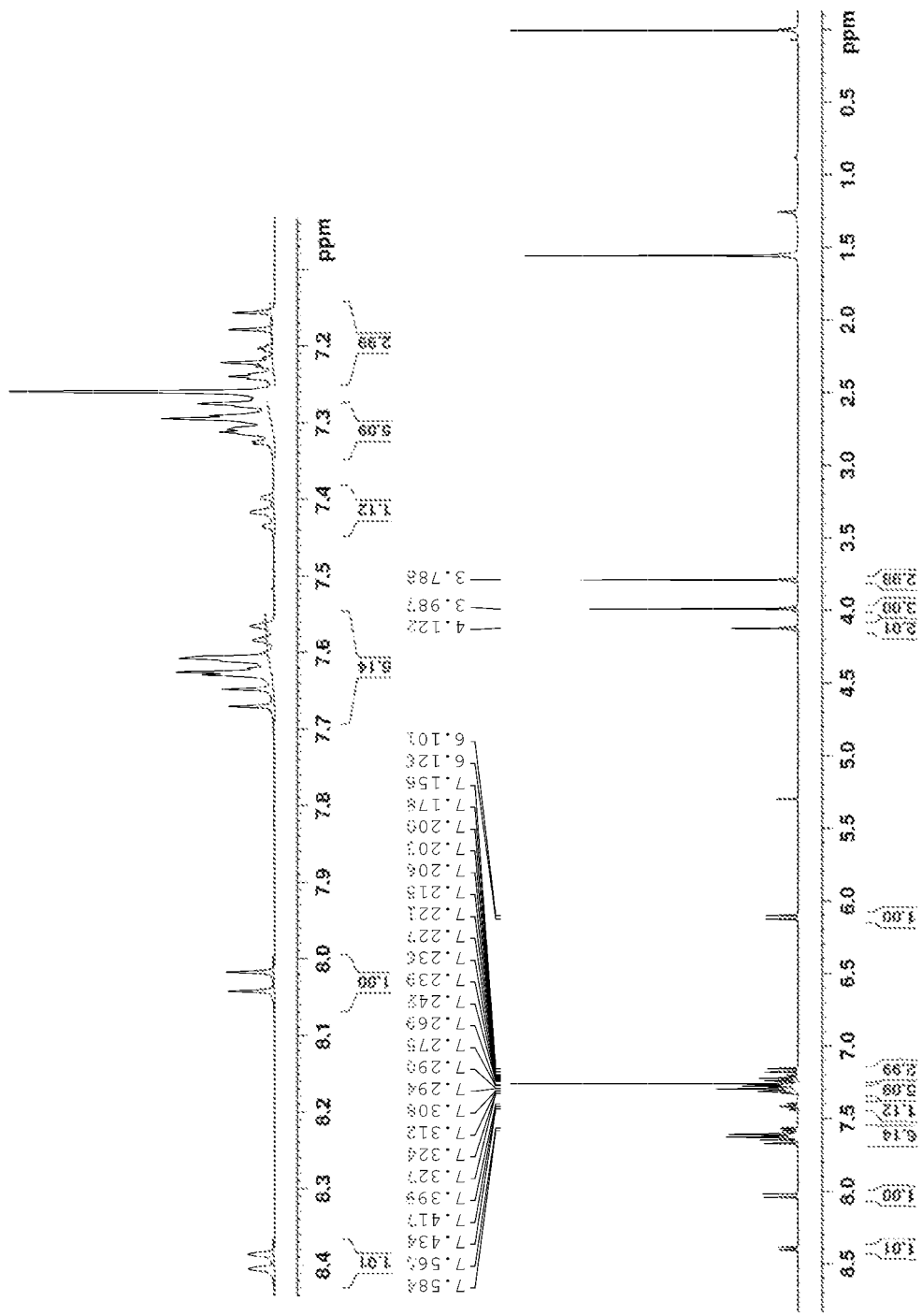
FIG. 10 is a graph of the $^1$H NMR spectrum (400 MHz) of 5,6-dimethoxy-2,2-diphenyl-2,9-dihydrobenzo[f]indeno[2,1-h]chromene (Compound 10), solvent: deuterated chloroform.
Figure 11:
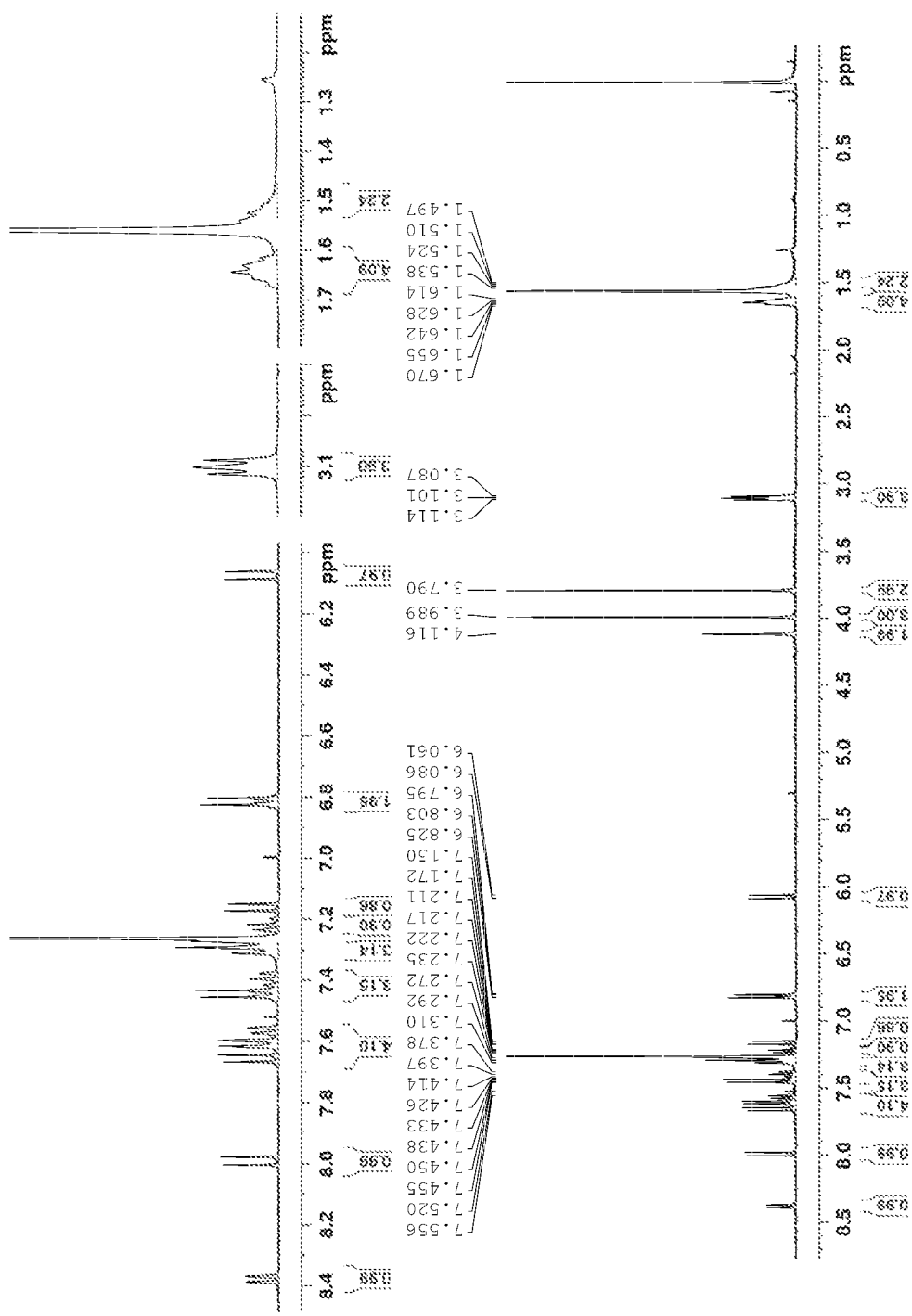
FIG. 11 is a graph of the $^1$H NMR spectrum (400 MHz) of 5,6-dimethoxy-2-phenyl-2-(4-(piperidin-1-yl)phenyl)-2,9-dihydrobenzo[f]indeno[2,1-h]chromene (Compound 11), solvent: deuterated chloroform.
Figure 12:
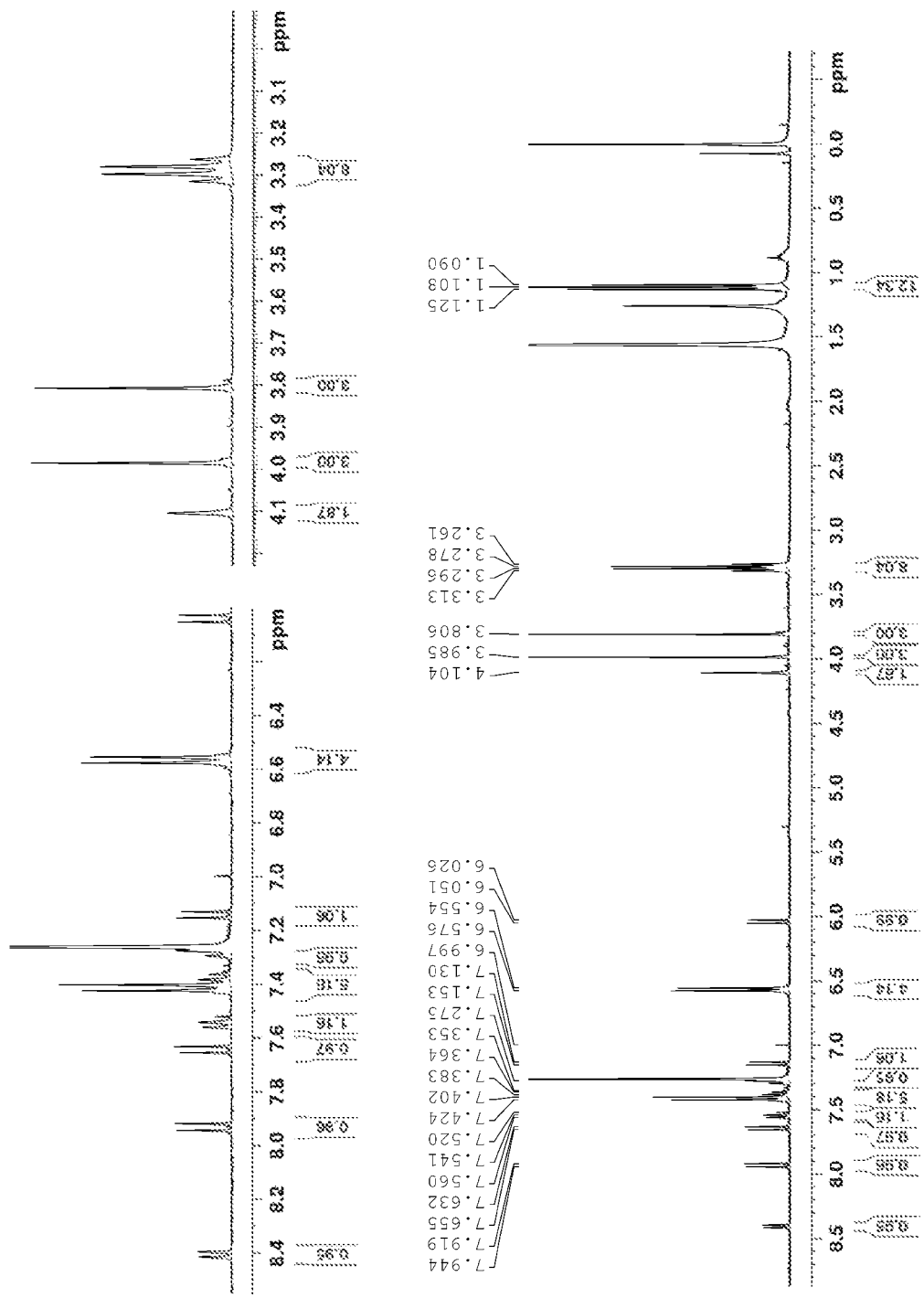
FIG. 12 is a graph of the $^1$H NMR spectrum (400 MHz) of 5,6-dimethoxy-2,2-di(4-diethylaminophenyl)-2,9-dihydrobenzo[f]indeno[2,1-h]chromene (Compound 12), solvent: deuterated chloroform.
Figure 13:
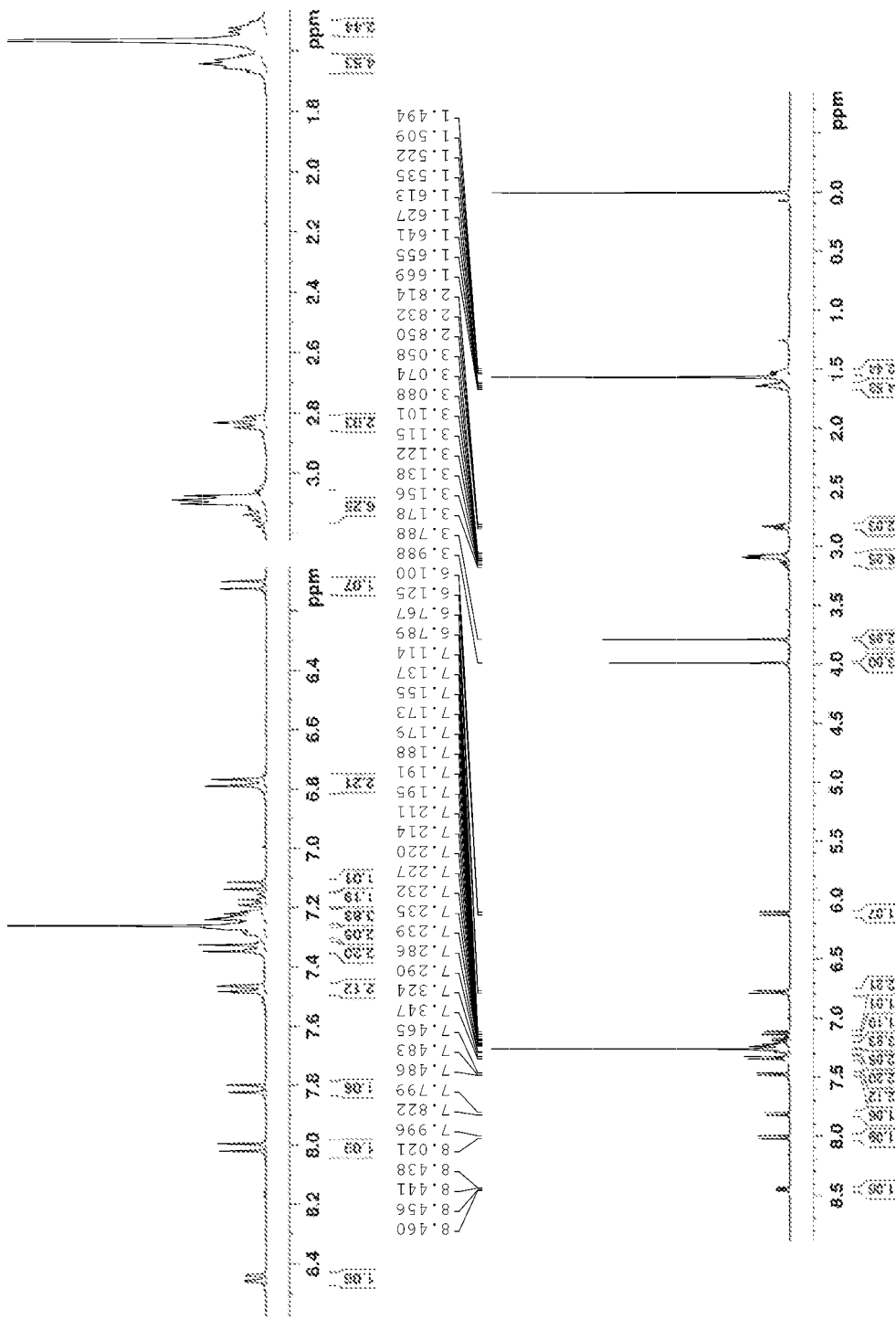
FIG. 13 is a graph of the $^1$H NMR spectrum (400 MHz) of 1,2-dimethoxy-12-phenyl-12-(4-(piperidin-1-yl)phenyl)-5,12-dihydro-6H-benzo[f]naphtho[2,1-h]chromene (compound 13), solvent: deuterated chloroform.
Figure 14:
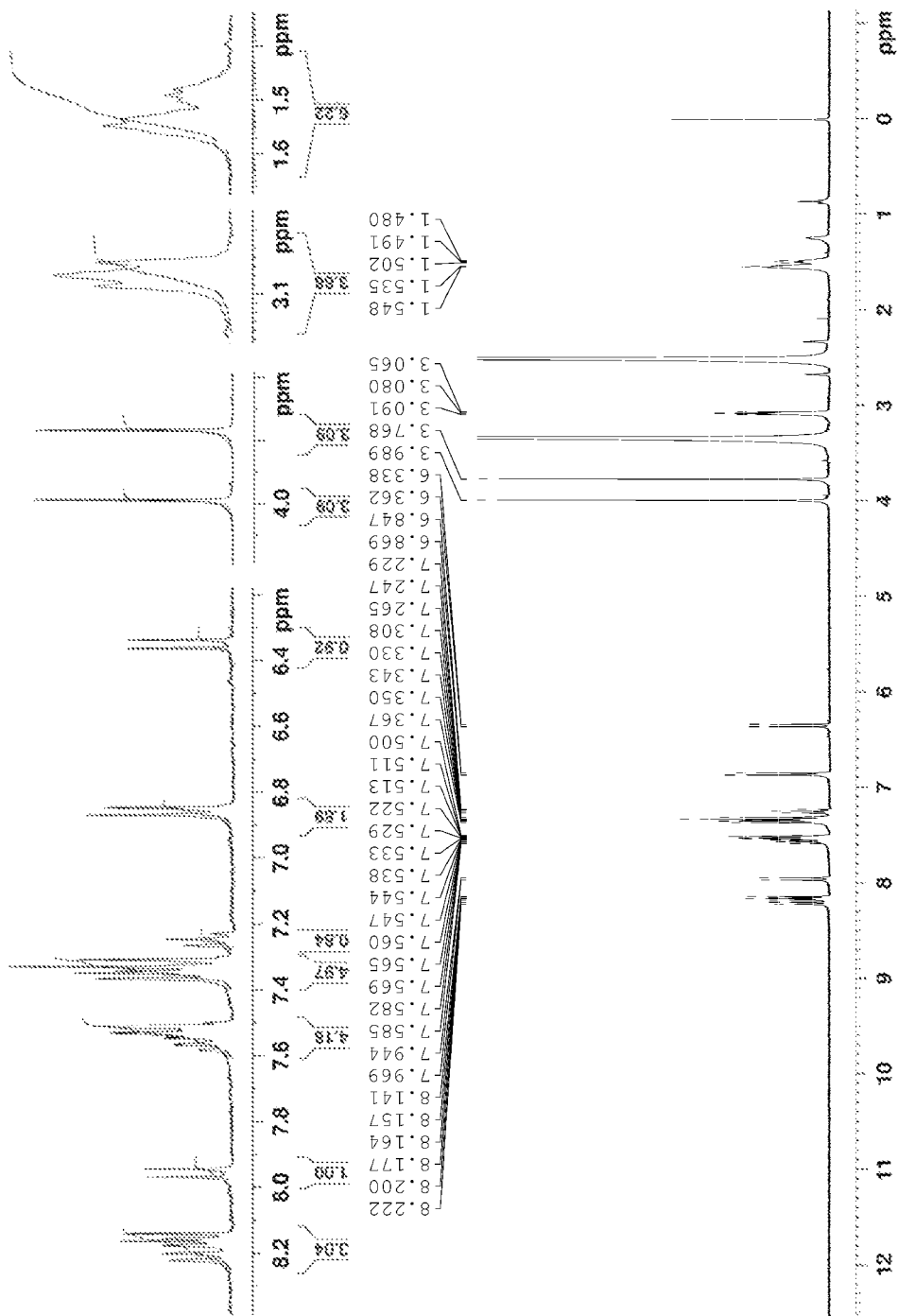
FIG. 14 is a graph of the $^1$H NMR spectrum (400 MHz) of 3-phenyl-3-(4-(piperidin-1-yl)phenyl)-3H-anthra[2,1-b]pyran (Compound 14), solvent: deuterated dimethyl sulfoxide.
Figure 15:
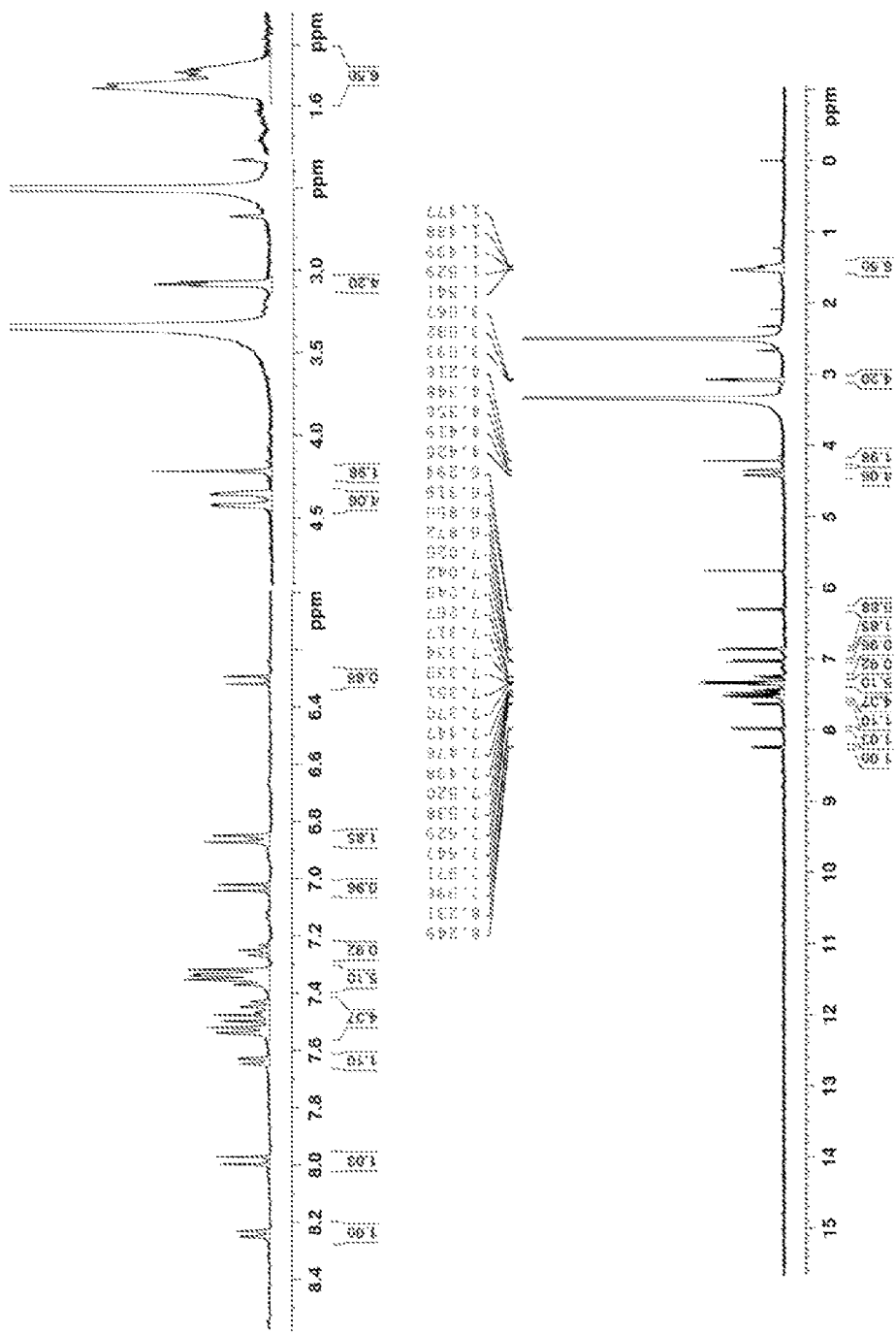
FIG. 15 is a graph of the $^1$H NMR spectrum (400 MHz) of 1-(4-(9-phenyl-4,5,9,15-tetrahydro-[1,4]dioxino[2',3':5,6]benzo6 [1,2-f]indeno[1,2-h]chromen-9-yl)phenyl)piperidine (Compound 15), solvent: deuterated dimethyl sulfoxide.
Figure 16:
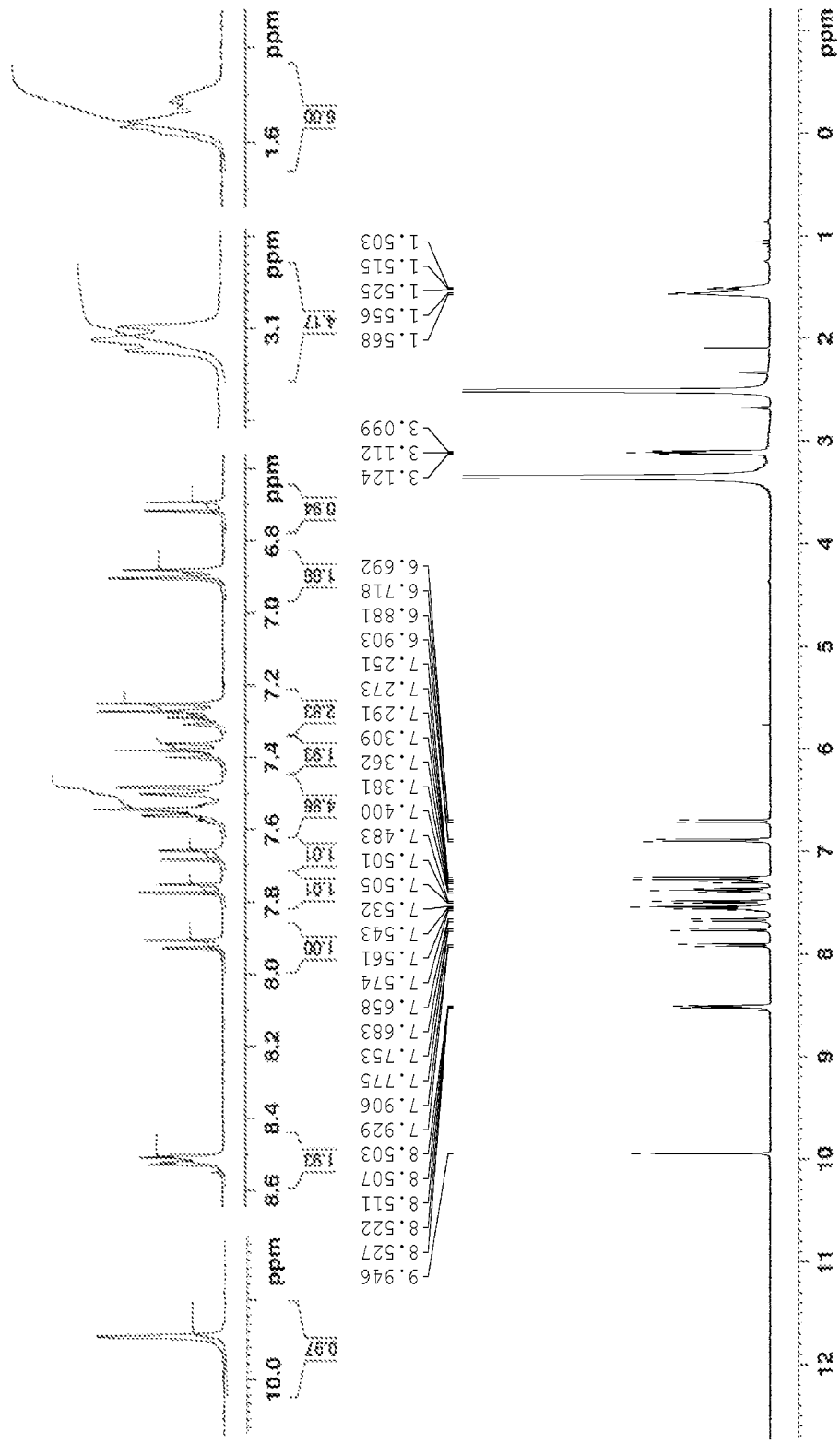
FIG. 16 is a graph of the H NMR spectrum (400 MHz) of 3,8-diphenyl-8-(4-(piperidin-1-yl)phenyl)-8H-pyrano[3,2-f]quinazoline (Compound 16), solvent: deuterated dimethyl sulfoxide.
Figure 17:
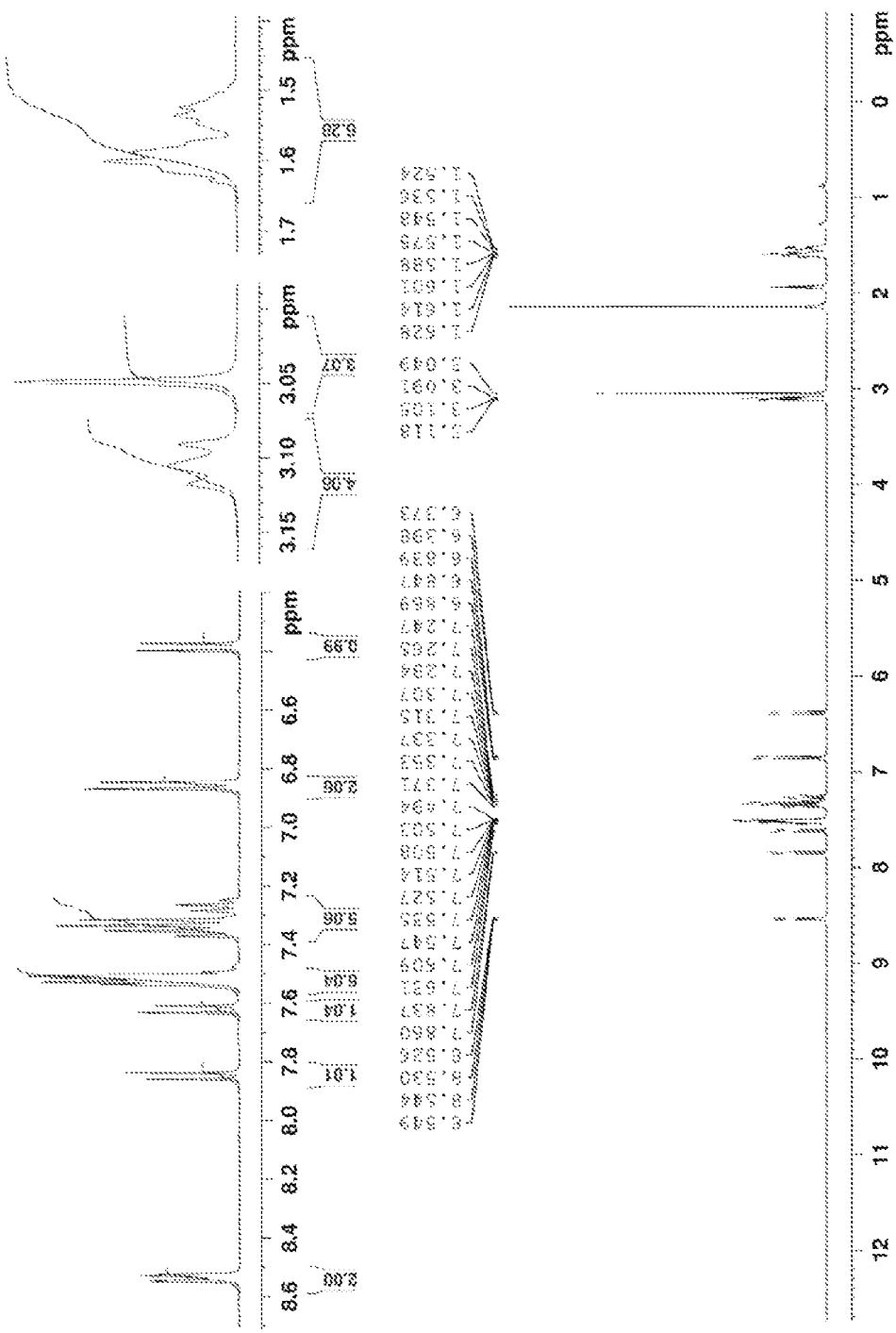
FIG. 17 is a graph of the $^1$H NMR spectrum (400 MHz) of 1-methyl-3,8-diphenyl-8-(4-(piperidin-1-yl)phenyl)-8H-pyrano[3,2-f]quinazoline (Compound 17), solvent: deuterated acetonitrile.
Figure 18:
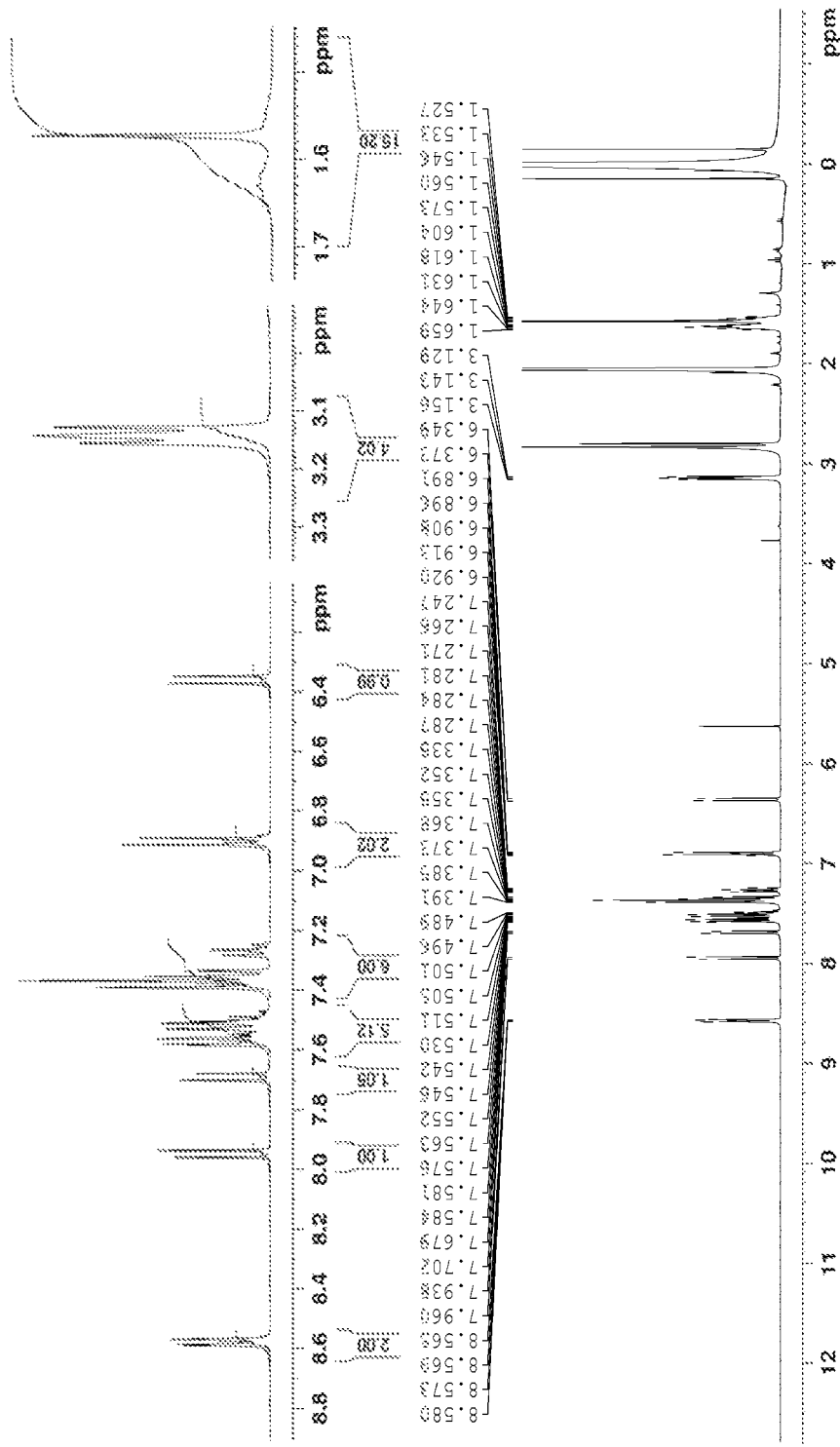
FIG. 18 is a graph of the H NMR spectrum (400 MHz) of 1-(tert-Butyl)-3,8-diphenyl-8-(4-(piperidin-1-yl)phenyl)-8H-pyrano[3,2-f]quinazoline (Compound 18), solvent: deuterated acetone.
Figure 19:
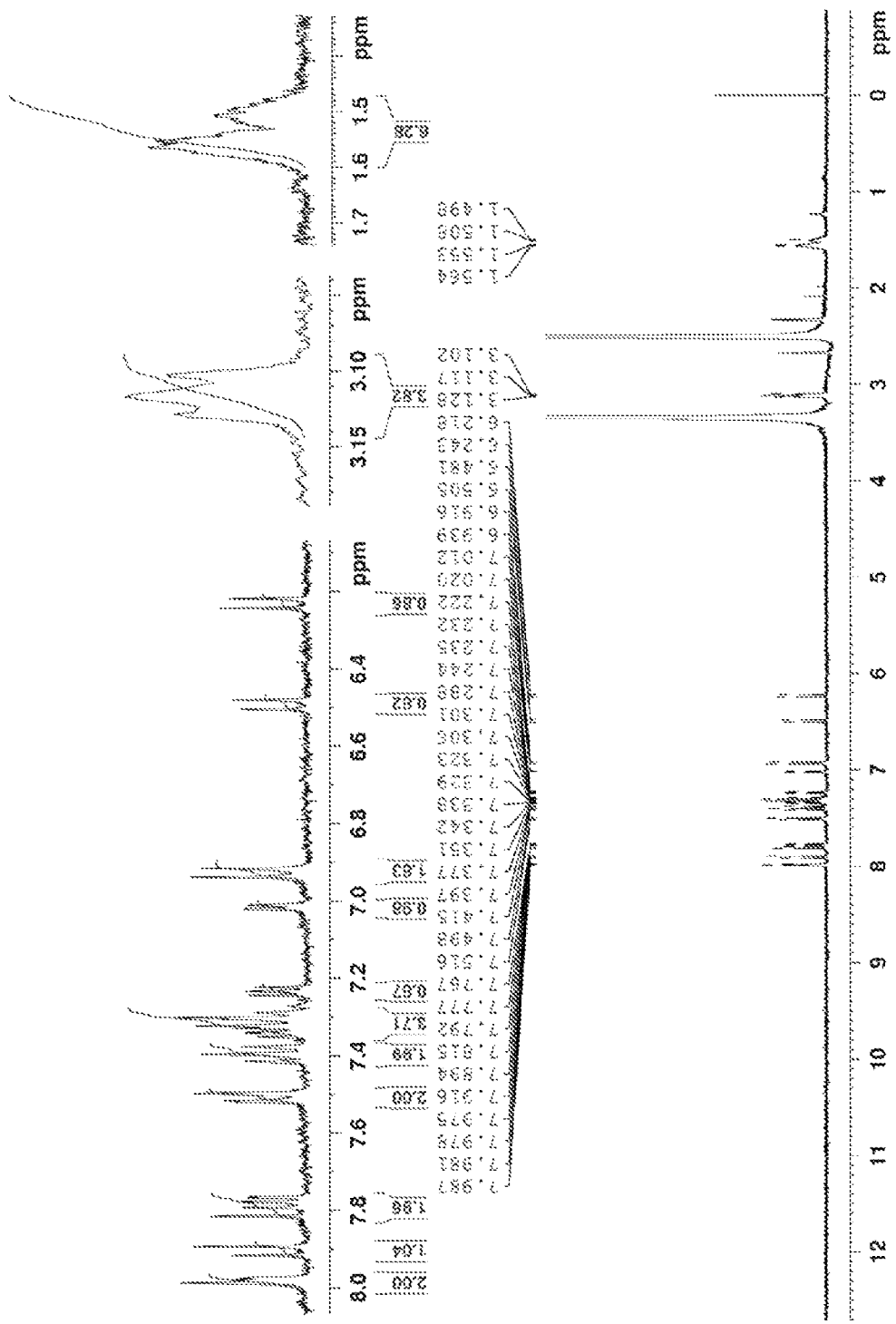
FIG. 19 is a graph of the $^1$H NMR spectrum (400 MHz) of 8-phenyl-8-(4-(piperidin-1-yl)phenyl)-1,3-di(thiophen-2-yl)-8H-pyrano[3,2-f]quinazoline (Compound 19), solvent: deuterated dimethyl sulfoxide.
Figure 20:
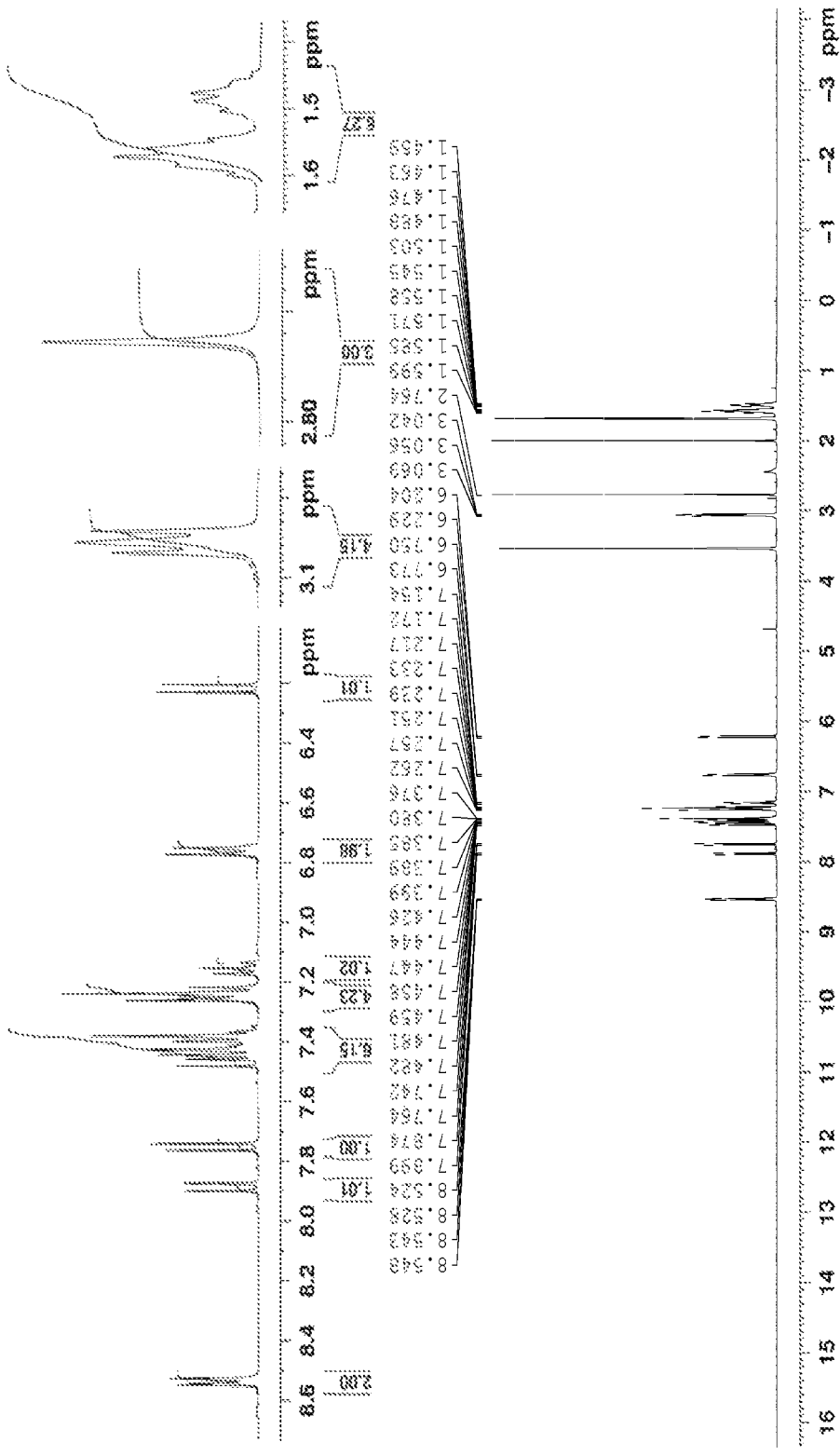
FIG. 20 is a graph of the $^1$H NMR spectrum (400 MHz) of 1-(methylthio)-3,8-diphenyl-8-(4-(piperidin-1-yl)phenyl)-8H-pyrano[3,2-f]quinazoline (Compound 20), solvent: deuterated tetrahydrofuran.
Figure 21:
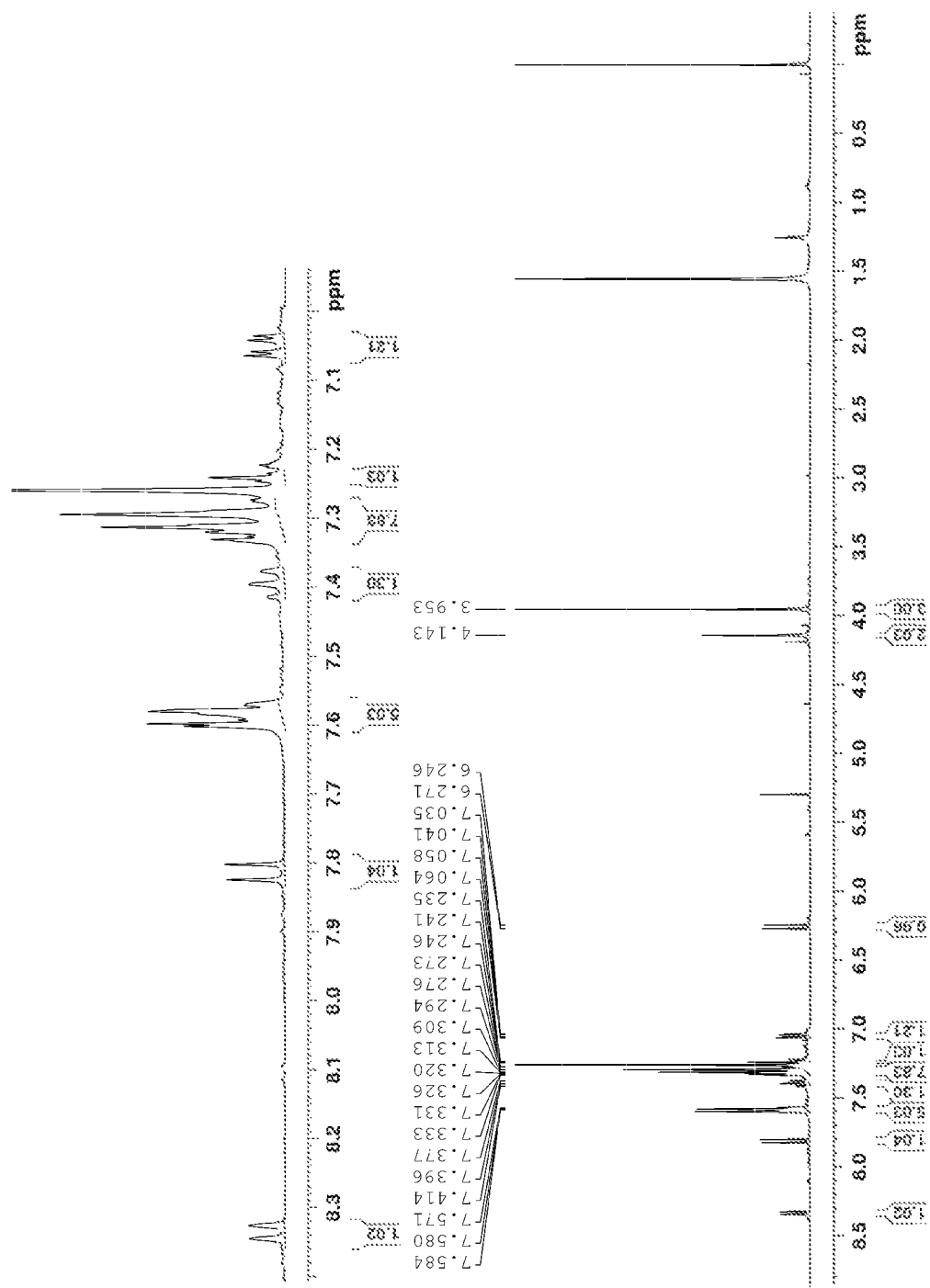
FIG. 21 is a graph of the $^1$H NMR spectrum (400 MHz) of 6-methoxy-2-phenyl-2-(4-(piperidin-1-yl)phenyl)-2,9-dihydrobenzo[f]indeno[2,1-h]chromene (Compound 22), solvent: deuterated chloroform.
Figure 22:
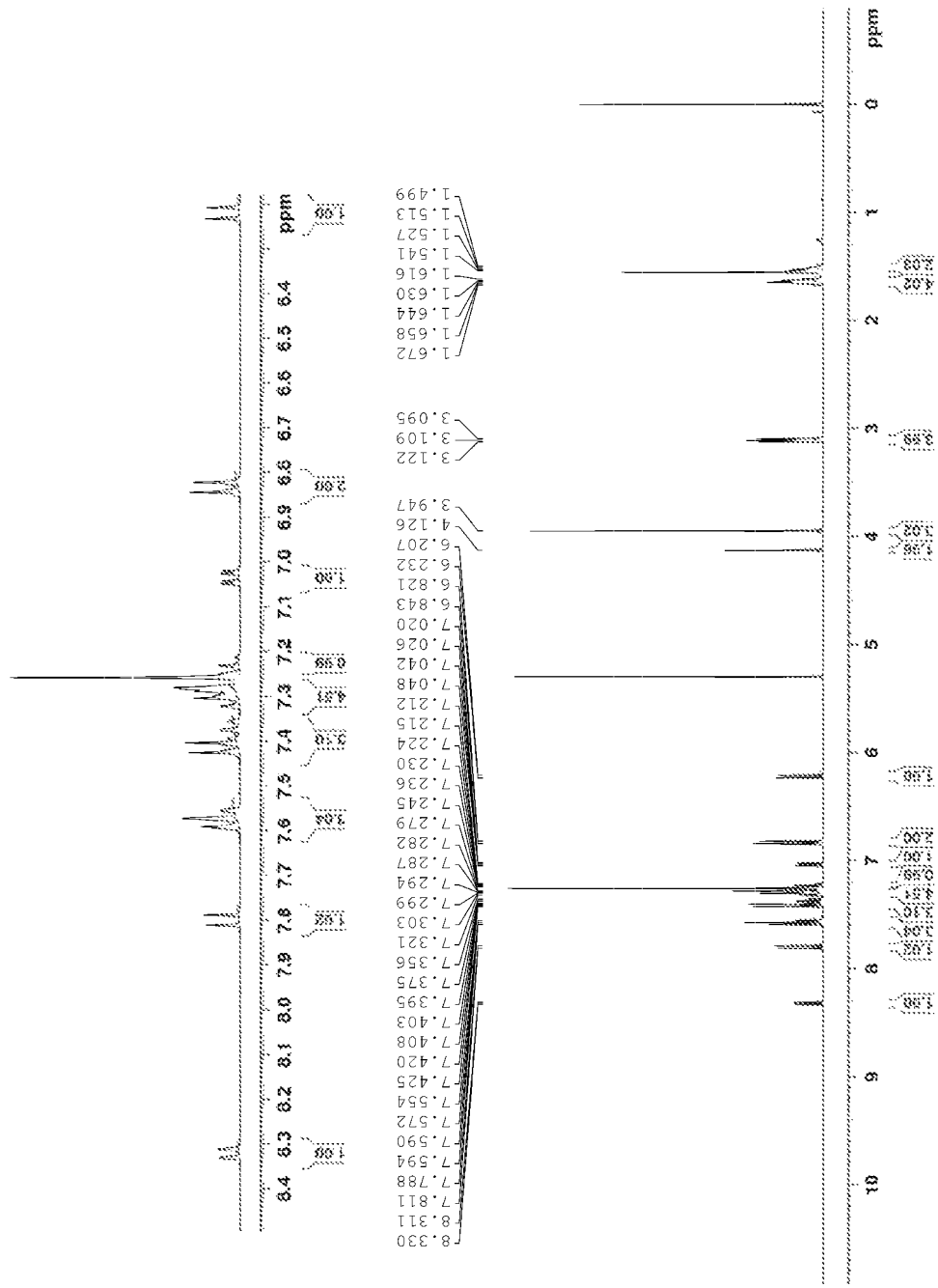
FIG. 22 is a graph of the $^1$H NMR spectrum (400 MHz) of 6-methoxy-2,2-diphenyl-2,9-dihydrobenzo[1]indeno[2,1-h]chromene (Compound 21), solvent: deuterated chloroform.

Hereinafter, embodiments of the present invention will be described in detail.

The compound of present invention is represented by the following general formulas (1), (2) or (3).

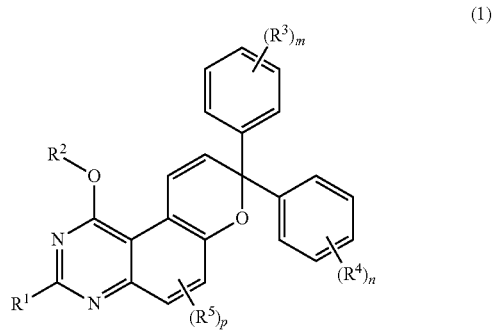

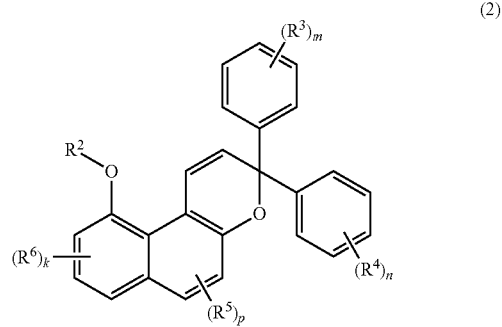

-continued

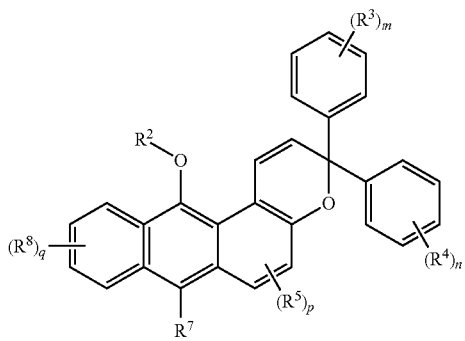
(3)

In the above formulas(1), (2) and (3), the substituent R1, R6 and R8 are alkyl group or alkoxy group, or alkyl group having substituent W or alkoxy group having substituent W; or aromatic group or heterocyclic group, or aromatic group having substituent W or heterocyclic group having substituent W, etc., in view of decolorizing speed, it is preferred to bond R2 with R6 or bond R2 with R8 to form 5- to 7-membered ring, or 5- to 7-membered ring having substituent W, in view of colorizing properties such as colorizing density and colorizing speed, it is preferable that the substituent R1, R6 and R8 are alkyl group or alkoxy group, or alkyl group having substituent W or alkoxy group having substituent W; or aromatic group or heterocyclic group, or aromatic group having substituent W or heterocyclic group having substituent W. The aromatic group or heterocyclic group forming aromatic group or heterocyclic group may be monocyclic or polycyclic, such as benzene ring, naphthalene ring, anthracene ring, pyrene ring, fluorene ring, phenanthrene ring, thiophene ring, thienothiophene ring, dithienothiophene ring, pyrrole ring, pyridine ring, pyrimidine ring, quinoline ring, isoquinoline ring, quinoxaline ring, furan ring and furofuran ring, etc.

The substituents W are independent to each other and are identical or different from each other, and the substituent(s) W is one or more substituent selected from the group consisting of hydrogen atom, halogen atom, nitro group, cyano group, trifluoromethyl group, hydroxyl group, thiol group, amino group and carbazole group, straight chain or branched chain alkyl group, alkylamino group, alkoxy group and cycloether ring having carbon number from 1 to 20, —Y1-SiZ1Z2Z3 group, —Y1-SiY2Z1Z2 group and —Y1-SiY2Y3Z1 group, aromatic ring, heterocyclic ring, and alicyclic ring which forms rings by combining with each other, wherein Y1 to Y3 and Z1 to Z3 are independent to each other and are identical to or different from each other, and Y1 to Y3 represent straight chain, branched chain or cyclic alkyl group or alkylene group having carbon number from 1 to 20, and Z1 to Z3 represent hydrogen atom or halogen atom, or straight chain or branched chain alkoxy group having carbon number from 1 to 8, or the substituent (s) W is one or more substituent selected from the group consisting of substituents represented by the following structural formulas (i), (ii) and (iii):

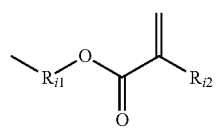
(i)

wherein Ri1 represents alkyl group, alkylene group or alkoxylene group having carbon number from 1 to 20, and Ri2 represents hydrogen or alkyl group having carbon number from 1 to 3;

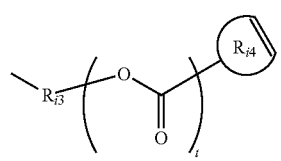
(ii)

wherein Ri3 represents alkyl group, alkylene group or alkoxylene group having carbon number from 1 to 20, Ri4 represents cyclic olefins having a total of carbon and silicon number of 5 to 10, and t represents of 0 or 1; and

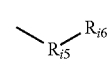
(iii)

wherein Ri5 represents alkyl group, alkylene group or alkoxylene group having carbon number from 1 to 20, Ri6 represents ethylene group or acetylene group.

Regarding the substituent R2, it is straight chain, branched chain or cyclic alkyl group, aromatic ring group or heterocyclic group having carbon number from 1 to 20, or straight chain, branched chain or cyclic alkyl group, aromatic ring group or heterocyclic group having substituent W and having carbon number from 1 to 20, in view of inhibiting trans-transoid generate, it is preferably straight chain or branched chain alkyl group or aryl group having carbon number from 1 to 20, more preferably, straight chain alkyl group, phenylalkyl group, or phenyl group having carbon number from 1 to 10, and further preferably, methyl group, ethyl group, propyl group, butyl group, pentyl group, hexyl group, heptyl group, or phenyl group.

Furthermore, the substituent $R^3$, $R^4$, $R^5$ and $R^7$ are independent to each other, identical or different from each other, and may be halogen atom, nitro group, cyano group, trifluoromethyl group, hydroxyl group, thiol group, amino group, carbazole group, and straight chain or branched chain alkyl group, alkylamino group and alkoxy group having carbon number from 1 to 20, —Y$_1$—SiZ$_1$Z$_2$Z$_3$ group, —Y$_1$—SiY$_2$Z$_1$Z$_2$ group and —Y$_1$—SiY$_2$Y$_3$Z$_1$ group, aromatic rings such as benzene ring, naphthalene ring, anthracene ring, etc., which are bonded together to form a ring, heterocyclic rings such as pyridine ring, pyrrole ring, furan ring, and thiophene ring, and cycloaliphatic rings such as cyclopentane ring and cyclohexane ring, wherein Y$_1$ to Y$_3$ are independent to each other, identical to or different from each other, and represent straight chain, branched chain or cyclic alkyl group or alkylene group having carbon number from 1 to 20, and Z$_1$ to Z$_3$ are independent to each other, identical to or different from each other, and represent hydrogen atom or halogen atom or straight chain or branched chain alkoxy group having carbon number from 1 to 8. One or more of these substituents may be used for substitution.

Bonding of R2 with R6 and bonding of R2 with R8 may form 5- to 7-membered ring, or 5- to 7-membered ring having substituent W. For example, bonding of R2 with R6 may form cyclic ethers such as 1,3-dioxole, 2,3-dihydrofuran, 1,4-dioxin, 2,3-dihydro-1,4-dioxin, 3,4-dihydro-2H-pyran, 6,7-dihydro-5H-1, 4-dioxepin, 2,3,4,5-tetrahydrooxepin, etc.

Bonding of two or more R5, bonding of two or more R6, bonding of one or more R5 and R6, bonding of one or more R5 and R7, and bonding of one or more R7 and R8 may form unsaturated 5- or 6-membered ring or aromatic ring, or unsaturated 5- or 6-membered ring having substituent W, furthermore, in the unsaturated 5- or 6-membered ring or aromatic ring formed by bonding of one or more R5 and R6, bonding of one or more R5 and R7 and bonding of one or more R7 and R8, unsaturated 5- or 6-membered ring or aromatic ring, or unsaturated 5-or 6-membered ring having substituent W may be formed. For example, a structure of an unsaturated 5- to 6-membered ring or a benzene ring is formed by any one of two R5, 5th position of R5 and 6th position of R5 and two R6 in the naphthopyran skeleton, furthermore, a structure of an unsaturated 5- to 6-membered ring or benzene ring is formed on the unsaturated 5-to 6-membered ring or benzene ring formed by any of two R5, 5th position of R5, 6th position of R5 and two R6, structures including a benzene ring is formed by 6th position of R6 and 7th position of R6; and an anthracene skeleton includes benzene formed by 8th position of R6 8 and 9th position of R6.

By introducing a substituent into the aryl moiety of the present compound in the general formulas (1), (2) and (3), the compound of the present invention can be optimally designed the molecular structure according to the use of the compound of the present invention, and photochromic characteristics such as speed, tone and density of colorizing, and decolorizing speed can be controlled more precisely. As the substituents W, R3, and R4 in this case, that is, the substituents introduced for the purpose of precise control of photochromic properties other than the substituents used for polymerization with functional groups contained in the main chain or side chain of the polymer compound, in view of color tone/decolorizing speed control, it is preferable to be selected from hydrogen atom, straight chain, branched chain or cyclic alkyl group having carbon number from 1 to 20, amino group, aliphatic heterocyclic ring, etc., and more preferably, selected from hydrogen atom, methyl group, methoxy group, biperidine, etc. One or more of these substituents may be used for substitution. Furthermore, the photochromic properties may be appropriately adjusted according to the use of the compound of the present invention depending on the number and type of substituents on the aryl group of the compound of the present invention and the structure of the aromatic ring formed by the substituent, etc.

In addition, the compound of the present invention can be introduced into a polymer compound as a functional site by condensation polymerization of 2 or 1 polymerizable substituents which selected from the substituent W and 2 or 1 polymerizable groups contained in the polymer main chain or side chain of the polymer compound, or the compound of the present invention can form a chain or network polymer compound by radical polymerization of the compounds of the present invention having two or more polymerizable substituents selected from the substituent W. In this case, the polymerizable substituent W is preferably selected from hydroxyl group, amino group, carboxyl group, isocyanate group, halogen group, azide group, vinyl group, ethynyl group, acrylic acid and methacrylic acid ester such as butyl methacrylate, butyl acrylate, and propoxy methacrylate represent by the following partial structural formula(iv):

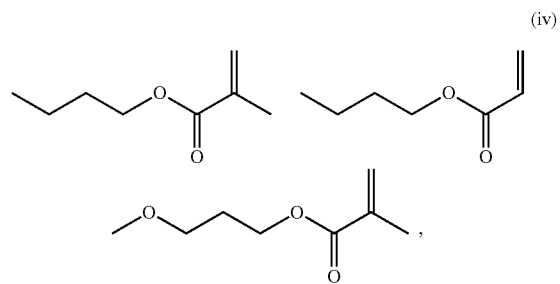

(iv)

and more preferably, the substituent can be selected from hydroxyl group and butyl methacrylate group, etc. One or more of these substituents may be used for substitution.

In addition, the above substituent can be integrate with the carbon atom to which the substituent is bonded, other substituent, or a carbon atom to which said other substituent is bonded to form heterocyclic ring such as benzene ring, naphthalene ring, anthracene ring, pyridine ring, pyrrole ring, furan ring or a thiophene ring, or form alicyclic ring such as cyclopentane ring or cyclohexane ring, and the ring may further have a substituent having the same meaning as other substituent having aryl group.

As compounds represented by the general formula (1), 1-methoxy-3,8-diphenyl-8-(4-(piperidin-1-yl)phenyl)-8H-pyrano[3,2-f]quinazoline (compound 1), 3-(dithieno[3,2-b: 2',3'-d]-1-methoxy-8-phenyl-8-(4-(piperidin-1-yl)phenyl)-8H-pyrano[3,2-f]quinazoline (compound 4), 3-(3a,8a-dihydropyren-1-yl)-1-methoxy-8-phenyl-8-(4-(piperidin-1-yl)phenyl)-8H-pyrano[3,2-f]quinazoline (Compound 5), 1-phenoxy-3,8-diphenyl-8-(4-(piperidin-1-yl)phenyl)-8H-pyrano[3,2-f]quinazoline (Compound 6) and derivatives of these compounds etc. can be given. As compounds represented by the general formula (2), 10-methoxy-3,3-bis(4-methoxyphenyl)-3H-benzo[f]chromene (compound 7) can be given.

As described above, the polymer compound of the present invention has repeating structural unit represent by following partial structural formula (v) or (vi) at the main chain and/or the side chain.

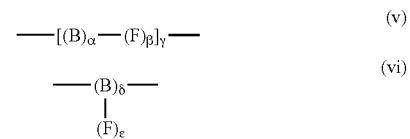

Specifically, the example represents repeating structural unit wherein B is one or more linking groups selected from the group consisting of carbon, nitrogen and oxygen atoms, F is a derivative of the compound of the present invention, F—B represents a bond between the linking group and one or two substituents selected from the substituents $R_C$ to $R_F$ of the derivative of the compound, and $\alpha$, $\beta$, $\gamma$, $\delta$ and $\epsilon$ are independent to each other and are an integer of 1 or more respectively.

The compound of the present invention can be introduced into a polymer compound as a functional site by condensation polymerization of 2 or 1 polymerizable substituents which selected from the substituent W such as hydroxyl group and 2 or 1 polymerizable groups contained in the polymer main chain or side chain of the polymer compound such as carboxyl group.

Since the compound of present invention has high-speed decolorizing property and high durability even in a solvent, it may be mixed with a specific solvent. As the solvent to be mixed, preferably, toluene, benzene, chloroform, methylene chloride, ethyl acetate, acetonitrile, etc can be given. In view of the stability of chromogen, toluene and benzene are more preferable. Two or more of these solvents may be mixed.

Since the compound of present invention has high-speed decolorizing property and high durability even in a solid phase such as a resin such as a plastic material or glass, it may be mixed with a solid such as a specific resin or glass, or it may be chemically bonded as a functional site to the main chain of the resin. As the resin to be mixed, preferably, polymethyl methacrylate, polybutyl methacrylate, acrylic block copolymer, polystyrene, polyimide, Teflon®, polycarbonate, polyurethane, etc. can be given. In view of stability of chromogen, polymethyl methacrylate, polybutyl methacrylate, polymethyl methacrylate-polynormal butyl acrylate block copolymer and polyurethane are more preferable.

As the use of the compound of present invention, the photochromic material containing the compound, the solvent, and the resin, light control lens material, hologram material, security ink material, optical switch material, and decorative article can be given.

The compound of present invention is a photochromic compound characterized by a high-speed decolorizing characteristic, and can also realize a photochromic characteristic that is visually decolorized simultaneously with light irradiation being stopped.

The decolorization speed of the compound of present invention is, for example, measured by a transient absorption SPECTRAL measurement method described later using a toluene as a solvent, and the half-life of the chromogen is preferably 1 to 3000 ms, more preferably, from 1 to 2000 ms, and further preferably, from 1 to 1000 ms.

EMBODIMENTS

The present invention will be explained more specifically with reference to the embodiments and comparative examples below, but the present invention is not intended to be limited to these examples and various modifications can be made without deviating from the technical spirit of the present invention.

Reference Example 1

Synthesis of 2-chloro-4-methoxyquinazolin-6-ol

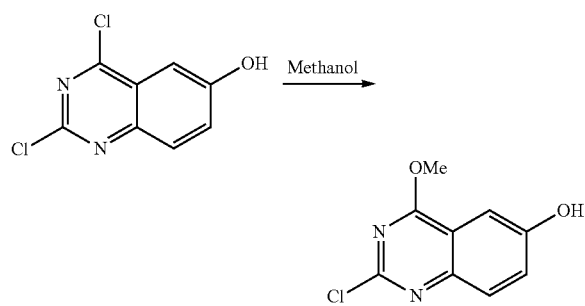

2,4-Dichloroquinazolin-6-ol (496 mg, 2.31 mmol) and methanol (10 mL) are mixed, and the mixture is stirred at 15° C. for 14.5 hours. Ethyl acetate is added to the reaction solution, and the resulting precipitate is removed by celite filtration, and the filtrate is washed with ion-exchanged water. After the organic layer is dried and the solvent is distilled off under reduced pressure, the residue is purified by silica gel column chromatography (tetrahydrofuran:dichloromethane=1:20), and pale yellow solid of 131 mg is obtained in 26% yield.

Reference Example 2

Synthesis of 3-chloro-1-methoxy-8-phenyl-8-(4-(piperidin-1-yl)phenyl)-8H-pyrano[3,2-f]quinazoline

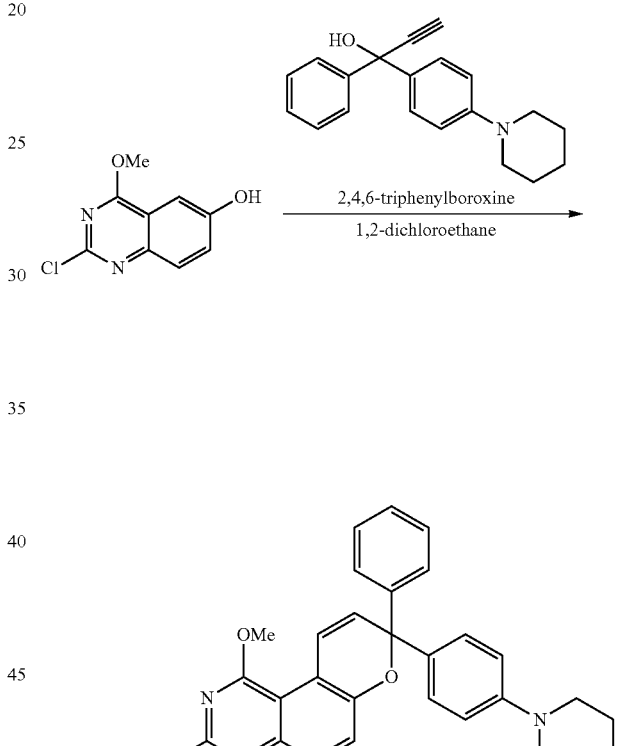

2-chloro-4-methoxyquinazolin-6-ol (151 mg, 0.72 mmol), 2,4,6-triphenylboroxine (147 mg, 0.47 mmol), 1-phenyl-1-[4-(1-Piperidinyl)-2-propyn-1-ol (321 mg, 1.10 mmol) and 1,2-dichloroethane (31 mL) are mixed, and the mixture is stirred at 80° C. for 11 hours. After the reaction solution is cooled to room temperature, sodium hydrogen carbonate is added, and the mixture is extracted with diethyl ether. The organic layer is washed with brine. After the organic layer is dried and the solvent is distilled off under reduced pressure, the residue is purified by silica gel column chromatography (ethyl acetate:dichloromethane:hexane=1:8:120) and alumina column chromatography (dichloromethane:hexane=4:6), and yellow solid of 183 mg is obtained in 53% yield.

Embodiment 1

Synthesis of 1-methoxy-3,8-diphenyl-8-(4-(piperidin-1-yl)phenyl)-8H-pyrano[3,2-f]quinazoline (Compound 1)

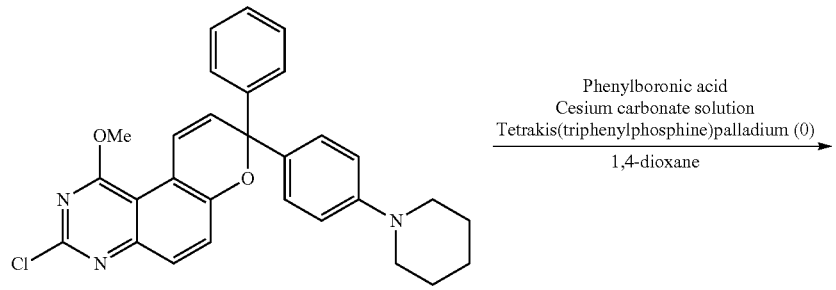

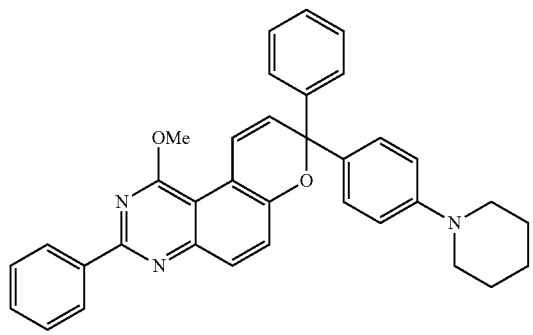

3-chloro-1-methoxy-8-phenyl-8-(4-(piperidin-1-yl)phenyl)-8H-pyrano[3,2-f]quinazoline (14 mg, 0.029 mmol) and phenylboronic acid (16 mg, 0.13 mmol) are dissolved in 1,4-dioxane (1 mL) and 1M aqueous cesium carbonate solution (0.090 mL, 0.090 mmol), and freeze degassed. Tetrakis (triphenylphosphine) palladium (0) (21 mg, 0.018 mmol) is added thereto and the mixture is stirred at 50° C. for 8.5 hours. After cooled to room temperature, the reaction solution is added with ethyl acetate and filtered through celite, and the filtrate is washed with water. After the organic layer is dried and the solvent is distilled off under reduced pressure, the residue is purified by silica gel column chromatography (ethyl acetate:hexane=1:10) and white solid of 10 mg (0.018 mmol) is obtained in 62% yield.

Embodiment 2

Synthesis of 1-methoxy-8-phenyl-8-(4-(piperidin-1-yl)phenyl)-3-(thiophen-2-yl)-8H-pyrano[3,2-f]quinazoline (Compound 2)

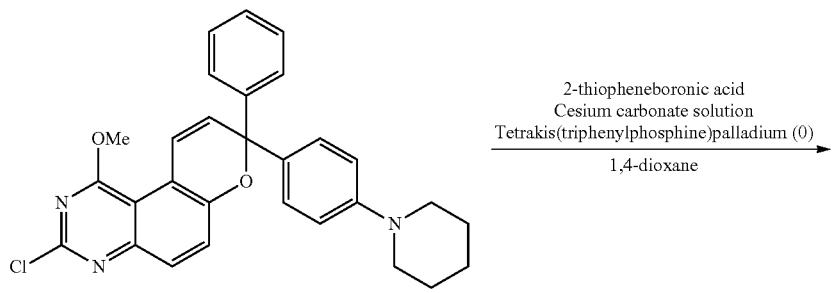

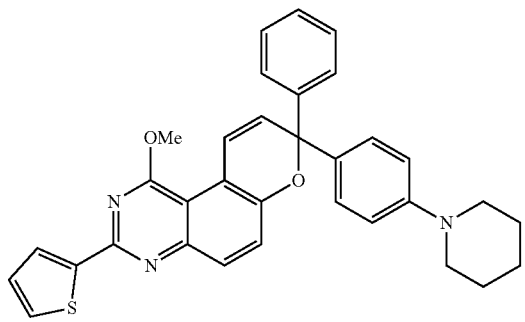

3-Chloro-1-methoxy-8-phenyl-8-(4-(piperidin-1-yl)phenyl)-8H-pyrano[3,2-f]quinazoline (11 mg, 0.023 mmol) and 2-thiopheneboron acid (7 mg, 0.052 mmol) are dissolved in 1,4-dioxane (0.75 mL) and 1M aqueous cesium carbonate (0.061 mL, 0.061 mmol), and freeze degassed. Tetrakis(triphenylphosphine) palladium (0) (11 mg, 0.0093 mmol) is added thereto and the mixture is stirred at 80° C. for 21 hours. After cooled to room temperature, the mixture is filtered through celite, and the filtrate is extracted with diethyl ether and washed with ion-exchanged water and brine. After the organic layer is dried and the solvent is distilled off under reduced pressure, the residue is purified by thin layer chromatography (ethyl acetate:dichloromethane:hexane=7:80:120) and yellow solid is obtained. The yellow solid is dissolved in a dichloromethane/hexane mixed solvent and cooled overnight and, as a precipitate, yellow solid of 2 mg is obtained in 16% yield.

Embodiment 3

Synthesis of 1-methoxy-8-phenyl-8-(4-(piperidin-1-yl)phenyl)-3-(thieno[3,2-b]thiophen-2-yl)-8H-pyrano[3,2-f]quinazoline (Compound 3)

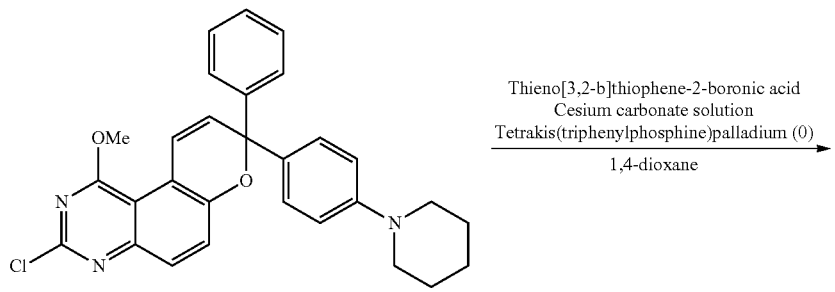

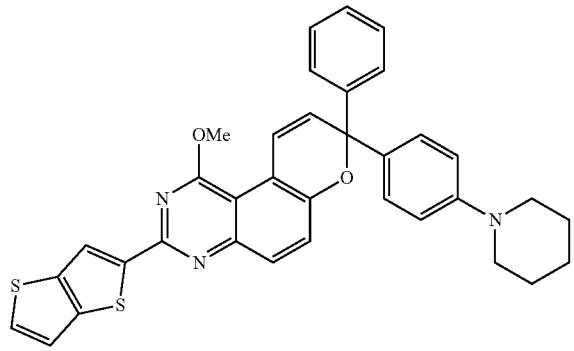

3-chloro-1-methoxy-8-phenyl-8-(4-(piperidin-1-yl)phenyl)-8H-pyrano[3,2-f]quinazoline (16 mg, 0.033 mmol) and thieno[3,2-b]thiophene-2-boronic acid (12 mg, 0.067 mmol) are dissolved in 1,4-dioxane (1.1 mL) and 1M aqueous cesium carbonate solution (0.096 mL, 0.096 mmol) and freeze-degassed. Tetrakis (triphenylphosphine) palladium (0) (11 mg, 0.0099 mmol) is added thereto, and the mixture is stirred at 80° C. for 27 hours. After filtration through celite, the filtrate is extracted with dichloromethane and washed with ion-exchanged water. The organic layer is dried, the solvent is distilled off under reduced pressure, the residue is purified by thin layer chromatography (ethyl acetate:dichloromethane:hexane=7:80:120), and yellow solid is obtained. The yellow solid is dissolved in a dichloromethane/hexane mixed solvent and cooled overnight, and gray solid of 3 mg is obtained as a precipitate in 15% yield.

Embodiment 4

Synthesis of 3-(Dithieno[3,2-b:2',3'-d]-1-methoxy-8-phenyl-8-(4-(piperidin-1-yl)phenyl)-8H-pyrano[3,2-f]quinazoline (Compound 4)

3-chloro-1-methoxy-8-phenyl-8-(4-(piperidin-1-yl)phenyl)-8H-pyrano[3,2-f]quinazoline (81 mg, 0.17 mmol) and dithieno[3,2-b:2',3'-d]thiophene-2-boronic acid (63 mg, 0.26 mmol) are dissolved in 1,4-dioxane (5.6 mL) and 1M aqueous cesium carbonate solution (0.49 mL, 0.49 mmol) and degassed by blowing nitrogen gas for 30 minutes. Tetrakis (triphenylphosphine) palladium (0) (44 mg, 0.038 mmol) is added thereto, and the mixture is stirred at 50° C. for 16.5 hours. Dithieno[3,2-b:2',3'-d]thiophene-2-boronic acid (20 mg, 0.082 mmol) and tetrakis (triphenylphosphine) palladium (0) (19 mg, 0.016 mmol) are added thereto, and the mixture is further stirred at 50° C. for 7 hours. After filtration through celite, the filtrate is extracted with ethyl acetate and washed with brine and ion-exchanged water. The organic layer is dried, the solvent is distilled off under reduced pressure, the residue is purified by silica gel column chromatography (dichloromethane), and yellowish green solid of 62 mg is obtained in 53% yield.

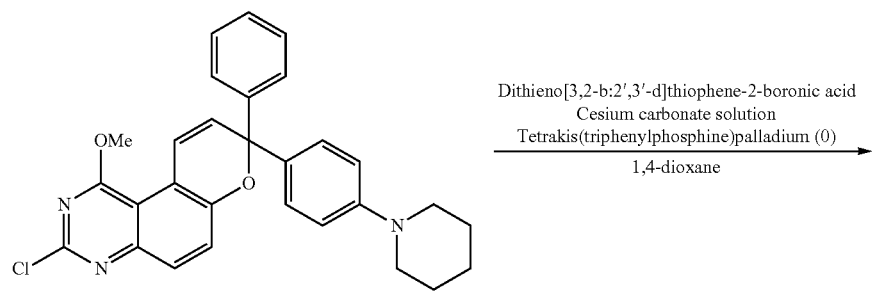

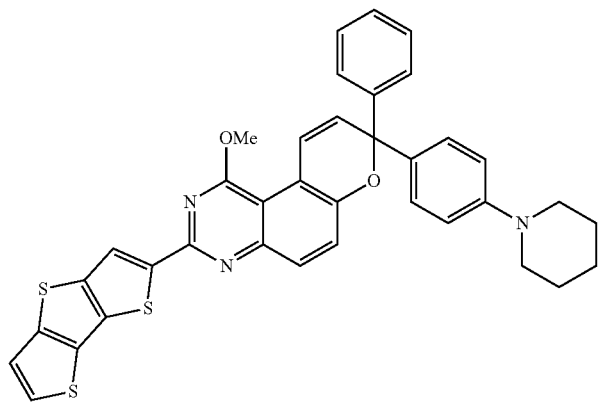

Embodiment 5

Synthesis of 3-(3a,8a-dihydropyren-1-yl)-1-methoxy-8-phenyl-8-(4-(piperidin-1-yl)phenyl)-8H-pyrano[3,2-f]quinazoline (Compound 5)

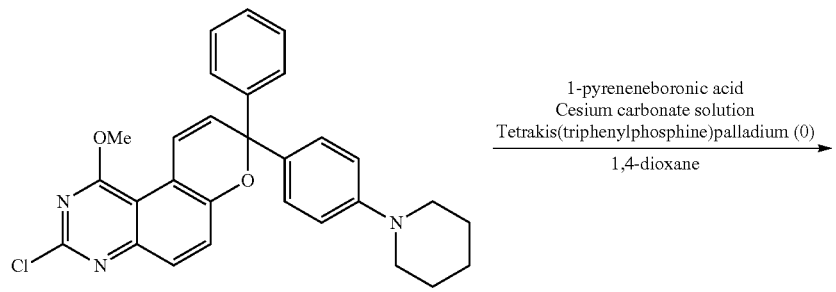

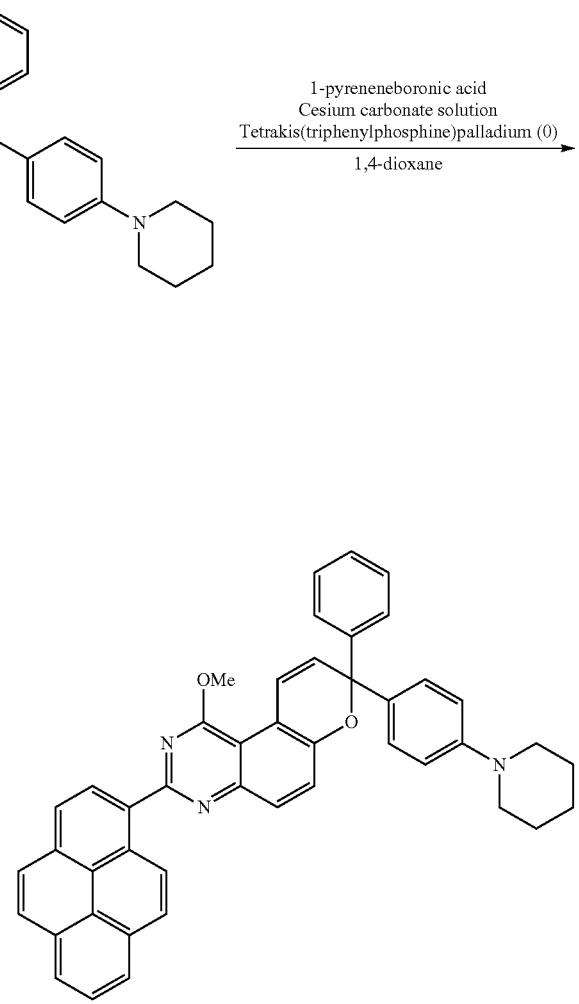

3-chloro-1-methoxy-8-phenyl-8-(4-(piperidin-1-yl)phenyl)-8H-pyrano[3,2-f]quinazoline (81 mg, 0.17 mmol) and 1-pyreneboronic acid (72 mg, 0.29 mmol) are dissolved in 1,4-dioxane (5.6 mL) and 1M aqueous cesium carbonate solution (0.49 mL, 0.49 mmol), and degassed by blowing nitrogen gas for 30 minutes. Tetrakis (triphenylphosphine) palladium (0) (59 mg, 0.050 mmol) is added thereto and the mixture is stirred at 50° C. for 11 hours. After filtration through celite, the filtrate is extracted with ethyl acetate and washed with ion-exchanged water. The organic layer is dried, the solvent is distilled off under reduced pressure, the residue is purified by silica gel column chromatography (ethyl acetate:dichloromethane=1:200), and yellow solid of 67 mg is obtained in 61% yield.

Reference Example 3

Synthesis of 3-chloro-1-phenoxy-8-phenyl-8-(4-(piperidin-1-yl)phenyl)-8H-pyrano[3,2-f]quinazoline

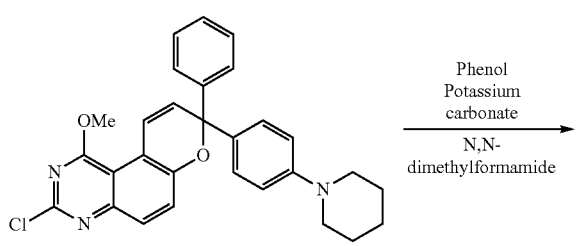

-continued

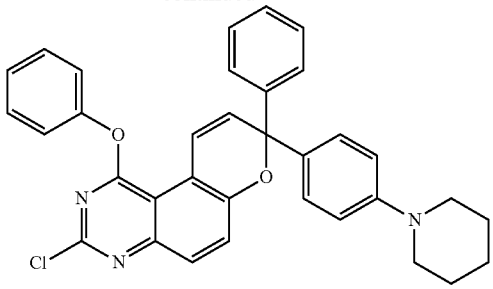

1,3-dichloro-1-phenoxy-8-phenyl-8-(4-(piperidin-1-yl)phenyl)-8H-pyran o[3,2-f]quinazoline (100 mg, 0.20 mmol), potassium carbonate (31 mg, 0.22 mmol) and phenol (0.02 mL, 0.21 mmol) are dissolved in N,N-dimethylformamide (0.6 mL), and the mixture is stirred at room temperature for 2.5 hours. Phenol (0.01 mL, 0.11 mmol) is further added thereto and the mixture is stirred at room temperature for 1 hour. Water and ethyl acetate are added thereto, and the aqueous layer is extracted with ethyl acetate. The combined organic layer is washed with water. The organic layer is dried, the solvent is distilled off under reduced pressure, the residue is purified by alumina column chromatography (dichloromethane:hexane=1:1), and yellow solid of 84 mg is obtained in 77% yield.

Embodiment 6

Synthesis of 1-phenoxy-3,8-diphenyl-8-(4-(piperidin-1-yl)phenyl)-8H-pyrano[3,2-f]quinazoline (Compound 6)

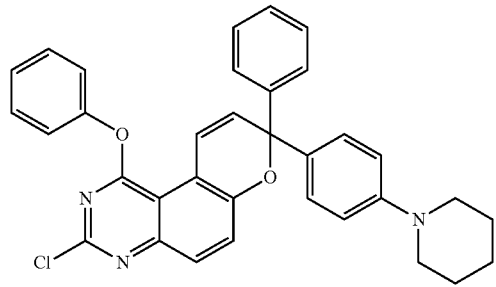

3-chloro-1-phenoxy-8-phenyl-8-(4-(piperidin-1-yl)phenyl)-8H-pyrano[3,2-f]quinazoline (43 mg, 0.079 mmol) and phenylboronic acid (15 mg, 0.12 mmol) are dissolved in 1,4-dioxane (2.2 mL) and 1M aqueous cesium carbonate solution (0.22 mL, 0.22 mmol), and degassed by blowing nitrogen gas for 30 minutes. Tetrakis (triphenylphosphine) palladium (0) (22 mg, 0.019 mmol) is added thereto, and the mixture is stirred at 50° C. for 13.5 hours. Tetrakis (triphenylphosphine) palladium (0) (12 mg, 0.010 mmol) is further added thereto, and the mixture is stirred at 70° C. for 5 hours. After filtration through celite, the filtrate is extracted with ethyl acetate and washed with water, the organic layer is dried, the solvent is removed under reduced pressure, the residue is purified by silica gel column chromatography (ethyl acetate:dichloromethane:hexane=1:24:6), and white solid of 13 mg is obtained in 28% yield.

Embodiment 7

Synthesis of 10-methoxy-3,3-bis(4-methoxyphenyl)-3H-benzo[f]chromene (Compound 7)

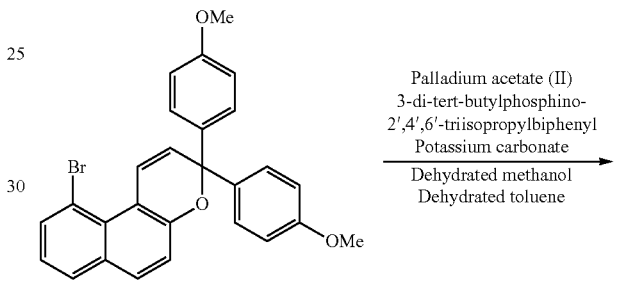

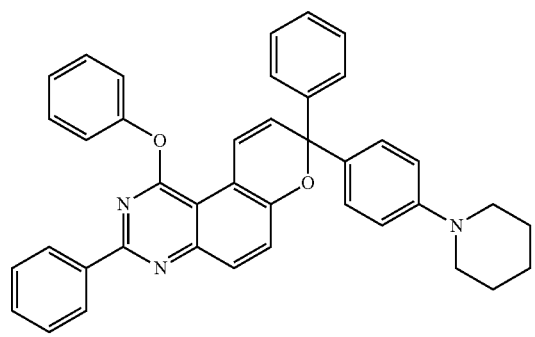

-continued

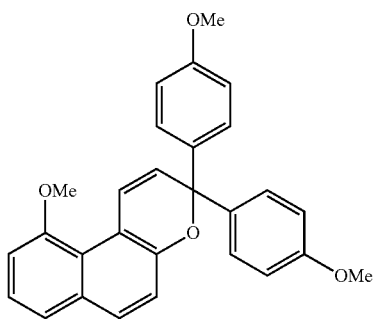

After 10-methoxy-3,3-bis(4-methoxyphenyl)-3H-benzo[f]chromene (32 mg, 0.068 mmol) synthesized according to the previous report (K. Arai, Y. Kobayashi, J. Abe, Chem. Commun., 51, 3057-3060, 2015), palladium acetate (2) (2 mg, 0.009 mmol), 2-di-tert-butylphosphino-2',4',6'-triisopropylbiphenyl (10 mg, 0.024 mmol) and cesium carbonate (32 mg, 0.098 mmol) are dissolved in dehydrated toluene (0.1 mL) and dehydrated methanol (0.1 mL) and freeze degassed, the mixture is stirred at 80° C. for 20 hours. The reaction solution is added with Ethyl acetate and filtered through celite, and the filtrate is washed with water. After the organic layer is dried, and the solvent is distilled off under reduced pressure, the residue is purified by silica gel column chromatography (dichloromethane:hexane=9:4) and pale orange solid of 21 mg is obtained in 72% yield.

Reference Example 4

Synthesis of 4-((tetrahydro-2H-pyran-2-yl)oxy)butan-1-ol

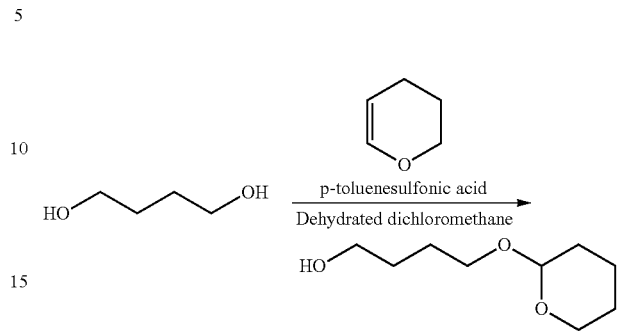

Butane-1,4-diol (2 mL, 22.6 mmol), 3,4-dihydro-2H-pyran (2.1 mL, 23.0 mmol) and p-toluenesulfonic acid (440 mg, 2.31 mmol) are dissolved in dehydrated dichloromethane (10 mL), and the mixture is stirred at 0° C. for 6 hours. Dichloromethane is added thereto, and the mixture is washed with a saturated aqueous sodium hydrogen carbonate solution and water. After the organic layer is dried and the solvent is distilled off under reduced pressure, the residue is purified by silica gel column chromatography (ethyl acetate:hexane=2:3) and colorless oil of 910 mg is obtained in 23% yield.

Reference Example 5

Synthesis of 3-chloro-8-phenyl-8-(4-(piperidin-1-yl)phenyl)-1-(4-((tetrahydro-2H-pyran-2-yl)oxy)butoxy)-8H-pyrano[3,2-]quinazoline

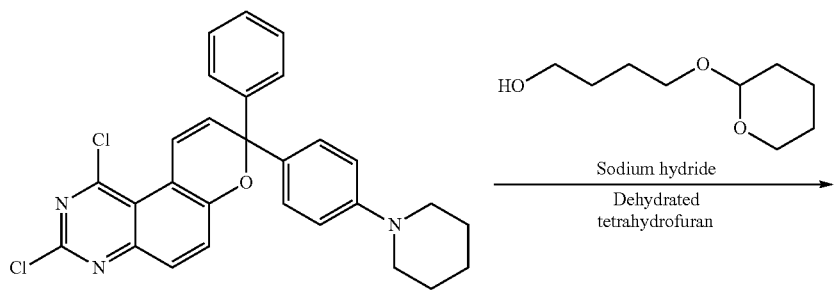

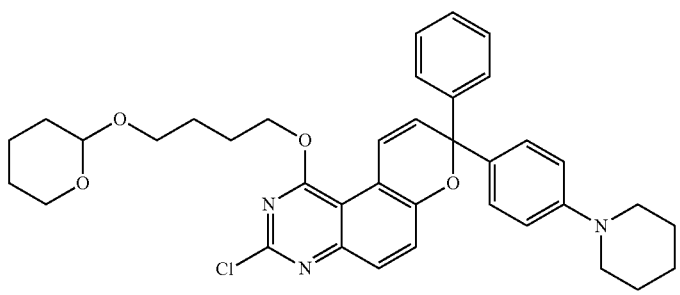

Sodium hydride (55%, dispersed in liquid paraffin) (29 mg, 0.66 mmol) and 4-((tetrahydro-2H-pyran-2-yl)oxy)butan-1-ol (0.3 mL) are mixed and the mixture is stirred at room temperature for 1 hour. Solution of 1,3-Dichloro-8-phenyl-8-(4-(piperidin-1-yl)phenyl)-8H-pyrano[3,2-f]quinazoline (300 mg, 0.61 mmol) dissolved in dehydrated tetrahydrofuran (4.5 mL) is added thereto, and the mixture is stirred at room temperature for 4 hours. Water and ethyl acetate are added to the reaction solution, and the aqueous layer is extracted with ethyl acetate. After the combined organic layers are washed with water and dried, and the solvent is distilled off under reduced pressure, the residue is purified by silica gel column chromatography (ethyl acetate:dichloromethane:hexane=1:10:3) and yellow oil of 302 mg is obtained in 79% yield.

Reference Example 6

Synthesis of 8-Phenyl-8-(4-(piperidin-1-yl)phenyl)-3-(pyren-1-yl)-1-(4-((tetrahydro-2H-pyran-2-yl)oxy)butoxy)-8H-pyrano[3,2-f]quinazoline 3-chloro-8-phenyl-8-(4-(piperidin-1-yl)phenyl)-1-(4-((tetrahydro-2H-pyran-2-yl)oxy)butoxy)-8H-pyrano[3,2-f]quinazoline (300 mg, 0.48 mmol) and 1-pyreneboronic acid (202 mg, 0.82 mmol) are dissolved in 1,4-dioxane (10 mL) and 1M aqueous cesium carbonate solution (1.4 mL, 1.4 mmol) and degassed by blowing nitrogen gas for 1 hour. Tetrakis (triphenylphosphine) palladium (0) (163 mg, 0.14 mmol) is added thereto and the mixture is stirred at 60° C. for 7.5 hours. After filtration through celite, the filtrate is extracted with ethyl acetate and washed with ion-exchanged water. The organic layer is dried, the solvent is distilled off under reduced pressure, the residue is purified by silica gel column chromatography (ethyl acetate:dichloromethane:hexane=3:50:15) and yellow solid of 261 mg is obtained in 69% yield.

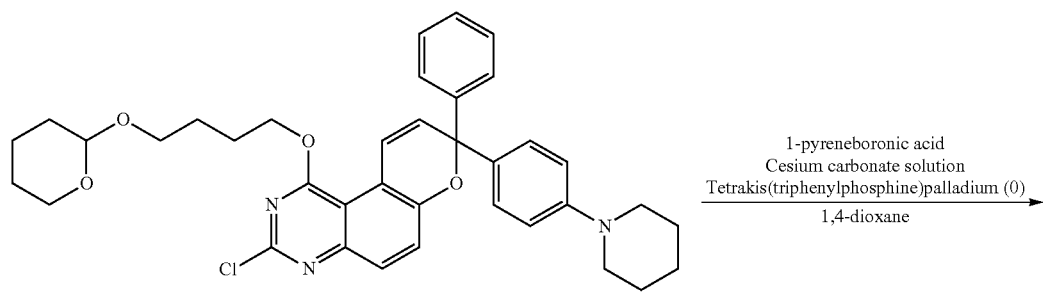

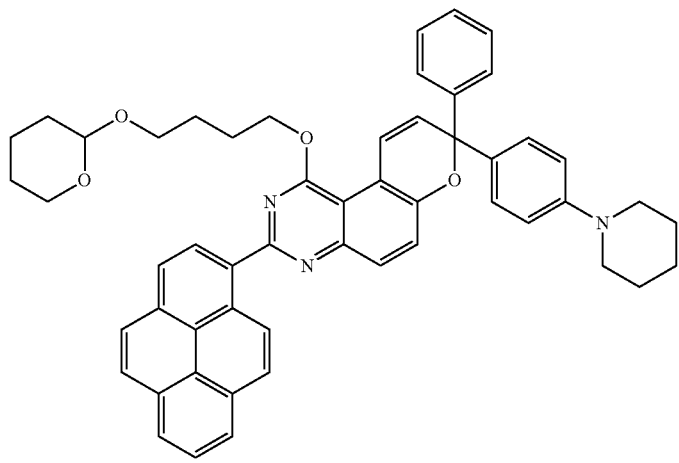

Reference Example

Synthesis of 4-((8-phenyl-8-(4-(piperidin-1-yl)phenyl)-3-(pyren-1-yl)-8H-pyrano[3,2-f]quinazolin-1-yl)oxy)butan-1-ol

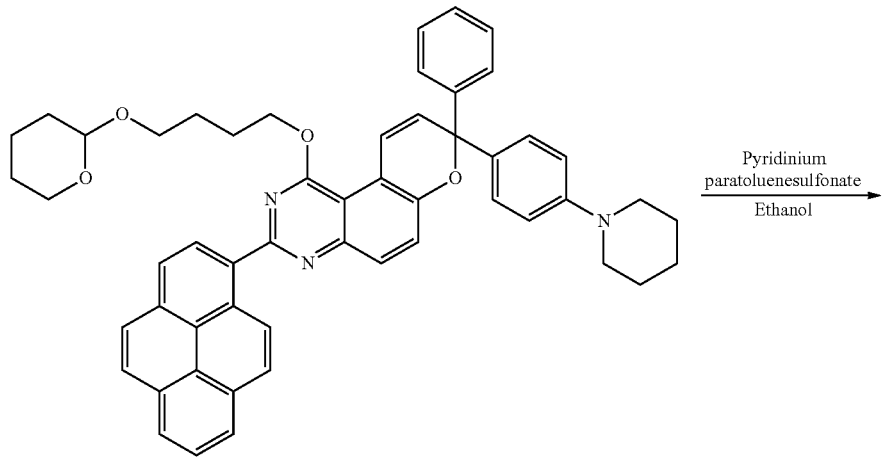

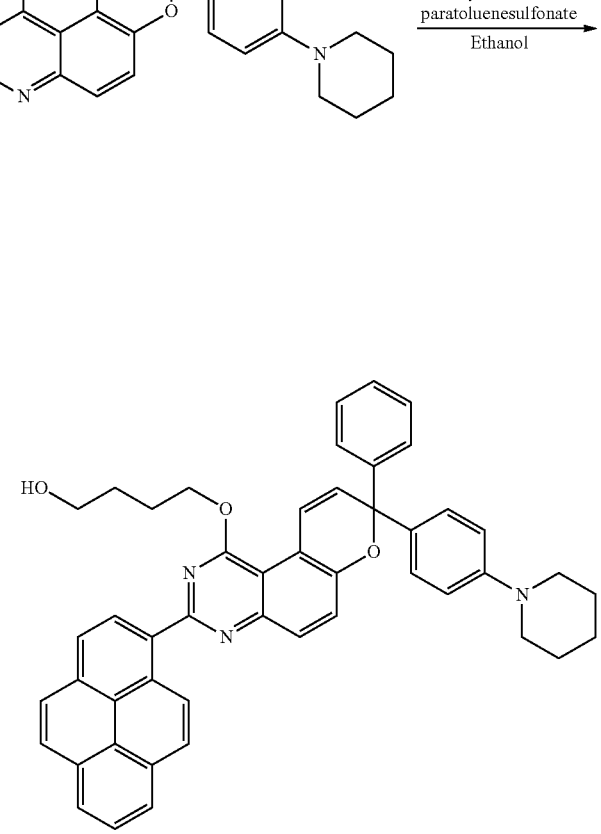

8-Phenyl-8-(4-(piperidin-1-yl)phenyl)-3-(pyren-1-yl)-1-(4-((tetrahydro-2H-pyran-2-yl)oxy)butoxy)-8H-pyrano[3,2-f]quinazoline (200 mg, 0.25 mmol) and pyridinium paratoluenesulfonate (14 mg, 0.06 mmol) are dissolved in ethanol (4 mL) and the mixture is stirred at 60° C. for 12 hours. After the solvent is distilled off under reduced pressure, dichloromethane and water are added, the aqueous layer is extracted with dichloromethane, and the combined organic layer is washed with water and brine. After the organic layer is dried and the solvent is distilled off under reduced pressure, the residue is purified by silica gel column chromatography (ethyl acetate:dichloromethane:hexane=1:10:1) and yellowish green solid of 86 mg is obtained in 49% yield.

Embodiment 8

Synthesis of 4-((8-phenyl-8-(4-(piperidin-1-yl)phenyl)-3-(pyren-1-yl)-8H-pyrano[3,2-f]quinazolin-1-yl)oxy)butyl methacrylate (Compound 8)

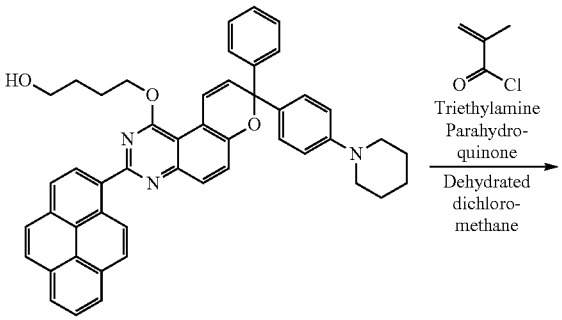

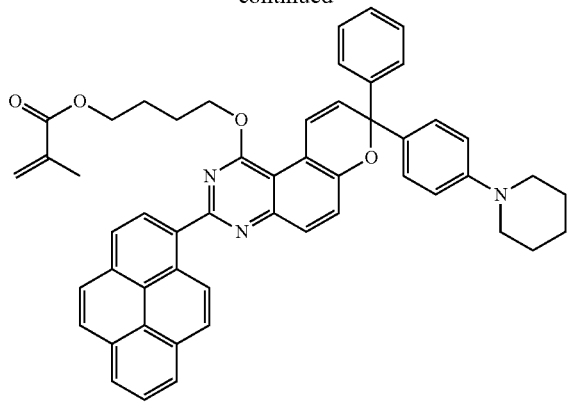

4-((8-phenyl-8-(4-(piperidin-1-yl)phenyl)-3-(pyren-1-yl)-8H-pyrano[3,2-J]quinazolin-1-yl)oxy)butan-1-ol (9 mg, 0.013 mmol), parahydroquinone (1 mg, 0.009 mmol) and triethylamine (0.015 mL, 0.11 mmol) are dissolved in dehydrated dichloromethane (0.3 mL) and cooled to 0° C. Methacryloyl chloride (0.1 mL, 1.1 mmol) is added thereto and the mixture is stirred at room temperature for 12 hours. The reaction solution is added to water, the aqueous layer is extracted with dichloromethane, and the combined organic layers are washed with water and brine. After the organic layer is dried and the solvent is distilled off under reduced pressure, the residue is purified by silica gel column chromatography (ethyl acetate:dichloromethane:hexane=1:28:12) and yellow solid of 2 mg is obtained in 20% yield.

Embodiment 9

Synthesis of 4-((8-phenyl-8-(4-(piperidin-1-yl)phenyl)-3-(pyren-1-yl)-8H-pyrano[3,2-f]quinazolin-1-yl)oxy)butyl methacrylate polymer (Compound 9)

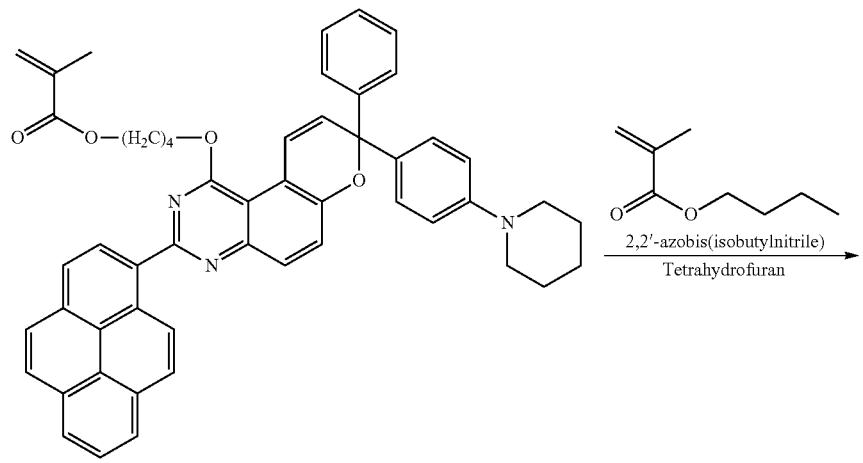

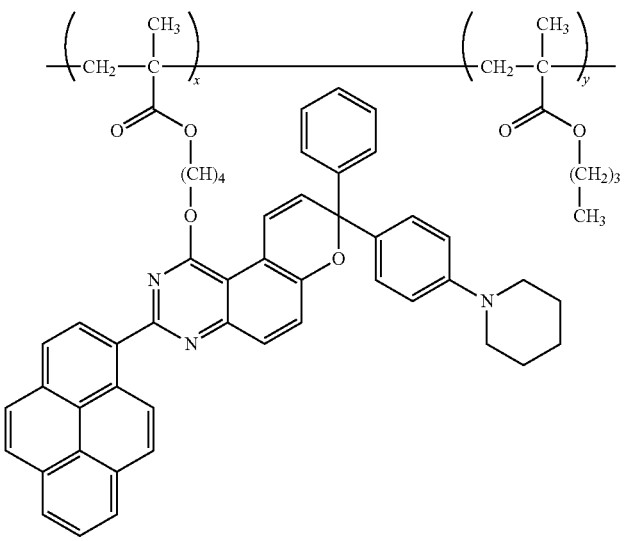

4-((8-phenyl-8-(4-(piperidin-1-yl)phenyl)-3-(pyren-1-yl)-8H-pyrano[3,2-f]quinazolin-1-yl)oxy)butyl methacrylate (1.6 mg, 0.002 mmol), butyl methacrylate (0.11 mL, 0.69 mmol) and 2,2'-azobis(isobutylnitrile) (5 mg, 0.030 mmol) are dissolved in 0.1 mL of tetrahydrofuran, the mixture is placed in a freezing ampoule, and the ampoule is sealed after 15 times of freezing and degassed. The solution is warmed to 60° C. and reacted overnight with stirring. Thereafter, the reaction solution is dissolved in tetrahydrofuran and dropped into methanol for reprecipitation purification. The precipitated solid is collected and photochromic polymer of 141 mg is obtained. By analyzing the ultraviolet/visible absorption spectrum of the toluene solution, x:y=1:1260 is obtained.

Reference Example 8

Synthesis of 2,3-dimethoxybenzyl alcohol

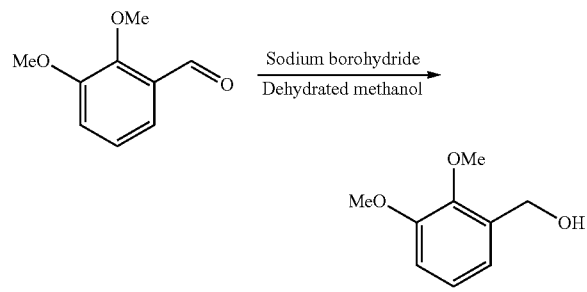

2,3-dimethoxybenzaldehyde (1515 mg, 9.1 mmol) is dissolved in dehydrated methanol (6 mL), sodium borohydride (201 mg, 5.3 mmol) is added thereto little by little, and the mixture is stirred at room temperature for 1 hour. The solvent is removed under reduced pressure, water is added, the mixture is extracted with dichloromethane, and the organic layer is washed with water. The organic layer is dried, the solvent is distilled off under reduced pressure and pale yellow liquid of 1442 mg is obtained in 94% yield.

Reference Example 9

Synthesis of 1-(chloromethyl)-2,3-dimethoxybenzene

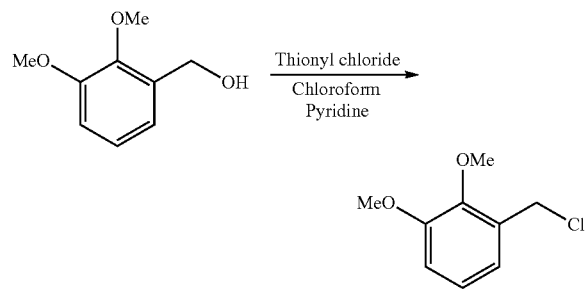

2,3-dimethoxybenzyl alcohol (1430 mg, 8.5 mmol) is dissolved in chloroform (10 mL), pyridine (6 mL) and thionyl chloride (1.22 mL, 17 mmol) are added thereto little by little, and the mixture is stirred at room temperature for 1 hour. The reaction solution is added with water and extracted with dichloromethane, and the organic layer is washed with aqueous sodium hydrogen carbonate solution. The organic layer is dried, the solvent is distilled off under reduced pressure, and pale yellow liquid of 1371 mg is obtained in 86% yield.

Reference Example 10

Synthesis of 2,3-dimethoxyphenylacetonitrile

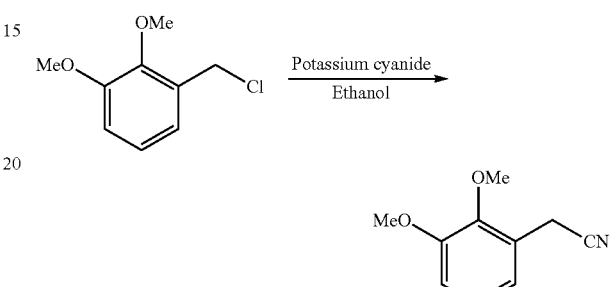

1-chlorophenyl-2,3-dimethoxybenzene (1360 mg, 7.3 mmol) and potassium cyanide (674 mg, 10.4 mmol) are dissolved in water (1.3 mL) and ethanol (3.26 mL) and the mixture is stirred at 110° C. for 1 hour. After cooled to room temperature, the reaction solution is added with water and extracted with dichloromethane, and the organic layer is washed with water. The organic layer is dried, the solvent is distilled off under reduced pressure, and pale yellow liquid (1132 mg, 6.4 mmol) is obtained in 88% yield.

Reference Example 11

Synthesis of 2,3-dimethoxyphenylacetic acid

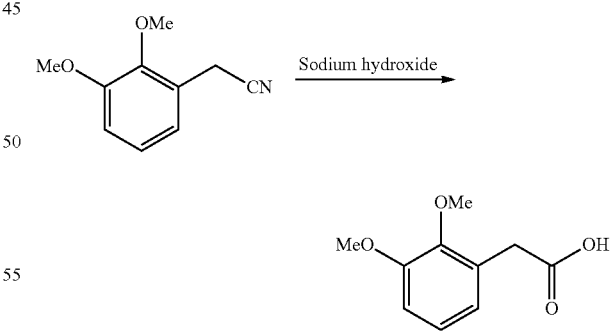

2,3-dimethoxyphenylacetonitrile (1120 mg, 6.3 mmol) and sodium hydroxide (1190 mg, 48 mmol) are dissolved in water (30 mL) and the mixture is stirred at 110° C. for 10.5 hours. The reaction solution is washed with diethyl ether, hydrochloric acid is added to the aqueous layer, and the mixture is extracted with ethyl acetate. The solvent is distilled off under reduced pressure and pale yellow liquid (1091 mg, 5.6 mmol) is obtained in 88% yield.

Reference Example 12

Synthesis of 2-(2,3-dimethoxyphenyl)-1-(2-hydroxy-1H-inden-3-yl)ethane-1-one

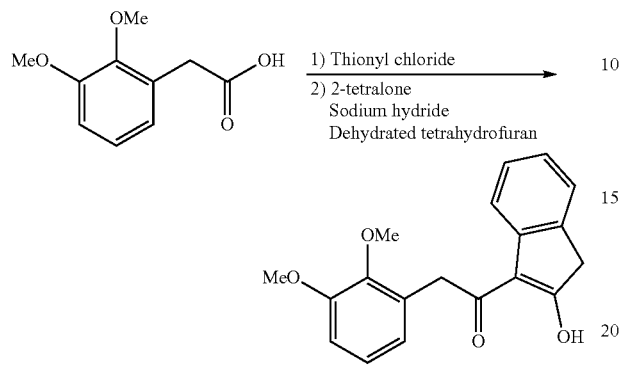

2,3-dimethoxyphenylacetic acid (1156 mg, 5.4 mmol) is dissolved in thionyl chloride (2 mL, 10.2 mmol) and the mixture is stirred at 60° C. for 2 hours. The solvent is distilled off under reduced pressure and pale yellow liquid is obtained.

After the pale yellow liquid and 2-indanone (808 mg, 6.1 mmol) are dissolved in dehydrated tetrahydrofuran (5 mL), and sodium hydride (55%, dispersed in liquid paraffin) (681 mg, 15.6 mmol) is carefully added, the mixture are stirred at 70° C. for 2 hours. After cooled to room temperature, the reaction solution is added with 1N hydrochloric acid (10 mL) and extracted with ethyl acetate, and the organic layer is washed with water. After the organic layer is dried and the solvent is distilled off under reduced pressure, the residue is purified by silica gel column chromatography (ethyl acetate: dichloromethane=1:200) and yellow solid of 906 mg is obtained in 54% yield.

Reference Example 13

Synthesis of 3,4-dimethoxy-11H-benzo[a]fluoren-6-ol

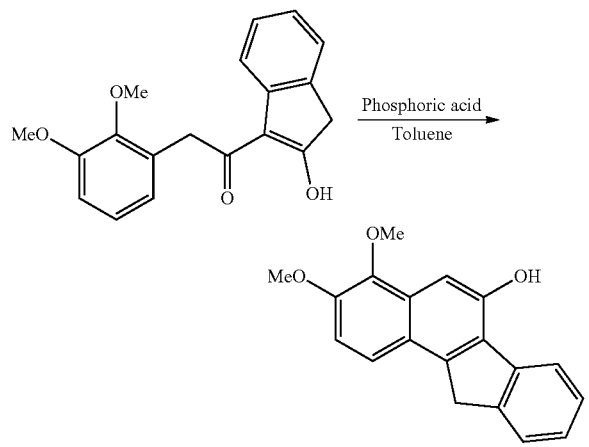

2-(2,3-dimethoxyphenyl)-1-(2-hydroxy 1H-inden-3-yl)ethane-1-one (808 mg, 2.4 mmol), 85% aqueous phosphoric acid (4 mL) and toluene (9 mL) are added, and the mixture is stirred at 110° C. for 6 hours while removing water in the system using the Dean-Stark apparatus. After cooled to room temperature, the reaction solution is added with cold water, and extracted with ethyl acetate, and the organic layer is washed with water. After the organic layer is dried, and the solvent is distilled off under reduced pressure, the residue is purified by silica gel column chromatography (ethyl acetate: dichloromethane=3.5:100) and yellow solid of 171 mg is obtained in 24% yield.

Embodiment 10

Synthesis of 5,6-dimethoxy-2,2-diphenyl-2,9-dihydrobenzo[f]indeno[2,1-h]chromene (Compound 10)

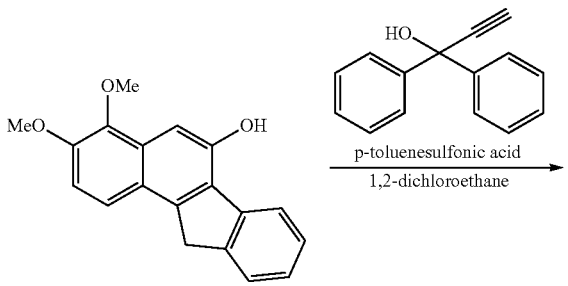

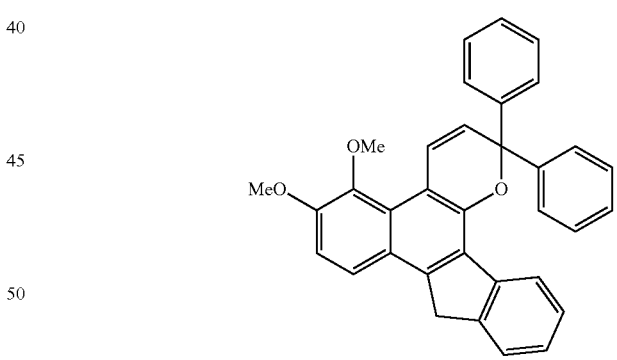

3,4-dimethoxy-11H-benzo[a]fluoren-6-ol (30 mg, 0.097 mmol), 1,1-diphenyl-2-propyn-1-ol (42 mg, 0.20 mmol) and p-toluenesulfonic acid (10 mg, 0.053 mmol) are dissolved in 1,2-dichloroethane (8 mL) and the mixture is stirred at room temperature for 18 hours. The reaction solution is extracted with dichloromethane, and the organic layer is washed with water. After the organic layer is dried and the solvent is distilled off under reduced pressure, the residue is purified by silica gel column chromatography (dichloromethane: hexane=20:1) and yellow solid of 50 mg is obtained in 59% yield.

Embodiment 11

Synthesis of 5,6-dimethoxy-2-phenyl-2-(4-(piperidin-1-yl)phenyl)-2,9-dihydrobenzo[f]indeno[2,1-h]chromene (Compound 11)

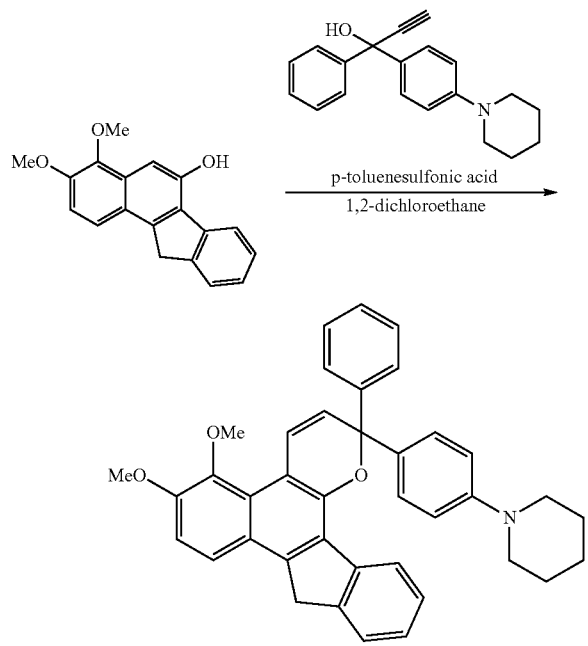

3,4-dimethoxy-11H-benzo[a]fluoren-6-ol (40 mg, 0.14 mmol), 1-phenyl-1-[4-(1-piperidinyl)phenyl]-2-propyn-1-ol (51 mg, 0.17 mmol) and paratoluenesulfonic acid (8 mg, 0.042 mmol) are dissolved in 1,2-dichloroethane (8 mL), and the mixture is stirred at 60° C. for 16.5 hours. After cooled to room temperature, the reaction solution is extracted with dichloromethane, and the organic layer is washed with water. After the organic layer is dried and the solvent is distilled off under reduced pressure, the residue is purified by silica gel column chromatography (dichloromethane:hexane=20:1) and red-purple solid of 50 mg is obtained in 64% yield.

Embodiment 12

Synthesis of 5,6-dimethoxy-2,2-di(4-diethylaminophenyl)-2,9-dihydrobenzo[f]indeno[2,1-h]chromene (Compound 12)

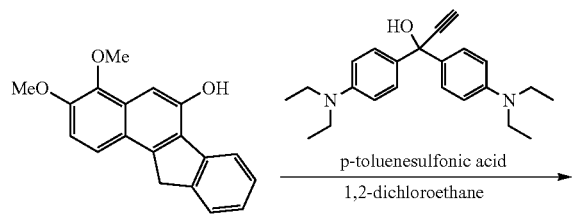

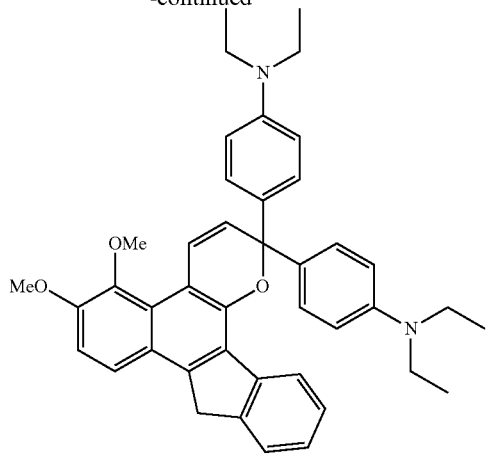

3,4-dimethoxy-11H-benzo[a]fluoren-6-ol (20 mg, 0.07 mmol), 1,1-bis-(4-(diethylamino)phenyl)prop-2-yn-1-ol (51 mg, 0.17 mmol) and paratoluenesulfonic acid (8 mg, 0.042 mmol) are dissolved in 1,2-dichloroethane (8 mL) and the mixture is stirred at 60° C. for 16.5 hours. After cooled to room temperature, the reaction solution is extracted with dichloromethane, and the organic layer is washed with water. After the organic layer is dried and the solvent is distilled off under reduced pressure, the residue is purified by silica gel column chromatography (dichloromethane) and purple solid of 3 mg is obtained in 8% yield.

Reference Example 14

Synthesis of 2-(2,3-dimethoxyphenyl)-1-(2-hydroxy-3,4-dihydronaphthalen-1-yl)ethane-1-one

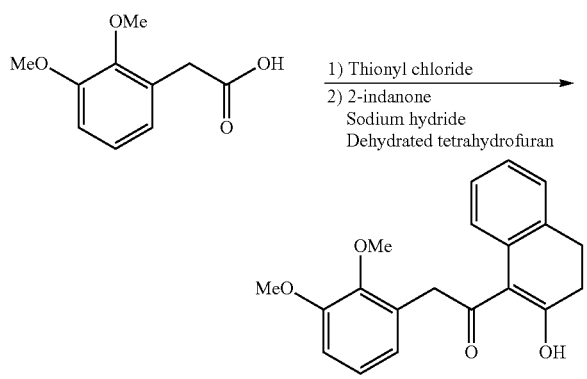

2,3-dimethoxyphenylacetic acid (505 mg, 2.5 mmol) is dissolved in thionyl chloride (0.4 mL, 10.2 mmol) and the mixture is stirred at 60° C. for 2 hours. The solvent is distilled off under reduced pressure and pale yellow liquid is obtained. After the pale yellow liquid and 2-tetralone (394 mg, 2.7 mmol) are dissolved in dehydrated tetrahydrofuran (5 mL), and sodium hydride (55%, dispersed in liquid paraffin) (525 mg, 12.0 mmol) is carefully added, the mixture is stirred at 70° C. for 2 hours. After cooled to room temperature, the reaction solution is added with 1N hydrochloric acid (14 mL) and extracted with ethyl acetate, and the organic layer is washed with water. After the organic layer is dried and the solvent is distilled off under reduced pressure, the residue is purified by silica gel column chromatography (hexane:dichloromethane=1:9) and yellow solid of 263 mg is obtained in 32% yield.

Reference Example 15

Synthesis of 7,8-dimethoxy-11,12-dihydrochrysen-5-ol

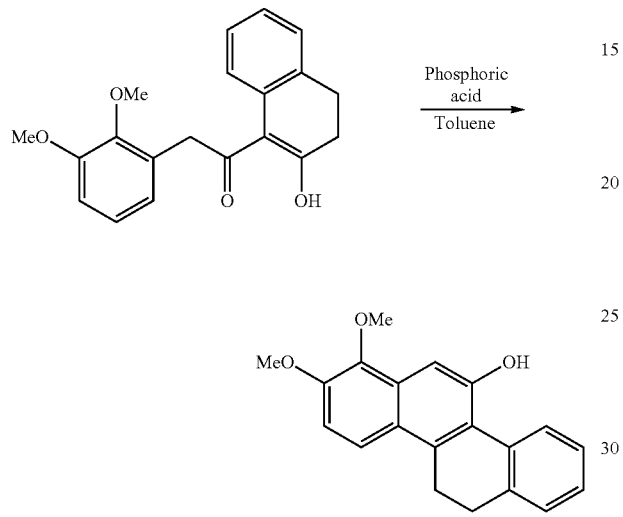

2-(2,3-dimethoxyphenyl)-1-(2-hydroxy-3,4-dihydronaphthalen-1-yl)ethane-1-one (263 mg, 0.81 mmol), 85% aqueous phosphoric acid (2.6 mL) and toluene (6 mL) are added, and the mixture is stirred at 110° C. for 5 hours while removing water in the system using a Dean-Stark apparatus. After cooled to room temperature, the reaction solution is added with cold water and extracted with ethyl acetate, and the organic layer is washed with water. After the organic layer is dried and the solvent is distilled off under reduced pressure, the residue is purified by silica gel column chromatography (ethyl acetate:dichloromethane=3:200) and orange solid of 140 mg is obtained in 57% yield.

Embodiment 13

Synthesis of 1,2-dimethoxy-12-phenyl-12-(4-(piperidin-1-yl)phenyl)-5,12-dihydro-6H-benzo[f]naphtho[2,1-h]chromene (Compound 13)

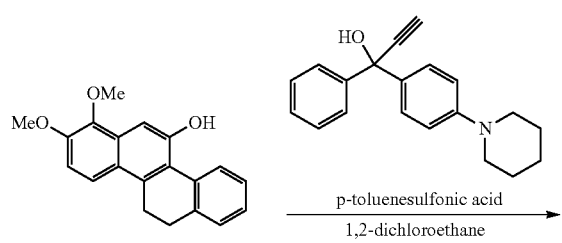

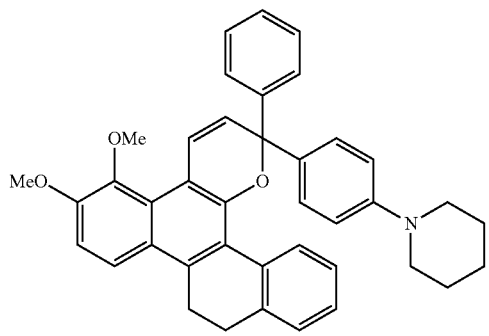

7,8-Dimethoxy-11,12-dihydrochrysen-5-ol (40 mg, 0.13 mmol), 1-phenyl-1-[4-(1-piperidinyl)phenyl]-2-propyn-1-ol (68 mg, 0.23 mmol) and paratoluenesulfonic acid (10 mg, 0.053 mmol) are dissolved in 1,2-dichloroethane (7 mL) and the mixture is stirred at 60° C. for 37 hours. The reaction solution is cooled to room temperature and extracted with dichloromethane, and the organic layer is washed with water. After the organic layer is dried and the solvent is distilled off under reduced pressure, the residue is purified by silica gel column chromatography (dichloromethane:hexane=7:3) and red solid of 36 mg obtained in 48% yield.

Reference Example 16

Synthesis of 2-((tetrahydro-2H-pyran-2-yl)oxy)anthraquinone

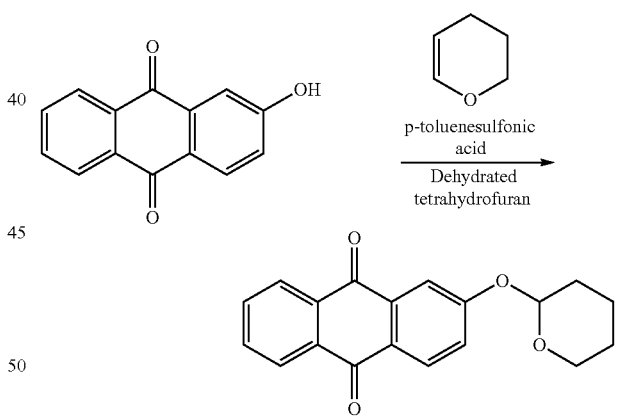

2-hydroxyanthraquinone (503 mg, 2.24 mmol), p-toluenesulfonic acid (31 mg, 0.16 mmol) and dihydropyran (1 mL, 10.9 mmol) are dissolved in dehydrated tetrahydrofuran (14 mL) and the mixture is stirred at room temperature for 4.5 hours. Dihydropyran (1 mL, 10.9 mmol) is further added thereto, and the mixture is stirred at room temperature for 12.5 hours. The reaction solution is added with 1M aqueous sodium hydroxide solution, extracted with dichloromethane, and then washed with water and brine. After the organic layer is dried and the solvent is distilled off under reduced pressure, the residue is purified by silica gel column chromatography (ethyl acetate:dichloromethane:hexane=1:20:20) and yellow solid of 494 mg is obtained in 72% yield.

Reference Example 17

Synthesis of 9,10-dimethoxyanthracen-2-ol

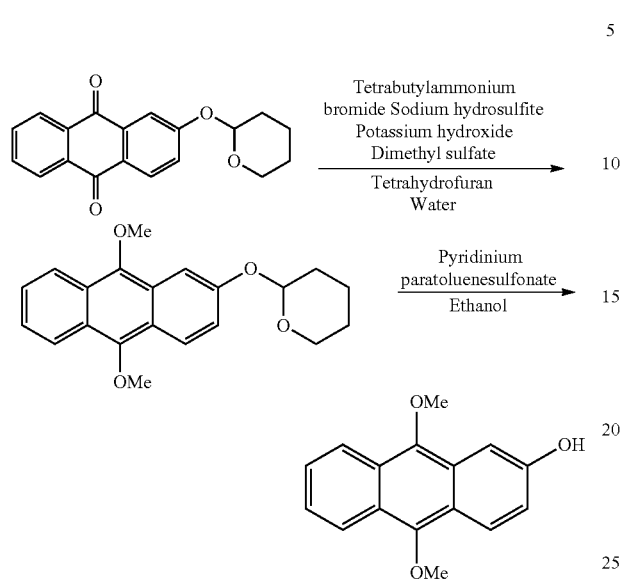

2-((Tetrahydro-2H-pyran-2-yl)oxy) anthraquinone (267 mg, 0.87 mmol) and tetrabutylammonium bromide (57 mg, 0.18 mmol) are dissolved in tetrahydrofuran (5.6 mL) and water (2 mL). Then, sodium hydrosulfite (454 mg, 2.61 mmol) is added thereto and the mixture is stirred at room temperature for 5 minutes. Potassium hydroxide (642 mg, 11.4 mmol) is added thereto, and furthermore, 5 minutes later, dimethyl sulfate (0.8 mL, 8.4 mmol) is added and the mixture is stirred at room temperature for 14 hours. A saturated aqueous ammonium chloride solution is added to the reaction solution, and the mixture is extracted with ethyl acetate. The organic layer is washed with water and dried, the solvent is distilled off under reduced pressure, and a crude product is obtained. This crude product and pyridinium paratoluenesulfonate (33 mg, 0.13 mmol) are dissolved in ethanol (19 mL) and the mixture is stirred at 60° C. for 3 hours. The reaction solution is added with ethyl acetate and washed with water. After the organic layer is dried and the solvent is distilled off under reduced pressure, the residue is purified by silica gel column chromatography (ethyl acetate:dichloromethane=1:30) and yellow solid of 169 mg is obtained in 76% yield.

Embodiment 14

Synthesis of 3-phenyl-3-(4-(piperidin-1-yl)phenyl)-3H-anthra[2,1-b]pyran (Compound 14)

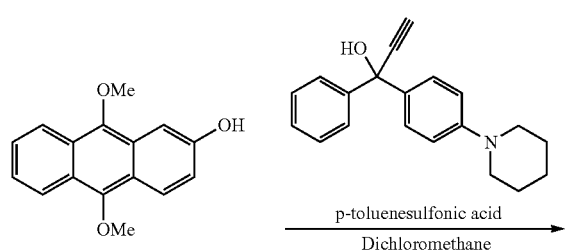

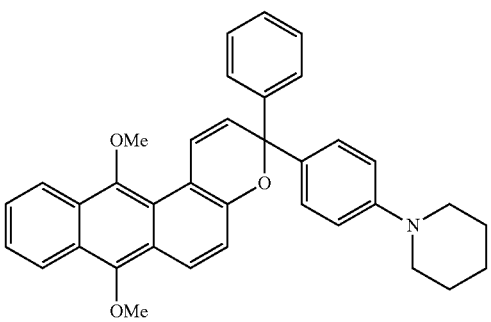

9,10-dimethoxyanthracen-2-ol (28 mg, 0.11 mmol), para-toluenesulfonic acid (7 mg, 0.04 mmol), 1-phenyl-1-[4-(1-piperidinyl)-2-propyne-1-ol (68 mg, 0.23 mmol) and dichloromethane (4 mL) are added and the mixture is stirred at room temperature for 22 hours. After added with water and extracted with ethyl acetate, the reaction solution is washed with water. After the organic layer is dried and the solvent is distilled off under reduced pressure, the residue is purified by silica gel column chromatography (ethyl acetate:hexane=3:20) and black solid of 31 mg is obtained in 63% yield.

Reference Example 18

Synthesis of 2,3-dihydrobenzo[b][1,4]dioxin-5-carbaldehyde

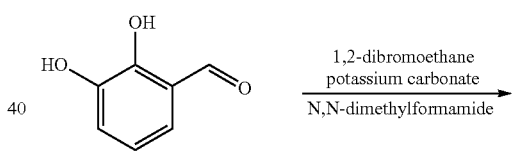

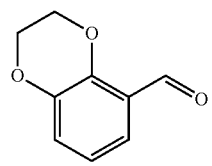

2,3-dihydroxybenzaldehyde (1003 mg, 7.24 mmol) is dissolved in N, N-dimethylformamide (70 mL), potassium carbonate (2701 mg, 19.5 mmol), 1,2-dibromoethane (0.75 mL, 8.7 mmol) is added thereto, and the mixture is stirred at 70° C. for 3 hours. After cooled to room temperature, the mixture is filtered through celite, and the solvent is removed under reduced pressure. The crude product is purified by silica gel column chromatography (hexane:ethyl acetate=5:1) and yellow solid of 644 mg is obtained in 54% yield.

Reference Example 19

Synthesis of (2,3-dihydrobenzo[b][1,4]dioxin-5-yl)methanol

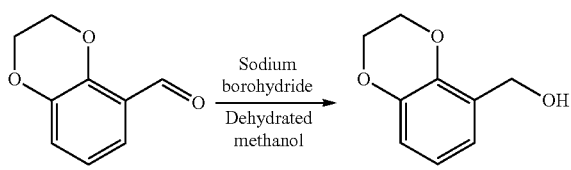 [SMILES: O=Cc1cccc2c1OCCO2 ; OCc1cccc2c1OCCO2]

2,3-dihydrobenzo[b][1,4]dioxin-5-carbaldehyde (615 mg, 3.74 mmol) is dissolved in dehydrated methanol (3 mL), sodium borohydride (270 mg, 7.1 mmol) is added thereto little by little, and the mixture is stirred at room temperature for 1 hour. The solvent is removed under reduced pressure, water is added, the mixture is extracted with dichloromethane, and the organic layer is washed with water. The organic layer is dried, the solvent is distilled off under reduced pressure, and pale yellow liquid of 556 mg is obtained in 89% yield.

Reference Example 20

Synthesis of 5-(chloromethyl)-2,3-dihydrobenzo[b][1,4]dioxin

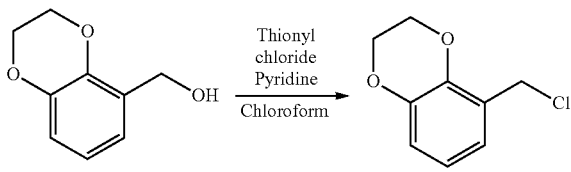 [SMILES: OCc1cccc2c1OCCO2 ; ClCc1cccc2c1OCCO2]

(2,3-Dihydrobenzo[b][1,4]dioxin-5-yl)methanol (533 mg, 3.20 mmol) is dissolved in chloroform (4 mL), pyridine (0.11 mL) and thionyl chloride (0.7 mL, 9.7 mmol) is added little by little and the mixture is stirred at room temperature for 1 hour. The reaction solution is added with water and extracted with dichloromethane, and the organic layer is washed with aqueous sodium hydrogen carbonate solution. The organic layer is dried, the solvent is distilled off under reduced pressure, and pale yellow liquid of 578 mg is obtained in 97% yield.

Reference Example 21

Synthesis of 2-(2,3-dihydrobenzo[b][1,4]dioxin-5-yl)acetonitrile

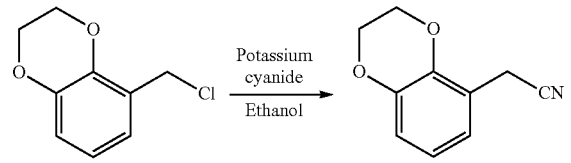 [SMILES: ClCc1cccc2c1OCCO2 ; N#CCc1cccc2c1OCCO2]

5-(chloromethyl)-2,3-dihydrobenzo[b][1,4]dioxin (552 mg, 2.96 mmol) and potassium cyanide (257 mg, 3.94 mmol) are dissolved in water (0.5 mL) and ethanol (2 mL), and the mixture is stirred at 110° C. for 1 hour. After cooled to room temperature, the reaction solution is added with water and extracted with dichloromethane, and the organic layer is washed with water. The organic layer is dried, the solvent is distilled off under reduced pressure, and pale yellow solid (481 mg, 2.74 mmol) is obtained in 93% yield.

Reference Example 22

Synthesis of 2-(2,3-dihydrobenzo[b][1,4]dioxin-5-yl)acetic acid

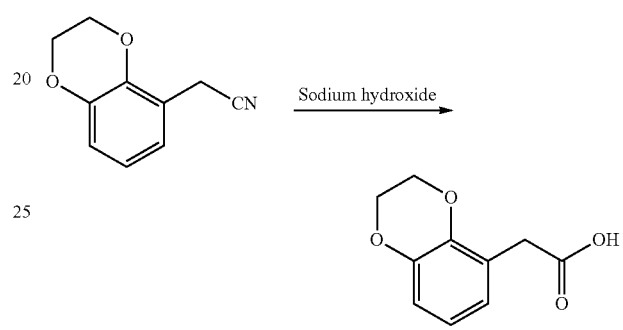

2-(2,3-dihydrobenzo[b][1,4]dioxin-5-yl)acetonitrile (453 mg, 2.51 mmol) and sodium hydroxide (557 mg, 14 mmol) is dissolved in water (9 mL) and the mixture is stirred at 110° C. for 7 hours. The reaction solution is washed with diethyl ether, hydrochloric acid is added to the aqueous layer, and the mixture is extracted with ethyl acetate. The solvent is distilled off under reduced pressure and pale yellow solid (388 mg, 2.0 mmol) is obtained in 80% yield.

Reference Example 23

Synthesis of 2-(2,3-dihydrobenzo[b][1,4]dioxin-5-yl)-1-(2-hydroxy-1H-inden-3-yl)ethan-1-one

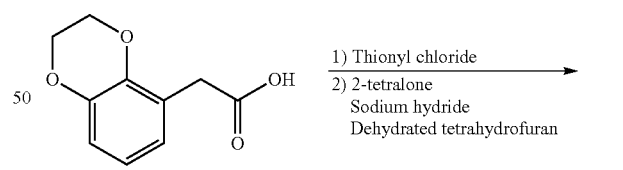

2-(2,3-dihydrobenzo[b][1,4]dioxin-5-yl)acetic acid (60 mg, 0.31 mmol) is dissolved in thionyl chloride (0.2 mL, 2.77 mmol) and the mixture is stirred at 60° C. for 2 hours. The solvent is distilled off under reduced pressure and pale yellow liquid is obtained. After the pale yellow liquid and 2-indanone (50 mg, 1.87 mmol) are dissolved in dehydrated tetrahydrofuran (1.8 mL) and sodium hydride (55%, dispersed in liquid paraffin) (681 mg, 6.26 mmol) is carefully added, the mixture is stirred at 70° C. for 2 hours. After cooled to room temperature, the reaction solution is added with 1N hydrochloric acid (5 mL) and extracted with ethyl acetate, and the organic layer is washed with water. After the organic layer is dried and the solvent is distilled off under reduced pressure, the residue is purified by silica gel column chromatography (ethyl acetate:hexane=1:3) and brown solid of 62 mg is obtained in 65% yield.

Reference Example 24

Synthesis of 4,5-dihydro-13H-indene[2',1':5,6]naphtho[1,2-b][1,4]dioxin-8-ol

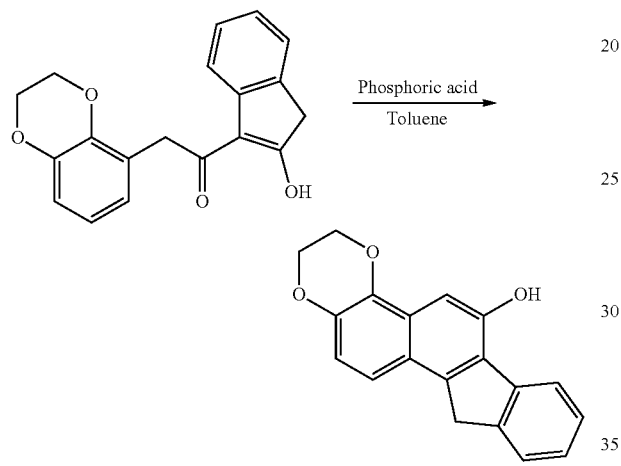

2-(2,3-dihydrobenzo[b][1,4]dioxin-5-yl)-1-(2-hydroxy-1H-inden-3-yl)ethan-1-one (55 mg, 1.68 mmol), 85% aqueous phosphoric acid solution (0.5 mL) and toluene (4.5 mL) are added, and the mixture is stirred at 110° C. for 6 hours while removing water in the system using a Dean-Stark apparatus. After cooled to room temperature, the reaction solution is added with cold water and extracted with ethyl acetate, and the organic layer is washed with water. After the organic layer is dried and the solvent is distilled off under reduced pressure, the crude product is dissolved in heated toluene and gradually cooled, and brown crystals of 33 mg are obtained in 65% yield.

Embodiment 15

Synthesis of 1-(4-(9-phenyl-4,5,9,15-tetrahydro-[1,4]dioxino[2',3':5,6]benzo[1,2-f]indeno[1,2-h]chromen-9-yl)phenyl)piperidine (Compound 15)

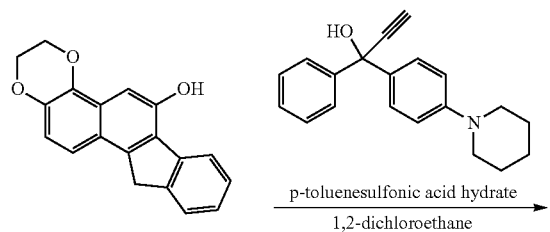

-continued

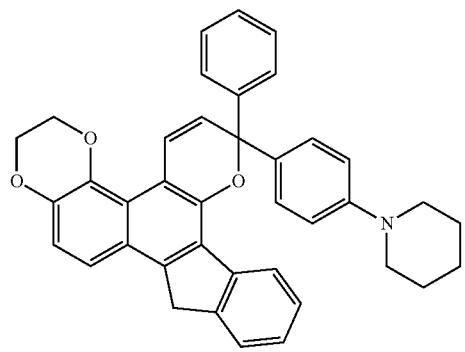

4,5-dihydro-13H-indene[2',1':5,6]naphtho[1,2-b][1,4]dioxin-8-ol (20 mg, 0.070 mmol), 1-phenyl-1-[4-(1-piperidinyl)phenyl]-2-propyn-1-ol (34 mg, 0.12 mmol) and p-toluenesulfonic acid (2 mg, 0.011 mmol) are dissolved in 1,2-dichloroethane (6 mL) and the mixture is stirred at 50° C. for 8 hours. The reaction solution is extracted with dichloromethane, and the organic layer is washed with water. After the organic layer is dried and the solvent is distilled off under reduced pressure, the residue is purified by silica gel column chromatography (dichloromethane:hexane=10:1) and red solid of 35 mg is obtained in 91% yield.

Reference Example 25

Synthesis of 2-phenylquinazolin-6-ol

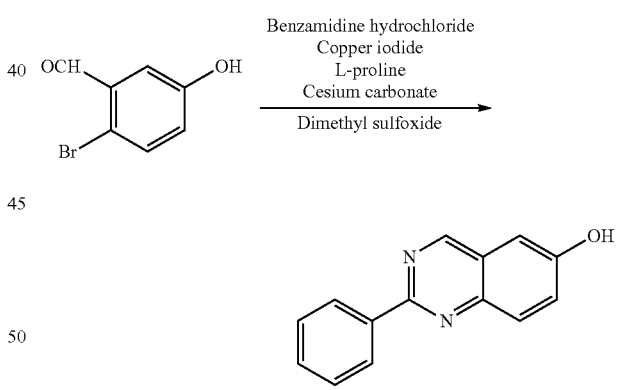

2-bromo-5-hydroxybenzaldehyde (301 mg, 1.50 mmol), benzamidine hydrochloride (389 mg, 2.48 mmol), copper iodide (66 mg, 0.35 mmol), L-proline (75 mg, 0.65 mmol) and cesium carbonate (1353 mg, 4.15 mmol) are dissolved in dehydrated dimethyl sulfoxide (3.6 mL) and the mixture is stirred at 70° C. for 1.5 hours. After cooled to room temperature, the reaction solution is added with water and extracted with ethyl acetate, and the combined organic layer is washed with water. After the organic layer is dried and the solvent is distilled off under reduced pressure, the residue is purified by silica gel column chromatography (methanol:ethyl acetate:dichloromethane=1:4:40) and pale yellow solid of 57 mg (0.26 mmol) is obtained in 17% yield.

Comparative Example 1

Synthesis of 3,8-diphenyl-8-(4-(piperidin-1-yl)phenyl)-8H-pyrano[3,2-f]quinazoline (Compound 16)

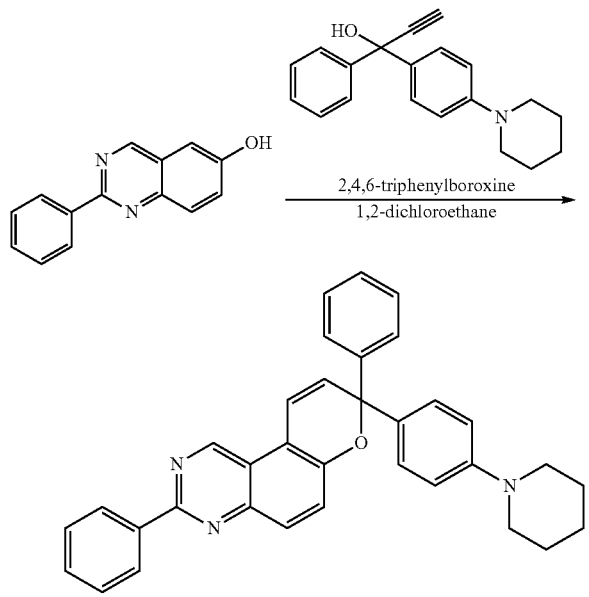

2-phenylquinazolin-6-ol (21 mg, 0.094 mmol), 1-phenyl-1-[4-(1-piperidinyl)phenyl]-2-propyn-1-ol (53 mg, 0.18 mmol) and 2,4,6-Triphenylboroxine (33 mg, 0.11 mmol) are dissolved in 1,2-dichloroethane (3.6 mL) and the mixture is stirred at 80° C. for 21.5 hours. After cooled to room temperature, the reaction solution is added with saturated aqueous sodium hydrogen carbonate solution and extracted with ethyl acetate, and the combined organic layer is washed with brine. After the organic layer is dried and the solvent is distilled off under reduced pressure, the residue is purified by alumina column chromatography (dichloromethane:hexane=2:3), the obtained yellow solid is washed with hexane, and pale yellow solid of 20 mg is obtained in 43% yield.

Reference Example 26

Synthesis of 1,3-dichloro-1-phenoxy-8-phenyl-8-(4-(piperidin-1-yl)phenyl)-8H-pyrano[3,2-f]quinazoline

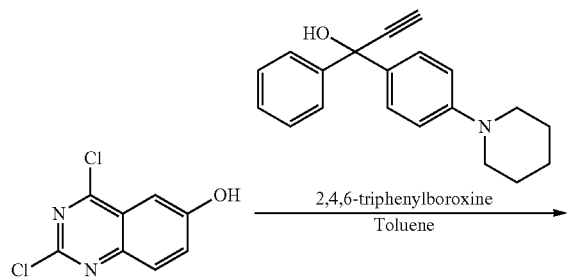

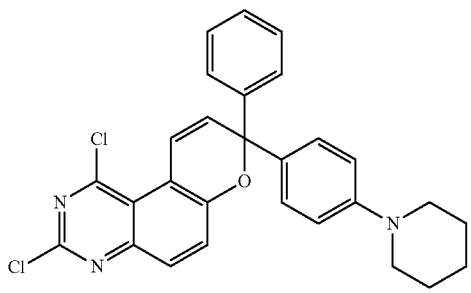

2,4-dichloroquinazolin-6-ol (344 mg, 1.60 mmol), 1-phenyl-1-[4-(1-piperidinyl)phenyl]-2-propyn-1-ol (891 mg, 3.06 mmol) and 2,4,6-Triphenylboroxine (506 mg, 1.62 mmol) are dissolved in toluene (28 mL) and the mixture is stirred at 100° C. for 3 days. After cooled to room temperature, the reaction solution is added with diethyl ether, the resulted precipitate is removed by celite filtration, and the filtrate is washed with a saturated aqueous sodium hydrogen carbonate solution and water. After the organic layer is dried and the solvent is distilled off under reduced pressure, the residue is purified by silica gel column chromatography (ethyl acetate:dichloromethane:hexane=1:28:12) and yellow solid of 314 mg is obtained in 40% yield.

Reference Example 27

Synthesis of 3-chloro-1-methyl-8-phenyl-8-(4-(piperidin-1-yl)phenyl)-8H-pyrano[3,2-f]quinazoline

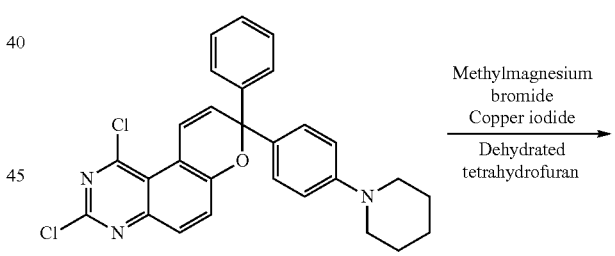

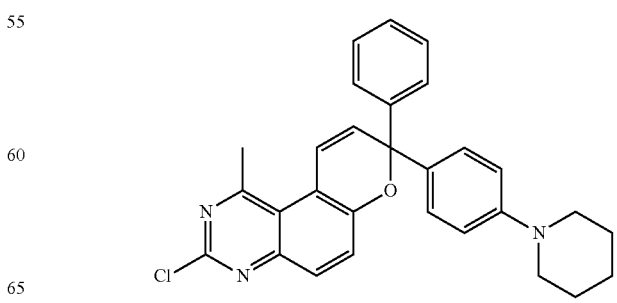

1,3-Dichloro-1-phenoxy-8-phenyl-8-(4-(piperidin-1-yl)phenyl)-8H-pyrano[3,2-f]quinazoline (48 mg, 0.098 mmol) and copper iodide (10 mg, 0.053 mmol) are dissolved in dehydrated tetrahydrofuran (0.4 mL) and the mixture is stirred at 0° C. The methyl magnesium bromide (0.15 mL, 0.14 mmol) is added to the tetrahydrofuran, and the mixture is stirred at 0° C. for 5 hours. A saturated aqueous ammonium chloride solution is added to the reaction solution, the mixture is extracted with ethyl acetate, and the combined organic layers are washed with water. After the organic layer is dried and the solvent is distilled off under reduced pressure, the residue is purified by silica gel column chromatography (acetone:ethyl acetate:methyl chloride=1:10:200) and brown solid of 21 mg is obtained in 46% yield.

Comparative Example 2

Synthesis of 1-methyl-3,8-diphenyl-8-(4-(piperidin-1-yl)phenyl)-8H-pyrano[3,2-f]quinazoline (Compound 17)

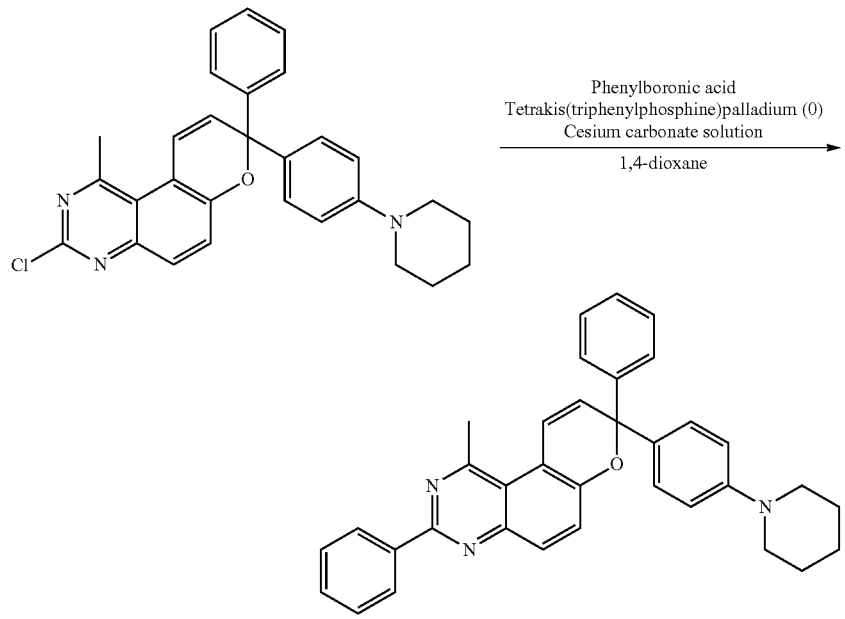

3-chloro-1-methyl-8-phenyl-8-(4-(piperidin-1-yl)phenyl)-8H-pyrano[3,2-f]quinazoline (20 mg, 0.043 mmol) and phenylboronic acid (14 mg, 0.11 mmol) are dissolved in 1,4-dioxane (1.4 mL) and 1M aqueous cesium carbonate solution (0.13 mL, 0.13 mmol), and the mixture is freeze degassed, and then tetrakis (triphenylphosphine) palladium (0) (16 mg, 0.014 mmol) is added and the mixture is stirred at 50° C. for 12.5 hours. Furthermore, tetrakis (triphenylphosphine) palladium (0) (12 mg, 0.010 mmol) is added, and the mixture is heated to 80° C. and is stirred for 5 hours. After cooled to room temperature, the reaction solution is added with ethyl acetate and filtered through celite, and the filtrate is washed with water. After the organic layer is dried and the solvent is distilled off under reduced pressure, the residue is purified by silica gel column chromatography (ethyl acetate:dichloroethane:hexane=1:28:12), the obtained white green solid is washed with hexane, and white solid of 2 mg is obtained in 9% yield.

Reference Example 28

Synthesis of 1-(tert-butyl)-3-chloro-8-phenyl-8-(4-(piperidin-1-yl)phenyl)-8H-pyrano[3,2-f]quinazoline

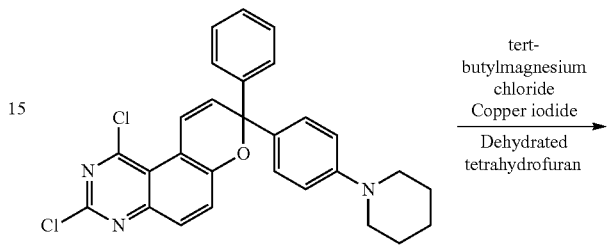

-continued

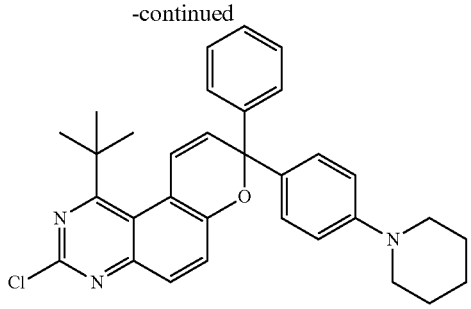

1,3-Dichloro-1-phenoxy-8-phenyl-8-(4-(piperidin-1-yl)phenyl)-8H-pyrano[3,2-f]quinazoline (50 mg, 0.10 mmol) and copper iodide (22 mg, 0.12 mmol) are dissolved in dehydrated tetrahydrofuran (1 mL) and the mixture is stirred at 0° C. Tert-butylmagnesium chloride (0.2 mL, 0.2 mmol) is added thereto, and the mixture is stirred at 0° C. for 5 minutes and then stirred at room temperature for 26 hours. A saturated aqueous ammonium chloride solution is added to the reaction solution, the mixture is extracted with ethyl acetate, and the combined organic layers are washed with water. After the organic layer is dried and the solvent is distilled off under reduced pressure, the mixture is appropriately purified by amine-treated silica gel column chromatography (ethyl acetate:dichloroethane:hexane=1:80:120), and 14 mg mixture of 1,3-dichloro-1-methyl-8-phenyl-8-(4-(piperidin-1-yl)phenyl)-8H-pyrano[3,2-f]quinazoline and 1-(tert-Butyl)-3-chloro-8-phenyl-8-(4-(piperidin-1-yl)phenyl)-8H-pyrano[3,2-f]quinazoline (1:8, $^1$H NMR) is obtained.

Comparative Example 3

Synthesis of 1-(tert-butyl)-3,8-diphenyl-8-(4-(piperidin-1-yl)phenyl)-8H-pyrano[3,2-f]quinazoline (Compound 18)

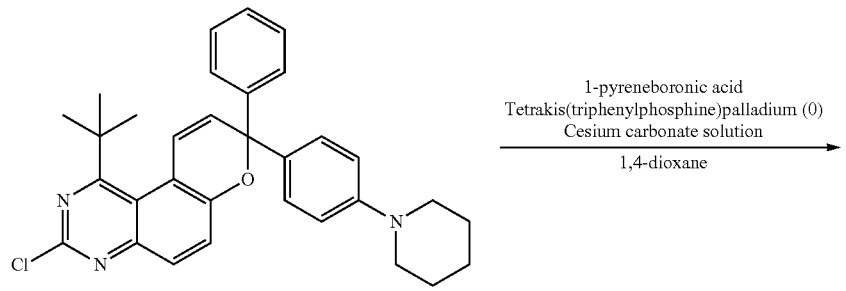

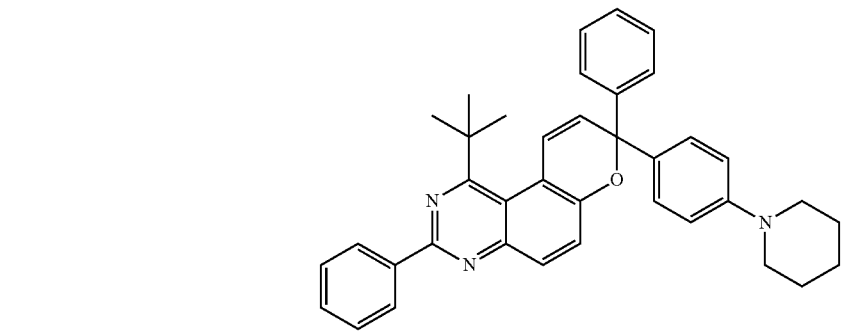

1-(tert-butyl)-3-chloro-8-phenyl-8-(4-(piperidin-1-yl)phenyl)-8H-pyrano[3,2-f]quinazoline (14 mg, 0.027 mmol) and phenylboronic acid (21 mg, 0.17 mmol) are dissolved in 1,4-dioxane (1.1 mL) and 1M aqueous cesium carbonate solution (0.081 mL, 0.081 mmol) and the mixture is freeze degassed, and then tetrakis (triphenylphosphine) palladium (0) (12 mg, 0.010 mmol) is added and the mixture is stirred at 80° C. for 16 hours. After cooled to room temperature, the reaction solution is added with ethyl acetate and filtered through celite, and the filtrate is washed with water. After the organic layer is dried and the solvent is distilled off under reduced pressure, the mixture is appropriately purified by silica gel column chromatography (ethyl acetate:dichloromethane:hexane=1:24:16), then purified by preparative reverse phase chromatography (acetonitrile), and white solid of 4 mg is obtained.

Reference Example 29

Synthesis of 2,4-di(thiophen-2-yl)quinazolin-6-ol

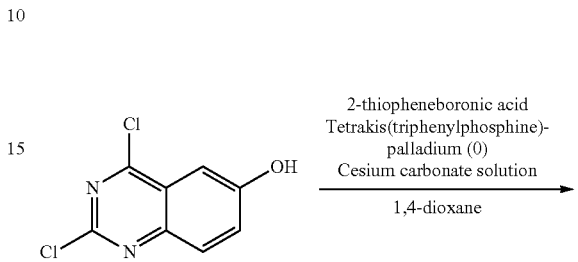

-continued

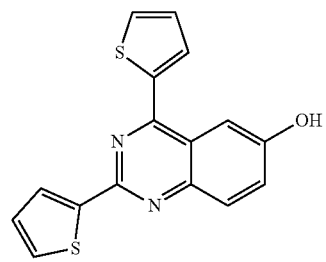

2,4-dichloroquinazolin-6-ol (32 mg, 0.15 mmol) and 2-thiopheneboronic acid (52 mg, 0.41 mmol) are dissolved in 4 mL 1,4-dioxane and 0.47 mL 1 M aqueous cesium carbonate solution. The mixture is degassed with nitrogen gas. Tetrakis (triphenylphosphine) palladium (0) (35 mg, 0.03 mmol) is added to the obtained solution and the solution is stirred at 100° C. for 13.5 hours. After filtration through celite, the filtrate is extracted with ethyl acetate and washed with water. After the organic layer is dried and the solvent is distilled off under reduced pressure, the crude mixture is purified by silica gel column chromatography (ethyl acetate:dichloromethane=1:10) and yellow solid of 31 mg is obtained in 64% yield.

Comparative Example 4

Synthesis of 8-phenyl-8-(4-(piperidin-1-yl)phenyl)-1,3-di(thiophen-2-yl)-8H-pyrano[3,2-f]quinazoline (Compound 19)

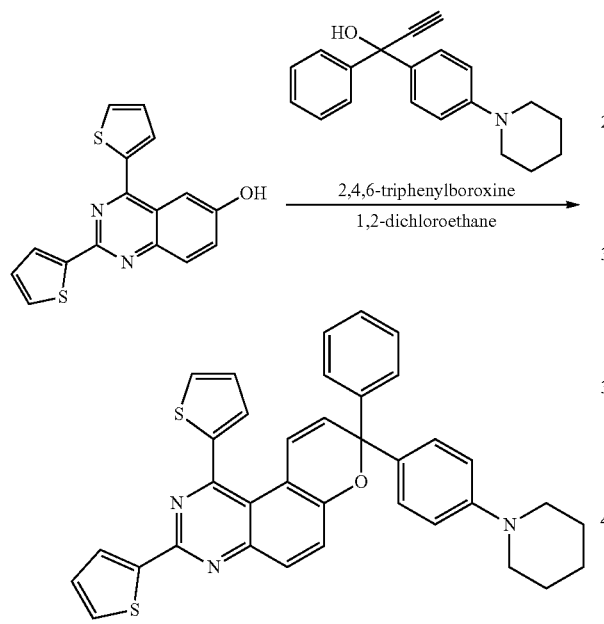

2,4-di(thiophen-2-yl)quinazolin-6-ol (30 mg, 0.097 mmol), 1-phenyl-1-[4-(1-piperidinyl)phenyl]-2-propyn-1-ol (46 mg, 0.16 mmol) and 2,4,6-triphenylboroxine (17 mg, 0.054 mmol) are dissolved in 1,2-dichloroethane (4 mL) and the mixture is stirred at 80° C. for 12.5 hours. The reaction solution is cooled to room temperature and extracted with diethyl ether, and the organic layer is washed with a saturated aqueous sodium hydrogen carbonate solution and water. After the organic layer is dried and the solvent is distilled off under reduced pressure, the mixture is purified by silica gel column chromatography (ethyl acetate:dichloromethane:hexane=1:8:12) and yellow solid of 38 mg is obtained in 67% yield.

Reference Example 30

Synthesis of 3-chloro-1-(methylthio)-8-phenyl-8-(4-(piperidin-1-yl)phenyl)-8H-pyrano[3,2-f]quinazoline

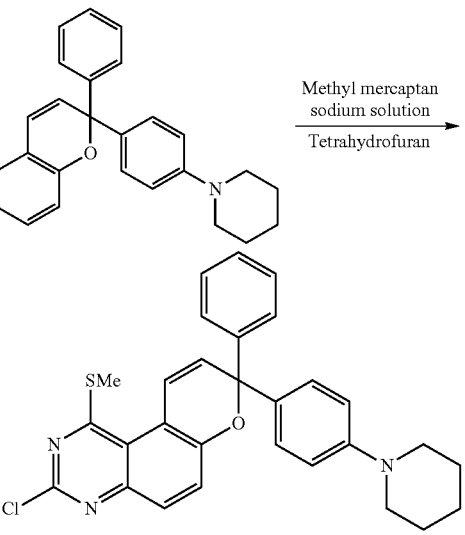

1,3-dichloro-8-phenyl-8-(4-(piperidin-1-yl)phenyl)-8H-pyrano[3,2-f]quinazoline (100 mg, 0.20 mmol) is dissolved in tetrahydrofuran (2 mL) and cooled to 0° C. Methyl mercaptan sodium (about 15% aqueous solution) (0.3 mL, 4.7 mmol) is added thereto, and the mixture is stirred at room temperature for 2 days. Water is added to the reaction solution, the aqueous layer is extracted with ethyl acetate, and the combined organic layer is washed with water and brine. After the organic layer is dried and the solvent is distilled off under reduced pressure, the residue is purified by silica gel column chromatography (ethyl acetate:dichloromethane:hexane=1:28:12) and yellow solid of 48 mg is obtained in 48% yield.

Comparative Example 5

Synthesis of 1-(methylthio)-3,8-diphenyl-8-(4-(piperidin-1-yl)phenyl)-8H-pyrano[3,2-f]quinazoline (Compound 20)

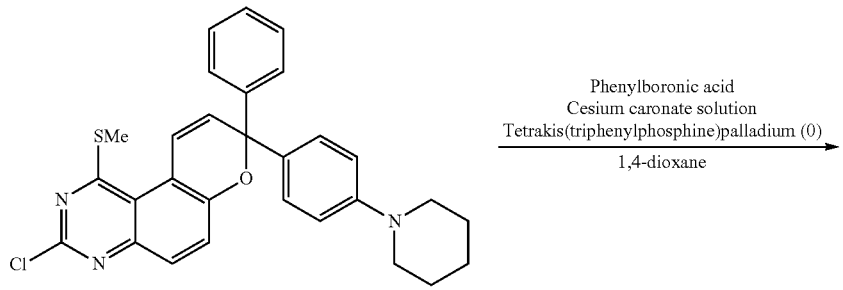

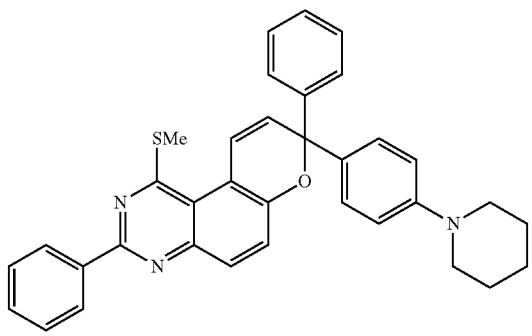

3-chloro-1-(methylthio)-8-phenyl-8-(4-(piperidin-1-yl)phenyl)-8H-pyrano[3,2-f]quinazoline (30 mg, 0.060 mmol) and phenylboron acid (14 mg, 0.11 mmol) are dissolved in 1,4-dioxane (1.3 mL) and 1M aqueous cesium carbonate solution (0.18 mL, 0.18 mmol), and the mixture is degassed by blowing nitrogen gas for 1 hour. Tetrakis (triphenylphosphine) palladium (0) (13 mg, 0.011 mmol) is added thereto and the mixture is stirred at 60° C. for 7 hours. After cooled to room temperature, the reaction solution is added with ethyl acetate and filtered through celite, and the filtrate is washed with water and brine. After the organic layer is dried and the solvent is distilled off under reduced pressure, the mixture is appropriately purified by silica gel column chromatography (ethyl acetate:dichloromethane:hexane=1:24:16), and then purified by preparative reverse phase chromatography (acetonitrile), and yellow solid of 9 mg is obtained in 15% yield.

Reference Example 31

Synthesis of 1-(2-hydroxy-1H-inden-3-yl)-2-(3-methoxyphenyl)ethan-1-one

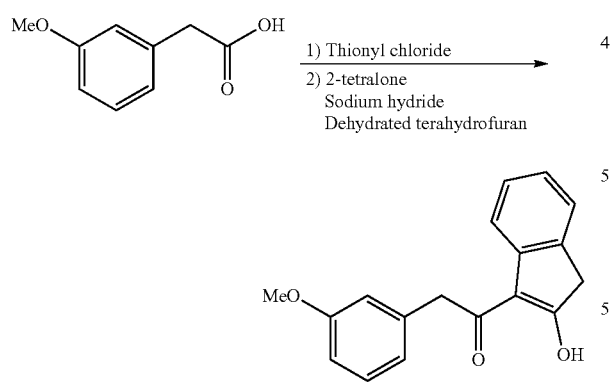

2-(3-methoxyphenyl)acetic acid (502 mg, 3.0 mmol) is dissolved in thionyl chloride (0.5 mL, 6.9 mmol) and the mixture is stirred at 60° C. for 2 hours. The solvent is distilled off under reduced pressure and pale yellow liquid is obtained. The pale yellow liquid and 2-indanone (529 mg, 4.0 mmol) are dissolved in dehydrated tetrahydrofuran (5 mL), and after sodium hydride 55%, (dispersed in liquid paraffin) (800 mg, 18.3 mmol) is carefully added, the mixture is stirred at 70° C. for 2 hours. After cooled to room temperature, the reaction solution is added with 1N hydrochloric acid (20 mL) and extracted with ethyl acetate, and the organic layer is washed with water. After the organic layer is dried and the solvent is distilled off under reduced pressure, the residue is purified by silica gel column chromatography (hexane:dichloromethane=1:2) and yellow solid of 400 mg is obtained in 47% yield.

Reference Example 32

Synthesis of 3-methoxy-11H-benzo[a]fluoren-6-ol

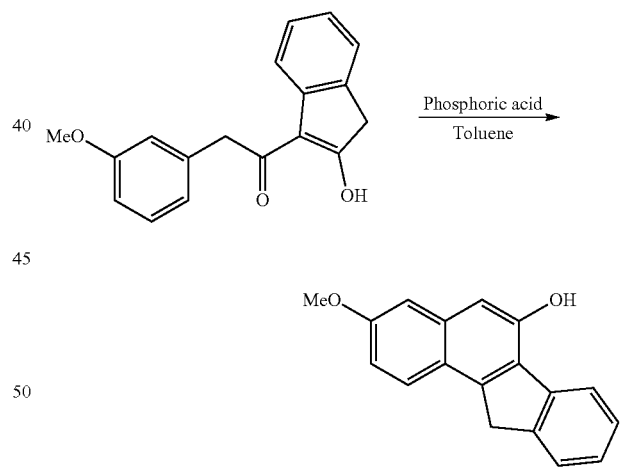

1-(2-Hydroxy-1H-inden-3-yl)-2-(3-methoxyphenyl)ethan-1-one (251 mg, 0.90 mmol), 85% aqueous phosphoric acid (2.3 mL) and toluene (5 mL) are added, and the mixture is stirred at 110° C. for 5 hours while removing water from the system using a Dean-Stark apparatus. After cooled to room temperature, the reaction solution is added with cold water and extracted with ethyl acetate, and the organic layer is washed with water. After the organic layer is dried and the solvent is distilled off under reduced pressure, the residue is purified by silica gel column chromatography (hexane:dichloromethane=1:4) and yellow solid of 96 mg is obtained in 41% yield.

Comparative Example 6

Synthesis of 6-methoxy-2,2-diphenyl-2,9-dihydrobenzo[f]indeno[2,1-h]chromene (Compound 21)

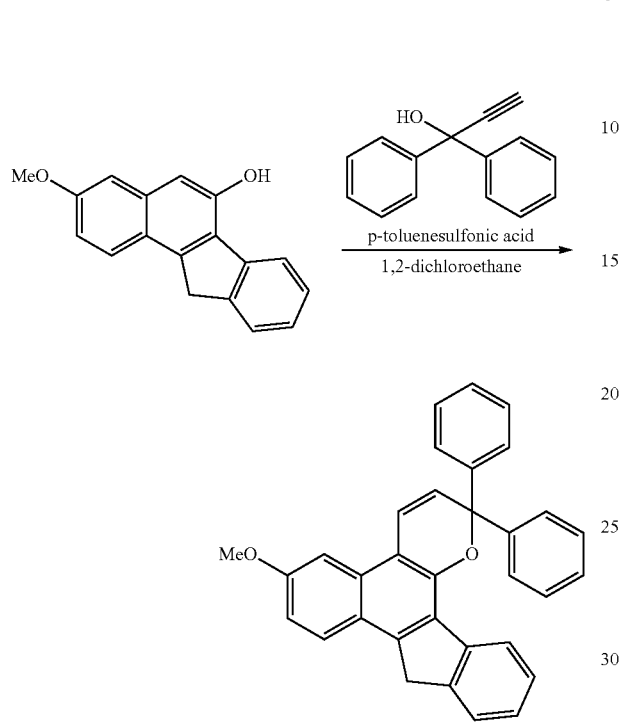

3-methoxy-11H-benzo[a]fluoren-6-ol (31 mg, 0.11 mmol), 1,1-diphenyl-2-propyn-1-ol (30 mg, 0.14 mmol) and paratoluenesulfonic acid (8 mg, 0.042 mmol) are dissolved in 1,2-dichloroethane (8 mL) and the mixture is stirred at room temperature for 15 hours. The reaction solution is extracted with dichloromethane, and the organic layer is washed with water. After the organic layer is dried and the solvent is distilled off under reduced pressure, the residue is purified by silica gel column chromatography (dichloromethane:hexane=3:4) and yellow solid of 16 mg is obtained in 31% yield.

Comparative Example 7

Synthesis of 6-methoxy-2-phenyl-2-(4-(piperidin-1-yl)phenyl)-2,9-dihydrobenzo[f]indeno[2,1-h]chromene (Compound 22)

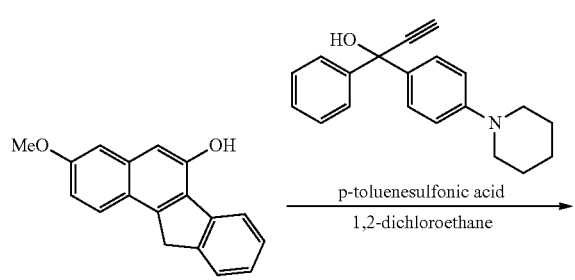

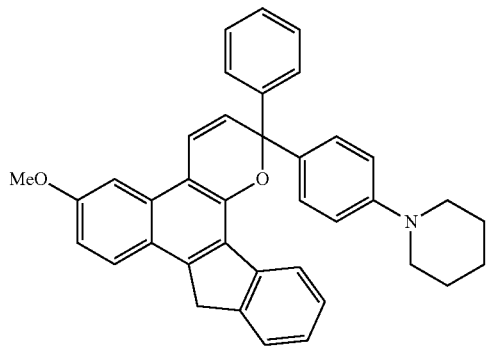

3-methoxy-11H-benzo[a]fluoren-6-ol (40 mg, 0.15 mmol), 1-phenyl-1-[4-(1-piperidinyl)phenyl]-2-propyn-1-ol (53 mg, 0.18 mmol) and paratoluenesulfonic acid (10 mg, 0.053 mmol) are dissolved in 1,2-dichloroethane (6 mL), and the mixture is stirred at 60° C. for 19 hours. The reaction solution is cooled to room temperature and extracted with dichloromethane, and the organic layer is washed with water. After the organic layer is dried and the solvent is distilled off under reduced pressure, the residue is purified by silica gel column chromatography (dichloromethane:hexane=1:1) and red-purple solid of 59 mg is obtained in 72% yield.

Embodiment 16

Photochromic Properties of Benzene Solutions of Compounds 1-5 and CR173.

Figure 23:
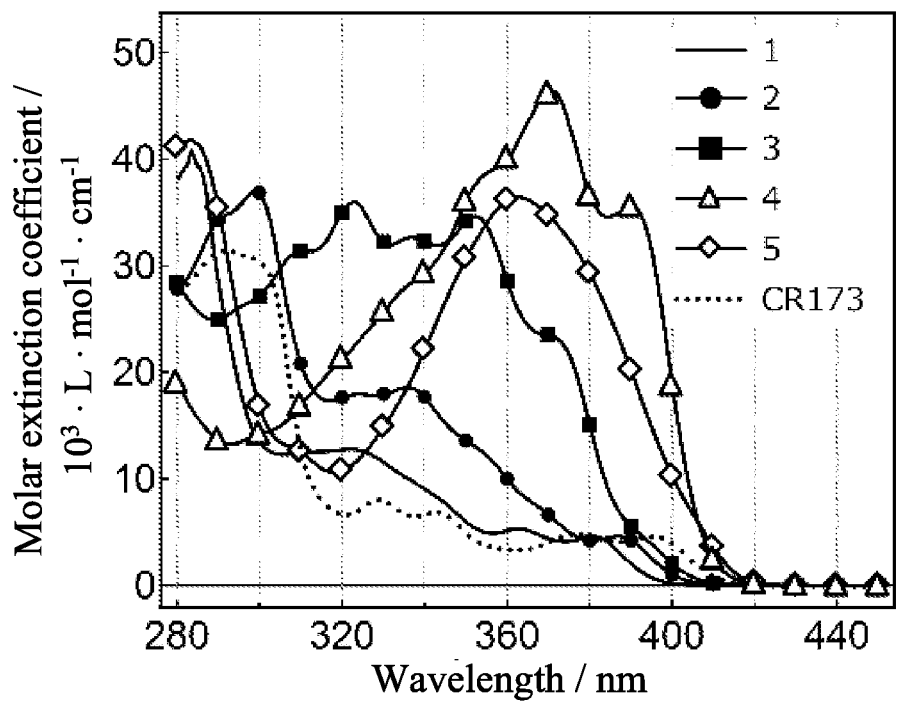
FIG. 23 is a graph of UV/visible absorption spectrum of benzene solutions of compounds 1 to 5 and CR173 decolorized body.
Figure 24:
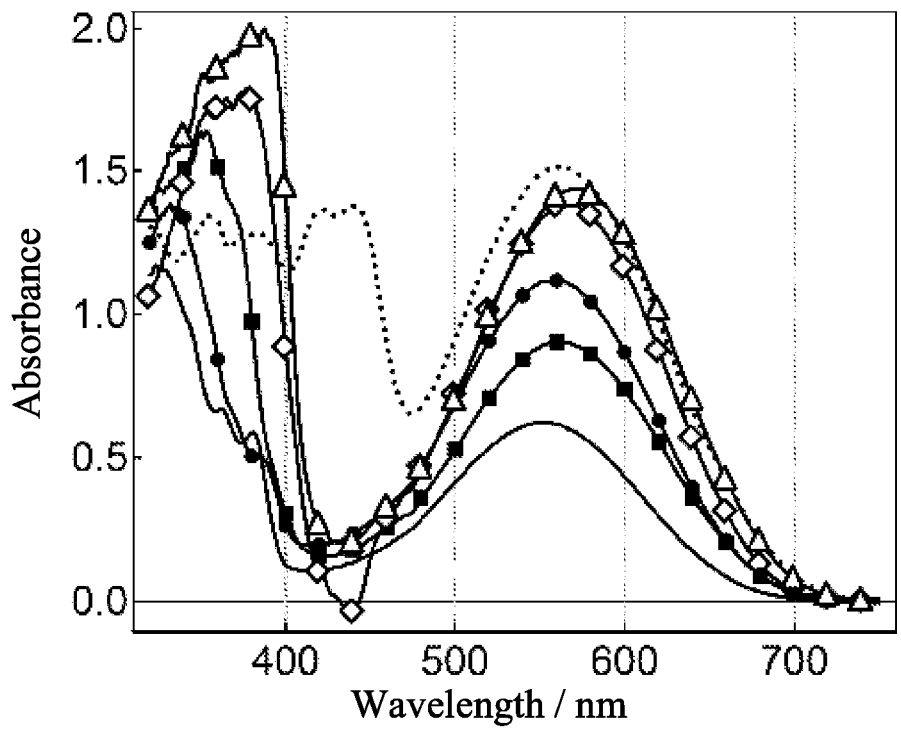
FIG. 24 is a graph of UV-visible/near-infrared absorption spectrum of benzene solutions of compounds 1 to 5 and CR173 chromogen.
Figure 25:
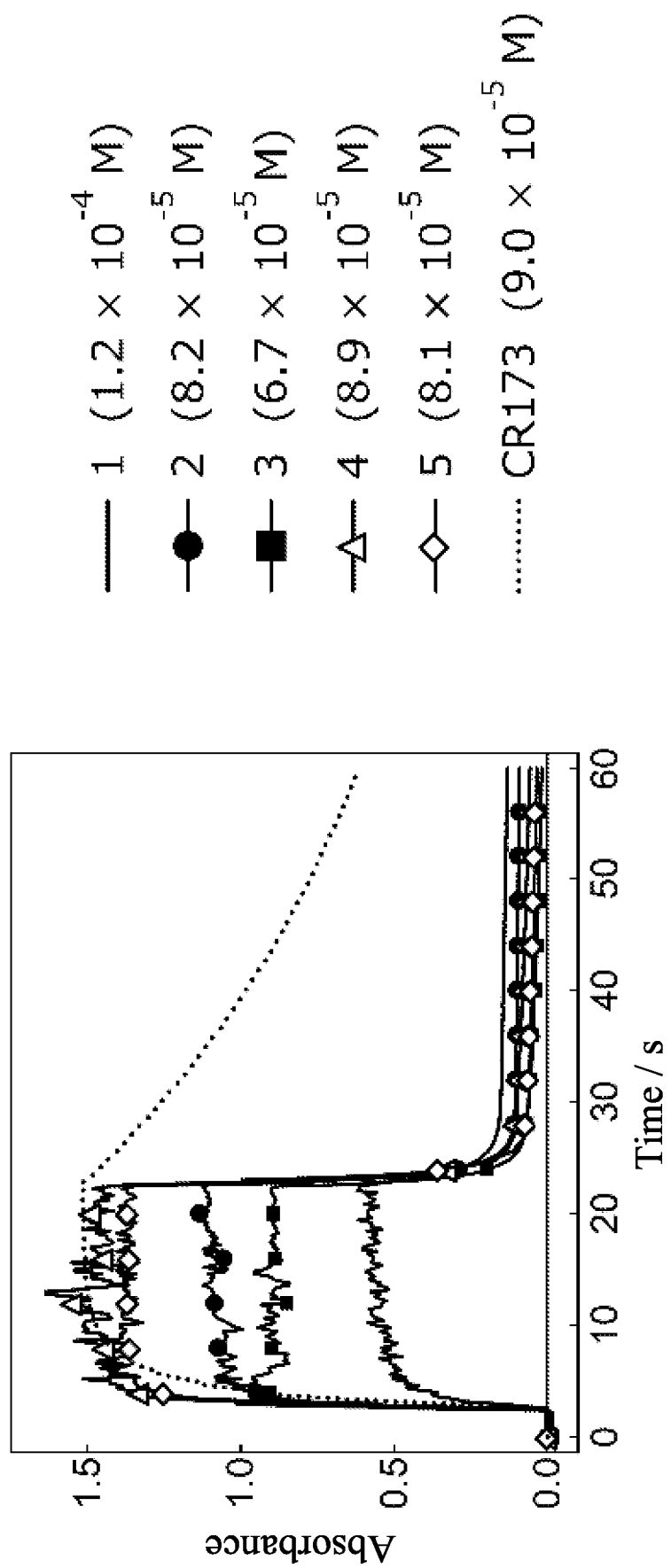
FIG. 25 is a graph of changes in absorbance by time at the maximum absorption wavelength of the chromogen when during the benzene solution of compounds 1 to 5 and CR173 is irradiated with UV and after UV irradiation is stopped.

Ultraviolet/visible absorption spectrum, and transient absorption spectrum measured using ultraviolet with a wavelength of 365 nm as excitation light of benzene solution of compound 1 to 5 and compound CR173 (Corning, Inc.) shown below (compound 1: concentration $1.2 \times 10^{-4}$ M, compound 2: concentration $8.2 \times 10^{-5}$ M, compound 3: concentration $6.7 \times 10^{-5}$ M, Compound 4: Concentration $8.9 \times 10^{-5}$ M, Compound 5: Concentration $8.1 \times 10^{-5}$ M, CR173: Concentration $9.0 \times 10^{-5}$ M) are shown in FIGS. 23 and 24. It is confirmed that compounds 2 to 5 strongly absorbed ultraviolet in the UVA region (wavelength 315 to 400 nm) and had higher sensitivity to sunlight as compared with compound CR173. Upon irradiation with ultraviolet, a reversible chromogen which each having a maximum absorption wavelength at wavelength mentioned above is generated at 552 nm for Compound 1, 558 nm for Compound 2, 560 nm for Compound 3, 570 nm for Compound 4, 565 nm for Compound 5, and 560 nm for Compound CR173. FIG. 25 shows the time change of absorbance at the maximum absorption wavelength of the chromogen when the benzene solution of each compound is irradiated with ultraviolet and when the irradiation is stopped. It is confirmed that for CR173, the half-life of the chromogen is 29 seconds and the colorization remains for a long time, whereas for compounds 1 to 5 in which an etheric oxygen atom is bonded to the 1st carbon atom of the pyranoquinazoline skeleton, the half-life of the chromophore is 0.6 to 0.8 seconds and the decolorizing reaction is significantly accelerated.

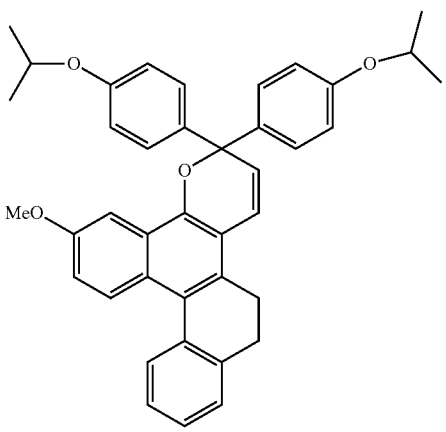 [SMILES: COc1ccc2c3c(c4c(c2c1)OC(c1ccc(OC(C)C)cc1)(c1ccc(OC(C)C)cc1)C=C4)CCc1ccccc1-3]

Embodiment 17

Photochromic Properties of Toluene Solutions of Compounds 1, 4, 5 and CR173

Figure 26:
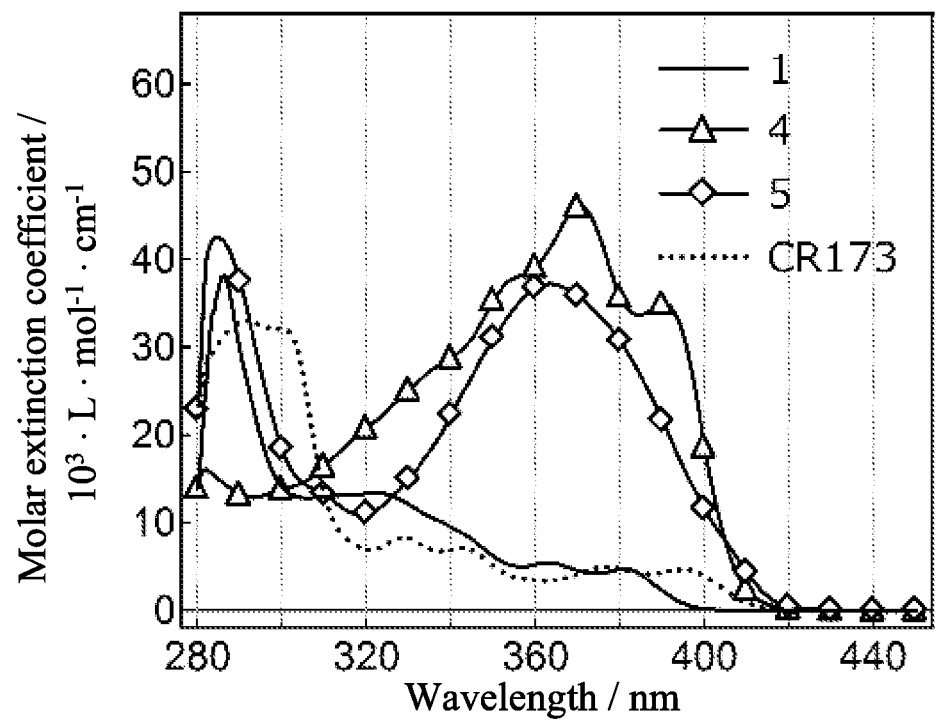
FIG. 26 is a graph of UV/visible absorption spectrum of toluene solutions of decolorized compounds 1, 4, 5 and CR173.
Figure 27:
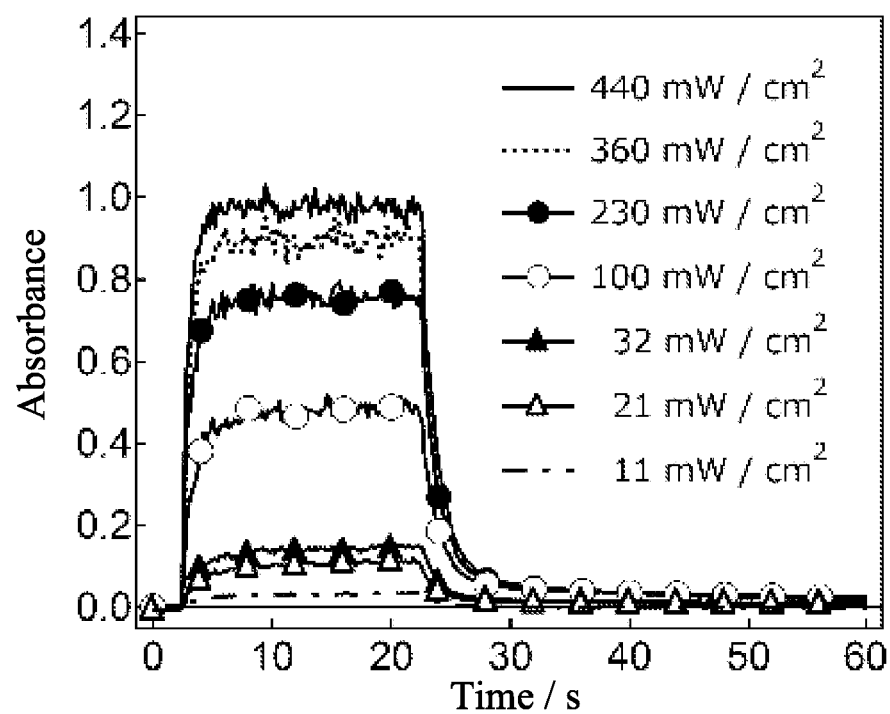
FIG. 27 is a graph of change of the absorbance by time at the maximum absorption wavelength during the toluene solution of compound 1 is irradiated with UV and after UV irradiation is stopped.
Figure 28:
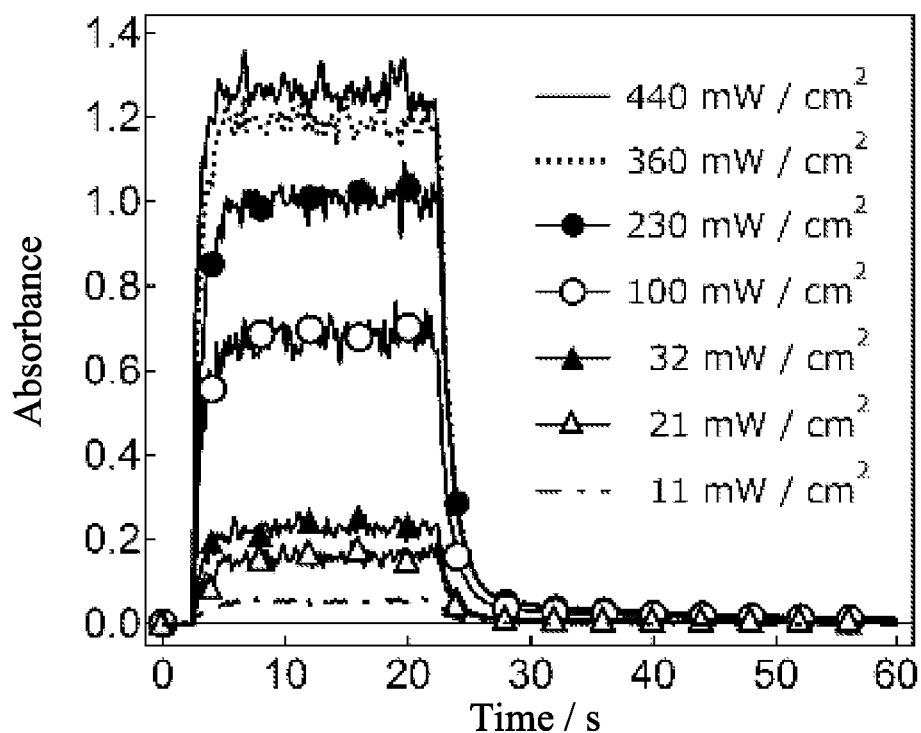
FIG. 28 is a graph of change of the absorbance by time at the maximum absorption wavelength during the toluene solution of compound 4 is irradiated with UV and after UV irradiation is stopped.
Figure 29:
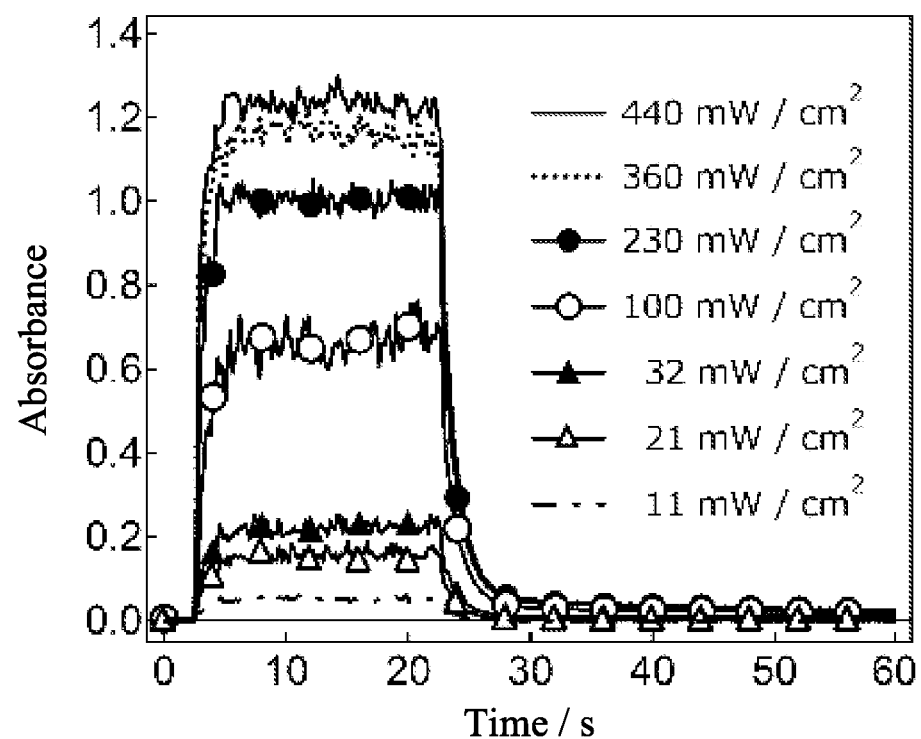
FIG. 29 is a graph of change of the absorbance by time at the maximum absorption wavelength during the toluene solution of compound 5 is irradiated with UV and after UV irradiation is stopped.
Figure 30:
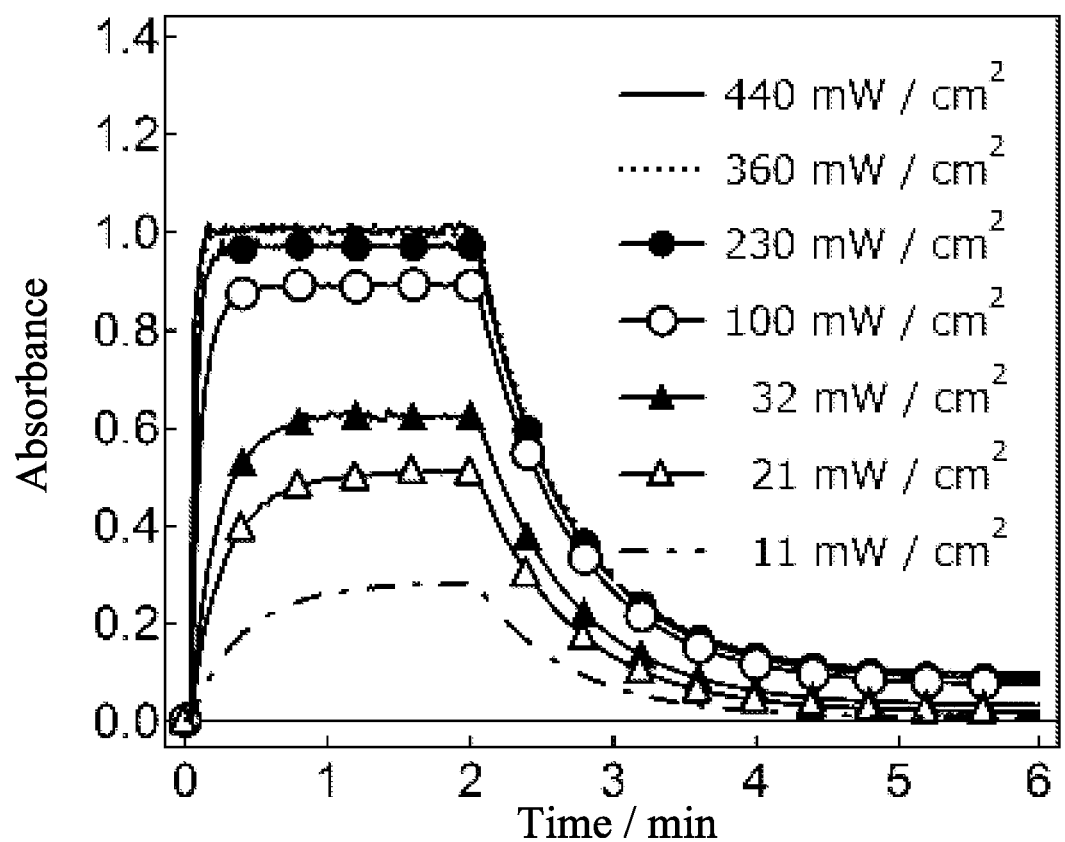
FIG. 30 is a graph of change of the absorbance by time at the maximum absorption wavelength during the toluene solution of compound CR173 is irradiated with UV and after UV irradiation is stopped.

FIG. 26 shows the ultraviolet/visible absorption spectrum of toluene solution of compound 1, 4, 5 and CR173 (compound 1: concentration $5.5 \times 10^{-5}$M, compound 4: concentration $5.5 \times 10^{-5}$M, compound 5: concentration $5.6 \times 10^{-5}$M, CR173: concentration $5.5 \times 10^{-5}$M). It is confirmed that compounds 4 and 5 strongly absorb ultraviolet in the UVA region (wavelength 315 to 400 nm) and have high sensitivity to sunlight even in toluene as compared with compound CR173. FIGS. 27 to 30 show the time change of the light absorbency in the maximum absorption wavelength of chromogen during toluene solution of each compound mentioned above is irradiated with various intensities of ultraviolet with wavelength of 365 nm (11 mW/cm$^2$, 21 mW/cm2, 32 mW/cm$^2$, 100 mW/cm$^2$, 230 mW/cm$^2$, and 360 mW/cm$^2$) and during ultraviolet irradiation stopped.

Figure 31:
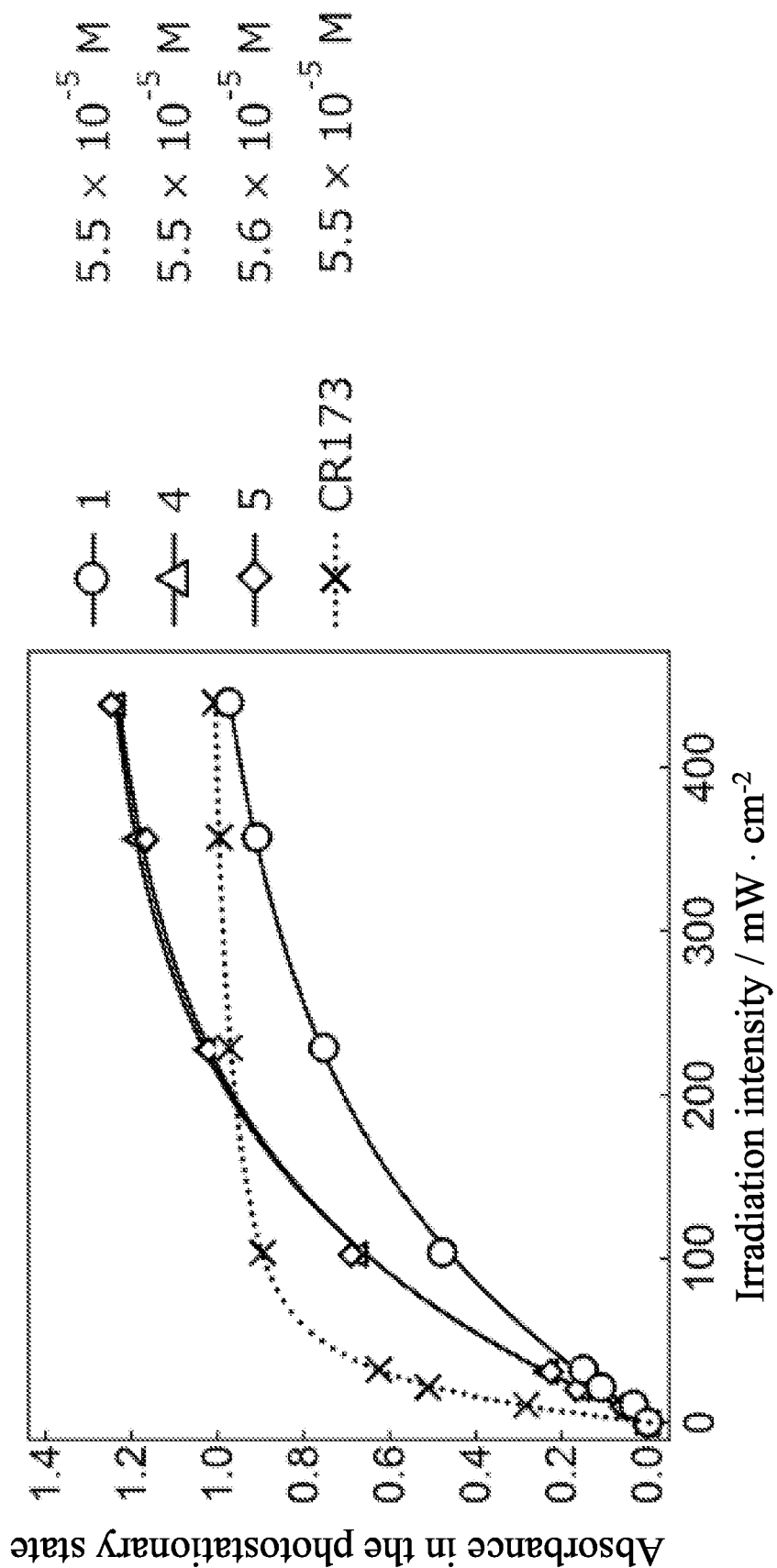
FIG. 31 is a graph of relationship between absorbance and irradiation intensity in the photo stationary state during the toluene solution of compounds 1, 4, 5 and CR173 is irradiated with UV.

FIG. 31 shows the relationship between the absorbance and the intensity of ultraviolet irradiation in photo stationary state during each toluene solution of compound 1, 4, 5 and CR173 (compound 1: concentration $5.5 \times 10^{-5}$M, compound 4: concentration $5.5 \times 10^{-5}$M, compound 5: concentration $5.6 \times 10^{-5}$M) is irradiated with ultraviolet with wavelength of 365 nm (11 m$^w$/cm$^2$, 21 m$^w$/cm$^2$, 32 m$^w$/cm$^2$, 100 m$^w$/cm$^2$, 230 m$^w$/cm$^2$, 360 m$^w$/cm$^2$ and 440 m$^w$/cm$^2$). It is confirmed the compounds 4 and 5 are colorized at a higher concentration than CR173 when the intensity of ultraviolet irradiation is stronger than about 200 mW/cm$^2$.

Embodiment 18

Photochromic Properties of Polymers Doped with Compounds 4, 5 and CR173.

Figure 32:
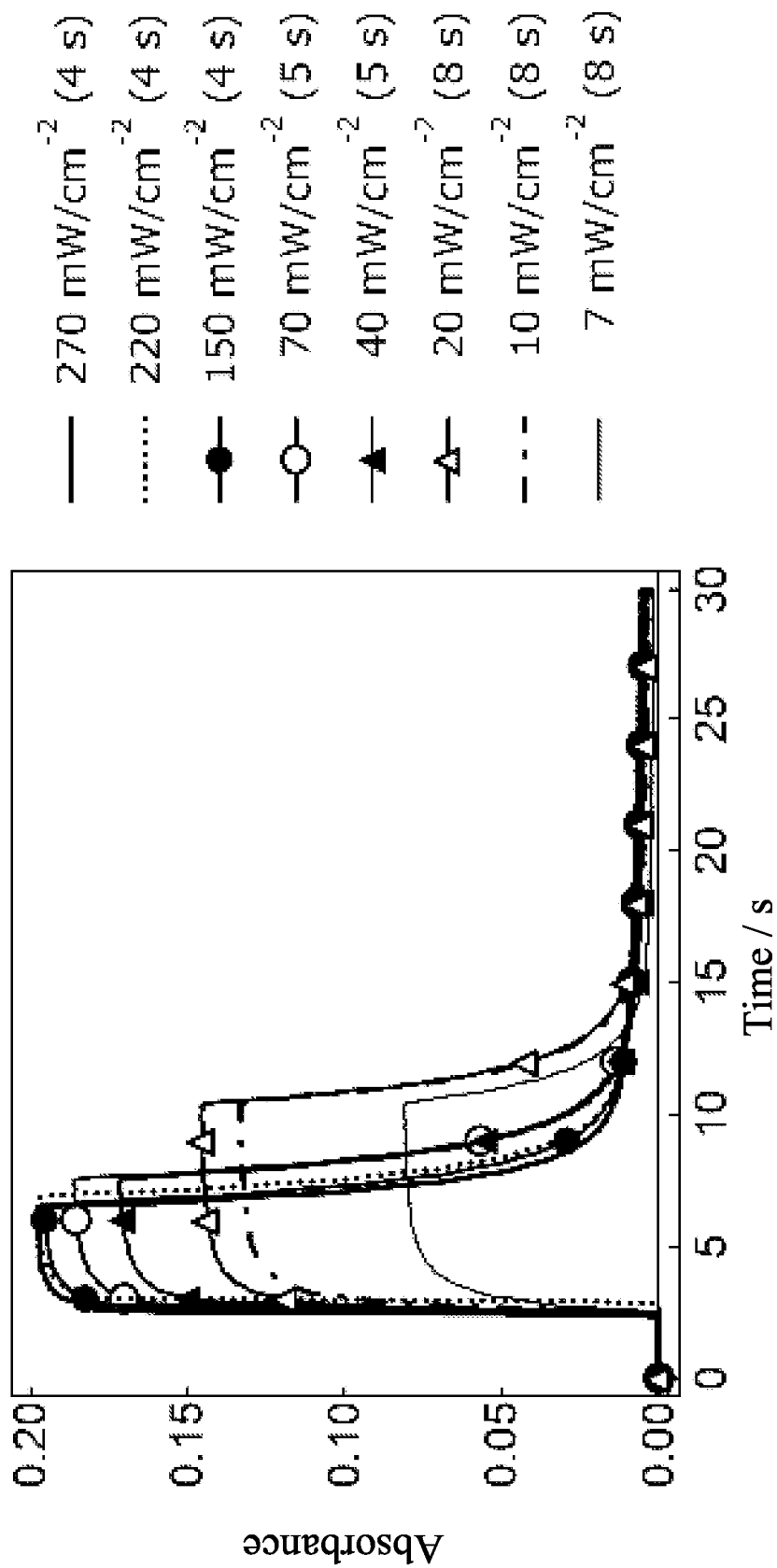
FIG. 32 is a graph of change in absorbance by time at the maximum absorption wavelength of the colored body during the polymer thin film doped with compound 4 is irradiated with UV and after UV irradiation is stopped.
Figure 33:
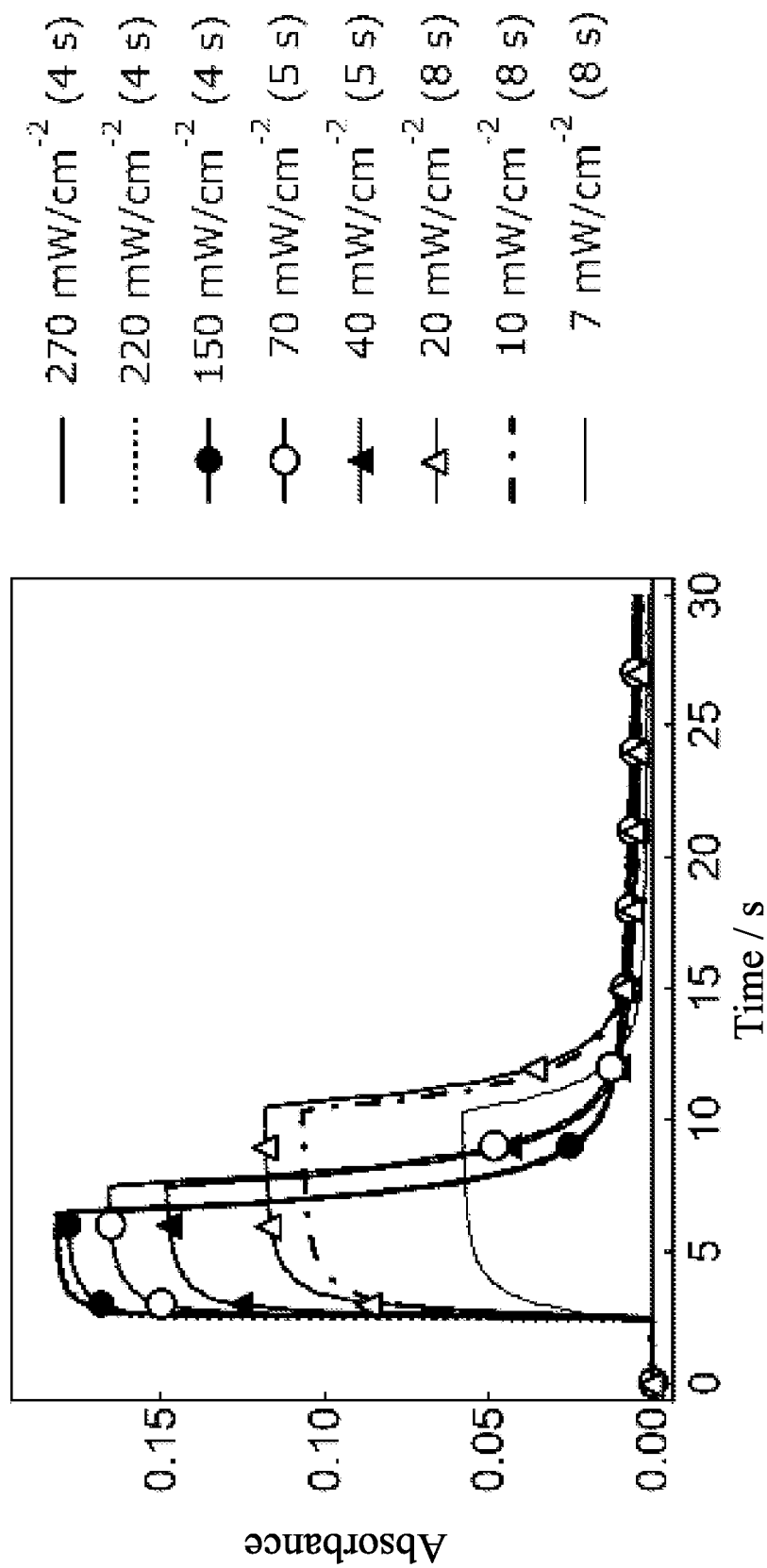
FIG. 33 is a graph of change in absorbance by time at the maximum absorption wavelength of the colored body during the polymer thin film doped with compound 5 is irradiated with UV and after UV irradiation is stopped.
Figure 34:
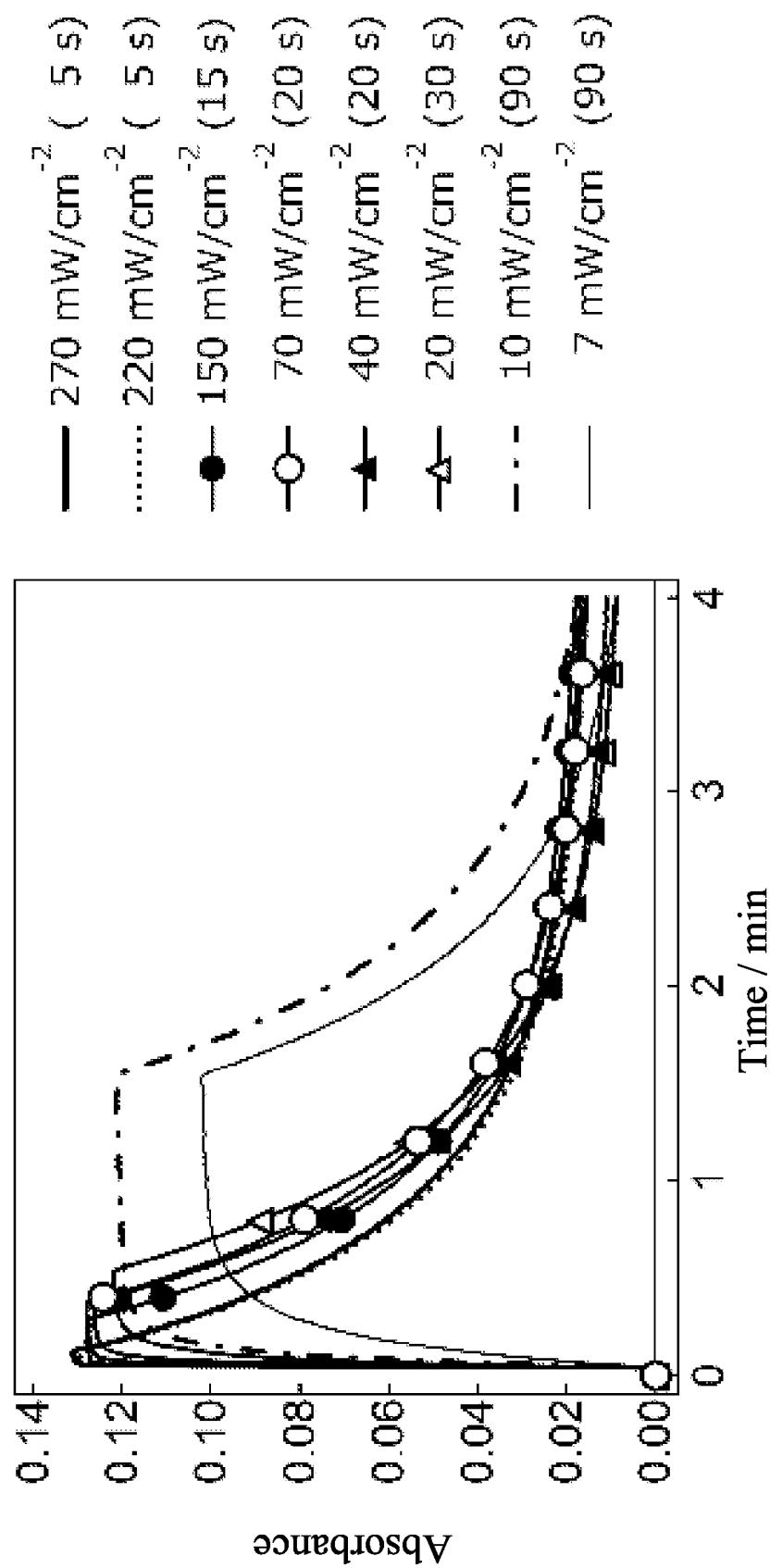
FIG. 34 is a graph of change in absorbance by time at the maximum absorption wavelength of the colored body during the polymer thin film doped with compound CR173 is irradiated with UV and after UV irradiation is stopped.

A 20% by mass toluene solution of a polymethyl methacrylate-polynormal butyl acrylate block copolymer (LA2330, Kuraray Co., Ltd.) containing 1% by mass of compounds 4, 5 and CR173 is prepared, and a polymer thin film is formed on a glass substrate by spin coating. FIGS. 32 to 34 show the time-dependent changes in absorbance at the maximum absorption of chromogen when polymer thin film doped with compound 4 (1% by mass, film thickness 4.5 m, maximum absorption of chromogen at wavelength of 574 nm), polymer thin film doped with compound 5 (1% by mass, film thickness 4.5 μm, maximum absorption of chromogen at wavelength of 567 nm) and polymer thin film doped with CR173 (1% by mass, film thickness of 4.5 μm, maximum absorption of chromogen at wavelength of 560 nm) were respectively irritated with various intensities of ultraviolet with wavelength of 365 nm (7 mW/cm$^2$, 10 mW/cm$^2$, 20 mW/cm$^2$, 40 mW/cm$^2$, 70 mW/cm$^2$, 150 mW/cm$^2$, 220 mW/cm$^2$, and 270 mW/cm$^2$) and when the irradiation is stopped. Similar to the measurement results of the solution, it is confirmed that as for CR173, after the ultraviolet irradiation is stopped, the chromogen remained for a long time, whereas as for compounds 1, 4, and 5, the decolorizing reaction proceeded at high speed.

Figure 35:
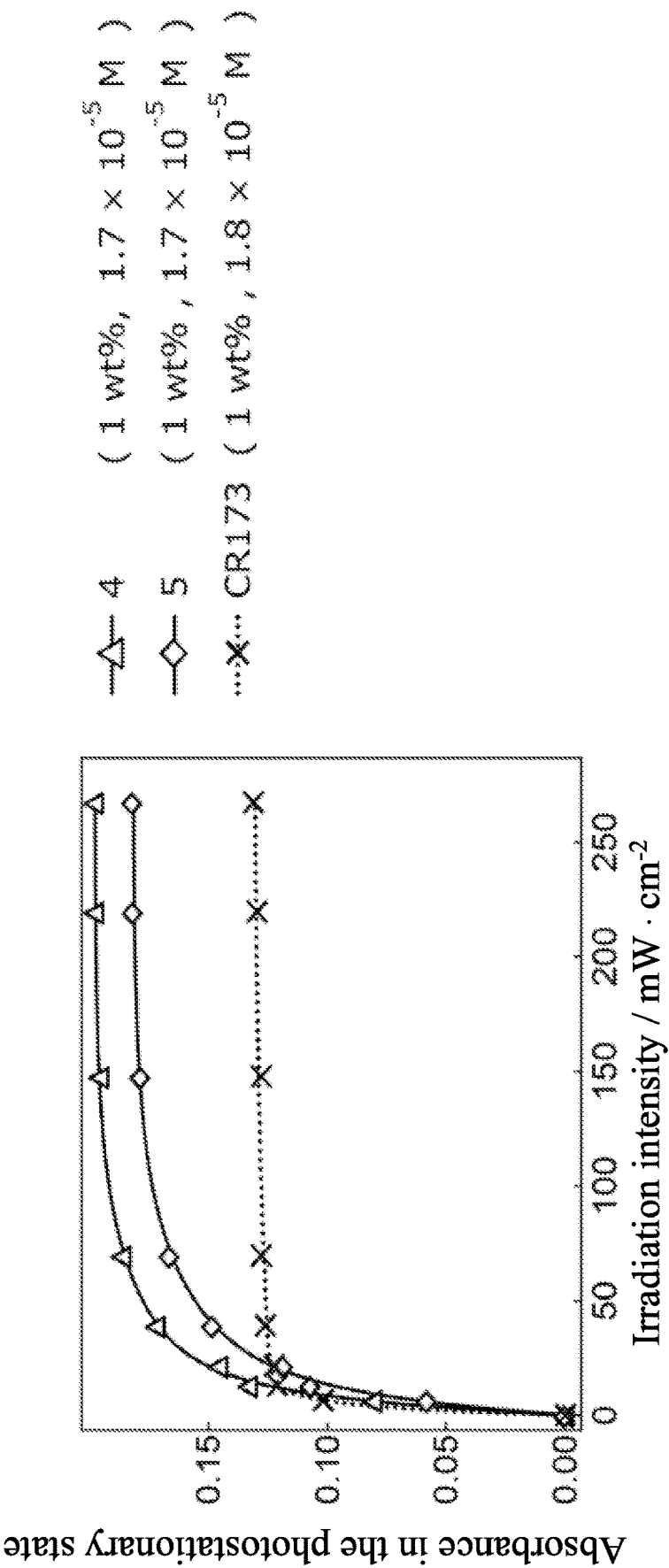
FIG. 35 is a graph of change in absorbance by time at the maximum absorption wavelength of the colored body during the polymer thin film doped with compound CR173 is irradiated with UV and after UV irradiation is stopped.

FIG. 35 shows the relationship between the absorbance and the intensity of ultraviolet irradiation in photo stationary state when the polymer thin film above is irradiated with various intensities of ultraviolet with wavelength of 365 nm (7 mW/cm$^2$, 10 mW/cm$^2$, 20 mW/cm$^2$, 40 mW/cm$^2$, 70 mW/cm$^2$, 150 mW/cm$^2$, 220 mW/cm$^2$, and 270 mW/cm$^2$). It is confirmed that when the intensity of ultraviolet irradiation is higher than about 13 mW/cm$^2$, the polymer thin film doped with compounds 4 and 5 develops a higher colorizing density than the polymer thin film doped with CR173.

Embodiment 19

Light Resistance Test of Polymer Thin Films Doped with Compounds 4, 5 and CR173.

Figure 36:
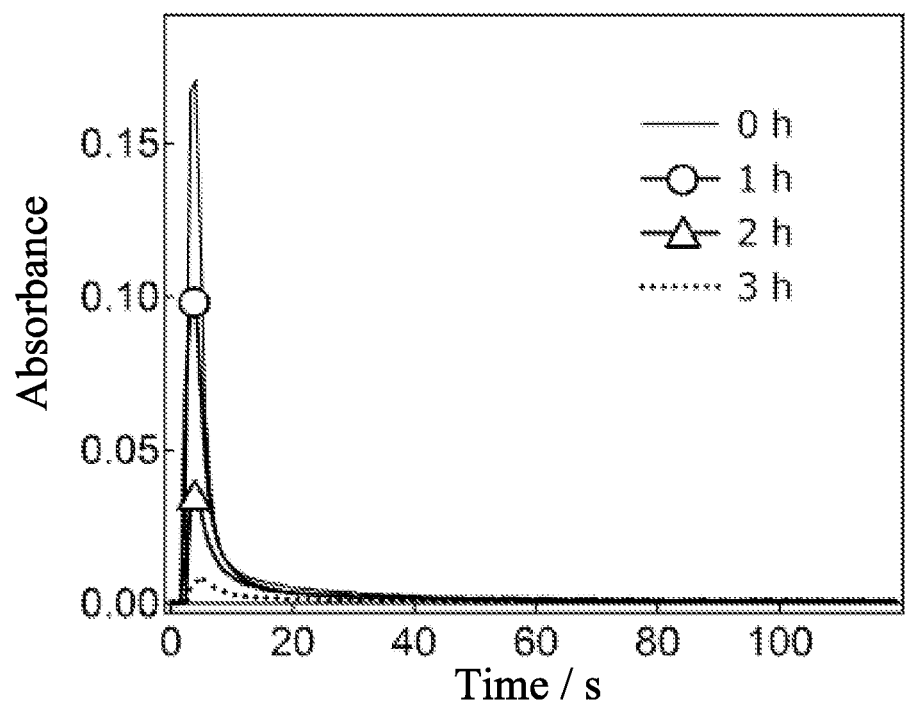
FIG. 36 is a graph of change of the light absorbency by time at the maximum absorption wavelength of the chromogen after repeatedly irradiating the polymer thin film doped with the compound 4 with white light.
Figure 37:
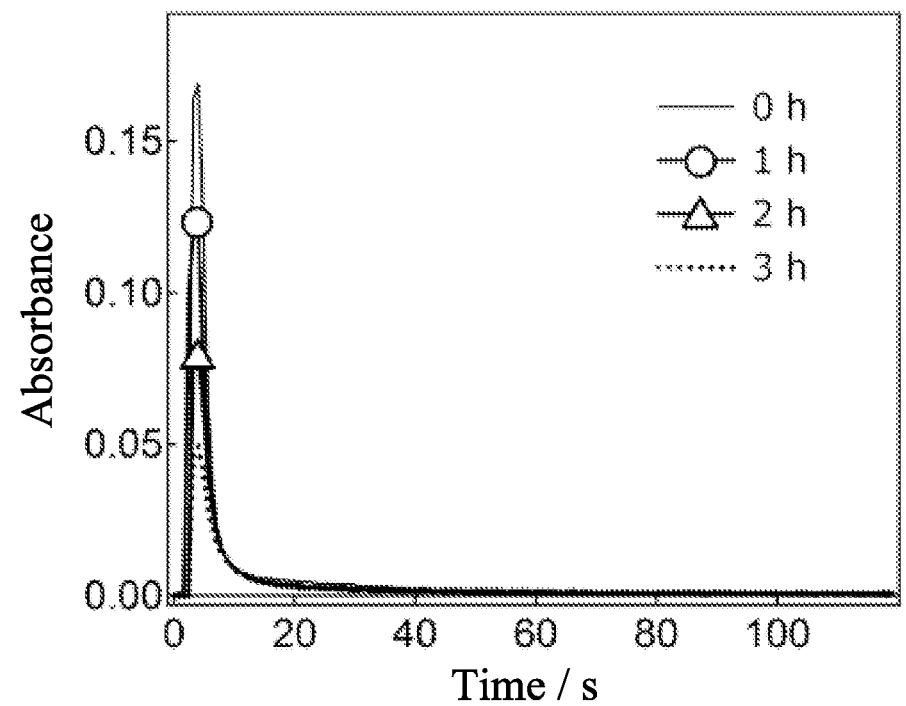
FIG. 37 is a graph of change of the light absorbency by time at the maximum absorption wavelength of the chromogen after repeatedly irradiating the polymer thin film doped with the compound 5 with white light.
Figure 38:
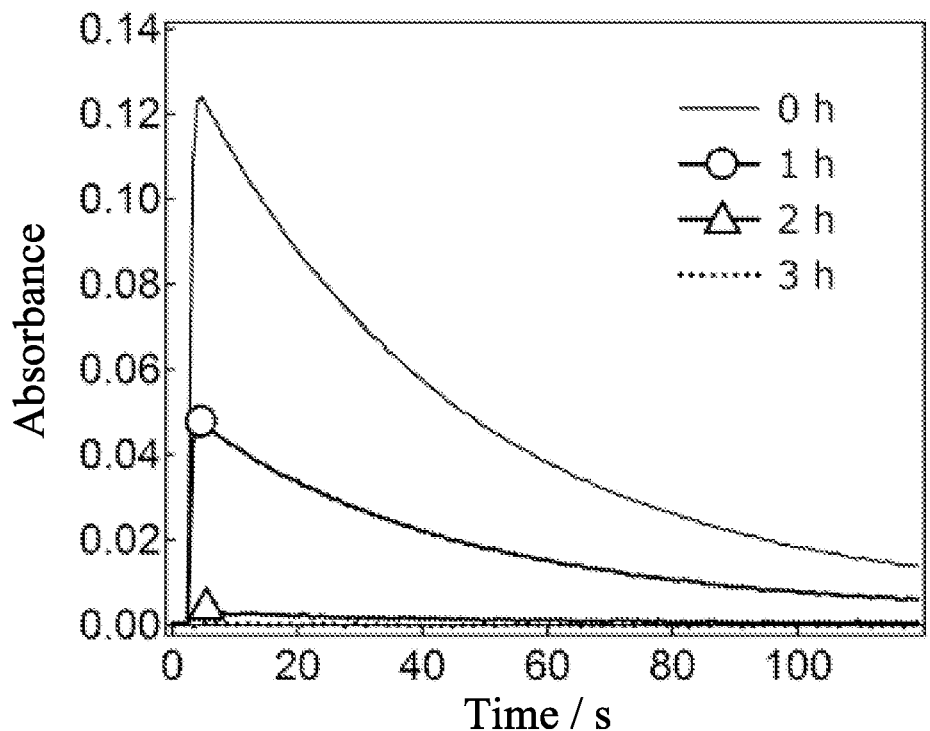
FIG. 38 is a graph of change of the light absorbency by time at the maximum absorption wavelength of the chromogen after repeatedly irradiating the polymer thin film doped with the compound CR173 with white light.

FIGS. 36 to 38 show the time-dependent change in absorbance at the maximum absorption wavelength of the chromogen during irradiated with ultraviolet for 2 seconds of the polymer thin film of compounds 4, 5 and CR173 made the same as that in embodiment 18 been irradiated with white light (xenon lamp 240 nm to 1000 nm, intensity 15.5 mW/cm$^2$) continuously (1 hour, 2 hours, 3 hours), then been completely colorless by irradiated with visible light with a wavelength of 550 nm for 3 minutes.

Figure 39:
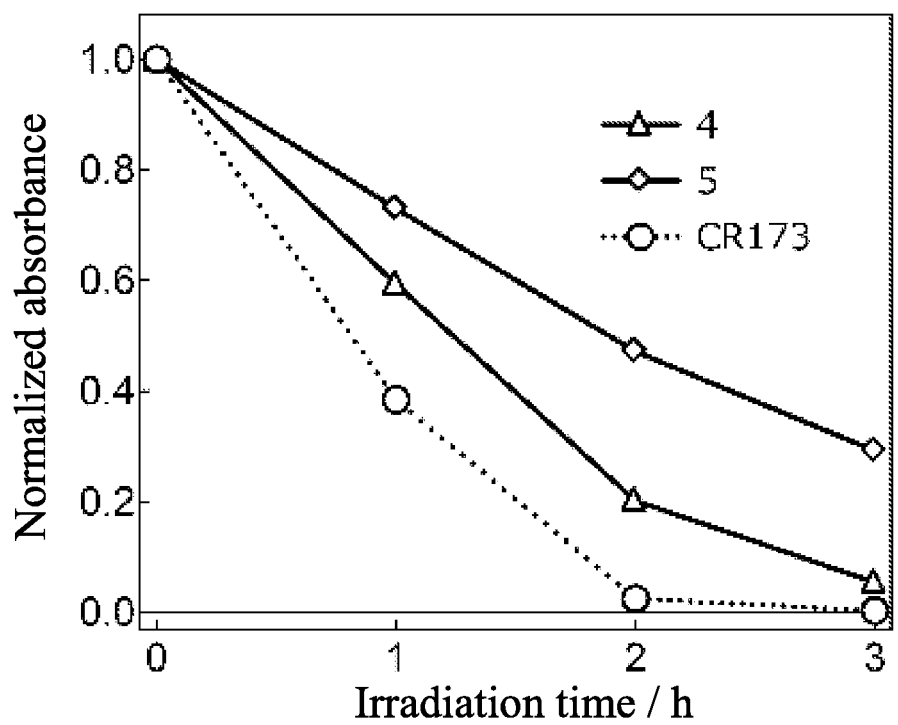
FIG. 39 is a graph of dependence of absorbance to the light irradiation time in the photo stationary state when the polymer thin film doped with compounds 4, 5 and CR173 is irradiated with UV, which normalized by the light absorbance in the photo stationary state when the polymer thin film not irradiated with white light is irradiated with UV.

Furthermore, FIG. 39 shows the absorbance at the maximum absorption wavelength of the chromogen when irradiated with ultraviolet for 2 seconds which is plotted on a graph having a vertical axis of the normalized absorbance at the maximum absorption wavelength of the chromogen when the polymer thin film not irradiated with white light is irradiated with ultraviolet for 2 seconds, and a horizontal axis of the irradiation time of white light, during the polymer thin film of compound 4, 5 and CR173 is irradiated with white light (xenon lamp 240 nm to 1000 nm, intensity 15.5 mW/cm$^2$) continuously (1 hour, 2 hours, 3 hours) and been completely colorless by irradiate visible light for 3 minutes. As for CR173, when CR173 is irradiated with white light for 2 hours or 3 hours, absorption of the chromogen is hardly confirmed, whereas as for compounds 4 and 5, the absorption of the chromogen is confirmed, and it has shown that compounds 4 and 5 have higher light resistance than CR173.

Embodiment 20

Photochromic Properties of Toluene Solution of Compound 1.

Figure 40:
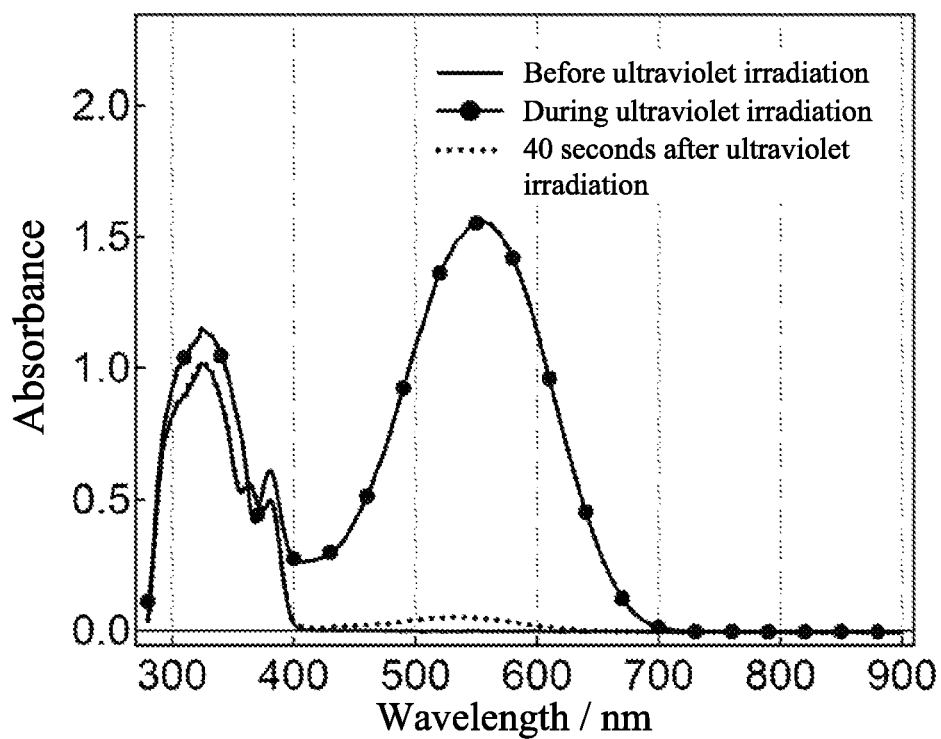
FIG. 40 is a graph of UV-visible/near-infrared absorption spectrum of toluene solution of compound 1 at the timing of before UV irradiation, during UV irradiation and 40 seconds after UV irradiation is stopped.
Figure 41:
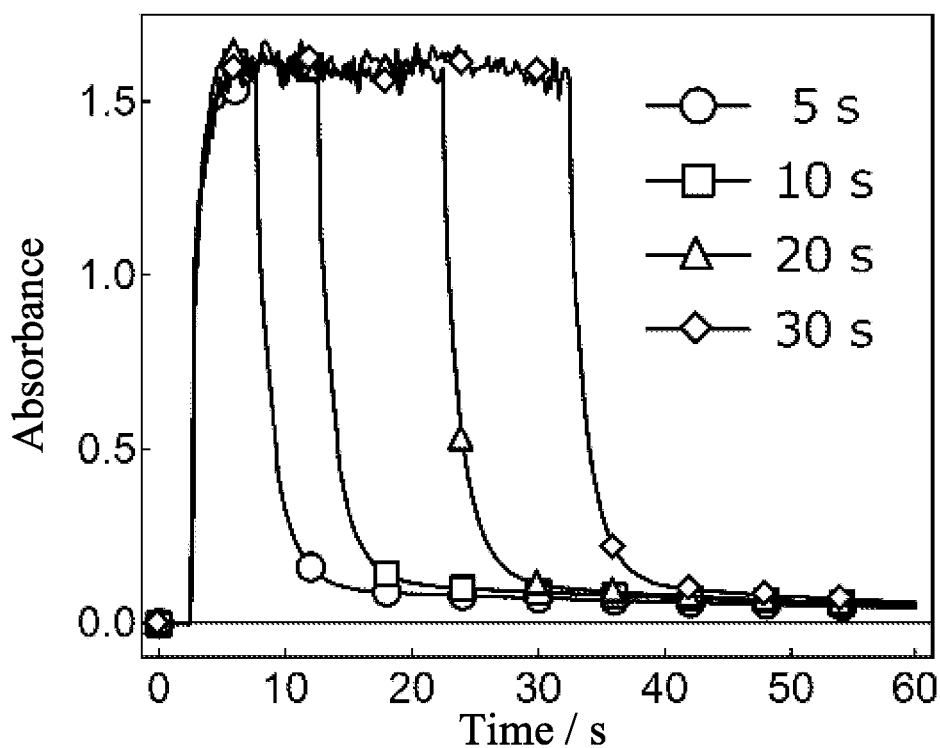
FIG. 41 is a graph of change in absorbance by time at the maximum absorption wavelength of the chromogen when the toluene solution of compound 1 is irradiated with UV for 5, 10, 20, and 30 seconds.

A transient absorption spectrum of a toluene solution of compound 1 (concentration $1.1 \times 10^{-4}$M) is measured using ultraviolet with wavelength of 365 nm as excitation light. FIG. 40 shows a transient absorption spectrum at the timing of before ultraviolet irradiation, during ultraviolet irradiation, and 40 seconds after ultraviolet irradiation is stopped. When a toluene solution of compound 1 is irradiated with ultraviolet, a chromogen having a maximum absorption wavelength at wavelength of 553 nm is formed reversibly. FIG. 41 shows changes with time in absorbance at the maximum absorption wavelength after irradiation with ultraviolet for 5, 10, 20, and 30 seconds. It is confirmed that at 25° C., after the ultraviolet irradiation is stopped, the chromogen rapidly decayed with a half-life of 0.90 s. At this time, it is confirmed that the production rate of the trans-transoid remained at about 4%. Also from the result of the photochromic property of compound 1, it is confirmed that the etheric oxygen atom is bonded to the carbon atom at the $1^{st}$ position of the pyranoquinazoline skeleton, thereby suppressing the generation of the trans-transoid.

Embodiment 21

Photochromic Properties of Compound 6 in Toluene.

Figure 42:
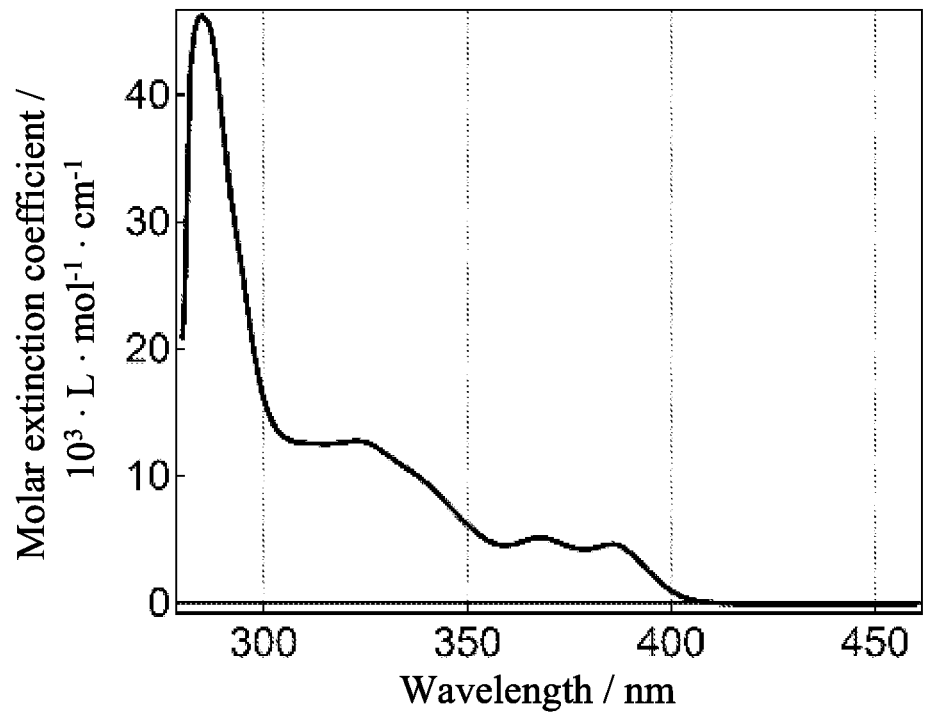
FIG. 42 is a graph of UV/visible absorption spectrum of the toluene solution of the decolorized compound 6.
Figure 43:
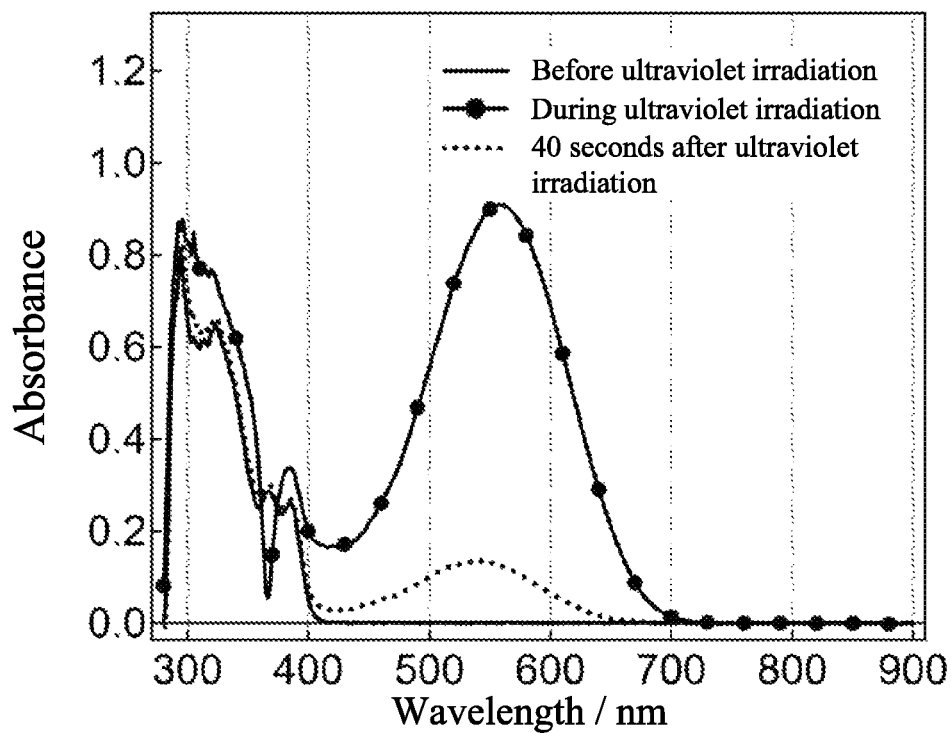
FIG. 43 is a graph of UV-visible/near-infrared absorption spectrum of toluene solution of compound 6 at the timing of before UV irradiation, during UV irradiation and 40 seconds after UV irradiation is stopped.
Figure 44:
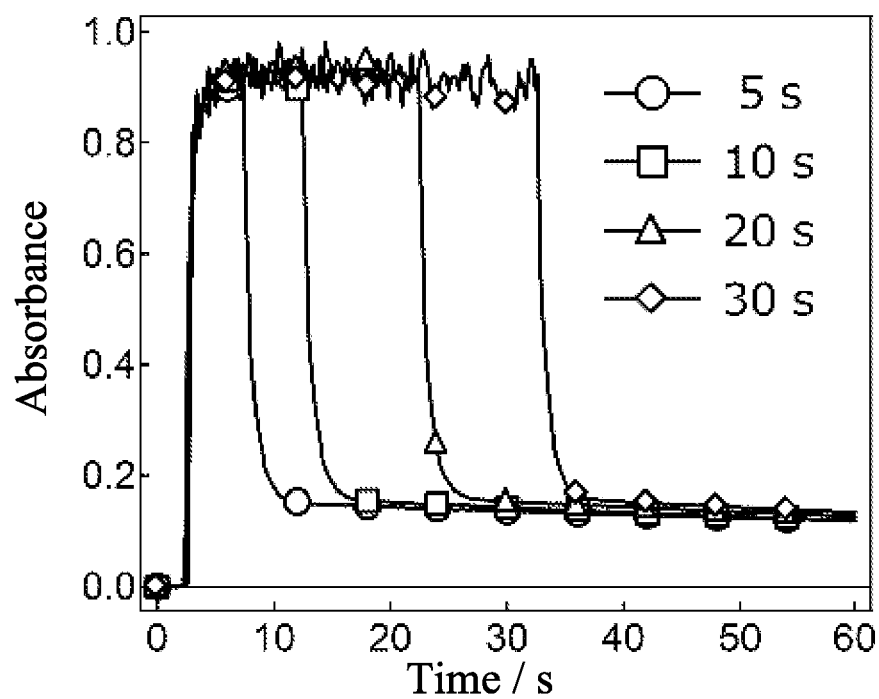
FIG. 44 is a graph of change in absorbance by time at the maximum absorption wavelength of the chromogen when the toluene solution of compound 6 is irradiated with UV for 5, 10, 20, and 30 seconds.

FIG. 42 shows the ultraviolet/visible absorption spectrum of the toluene solution of compound 6 (concentration $5.6 \times 10^{-5}$M). The transient absorption spectrum of the above toluene solution of compound 6 is measured using ultraviolet with wavelength of 365 nm as excitation light. FIG. 43 shows transient absorption spectra before ultraviolet irradiation, during ultraviolet irradiation, and 40 seconds after ultraviolet irradiation is stopped. When a toluene solution of compound 6 is irradiated with ultraviolet, a chromogen having a maximum absorption wavelength at a wavelength of 557 nm is produced reversibly. FIG. 44 shows changes with time in absorbance at the maximum absorption wavelength after irradiation with ultraviolet for 5, 10, 20, and 30 seconds. It is confirmed that at 25° C., after the ultraviolet irradiation is stopped, the chromogen rapidly decayed with a half-life of 0.47 s. At this time, it is confirmed that the production rate of the trans-transoid remained at about 16%. Also from the result of the photochromic property of compound 6, it is confirmed that the etheric oxygen atom is bonded to the carbon atom at the $1^{st}$ position of the pyranoquinazoline skeleton, thereby suppressing the generation of the trans-transoid.

Embodiment 22

Photochromic Properties of Compound 7 in Toluene.

Figure 45:
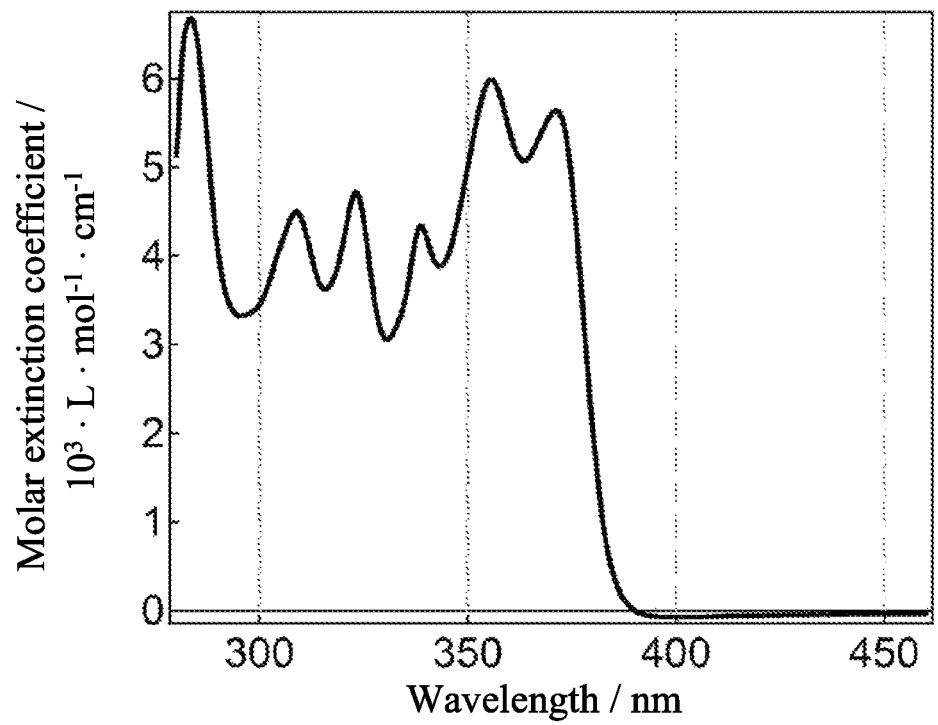
FIG. 45 is a graph of UV/visible absorption spectrum of the toluene solution of the decolorized compound 7.
Figure 46:
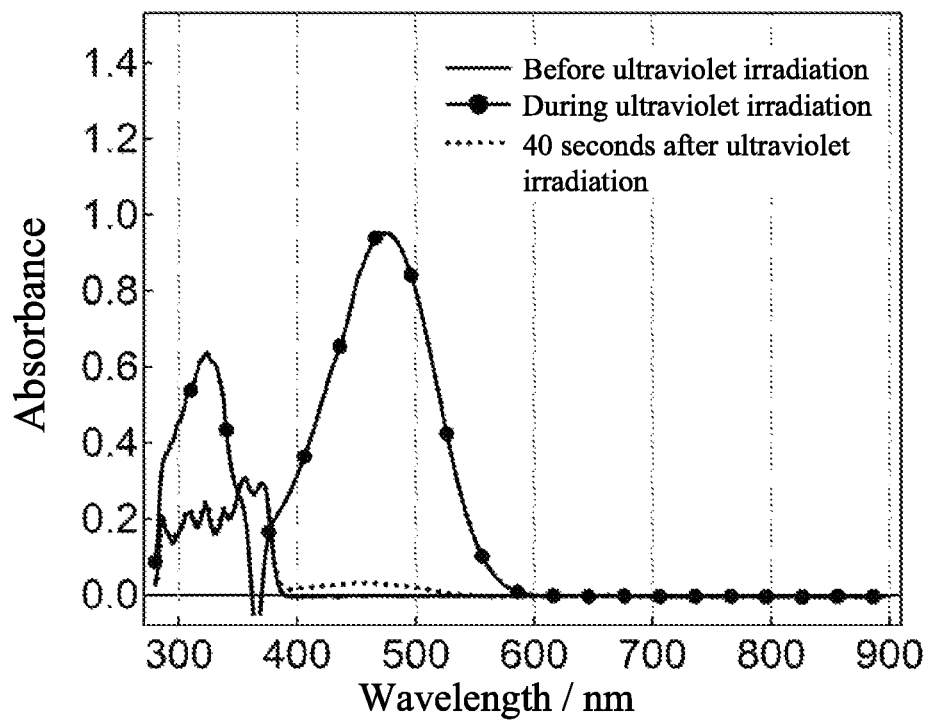
FIG. 46 is a graph of UV-visible/near-infrared absorption spectrum of toluene solution of compound 7 at the timing of before UV irradiation, during UV irradiation and 40 seconds after UV irradiation is stopped.
Figure 47:
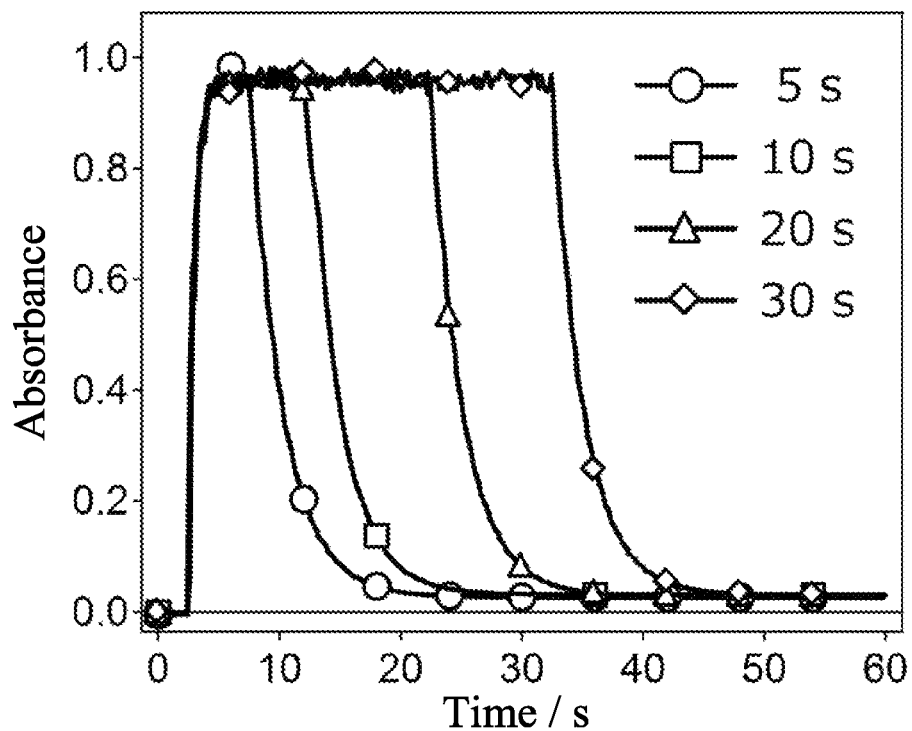
FIG. 47 is a graph of change in absorbance by time at the maximum absorption wavelength of the chromogen when the toluene solution of compound 7 is irradiated with UV for 5, 10, 20, and 30 seconds.

FIG. 45 shows the ultraviolet/visible absorption spectrum of the toluene solution of compound 7 (concentration $5.4 \times 10^{-5}$M). The transient absorption spectrum of the above toluene solution of compound 7 is measured using ultraviolet with wavelength of 365 nm as excitation light. FIG. 46 shows transient absorption spectra before ultraviolet irradiation, during ultraviolet irradiation, and 40 seconds after ultraviolet irradiation is stopped. When a toluene solution of compound 7 is irradiated with ultraviolet, a chromogen having a maximum absorption wavelength at a wavelength of 472 nm is produced reversibly. FIG. 47 shows changes with time in absorbance at the maximum absorption wavelength after irradiation with ultraviolet for 5, 10, 20, and 30 seconds. It is confirmed that at 25° C., after the ultraviolet irradiation is stopped, the chromogen rapidly decayed with a half-life of 1.8 s. At this time, it is confirmed that the production rate of the trans-transoid remained at about 5%. Also from the result of the photochromic property of compound 7, it is confirmed that the etheric oxygen atom is bonded to the carbon atom at the $1^{st}$ position of the pyranoquinazoline skeleton, thereby suppressing the generation of the trans-transoid.

Embodiment 23

Photochromic Properties of Compound 8 in Toluene.

Figure 48:
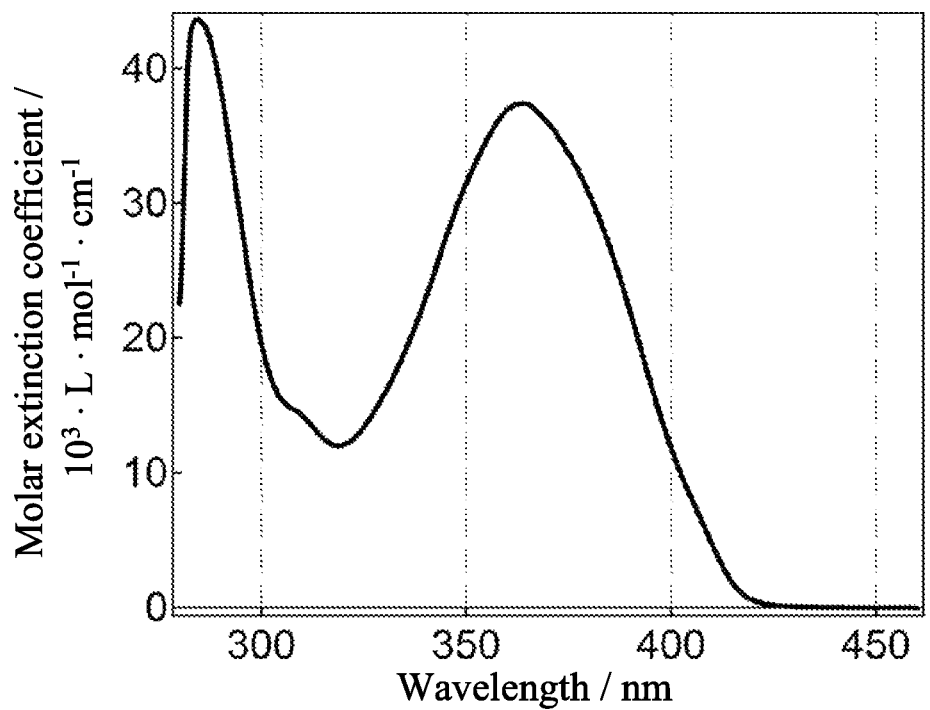
FIG. 48 is a graph of UV/visible absorption spectrum of the toluene solution of the decolorized compound 8.
Figure 49:
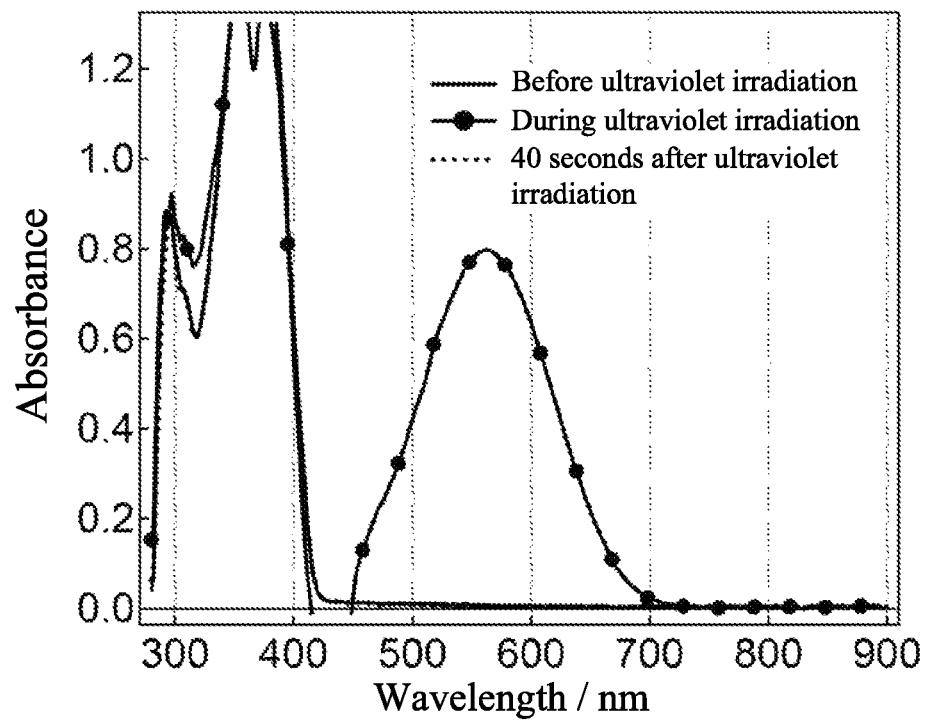
FIG. 49 is a graph of UV-visible/near-infrared absorption spectrum of toluene solution of compound 8 at the timing of before UV irradiation, during UV irradiation and 40 seconds after UV irradiation is stopped.
Figure 50:
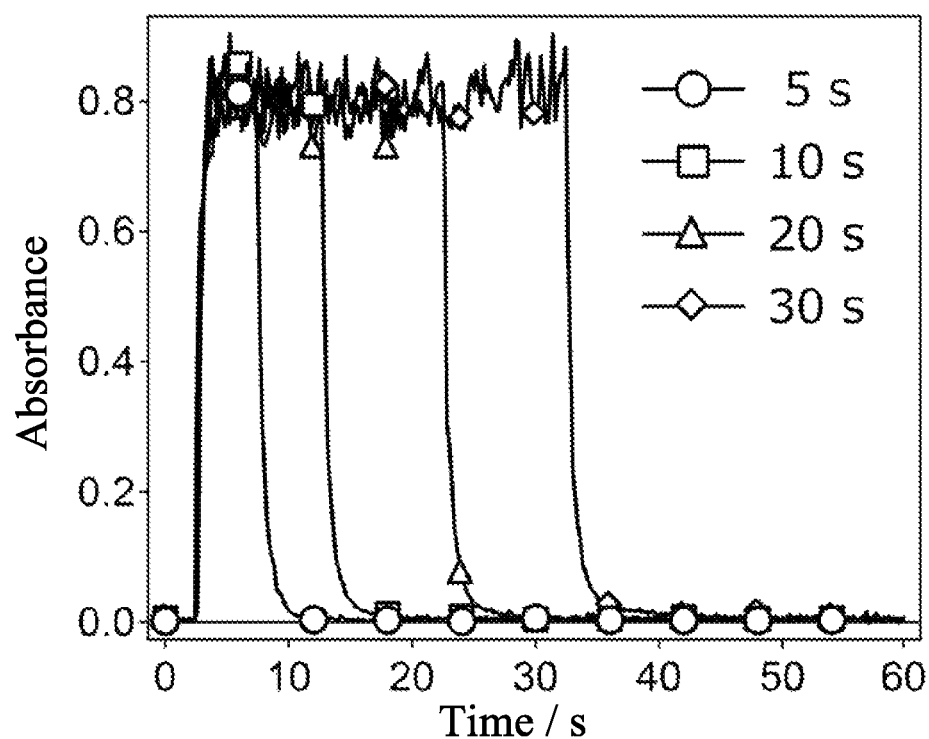
FIG. 50 is a graph of change in absorbance by time at the maximum absorption wavelength of the chromogen when the toluene solution of compound 8 is irradiated with UV for 5, 10, 20, and 30 seconds.
Figure 51:
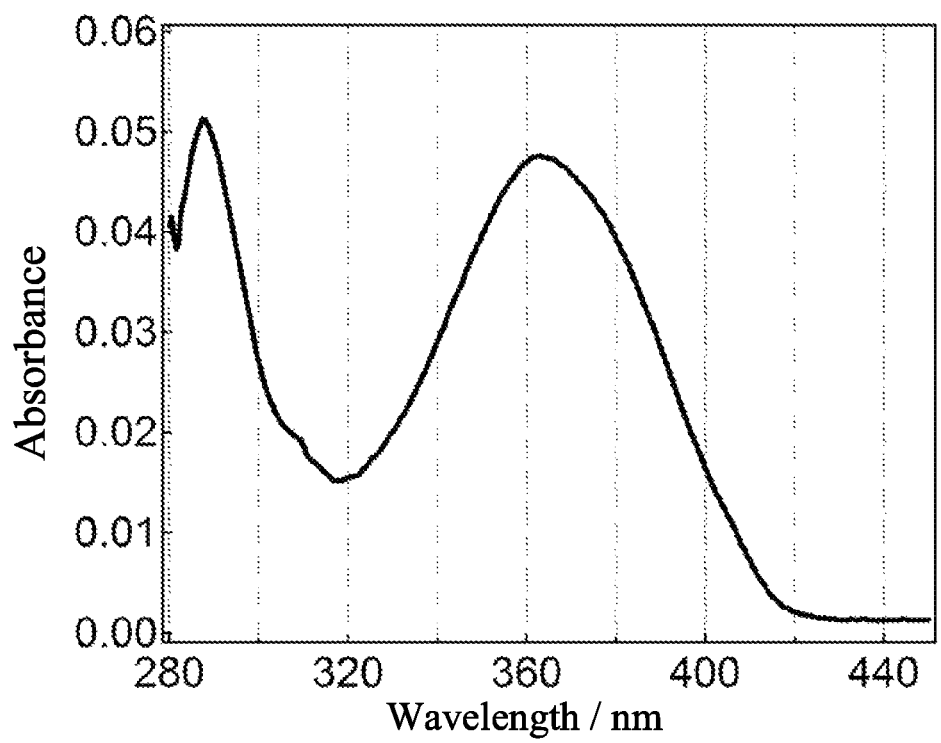
FIG. 51 is a graph of UV/visible absorption spectrum of the toluene solution of decolorized compound 9.

FIG. 48 shows the ultraviolet/visible absorption spectrum of the toluene solution of compound 8 (concentration $5.5 \times 10^{-5}$M). The transient absorption spectrum of the above toluene solution of compound 8 is measured using ultraviolet with wavelength of 365 nm as excitation light. FIG. 49 shows transient absorption spectra before ultraviolet irradiation, during ultraviolet irradiation, and 40 seconds after ultraviolet irradiation is stopped. When a toluene solution of compound 8 is irradiated with ultraviolet, a chromogen having a maximum absorption wavelength at a wavelength of 564 nm is produced reversibly. FIG. 50 shows changes with time in absorbance at the maximum absorption wavelength after irradiation with ultraviolet for 5, 10, 20, and 30 seconds. It is confirmed that at 25° C., after the ultraviolet irradiation is stopped, the chromogen rapidly decayed with a half-life of 0.28 s. At this time, it is confirmed that the production rate of the trans-transoid remained at about 3%. Also from the result of the photochromic property of compound 8, it is confirmed that the etheric oxygen atom is bonded to the carbon atom at the 1 st position of the pyranoquinazoline skeleton, thereby suppressing the generation of the trans-transoid.

Embodiment 24

Figure 52:
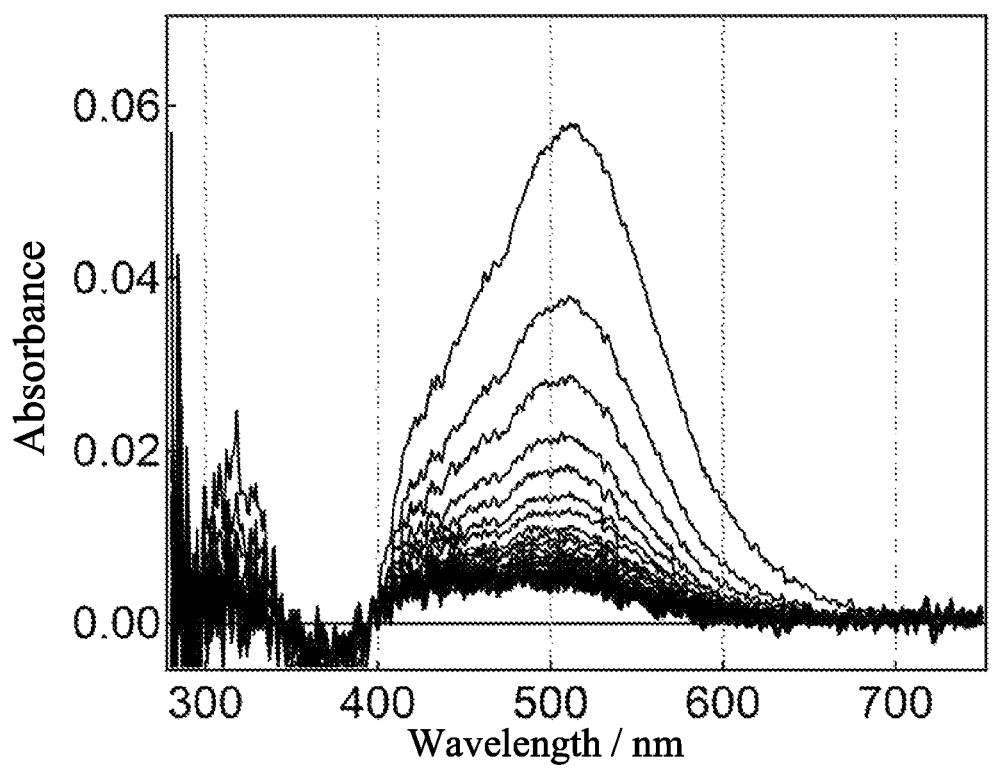
FIG. 52 is a graph of the transient absorption spectrum of the toluene solution of compound 9. The SPECTRAL measurement interval is 0.6 seconds.
Figure 53:
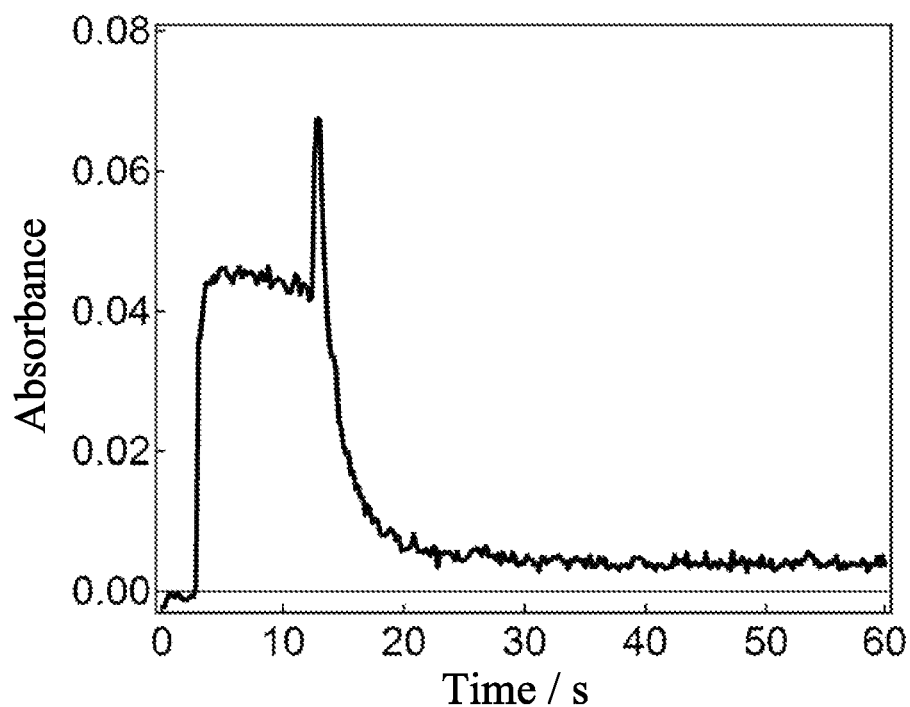
FIG. 53 is a graph of the change of the light absorbance by time in the maximum absorption wavelength of the chromogen when a toluene solution of compound 9 is irradiated with UV for 10 seconds.

Photochromic Properties of Compound 9 in Toluene 1.646 mg of the polymer (compound 9) obtained by copolymerization of compound 8 and butyl methacrylate is measured and dissolved in 2 mL of toluene. FIG. 52 shows a transient absorption spectrum of the toluene solution obtained by time-resolved spectroscopy. When a toluene solution of compound 9 is irradiated with ultraviolet, a chromogen having a maximum absorption wavelength at a wavelength of 511 nm is produced reversibly. FIG. 53 shows changes with time in absorbance at the maximum absorption wavelength after irradiation with ultraviolet for 10 seconds. It is confirmed that at 25° C., after the ultraviolet irradiation is stopped, the chromogen rapidly decayed with a half-life of 1.62 s. At this time, it is confirmed that the production rate of the trans-transoid remained at about 6%. Also from the result of the photochromic property of compound 9, it is confirmed that as the monomer do, the polymer also suppressing the generation of the trans-transoid.

Embodiment 25

Photochromic Properties of Compound 10 in Toluene.

Figure 54:
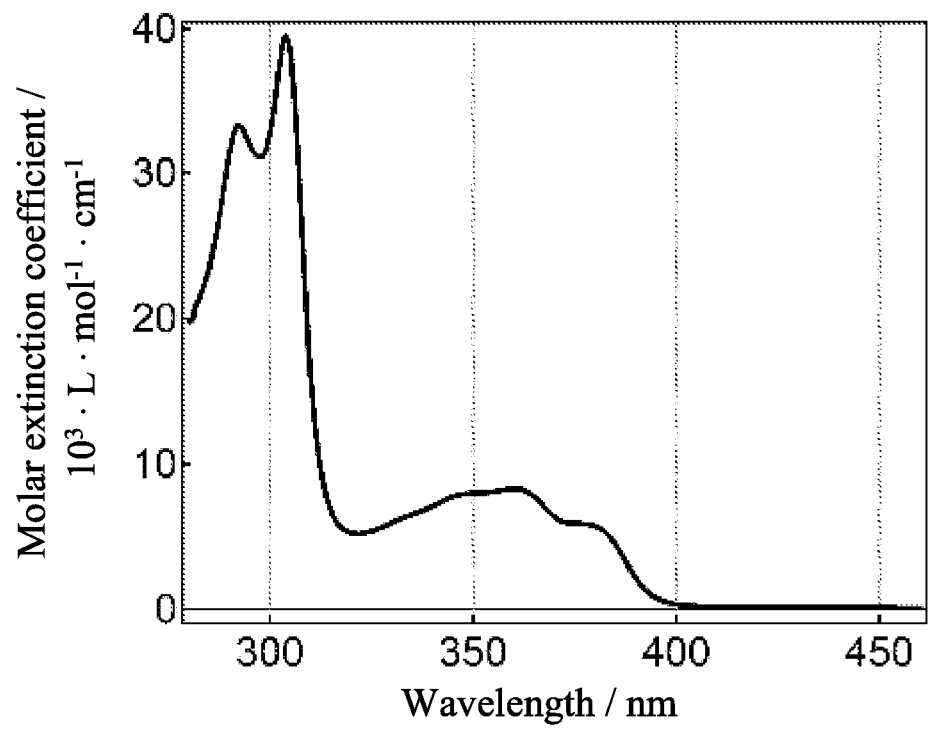
FIG. 54 is a graph of UV/visible absorption spectrum of the toluene solution of decolorized compound 10.
Figure 55:
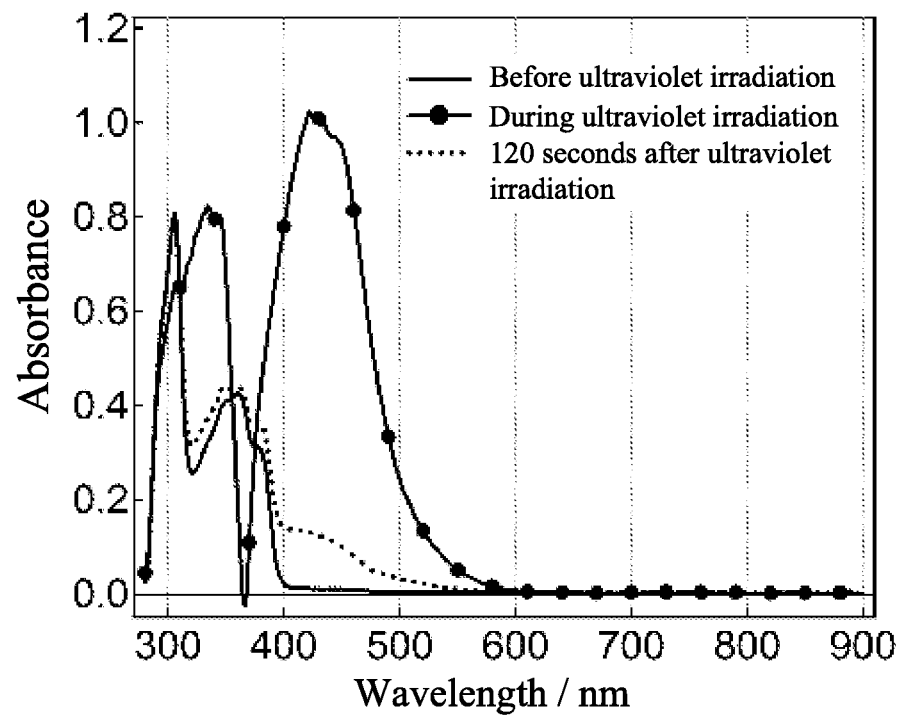
FIG. 55 is a graph of UV-visible/near-infrared absorption spectrum of toluene solution of compound 10 at the timing of before UV irradiation, during UV irradiation and 120 seconds after UV irradiation is stopped.
Figure 56:
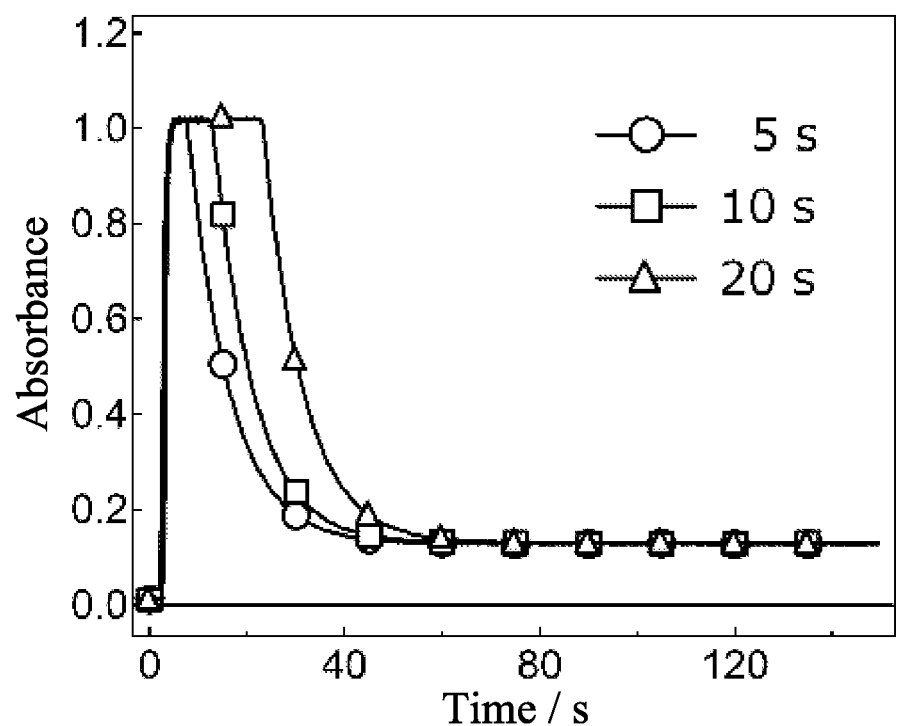
FIG. 56 is a graph of change in absorbance by time at the maximum absorption wavelength of the chromogen when the toluene solution of compound 10 is irradiated with UV for 5, 10, and 20 seconds.

FIG. 54 shows the ultraviolet/visible absorption spectrum of the toluene solution of compound 10 (concentration $5.6 \times 10^{-5}$M). The transient absorption spectrum of the above toluene solution of compound 10 is measured using ultraviolet with wavelength of 365 nm as excitation light. FIG. 55 shows transient absorption spectra before ultraviolet irradiation, during ultraviolet irradiation, and 120 seconds after ultraviolet irradiation is stopped. When a toluene solution of compound 10 is irradiated with ultraviolet, a chromogen having a maximum absorption wavelength at a wavelength of 423 nm is produced reversibly. FIG. 56 shows changes with time in absorbance at the maximum absorption wavelength after irradiation with ultraviolet for 5, 10 and 20 seconds. It is confirmed that at 25° C., after the ultraviolet irradiation is stopped, the chromogen rapidly decayed with a half-life of 5.7 s. At this time, it is confirmed that the production rate of the trans-transoid remained at about 12%.

Embodiment 26

Photochromic Properties of Compound 11 in Toluene.

Figure 57:
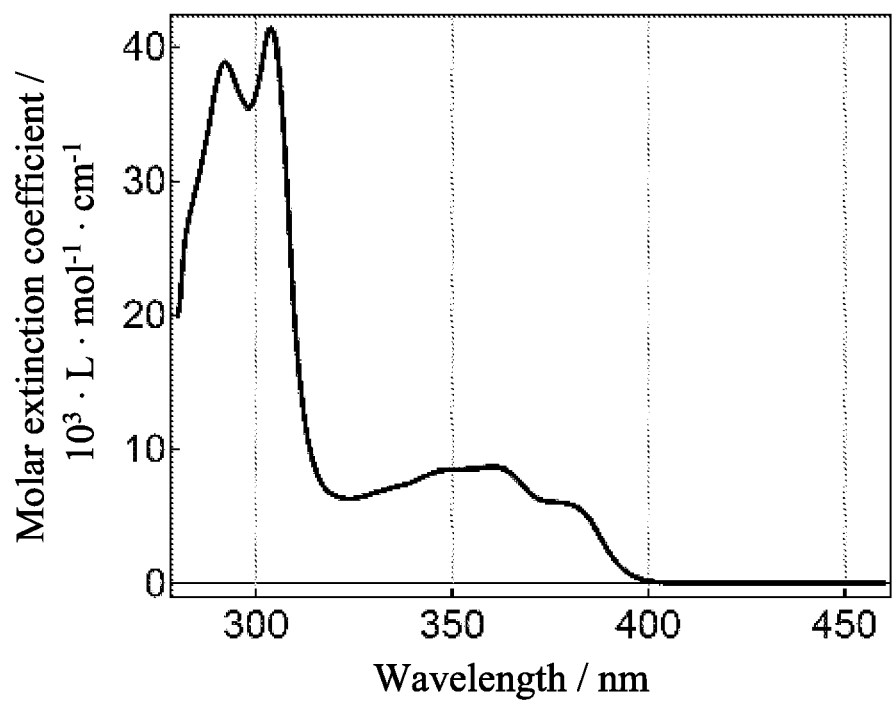
FIG. 57 is a graph of UV/visible absorption spectrum of the toluene solution of decolorized compound 11.
Figure 58:
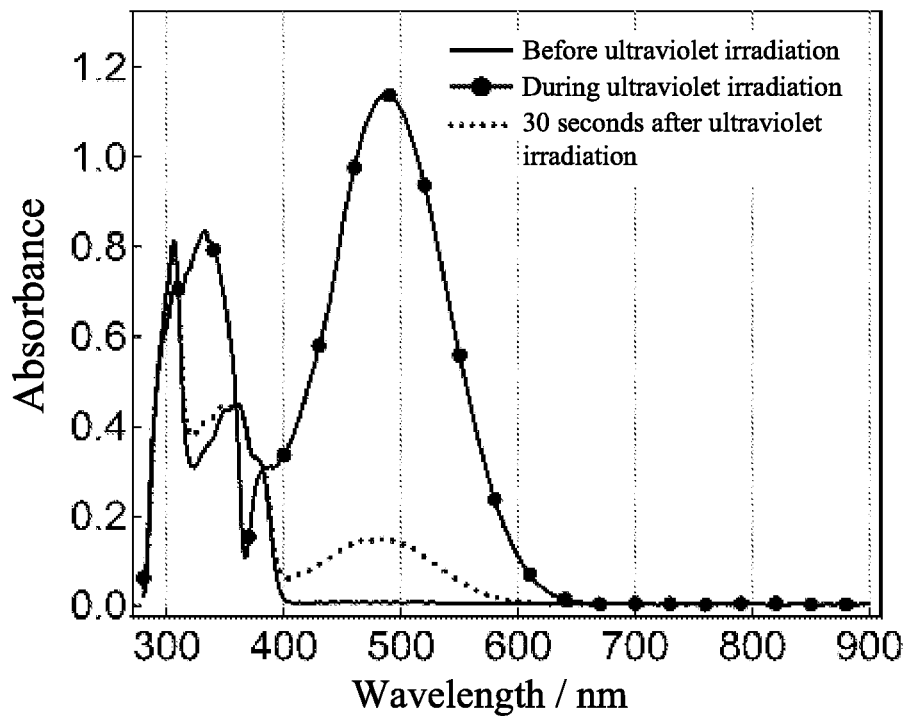
FIG. 58 is a graph of UV-visible/near-infrared absorption spectrum of toluene solution of compound 11 at the timing of before UV irradiation, during UV irradiation and 30 seconds after UV irradiation is stopped.
Figure 59:
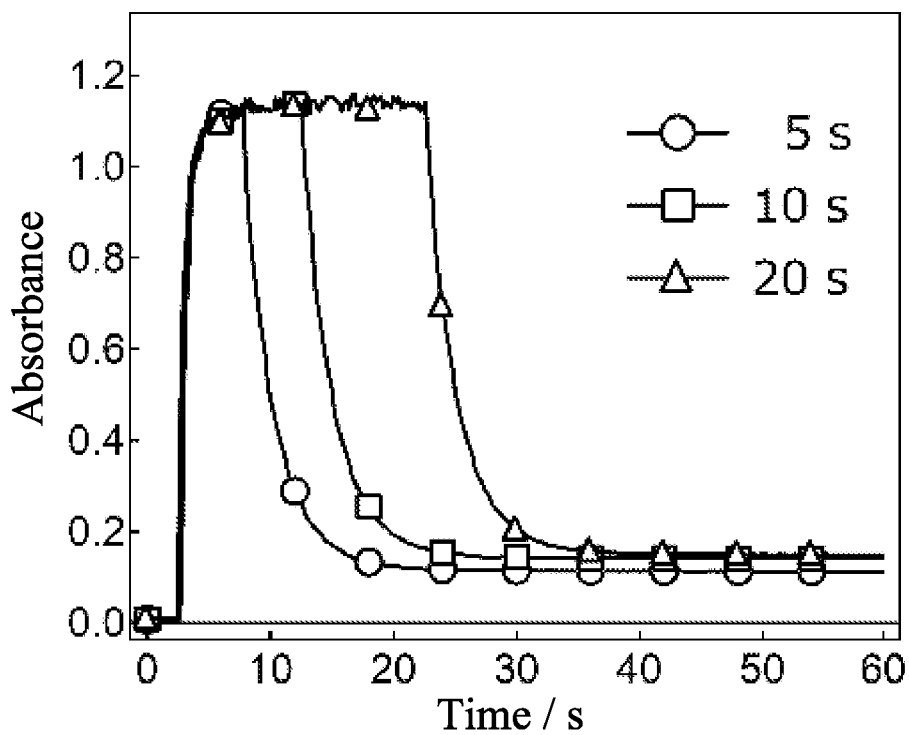
FIG. 59 is a graph of change in absorbance by time at the maximum absorption wavelength of the chromogen when the toluene solution of compound 11 is irradiated with UV for 5, 10, and 20 seconds.

FIG. 57 shows the ultraviolet/visible absorption spectrum of the toluene solution of compound 11 (concentration $5.5\times10^{-5}$M). The transient absorption spectrum of the above toluene solution of compound 11 is measured using ultraviolet with wavelength of 365 nm as excitation light. FIG. 58 shows transient absorption spectra before ultraviolet irradiation, during ultraviolet irradiation, and 30 seconds after ultraviolet irradiation is stopped. When a toluene solution of compound 11 is irradiated with ultraviolet, a chromogen having a maximum absorption wavelength at a wavelength of 488 nm is produced reversibly. FIG. 59 shows changes with time in absorbance at the maximum absorption wavelength after irradiation with ultraviolet for 5, 10 and 20 seconds. It is confirmed that at 25° C., after the ultraviolet irradiation is stopped, the chromogen rapidly decayed with a half-life of 1.7 s. At this time, it is confirmed that the production rate of the trans-transoid remained at about 14%.

Embodiment 27

Photochromic Properties of Compound 12 in Toluene.

Figure 60:
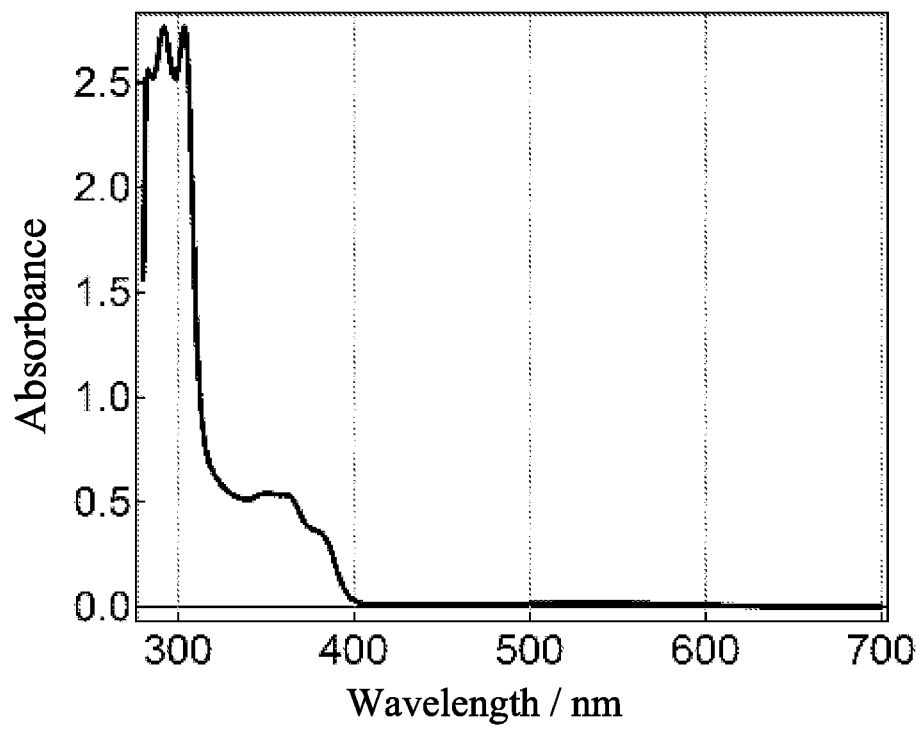
FIG. 60 is a graph of UV/visible absorption spectrum of the toluene solution of decolorized compound 12.
Figure 61:
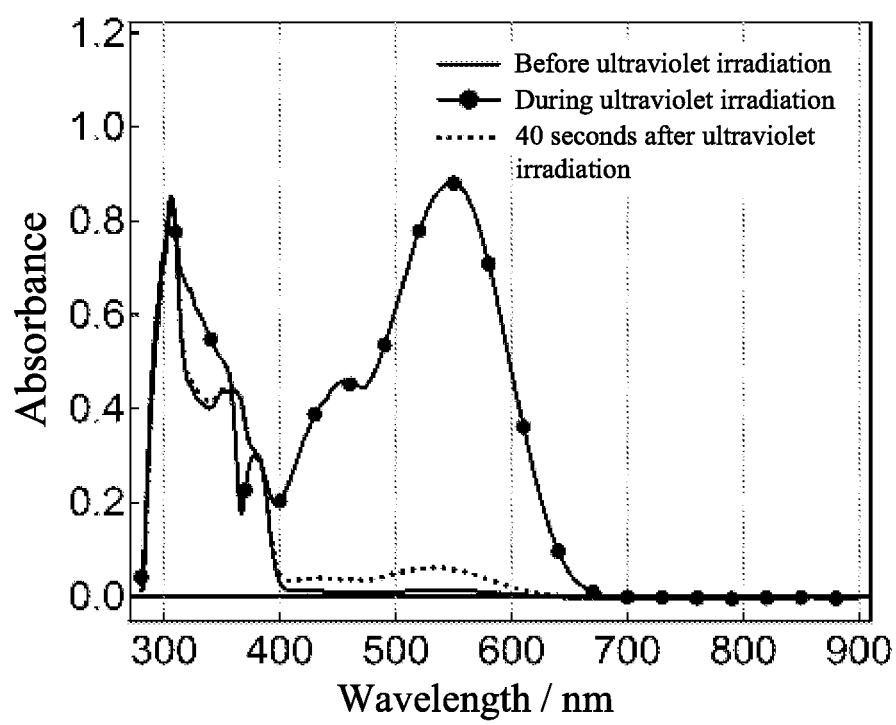
FIG. 61 is a graph of UV-visible/near-infrared absorption spectrum of toluene solution of compound 12 at the timing of before UV irradiation, during UV irradiation and 20 seconds after UV irradiation is stopped.
Figure 62:
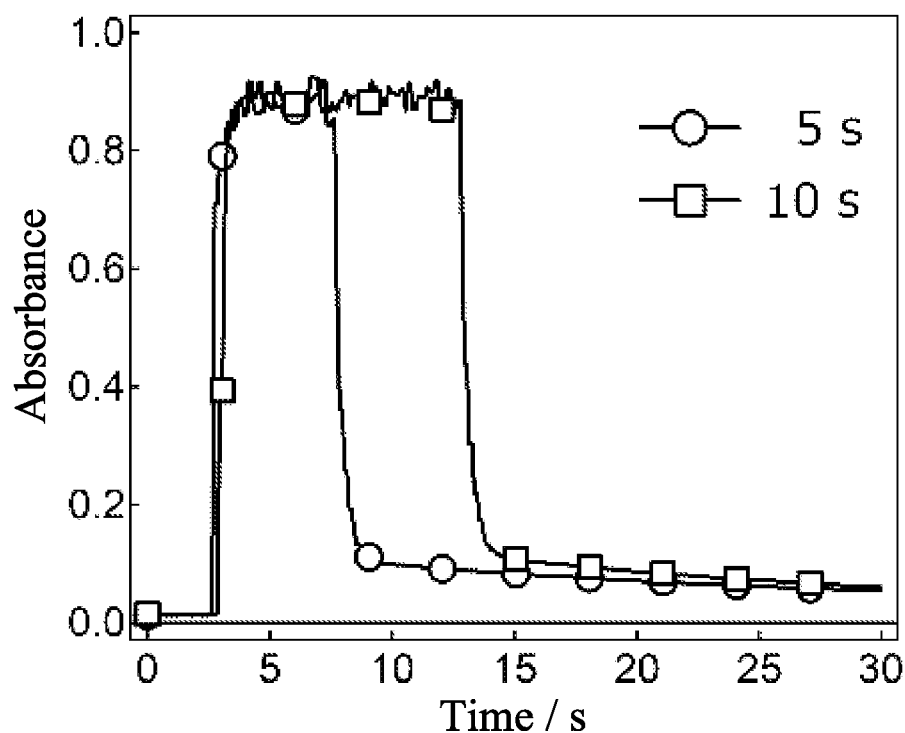
FIG. 62 is a graph of change in absorbance by time at the maximum absorption wavelength of the chromogen when the toluene solution of compound 12 is irradiated with UV for 5 and 10 seconds.

FIG. 60 shows the ultraviolet/visible absorption spectrum of the toluene solution of compound 12 (concentration $5.5\times10^{-5}$M). The transient absorption spectrum of the above toluene solution of compound 12 is measured using ultraviolet with wavelength of 365 nm as excitation light. FIG. 61 shows transient absorption spectra before ultraviolet irradiation, during ultraviolet irradiation, and 20 seconds after ultraviolet irradiation is stopped. When a toluene solution of compound 12 is irradiated with ultraviolet, a chromogen having a maximum absorption wavelength at a wavelength of 548 nm is produced reversibly. FIG. 62 shows changes with time in absorbance at the maximum absorption wavelength after irradiation with ultraviolet for 5 and 10 seconds. It is confirmed that at 25° C., after the ultraviolet irradiation is stopped, the chromogen rapidly decayed with a half-life of 0.2 s. At this time, it is confirmed that the production rate of the trans-transoid remained at about 14%.

Embodiment 28

Photochromic Properties of Compound 13 in Toluene.

Figure 63:
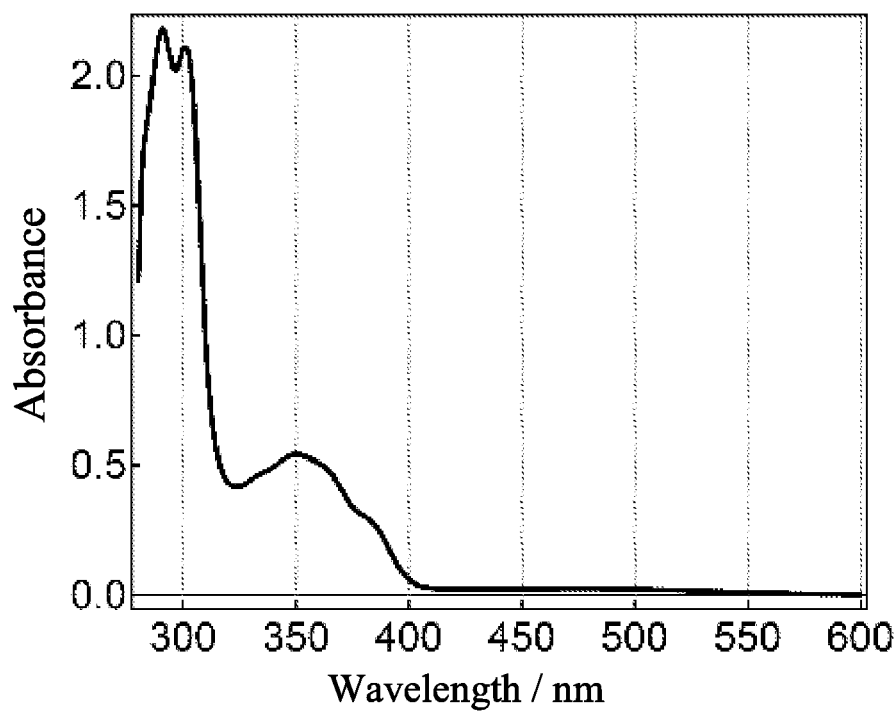
FIG. 63 is a graph of UV/visible absorption spectrum of the toluene solution of decolorized compound 13.
Figure 64:
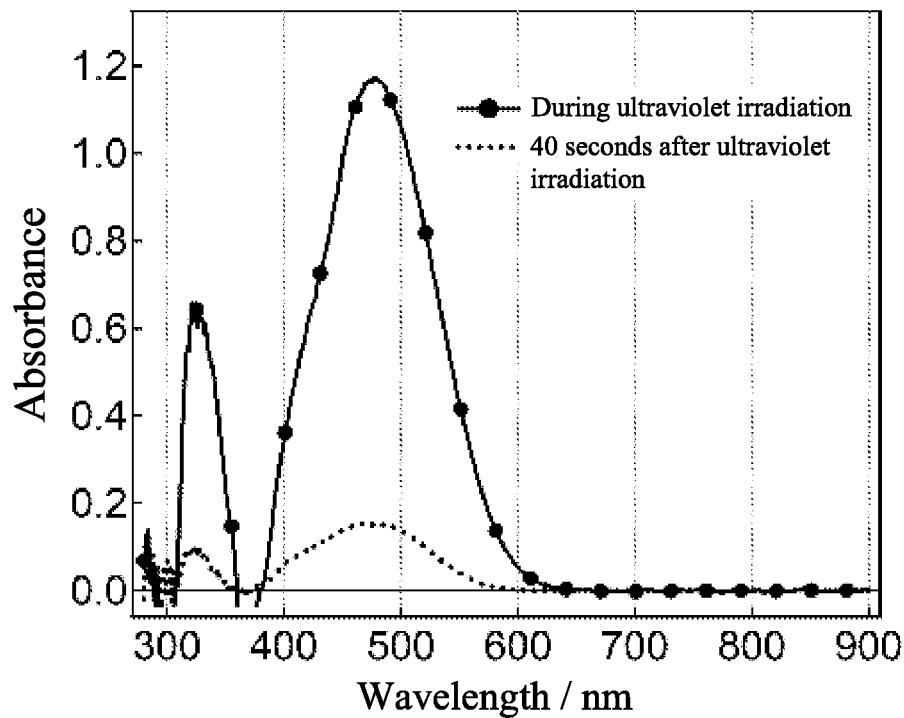
FIG. 64 is a graph of UV-visible/near-infrared absorption spectrum of toluene solution of compound 13 at the timing of before UV irradiation, during UV irradiation and 80 seconds after UV irradiation is stopped.
Figure 65:
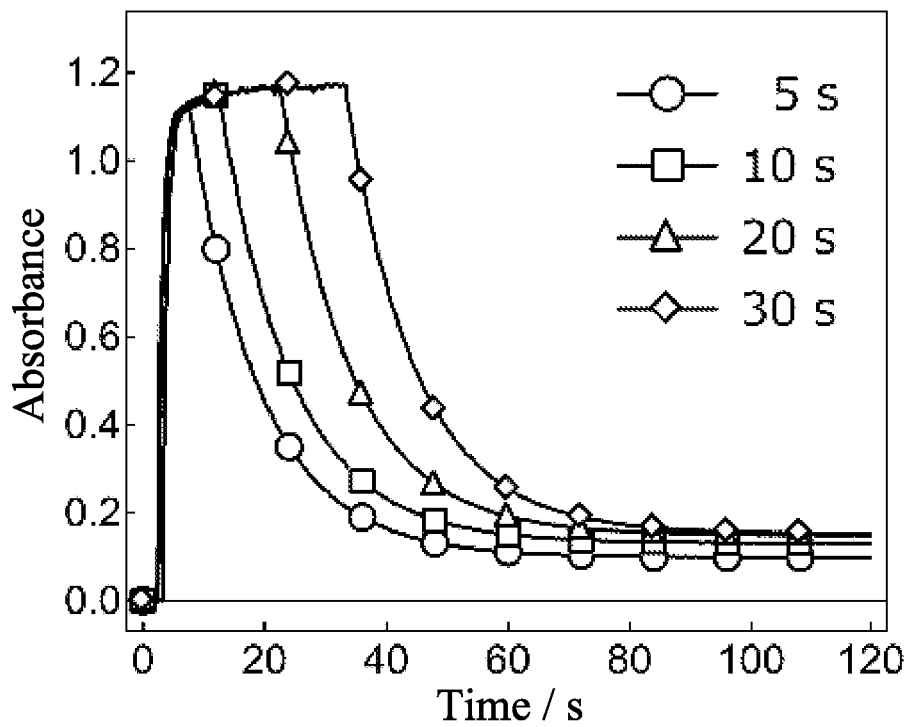
FIG. 65 is a graph of change in absorbance by time at the maximum absorption wavelength of the chromogen when the toluene solution of compound 13 is irradiated with UV for 5, 10, 20, and 30 seconds.

FIG. 63 shows the ultraviolet/visible absorption spectrum of the toluene solution of compound 13 (concentration $5.5\times10^{-5}$M). The transient absorption spectrum of the above toluene solution of compound 13 is measured using ultraviolet with wavelength of 365 nm as excitation light. FIG. 64 shows transient absorption spectra before ultraviolet irradiation, during ultraviolet irradiation, and 80 seconds after ultraviolet irradiation is stopped. When a toluene solution of compound 6 is irradiated with ultraviolet, a chromogen having a maximum absorption wavelength at a wavelength of 479 nm is produced reversibly. FIG. 65 shows changes with time in absorbance at the maximum absorption wavelength after irradiation with ultraviolet for 5, 10, 20 and 30 seconds. It is confirmed that at 25° C., after the ultraviolet irradiation is stopped, the chromogen rapidly decayed with a half-life of 8.0 s. At this time, it is confirmed that the production rate of the trans-transoid remained at about 14%.

Embodiment 29

Photochromic Properties of Compound 14 in Toluene.

Figure 66:
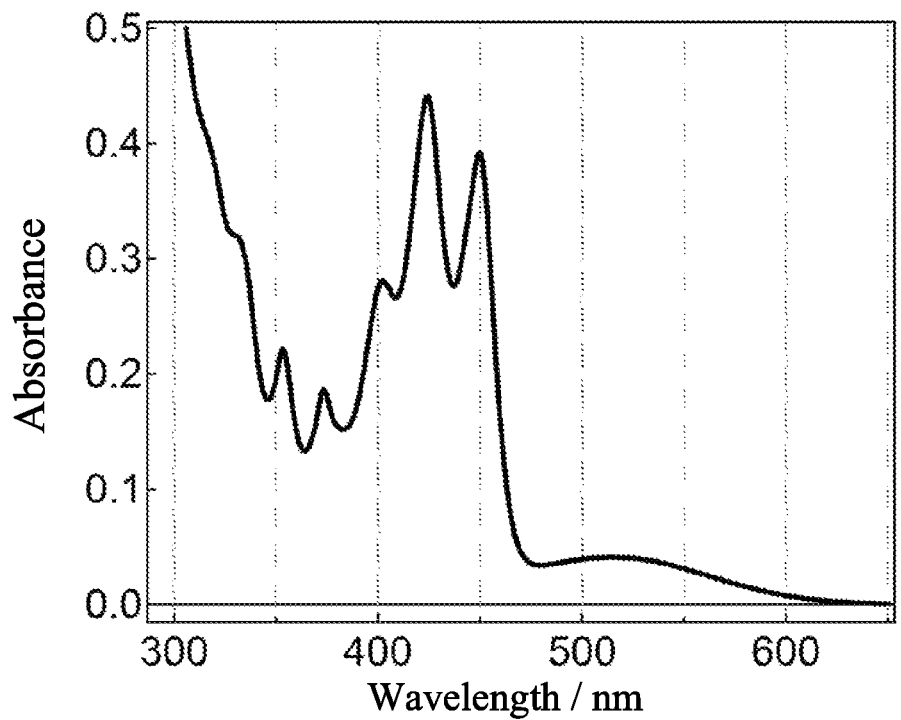
FIG. 66 is a graph of UV/visible absorption spectrum of the toluene solution of decolorized compound 14.
Figure 67:
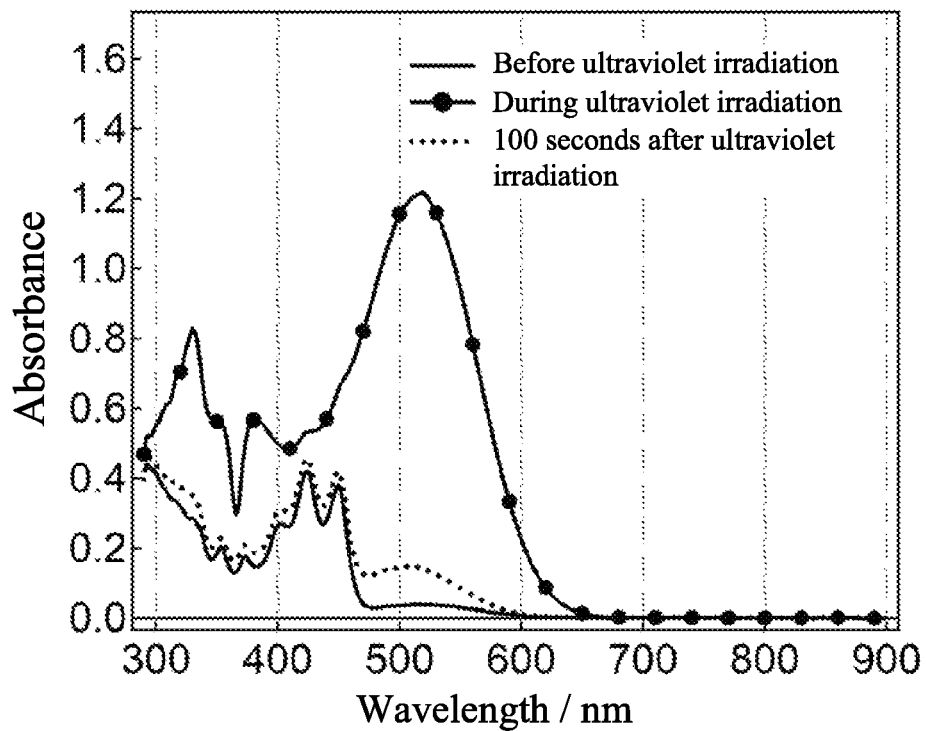
FIG. 67 is a graph of UV-visible/near-infrared absorption spectrum of toluene solution of compound 14 at the timing of before UV irradiation, during UV irradiation and 20 seconds after UV irradiation is stopped.
Figure 68:
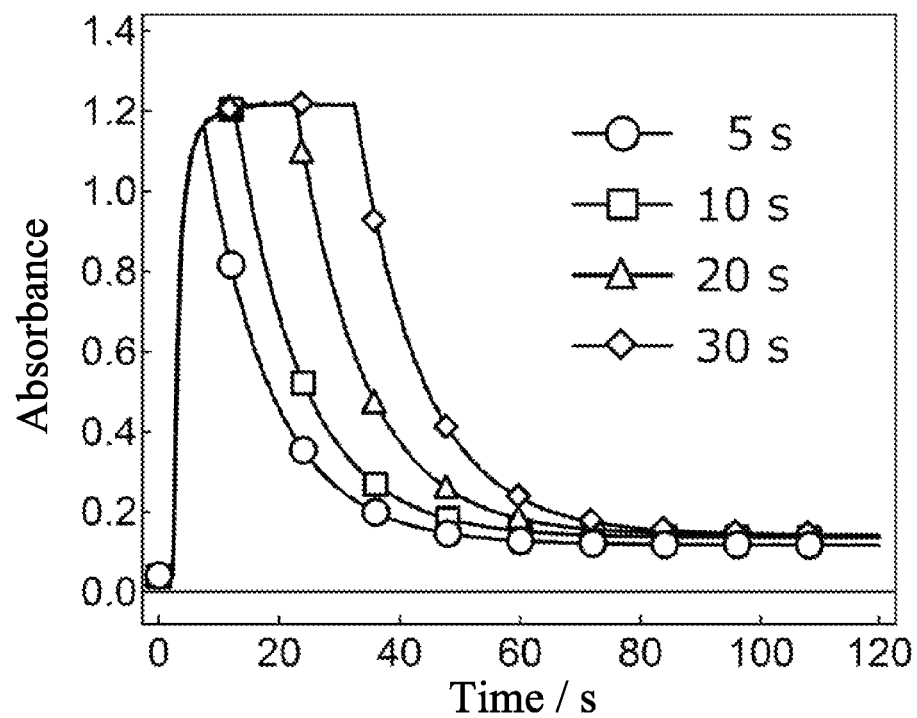
FIG. 68 is a graph of change in absorbance by time at the maximum absorption wavelength of the chromogen when the toluene solution of compound 14 is irradiated with UV for 5, 10, 20, and 30 seconds.

FIG. 66 shows the ultraviolet/visible absorption spectrum of the toluene solution of compound 14 (concentration $5.5\times10^{-5}$M). The transient absorption spectrum of the above toluene solution of compound 14 is measured using ultraviolet with wavelength of 365 nm as excitation light. FIG. 67 shows transient absorption spectra before ultraviolet irradiation, during ultraviolet irradiation, and 100 seconds after ultraviolet irradiation is stopped. When a toluene solution of compound 14 is irradiated with ultraviolet, a chromogen having a maximum absorption wavelength at a wavelength of 518 nm is produced reversibly. FIG. 68 shows changes with time in absorbance at the maximum absorption wavelength after irradiation with ultraviolet for 5, 10, 20, and 30 seconds. It is confirmed that at 25° C., after the ultraviolet irradiation is stopped, the chromogen relatively rapidly decayed with a half-life of 7.6 s. At this time, it is confirmed that the production rate of the trans-transoid remained at about 12%.

Embodiment 30

Photochromic Properties of Compound 15 in Toluene.

Figure 69:
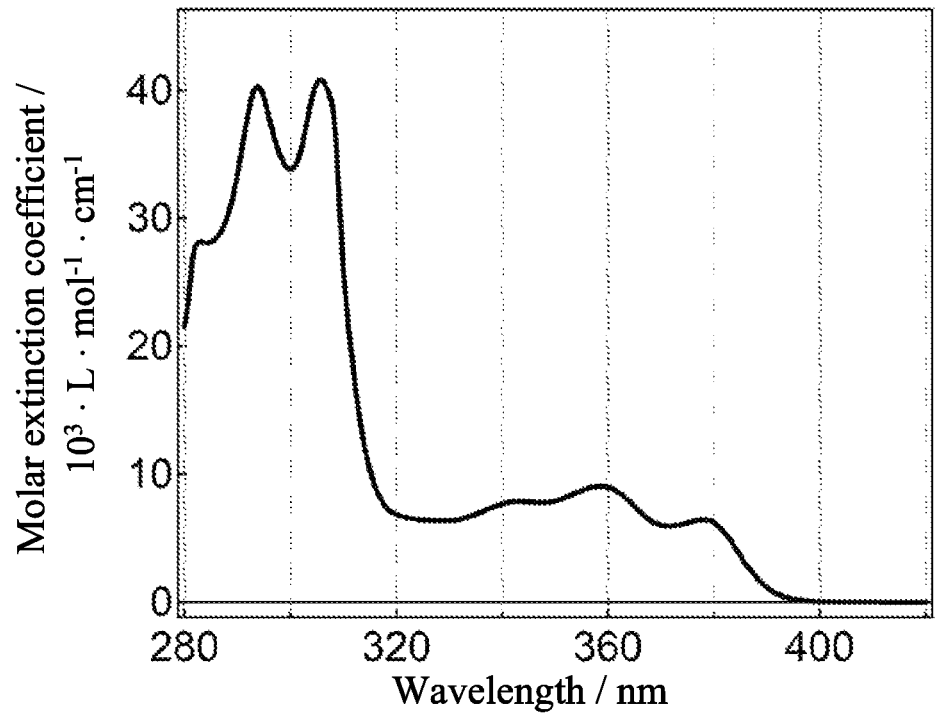
FIG. 69 is a graph of UV/visible absorption spectrum of the toluene solution of decolorized compound 15.
Figure 70:
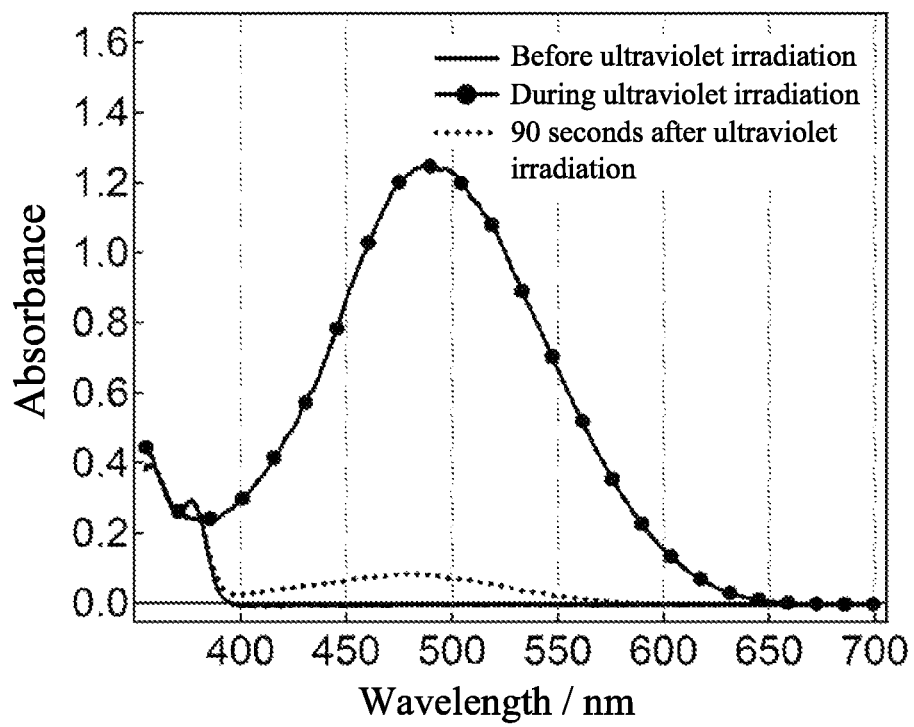
FIG. 70 is a graph of UV-visible/near-infrared absorption spectrum of toluene solution of compound 15 at the timing of before UV irradiation, during UV irradiation and 90 seconds after UV irradiation is stopped.
Figure 71:
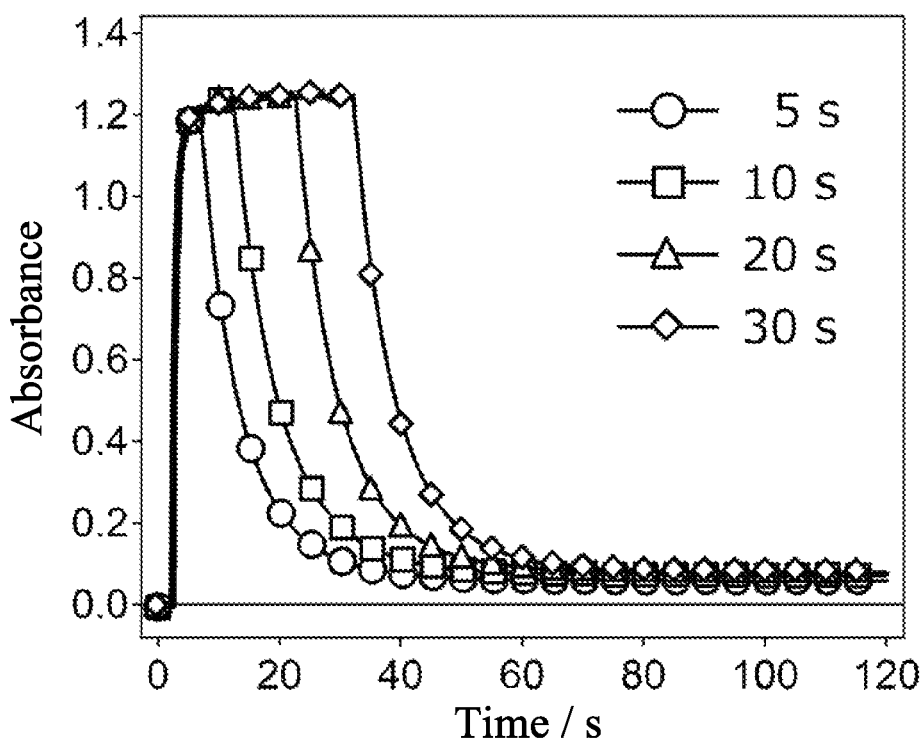
FIG. 71 is a graph of change in absorbance by time at the maximum absorption wavelength of the chromogen when the toluene solution of compound 15 is irradiated with UV for 5, 10, 20, and 30 seconds.

FIG. 69 shows the ultraviolet/visible absorption spectrum of the toluene solution of compound 15 (concentration $5.5\times10^{-5}$M). The transient absorption spectrum of the above toluene solution of compound 15 is measured using ultraviolet with wavelength of 365 nm as excitation light. FIG. 70 shows transient absorption spectra before ultraviolet irradiation, during ultraviolet irradiation, and 90 seconds after ultraviolet irradiation is stopped. When a toluene solution of compound 15 is irradiated with ultraviolet, a chromogen having a maximum absorption wavelength at a wavelength of 491 nm is produced reversibly. FIG. 71 shows changes with time in absorbance at the maximum absorption wavelength after irradiation with ultraviolet for 5, 10, 20, and 30 seconds. It is confirmed that at 25° C., after the ultraviolet irradiation is stopped, the chromogen relatively rapidly decayed with a half-life of 4.8 s. At this time, it is confirmed that the production rate of the trans-transoid remained at about 8%. From the results of the photochromic properties of Compound 15, it is confirmed that the generation of trans-transoid can be efficiently suppressed by suppressing the rotation of the corresponding etheric oxygen atoms.

Comparative Example 8

Photochromic Properties of Compound 16 in Toluene.

Figure 72:
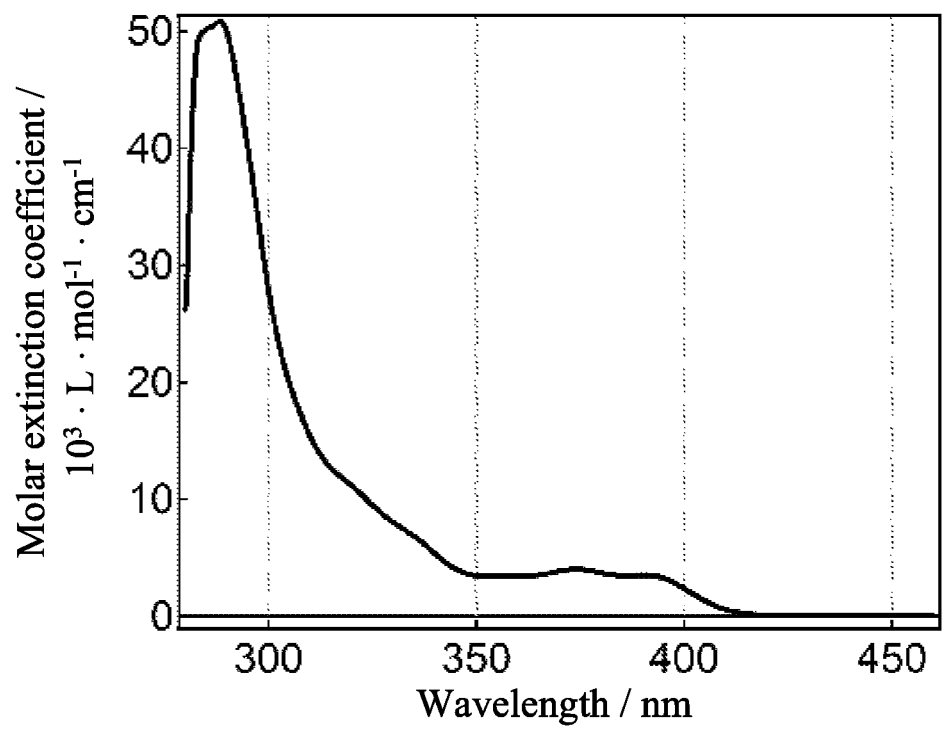
FIG. 72 is a graph of UV/visible absorption spectrum of the toluene solution of decolorized compound 16.
Figure 73:
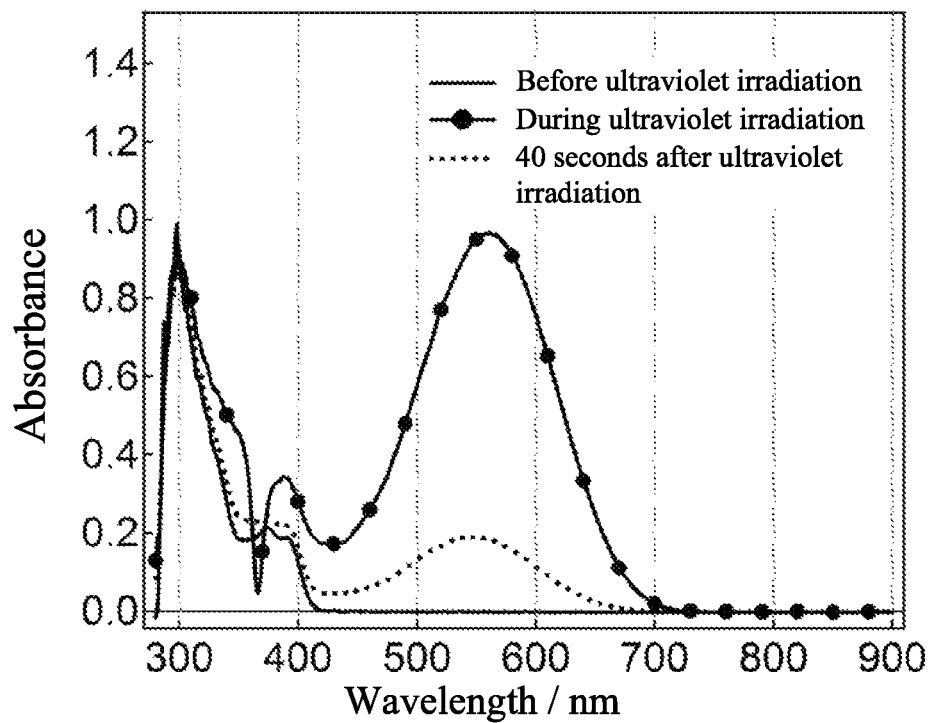
FIG. 73 is a graph of UV-visible/near-infrared absorption spectrum of toluene solution of compound 16 at the timing of before UV irradiation, during UV irradiation and 40 seconds after UV irradiation is stopped.
Figure 74:
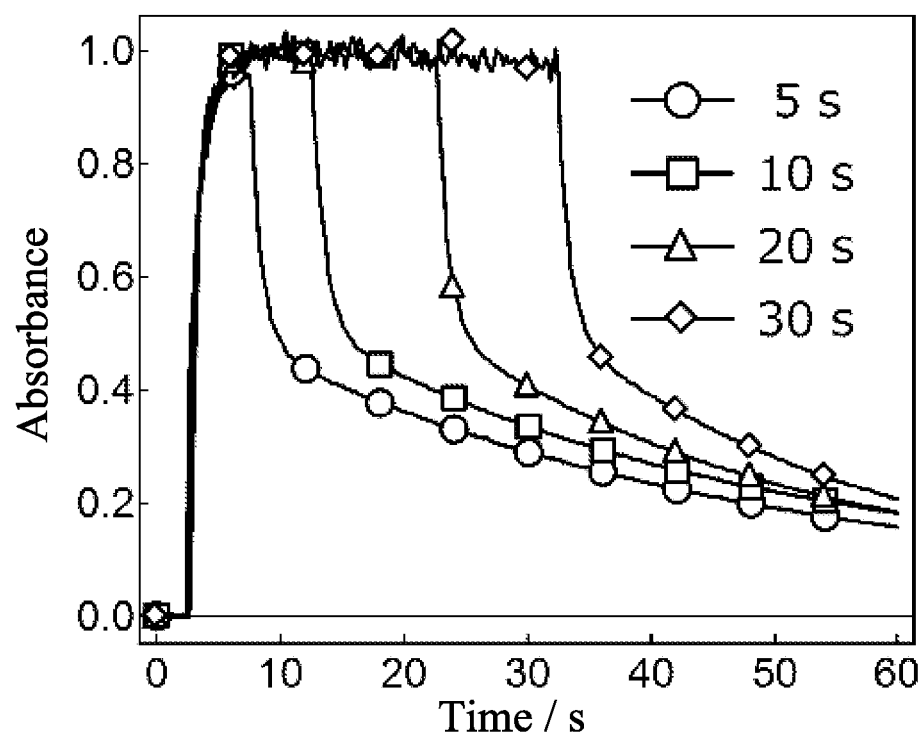
FIG. 74 is a graph of change in absorbance by time at the maximum absorption wavelength of the chromogen when the toluene solution of compound 16 is irradiated with UV for 5, 10, 20, and 30 seconds.

FIG. 72 shows the ultraviolet/visible absorption spectrum of the toluene solution of compound 16 (concentration $5.5\times10^{-5}$M). The transient absorption spectrum of the above toluene solution of compound 16 is measured using ultraviolet with wavelength of 365 nm as excitation light. FIG. 73 shows transient absorption spectra before ultraviolet irradiation, during ultraviolet irradiation, and 40 seconds after ultraviolet irradiation is stopped. When a toluene solution of compound 16 is irradiated with ultraviolet, a chromogen having a maximum absorption wavelength at a wavelength of 561 nm is produced reversibly. FIG. 74 shows changes with time in absorbance at the maximum absorption wavelength after irradiation with ultraviolet for 5, 10, 20, and 30 seconds. It is confirmed that at 25° C., after the ultraviolet irradiation is stopped, the chromogen rapidly decayed with a half-life of 0.75 s. It is confirmed that 44% of the trans-transoid is generated in the compound 16 in which a hydrogen atom is bonded to the carbon atom at the $1^{st}$ position of the pyranoquinazoline skeleton.

Comparative Example 9

Photochromic Properties of Compound 17 in Toluene.

Figure 75:
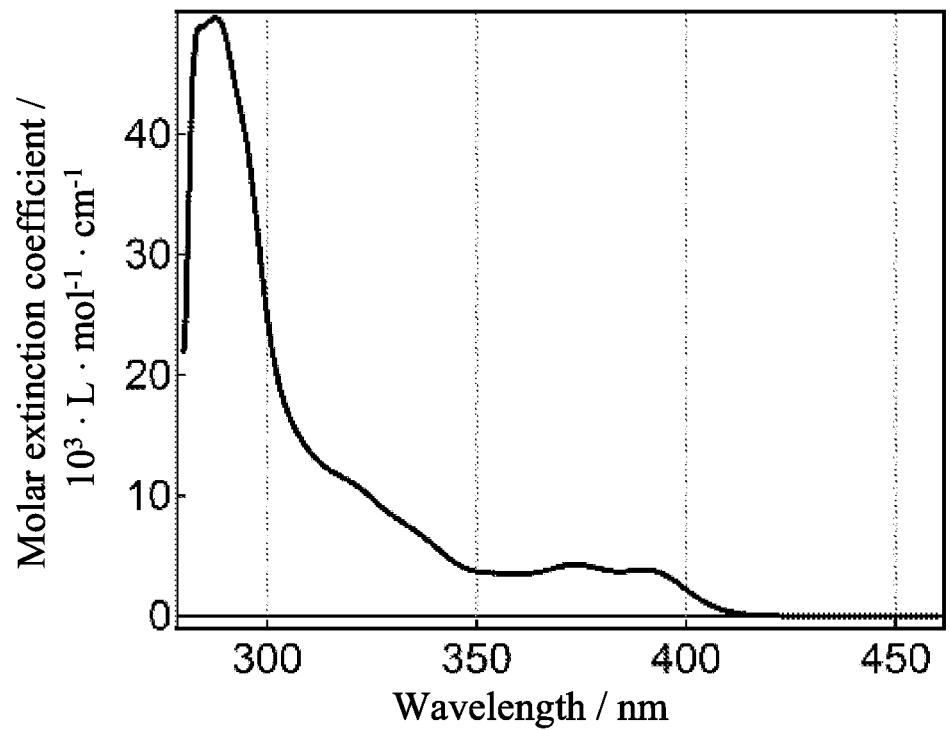
FIG. 75 is a graph of UV/visible absorption spectrum of the toluene solution of decolorized compound 17.
Figure 76:
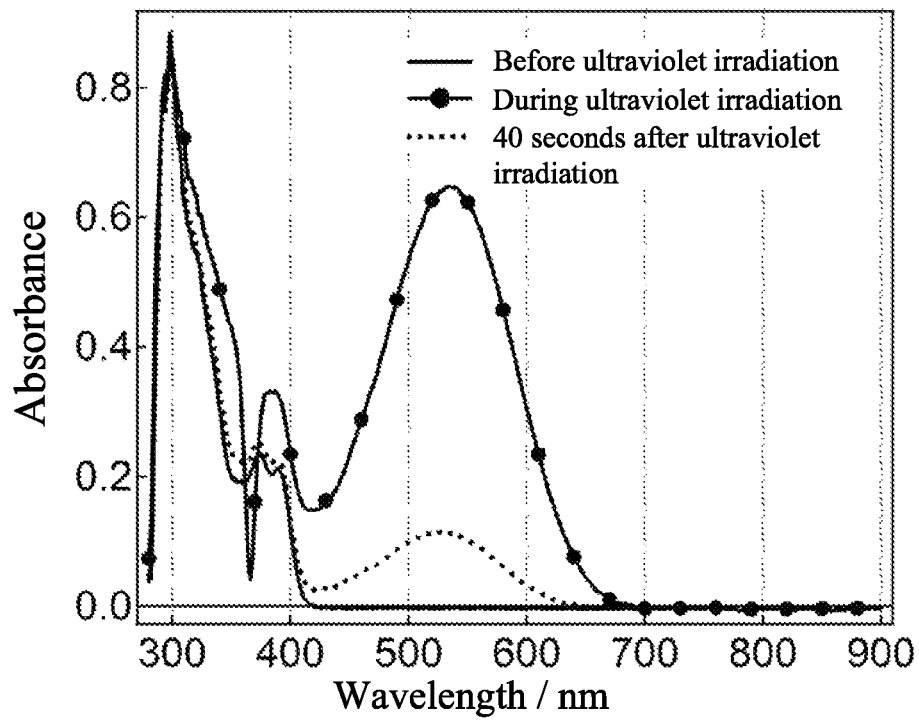
FIG. 76 is a graph of UV-visible/near-infrared absorption spectrum of toluene solution of compound 17 at the timing of before UV irradiation, during UV irradiation and 40 seconds after UV irradiation is stopped.
Figure 77:
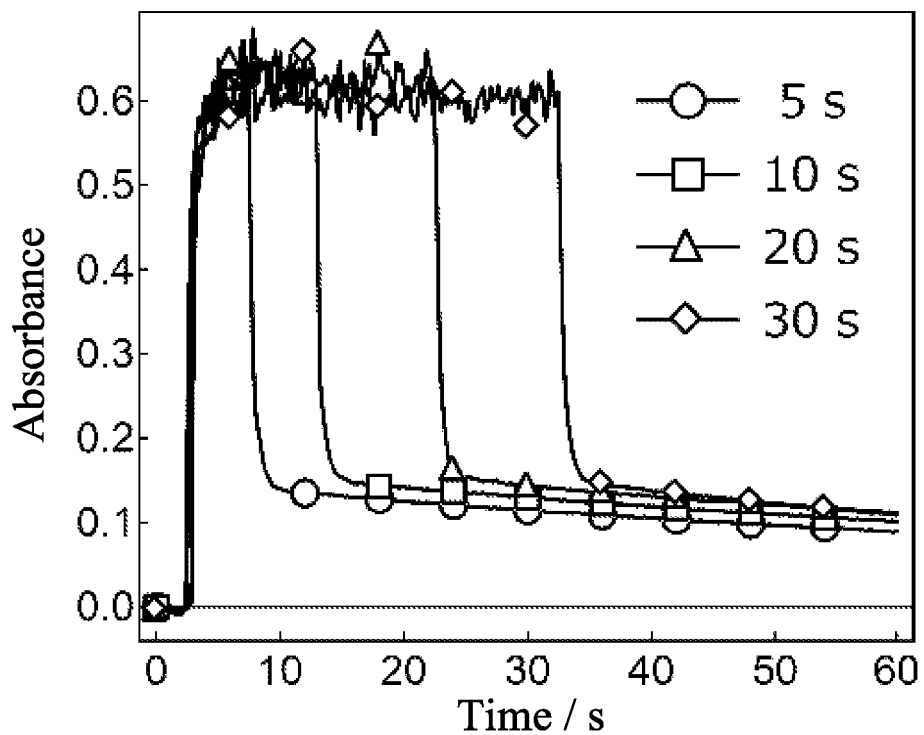
FIG. 77 is a graph of change in absorbance by time at the maximum absorption wavelength of the chromogen when the toluene solution of compound 17 is irradiated with UV for 5, 10, 20, and 30 seconds.

FIG. 75 shows the ultraviolet/visible absorption spectrum of the toluene solution of compound 17 (concentration $5.6 \times 10^{-5}$M). The transient absorption spectrum of the above toluene solution of compound 17 is measured using ultraviolet with wavelength of 365 nm as excitation light. FIG. 76 shows transient absorption spectra before ultraviolet irradiation, during ultraviolet irradiation, and 40 seconds after ultraviolet irradiation is stopped. When a toluene solution of compound 17 is irradiated with ultraviolet, a chromogen having a maximum absorption wavelength at a wavelength of 535 nm is produced reversibly. FIG. 74 shows changes with time in absorbance at the maximum absorption wavelength after irradiation with ultraviolet for 5, 10, 20, and 30 seconds. It is confirmed that at 25° C., after the ultraviolet irradiation is stopped, the chromogen rapidly decayed with a half-life of 0.31 s. It is confirmed that 24% of the trans-transoid is generated in the compound 17 in which a methyl group is bonded to the carbon atom at the 1st position of the pyranoquinazoline skeleton.

Comparative Example 10

Photochromic Properties of Compound 18 in Toluene.

Figure 78:
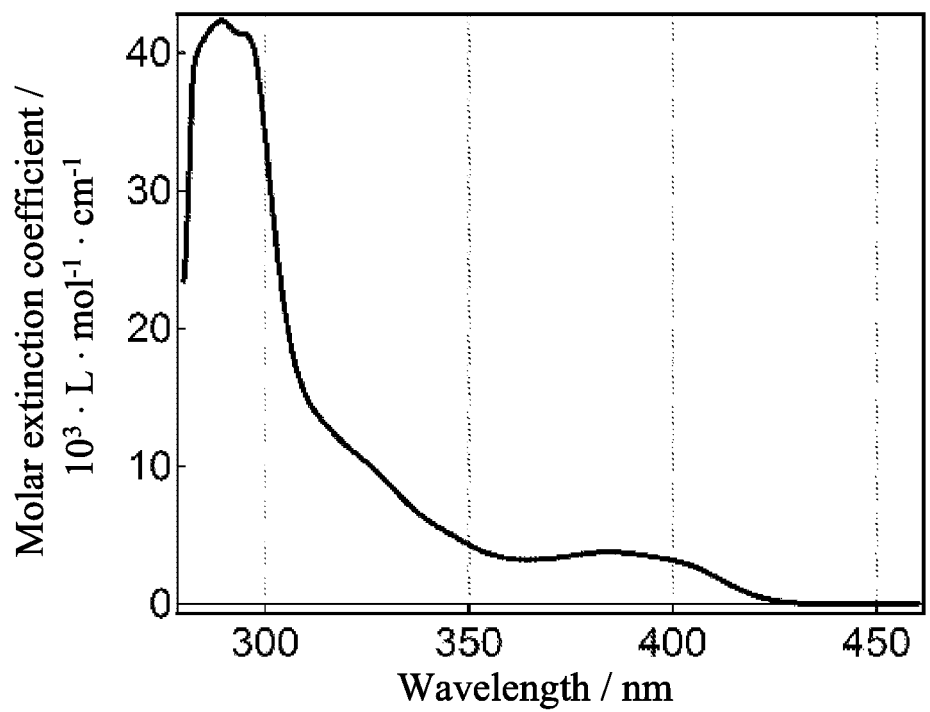
FIG. 78 is a graph of UV/visible absorption spectrum of the toluene solution of decolorized compound 18.
Figure 79:
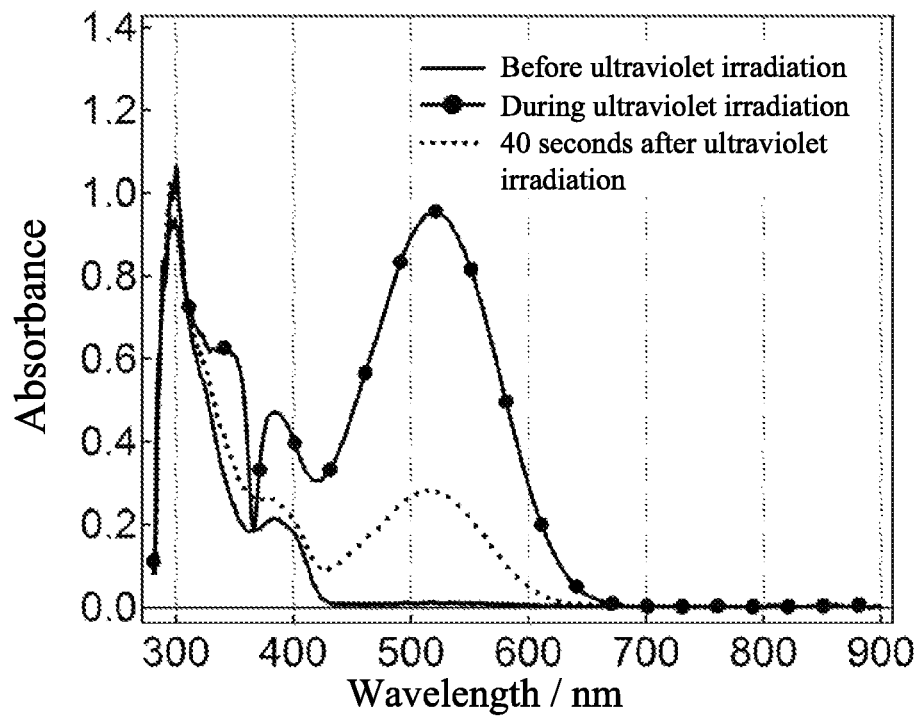
FIG. 79 is a graph of UV-visible/near-infrared absorption spectrum of toluene solution of compound 18 at the timing of before UV irradiation, during UV irradiation and 40 seconds after UV irradiation is stopped.
Figure 80:
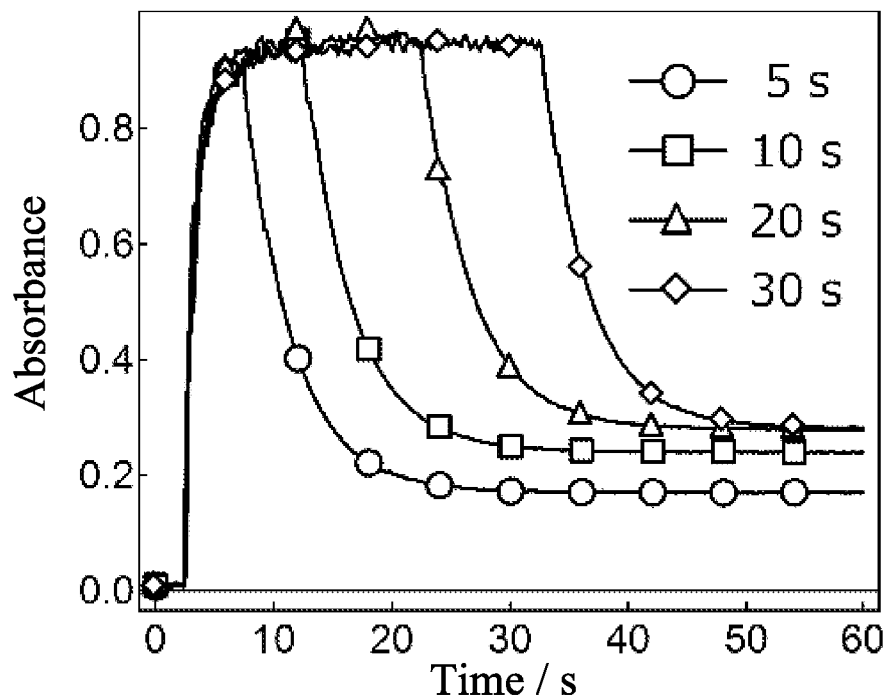
FIG. 80 is a graph of change in absorbance by time at the maximum absorption wavelength of the chromogen when the toluene solution of compound 18 is irradiated with UV for 5, 10, 20, and 30 seconds.

FIG. 78 shows the ultraviolet/visible absorption spectrum of the toluene solution of compound 18 (concentration $5.5 \times 10^{-5}$M). The transient absorption spectrum of the above toluene solution of compound 18 is measured using ultraviolet with wavelength of 365 nm as excitation light. FIG. 79 shows transient absorption spectra before ultraviolet irradiation, during ultraviolet irradiation, and 40 seconds after ultraviolet irradiation is stopped. When a toluene solution of compound 18 is irradiated with ultraviolet, a chromogen having a maximum absorption wavelength at a wavelength of 520 nm is produced reversibly. FIG. 80 shows changes with time in absorbance at the maximum absorption wavelength after irradiation with ultraviolet for 5, 10, 20, and 30 seconds. It is confirmed that at 25° C., after the ultraviolet irradiation is stopped, the chromogen slowly decayed with a half-life of 2.9 s. It is confirmed that 29% of the trans-transoid is generated in the compound 18 in which a tert-butyl group is bonded to the carbon atom at the $1^{st}$ position of the pyranoquinazoline skeleton.

Comparative Example 11

Photochromic Properties of Compound 19 in Toluene.

Figure 81:
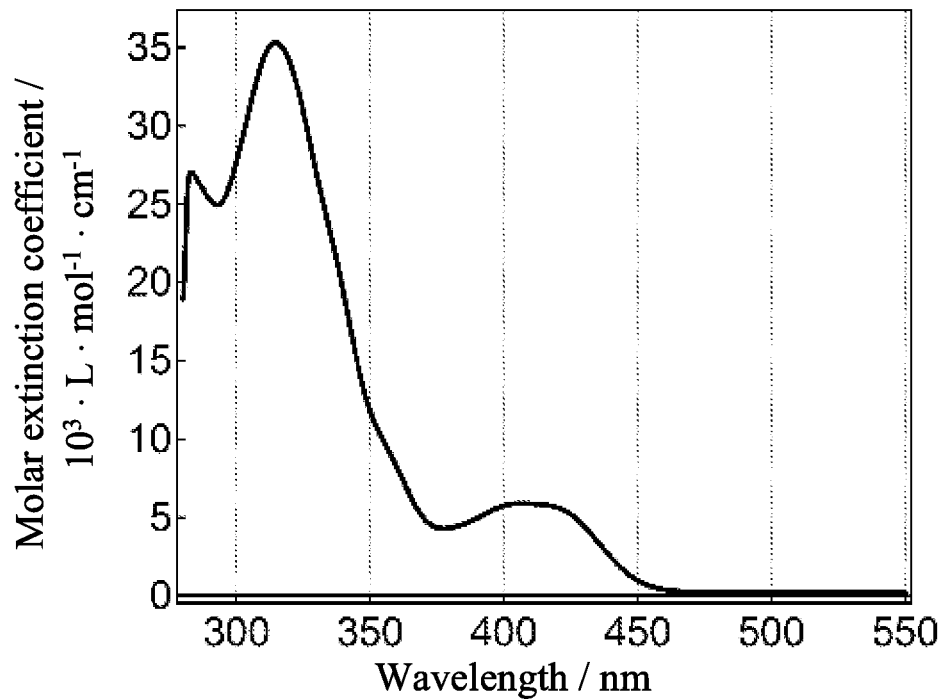
FIG. 81 is a graph of UV/visible absorption spectrum of the toluene solution of decolorized compound 19.
Figure 82:
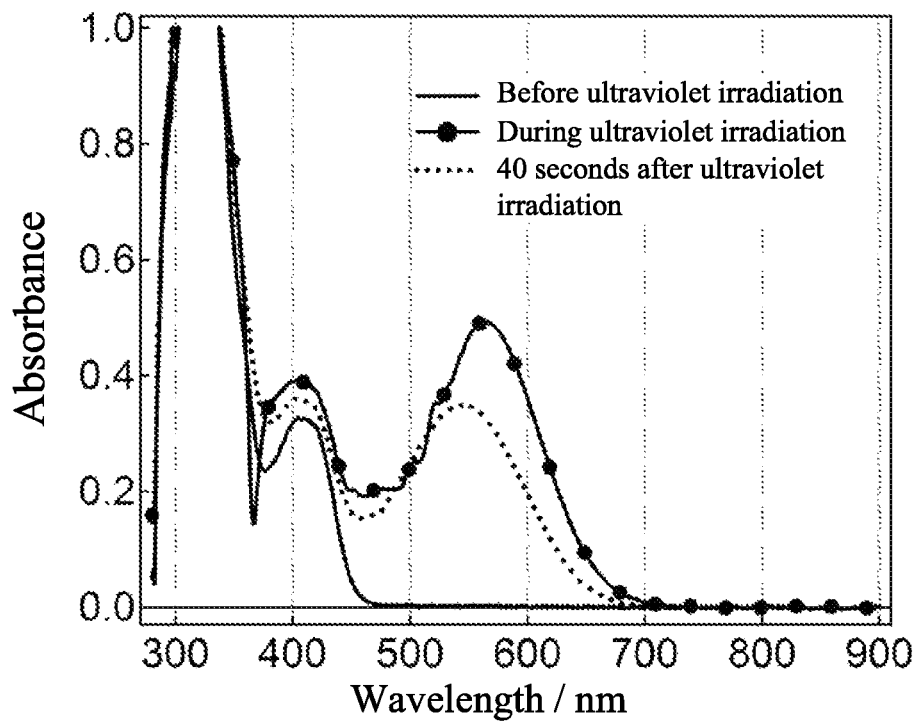
FIG. 82 is a graph of UV-visible/near-infrared absorption spectrum of toluene solution of compound 19 at the timing of before UV irradiation, during UV irradiation and 40 seconds after UV irradiation is stopped.
Figure 83:
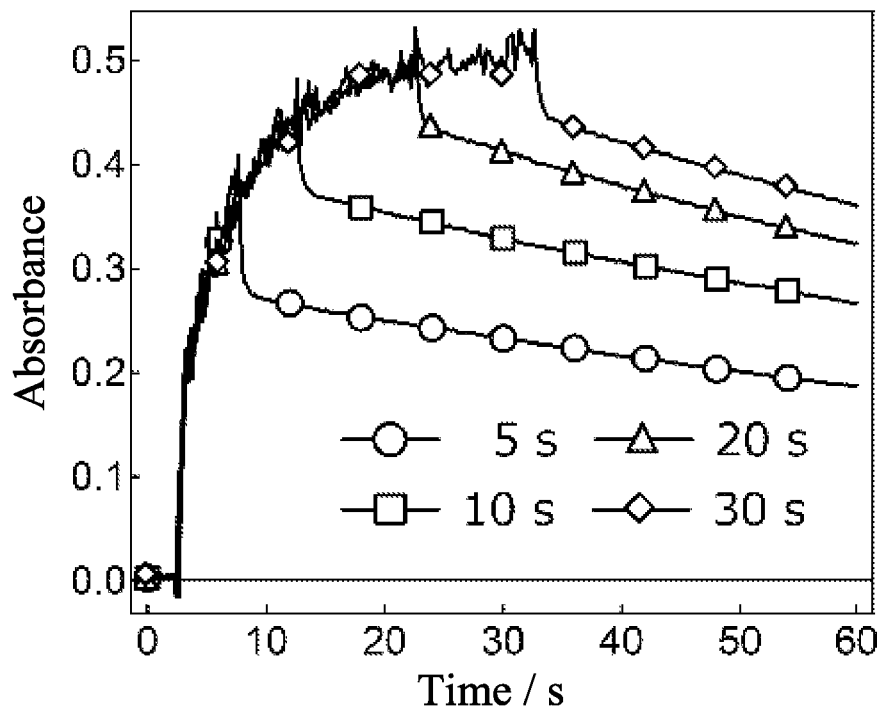
FIG. 83 is a graph of change in absorbance by time at the maximum absorption wavelength of the chromogen when the toluene solution of compound 19 is irradiated with UV for 5, 10, 20, and 30 seconds.

FIG. 81 shows the ultraviolet/visible absorption spectrum of the toluene solution of compound 18 (concentration $5.7 \times 10^{-5}$M). The transient absorption spectrum of the above toluene solution of compound 19 is measured using ultraviolet with wavelength of 365 nm as excitation light. FIG. 82 shows transient absorption spectra before ultraviolet irradiation, during ultraviolet irradiation, and 40 seconds after ultraviolet irradiation is stopped. When a toluene solution of compound 19 is irradiated with ultraviolet, a chromogen having a maximum absorption wavelength at a wavelength of 565 nm is produced reversibly. FIG. 83 shows changes with time in absorbance at the maximum absorption wavelength after irradiation with ultraviolet for 5, 10, 20, and 30 seconds. It is confirmed that at 25° C., after the ultraviolet irradiation is stopped, the chromogen rapidly decayed with a half-life of 0.17 s. It is confirmed that 86% of the trans-transoid is generated in the compound 19 in which a thienyl group is bonded to the carbon atom at the 1st position of the pyranoquinazoline skeleton.

Comparative Example 12

Photochromic Properties of Compound 20 in Toluene.

Figure 84:
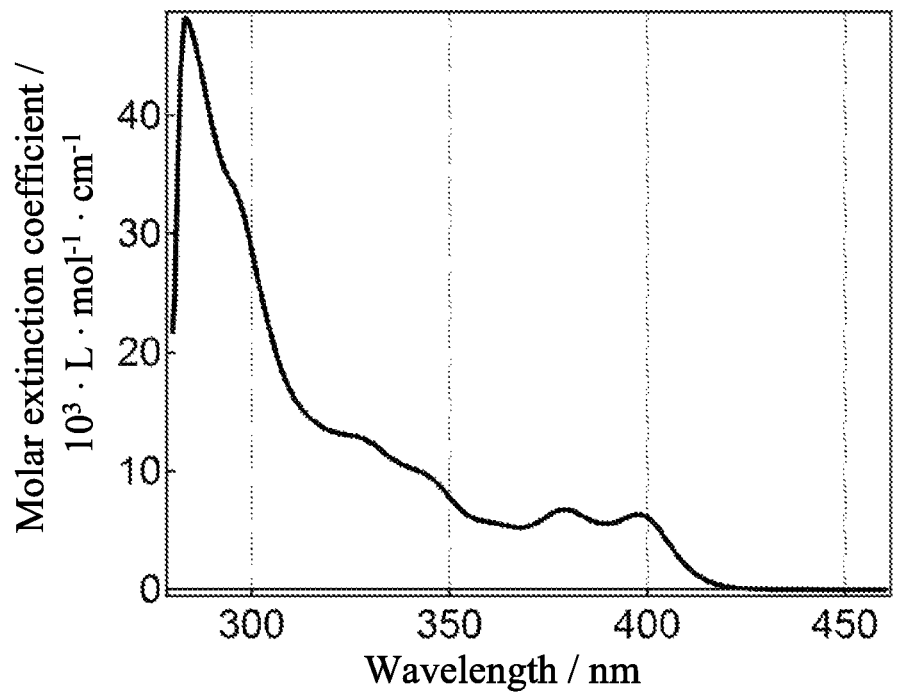
FIG. 84 is a graph of UV/visible absorption spectrum of the toluene solution of decolorized compound 20.
Figure 85:
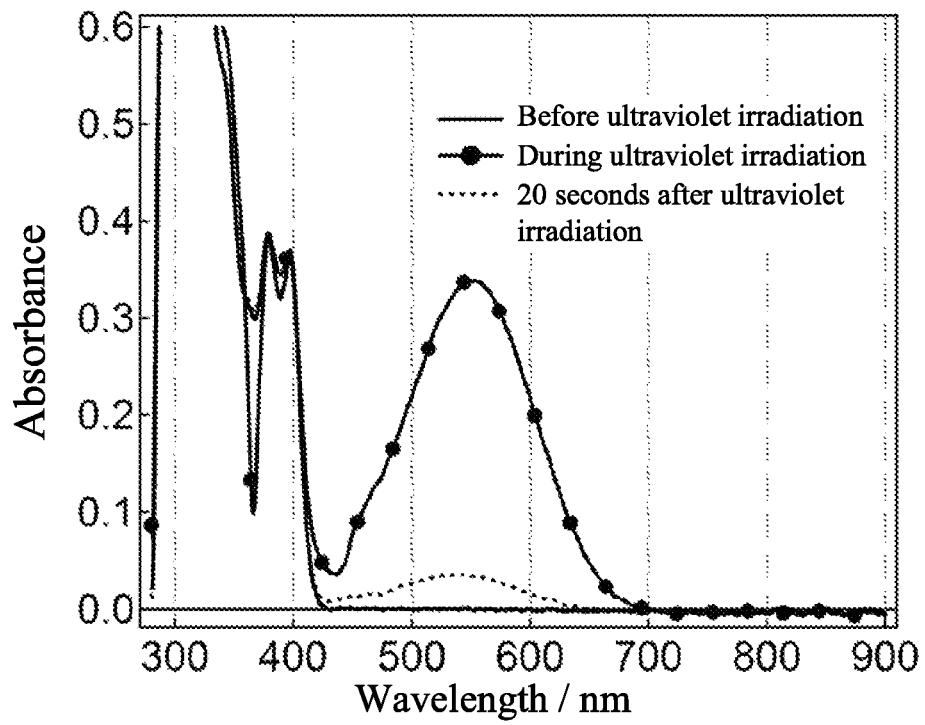
FIG. 85 is a graph of UV-visible/near-infrared absorption spectrum of toluene solution of compound 20 at the timing of before UV irradiation, during UV irradiation and 20 seconds after UV irradiation is stopped.
Figure 86:
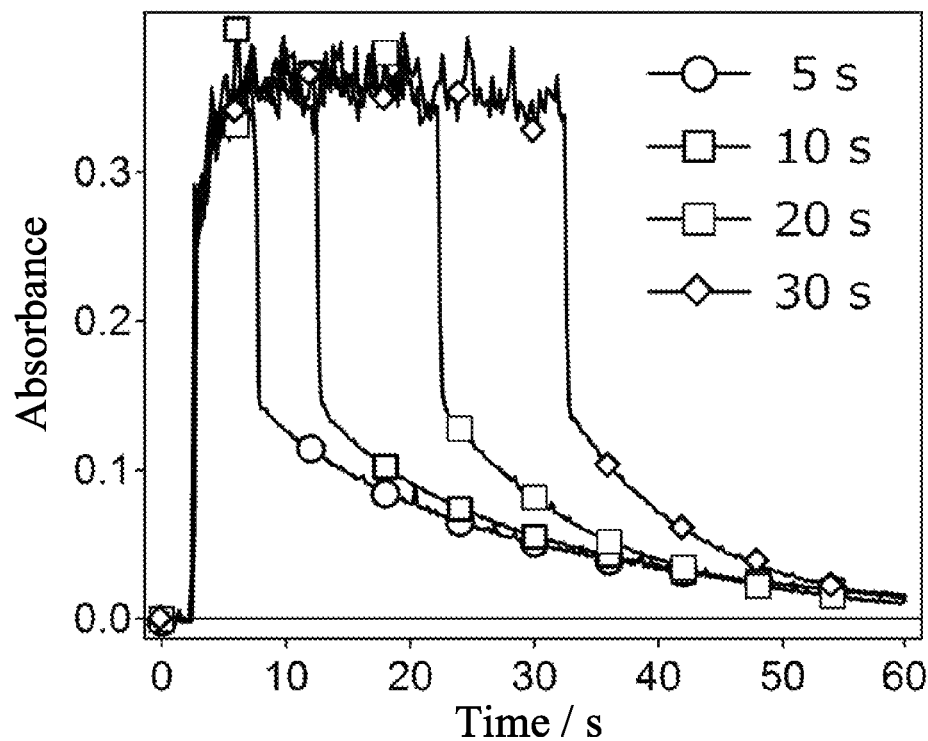
FIG. 86 is a graph of change in absorbance by time at the maximum absorption wavelength of the chromogen when the toluene solution of compound 20 is irradiated with UV for 5, 10, 20, and 30 seconds.

FIG. 84 shows the ultraviolet/visible absorption spectrum of the toluene solution of compound 20 (concentration 5.9×10-M). The transient absorption spectrum of the above toluene solution of compound 20 is measured using ultraviolet with wavelength of 365 nm as excitation light. FIG. 85 shows transient absorption spectra before ultraviolet irradiation, during ultraviolet irradiation, and 20 seconds after ultraviolet irradiation is stopped. When a toluene solution of compound 20 is irradiated with ultraviolet, a chromogen having a maximum absorption wavelength at a wavelength of 552 nm is produced reversibly. FIG. 86 shows changes with time in absorbance at the maximum absorption wavelength after irradiation with ultraviolet for 5, 10, 20, and 30 seconds. It is confirmed that at 25° C., after the ultraviolet irradiation is stopped, the chromogen rapidly decayed with a half-life of 0.10 s. It is confirmed that 39% of the trans-transoid is generated in the compound 20 in which a thioether group is bonded to the carbon atom at the $1^{st}$ position of the pyranoquinazoline skeleton.

Comparative Example 13

Photochromic Properties of Compound 21 in Toluene.

Figure 87:
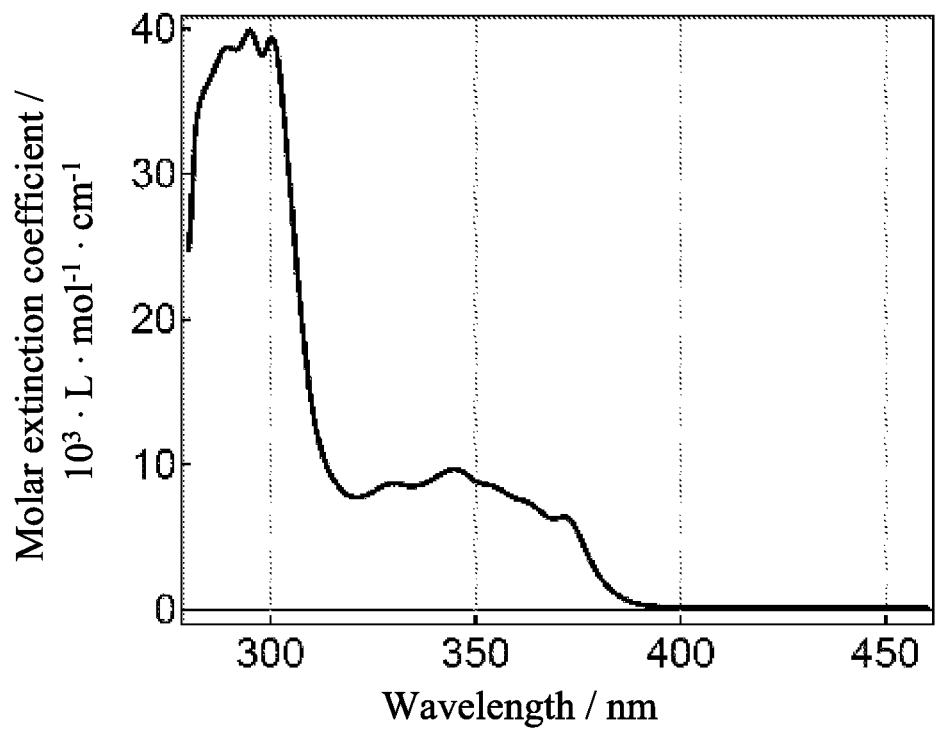
FIG. 87 is a graph of UV/visible absorption spectrum of the toluene solution of decolorized compound 21.
Figure 88:
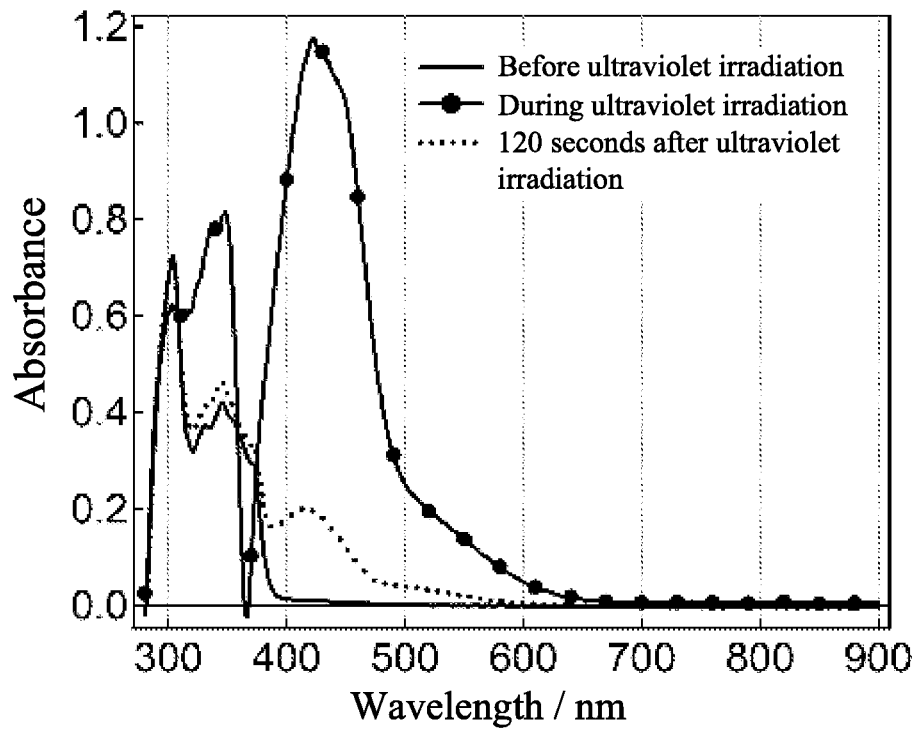
FIG. 88 is a graph of UV-visible/near-infrared absorption spectrum of toluene solution of compound 21 at the timing of before UV irradiation, during UV irradiation and 120 seconds after UV irradiation is stopped.
Figure 89:
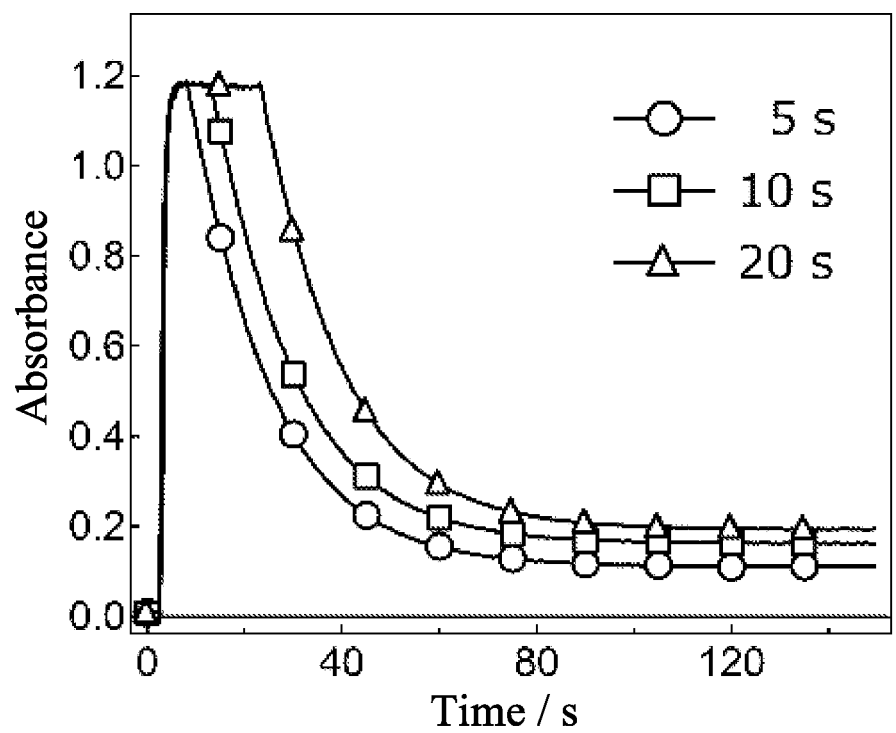
FIG. 89 is a graph of change in absorbance by time at the maximum absorption wavelength of the chromogen when the toluene solution of compound 21 is irradiated with UV for 5, 10, and 20 seconds.

FIG. 87 shows the ultraviolet/visible absorption spectrum of the toluene solution of compound 21 (concentration $5.5 \times 10^{-5}$M). The transient absorption spectrum of the above toluene solution of compound 21 is measured using ultraviolet with wavelength of 365 nm as excitation light. FIG. 88 shows transient absorption spectra before ultraviolet irradiation, during ultraviolet irradiation, and 120 seconds after ultraviolet irradiation is stopped. When a toluene solution of compound 21 is irradiated with ultraviolet, a chromogen having a maximum absorption wavelength at a wavelength of 423 nm is produced reversibly. FIG. 89 shows changes with time in absorbance at the maximum absorption wavelength after irradiation with ultraviolet for 5, 10 and 20 seconds. It is confirmed that at 25° C., after the ultraviolet irradiation is stopped, the chromogen rapidly decayed with a half-life of 12 s. It is confirmed that 39% of the trans-transoid is generated in the compound 21 in which a thioether group is bonded to the carbon atom at the $1^{st}$ position of the pyranoquinazoline skeleton. At this time, it is confirmed that the production rate of the trans-transoid remained at about 15%.

Comparative Example 14

Photochromic properties of compound 22 in toluene.

Figure 90:
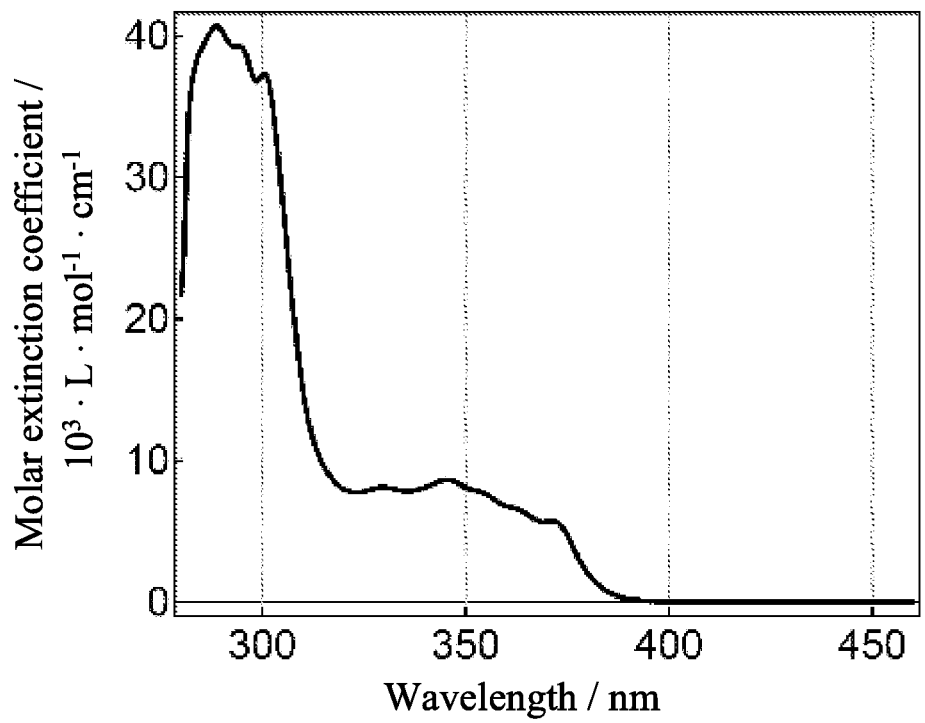
FIG. 90 is a graph of UV/visible absorption spectrum of the toluene solution of decolorized compound 22.
Figure 91:
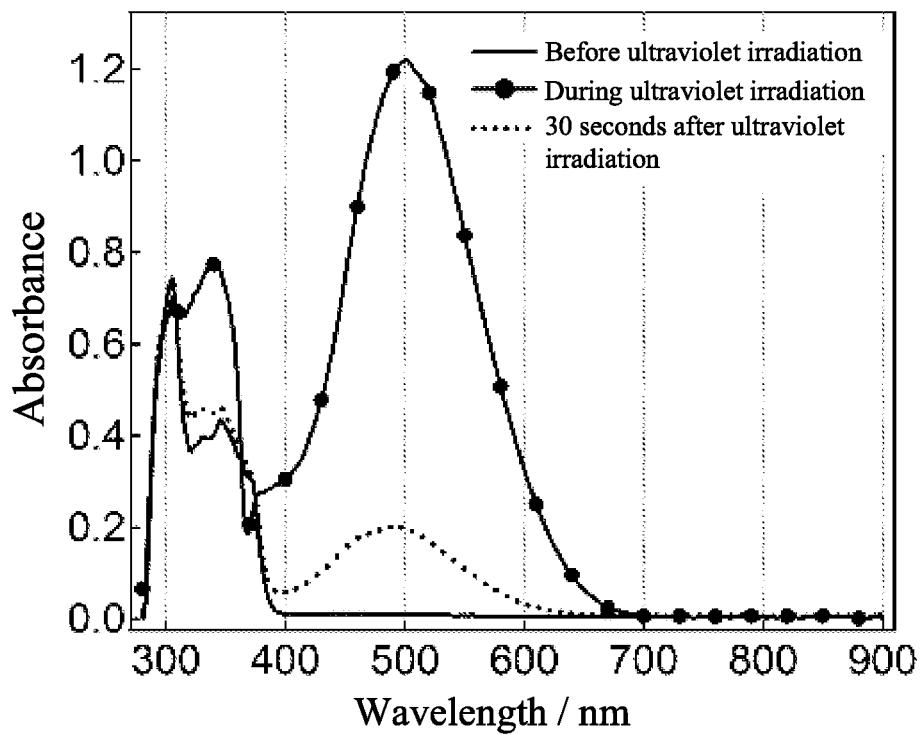
FIG. 91 is a graph of UV-visible/near-infrared absorption spectrum of toluene solution of compound 22 at the timing of before UV irradiation, during UV irradiation and 30 seconds after UV irradiation is stopped.
Figure 92:
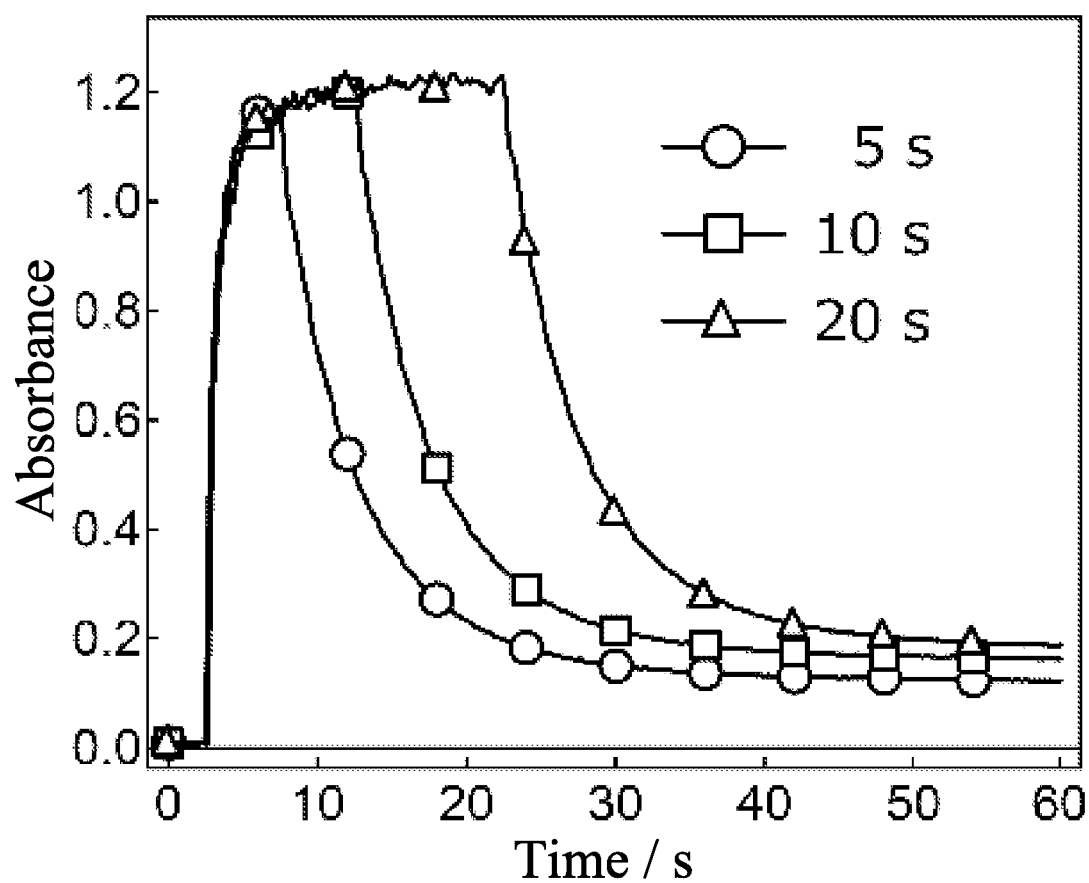
FIG. 92 is a graph of change in absorbance by time at the maximum absorption wavelength of the chromogen when the toluene solution of compound 22 is irradiated with UV for 5, 10, and 20 seconds.

FIG. 90 shows the ultraviolet/visible absorption spectrum of the toluene solution of compound 22 (concentration $5.5 \times 10^{-5}$M). The transient absorption spectrum of the above toluene solution of compound 21 is measured using ultraviolet with wavelength of 365 nm as excitation light. FIG. 91 shows transient absorption spectra before ultraviolet irradiation, during ultraviolet irradiation, and 30 seconds after ultraviolet irradiation is stopped. When a toluene solution of compound 22 is irradiated with ultraviolet, a chromogen having a maximum absorption wavelength at a wavelength of 501 nm is produced reversibly. FIG. 92 shows changes with time in absorbance at the maximum absorption wavelength after irradiation with ultraviolet for 5, 10 and 20 seconds. It is confirmed that at 25° C., after the ultraviolet irradiation is stopped, the chromogen relatively rapidly decayed with a half-life of 3.3 s. It is confirmed that 39% of the trans-transoid is generated in the compound 22 in which a thioether group is bonded to the carbon atom at the $1^{st}$ position of the pyranoquinazoline skeleton. At this time, it is confirmed that the production rate of the trans-transoid remained at about 21%.

The pyranoquinazoline derivative and naphthopyran derivative of the present invention have a high-speed colorizing/decolorizing reaction and high durability as compared with conventional photochromic materials. Furthermore, the photochromic characteristics such as the decolorizing reaction rate and colorizing density may be adjusting appropriately depending on the use of the compound of the present invention according to the number and type of substituents on the aryl group of the compound of the present invention, the structure of the aromatic ring formed by the substituent, etc. Therefore, the photochromic compound in which the first carbon atom of the pyranoquinazoline (8H-pyrano[3,2-f]quinazoline) skeleton and the carbon atom at the $10^{th}$ position of the naphthopyran(3H-naphtho[2,1-b]pyran) skeleton are bonded to a etheric oxygen atom has high industrial applicability as an excellent photochromic compound, particularly in the fields of light control material, hologram material, security ink material and the like.

What is claimed is:
1. A compound represented by the following general formula:

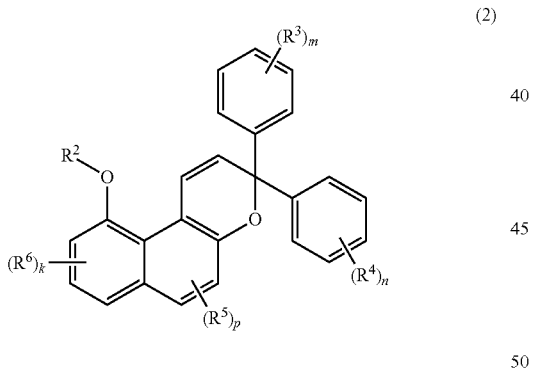

(2)

wherein, in the formulas:
the substituent $R^6$ is:
alkyl group or alkoxy group, or alkyl group having substituent W or alkoxy group having substituent W; or
aromatic group or heterocyclic group, or aromatic group having substituent W or heterocyclic group having substituent W,
wherein the substituents W are independent to each other and are identical or different from each other, and:
(1) the substituent(s) W is one or more substituent selected from the group consisting of:
hydrogen atom, halogen atom, nitro group, cyano group, trifluoromethyl group, hydroxyl group, thiol group, amino group and carbazole group,
straight chain or branched chain alkyl group, alkylamino group, alkoxy group and cycloether ring having carbon number from 1 to 20, and
—$Y_1$-$SiZ_1Z_2Z_3$ group, —$Y_1$-$SiY_2Z_1Z_2$ group and —$Y_1$-$SiY_2Y_3Z_1$ group, aromatic ring, heterocyclic ring, and alicyclic ring, each of which is formed by multiple substituent W combining with each other, wherein $Y_1$ to $Y_3$ and $Z_1$ to $Z_3$ are independent to each other and are identical to or different from each other, and $Y_1$ to $Y_3$ represent straight chain, branched chain or cyclic alkyl group or alkylene group having carbon number from 1 to 20, and $Z_1$ to $Z_3$ represent hydrogen atom or halogen atom, or straight chain or branched chain alkoxy group having carbon number from 1 to 8, or (2) the substituent(s) W is one or more substituent selected from the group consisting of substituents represented by the following structural formulas (i), (ii) and (iii):

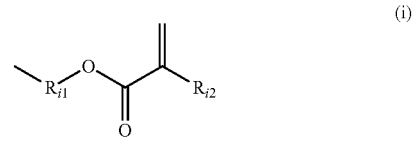

(i)

wherein $R_{i1}$ represents alkyl group, alkylene group or alkoxylene group having carbon number from 1 to 20, and $R_{i2}$ represents hydrogen or alkyl group having carbon number from 1 to 3;

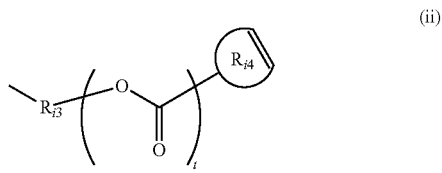

(ii)

wherein $R_{i3}$ represents alkyl group, alkylene group or alkoxylene group having carbon number from 1 to 20, $R_{i4}$ represents cyclic olefins having a total of carbon and silicon number of 5 to 10, and t represents of 0 or 1; and

(iii)

wherein $R_{i5}$ represents alkyl group, alkylene group or alkoxylene group having carbon number from 1 to 20, $R_{i6}$ represents ethylene group or acetylene group, the substituent W integrates the carbon atom and other substituent W as a whole to form or not to form aromatic ring, heterocyclic ring or alicyclic ring, wherein the aromatic ring, the heterocyclic ring and the alicyclic ring, if formed, is further with or without a substituent which has the same meaning as the substituent having aryl group, $R^2$ is:
  straight chain, branched chain or cyclic alkyl group, aromatic ring group or heterocyclic group having carbon number from 1 to 20, or
  straight chain, branched chain or cyclic alkyl group, aromatic ring group or heterocyclic group having substituent W and having carbon number from 1 to 20, $R^3$, $R^4$, and $R^5$ are independent to each other, identical or different from each other, and one or more substituent selected from the group consisting of:
  hydrogen atom, halogen atom, nitro group, cyano group, trifluoromethyl group, hydroxyl group, thiol group, amino group, carbazole group, and straight chain or branched chain alkyl group, alkylamino group and alkoxy group having carbon number from 1 to 20, —$Y_1$-Si$Z_1Z_2Z_3$ group, —$Y_1$-Si$Y_2Z_1Z_2$ group —$Y_1$-Si$Y_2Y_3Z_1$ group, aromatic ring, heterocyclic ring, and alicyclic ring which forms rings by combining with each other, wherein Yi to $Y_3$ are independent to each other, identical to or different from each other, and represent straight chain, branched chain or cyclic alkyl group or alkylene group having carbon number from 1 to 20, and $Z_1$ to $Z_3$ are independent to each other, identical to or different from each other, and represent hydrogen atom or halogen atom or straight chain or branched chain alkoxy group having carbon number from 1 to 8, and aromatic ring, heterocyclic ring and alicyclic ring, each of which is formed by multiple substituent $R^3$, $R^4$, and $R^5$ combining with each other, bonding of $R^2$ with $R^6$ may form 5- to 7-membered ring, or 5- to 7-membered ring having substituent W, bonding of two or more $R^5$, bonding of two or more $R^6$, bonding of one or more $R^5$ and $R^6$, may form unsaturated 5- or 6-membered ring or aromatic ring, or unsaturated 5- or 6-membered ring having substituent W, in the unsaturated 5- or 6-membered ring or aromatic ring formed by bonding of one or more $R^5$ and $R^6$, bonding of one or more $R^5$ and $R^7$ and bonding of one or more $R^7$ and $R^8$, unsaturated 5- or 6-membered ring or aromatic ring, or unsaturated 5- or 6-membered ring having substituent W may be formed, m and n are an integer from 1 to 5, k is an integer from 1 to 3, and p is an integer from 1 to 2.

2. A compound formed by copolymerizing the compound as claimed in claim 1.

* * * * *